United States Patent
Brown et al.

(10) Patent No.: US 12,252,691 B2
(45) Date of Patent: Mar. 18, 2025

(54) COMPOSITIONS AND METHODS FOR INHIBITING LPA EXPRESSION

(71) Applicant: Dicerna Pharmaceuticals, Inc., Lexington, MA (US)

(72) Inventors: Bob Dale Brown, Littleton, MA (US); Henryk T. Dudek, Belmont, MA (US); Marc Abrams, Natick, MA (US); Wen Han, Boston, MA (US); Anton Turanov, Revere, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 18/807,591

(22) Filed: Aug. 16, 2024

(65) Prior Publication Data
US 2024/0401053 A1  Dec. 5, 2024

Related U.S. Application Data

(63) Continuation of application No. 18/040,302, filed as application No. PCT/US2021/071109 on Aug. 5, 2021.

(60) Provisional application No. 63/074,779, filed on Sep. 4, 2020, provisional application No. 63/061,676, filed on Aug. 5, 2020.

(51) Int. Cl.
 C12N 15/113 (2010.01)

(52) U.S. Cl.
 CPC ........ *C12N 15/113* (2013.01); *C12N 2310/14* (2013.01); *C12N 2310/315* (2013.01); *C12N 2310/321* (2013.01); *C12N 2310/322* (2013.01); *C12N 2310/351* (2013.01); *C12N 2310/531* (2013.01)

(58) Field of Classification Search
 CPC .............. C12N 15/113; C12N 2310/14; C12N 2310/315; C12N 2310/321; C12N 2310/322; C12N 2310/351; C12N 2310/531
See application file for complete search history.

(56) References Cited

U.S. PATENT DOCUMENTS

| | | |
|---|---|---|
| 8,372,968 B2 | 2/2013 | Tuschl et al. |
| 8,513,207 B2 | 8/2013 | Brown |
| 8,883,996 B2 | 11/2014 | Rossi et al. |
| 8,927,513 B2 | 1/2015 | Manoharan et al. |
| 8,927,705 B2 | 1/2015 | Brown |
| 9,012,138 B2 | 4/2015 | Tuschl et al. |
| 9,012,621 B2 | 4/2015 | Tuschl et al. |
| 9,193,753 B2 | 11/2015 | Tuschl et al. |
| 11,414,659 B2 | 8/2022 | Wang et al. |
| 2009/0099115 A1 | 4/2009 | McSwiggen et al. |

FOREIGN PATENT DOCUMENTS

| | | | |
|---|---|---|---|
| WO | WO-2010033225 A2 | 3/2010 | |
| WO | WO-2011133871 A2 | 10/2011 | |
| WO | WO-2016100401 A1 * | 6/2016 | .......... A61K 47/549 |
| WO | WO-2017059223 A2 | 4/2017 | |
| WO | WO-2018045317 A1 | 3/2018 | |
| WO | WO-2019092283 A1 | 5/2019 | |
| WO | WO-2019118638 A2 | 6/2019 | |
| WO | WO-2021119034 A1 | 6/2021 | |
| WO | WO-2022032288 A1 | 2/2022 | |

OTHER PUBLICATIONS

Hu et al. "Therapeutic siRNA: state of the art." Sig Transduct Target Ther 5, 101 (2020). (Year: 2020).*
Foster et al. "Advanced siRNA Designs Further Improve In Vivo Performance of GalNAc-siRNA Conjugates." Molecular Therapy, vol. 26, Issue 3, 708-717 (2018) (Year: 2018).*
PCT International Search Report from PCT/US2021/071109 dated Nov. 18, 2021.
Prakash, et al., "Identification of metabolically stable 5'-phosphate analogs that support single-stranded siRNA activity," Nucleic Acids Research. 2015; 43(6):2993-3011.
Woese, et al., "Architecture of ribosomal RNA: Constraints of the sequence of "tetra-loops"," Proc. Natl. Acad. Sci. 1990; 87:8467-8471.
Antao, et al., "A thermodynamic study of unusually stable RNA and DNA hairpins," Nucleic Acids Research. 1991; 19(21):5901-5905.
Nakano, et al., "Selection for Thermodynamically Stable DNA Tetraloops Using Temperature Gradient Gel Electrophoresis Reveals Four Motifs: d(cGNNAg), d(cGNABg), d(cCNNGg), and d(gCNNGc)," Biochemistry. 2002; 41:14281-14292.
Moore, et al., "Short Hairpin RNA (shRNA): Design, Delivery, and Assessment of Gene Knockdown," Methods Mol. Biol. 2010; 619:141-158.
Kraynack and Baker, "Small interfering RNAs containing full 2'-O-methylribonucleotide-modified sense strands display Argonaute2/eIF2C2-dependent activity," RNA. 2006; 12:163-176.
Sun et al., "Asymmetric RNA duplexes mediate RNA interference in mammalian cells," Nature Biotechnology. 2008; 26:1379-1382.
Chang, et al., "Asymmetric Shorter-duplex siRNA Structures Triggers Efficient Gene Silencing with Reduced Nonspecific Effects," Molecular Therapy. 2009; 4:725-732.
Hamilton, et al., "Two classes of short interfering RNA in RNA silencing," EMBO J. 2002; 21(17):4671-4679.
U.S. Appl. No. 18/040,302, filed Feb. 2, 2023.
Yu, et al., "Disposition and Pharmacokinetics of a GalNAc3-Conjugated Antisense Oligonucleotide Targeting Human Lipoprotein (a) in Monkeys," Nucleic Acid Therapeutics. 2016;26(6):372-384.

* cited by examiner

*Primary Examiner* — Stephen T Kapushoc
*Assistant Examiner* — Amanda M Zahorik
(74) *Attorney, Agent, or Firm* — Dechert LLP; Andrea L.C. Reid; Gang Wang

(57) ABSTRACT

Oligonucleotides are provided herein that inhibit apolipoprotein(a) (LPA) expression. Also provided are compositions including the same and uses thereof, particularly uses relating to treating diseases, disorders and/or conditions associated with LPA expression.

4 Claims, 12 Drawing Sheets

Specification includes a Sequence Listing.

COMPOSITIONS AND METHODS FOR INHIBITING LPA EXPRESSION

CROSS-REFERENCE TO RELATED APPLICATIONS

This application is a continuation application of U.S. application Ser. No. 18/040,302, filed Feb. 2, 2023, which is a National Stage of International Application No. PCT/US2021/071109, filed Aug. 5, 2021, which claims the benefit under 35 U.S.C. § 119 (e) of U.S. Provisional Patent Application No. 63/061,676, filed Aug. 5, 2020, and claims the benefit under 35 U.S.C. § 119 (e) of U.S. Provisional Patent Application No. 63/074,779, filed Sep. 4, 2020, the contents of each of which are incorporated herein by reference in their entirety.

TECHNICAL FIELD

The disclosure relates to oligonucleotides that inhibit apolipoprotein(a) ("LPA") expression and uses thereof, particularly uses relating to treating diseases, disorders and/or conditions associated with LPA expression.

REFERENCE TO SEQUENCE LISTING

The instant application contains a Sequence Listing which has been submitted electronically in XML file format and is hereby incorporated by reference in its entirety. Said XML copy, created on Aug. 15, 2024, is named "400930_026USC1_211985_SL.xml" and is 1,325,553 bytes in size.

BACKGROUND

Lipoprotein (a) (Lp(a)) is a heterogeneous low density lipoprotein (LDL)-like particle containing a lipid core and apolipoprotein B (apoB-100) with a unique constituent, apolipoprotein(a) (apo(a)), that is attached to apoB-100 through a disulfide bond. The apo(a) gene (LPA) is expressed predominantly in the liver and expression is restricted to human and non-human primates. Lp(a) levels in humans are genetically defined and do not change significantly with diet, exercise, or other lifestyle changes. LPA varies in length depending upon the number of Kringle KIV2 domains present and its expression is inversely correlated with the number of domains present. Normal Lp(a) levels range from 0.1-25 mg/dl, with about 25% of the population in the United States of America having Lp(a) levels of 30 mg/dl or higher. Analysis of Lp(a) levels in multiple studies have implicated high Lp(a) levels as an independent risk factor for cardiovascular disease, stroke, and other related disorders including atherosclerotic stenosis. In addition, genome-wide association analyses have also implicated LPA as a genetic risk factor for diseases such as atherosclerotic stenosis. When therapeutic lipoprotein apheresis is used to lower both Lp(a) and LDL levels in hyperlipidemic patients, significant reductions of cardiovascular events have been observed.

Therefore, there exists a need for therapeutics and treatments related to these and other LPA-related diseases.

BRIEF SUMMARY OF THE INVENTION

Embodiments of the disclosure relate to compositions and methods for treating a disease, disorder and/or condition related to LPA expression. The disclosure is based, in part, on the discovery and development of oligonucleotides that selectively inhibit and/or reduce LPA expression in the liver. Accordingly, target sequences within LPA mRNA were identified and RNAi oligonucleotides that bind to these target sequences and inhibit LPA mRNA expression were generated. As demonstrated herein, the RNAi oligonucleotides inhibited monkey and human LPA expression in the liver. Without being bound by theory, the RNAi oligonucleotides described herein are useful for treating a disease, disorder or condition associated with LPA expression (e.g., cardiometabolic diseases, atherosclerosis, dyslipidemia, NAFLD and NASH).

Accordingly, in some embodiments, the present disclosure provides an RNAi oligonucleotide for reducing LPA expression, the oligonucleotide comprising a sense strand and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is at least 15 contiguous nucleotides in length.

In any of the foregoing or related embodiments, the sense strand is 15 to 50 nucleotides in length. In some embodiments, the sense strand is 18 to 36 nucleotides in length.

In any of the foregoing or related aspects, the antisense strand is 15 to 30 nucleotides in length.

In any of the foregoing or related aspects, the antisense strand is 22 nucleotides in length and wherein antisense strand and the sense strand form a duplex region of at least 19 nucleotides in length, optionally at least 20 nucleotides in length.

In any of the foregoing or related aspects, the region of complementarity is at least 19 contiguous nucleotides in length, optionally at least 20 nucleotides in length.

In any of the foregoing or related aspects, the 3' end of the sense strand comprises a stem-loop set forth as S1-L-S2, wherein S1 is complementary to S2, and wherein L forms a loop between S1 and S2 of 3-5 nucleotides in length.

In some aspects, the disclosure provides an RNAi oligonucleotide for reducing LPA expression, the oligonucleotide comprising a sense strand of 15 to 50 nucleotides in length and an antisense strand, wherein the sense strand and the antisense strand form a duplex region, wherein the wherein the antisense strand comprises a region of complementarity to a LPA mRNA target sequence of any one of SEQ ID NOs: 4-387, and wherein the region of complementarity is at least 15 contiguous nucleotides in length.

In other aspects, the disclosure provides an RNAi oligonucleotide for reducing LPA expression, the oligonucleotide comprising a sense strand of 15 to 50 nucleotides in length and an antisense strand of 15 to 30 nucleotides in length, wherein the sense strand and the antisense strand form a duplex region, wherein the antisense strand comprises a region of complementarity to a LPA mRNA target sequence of any one of SEQ ID NOs: 4-387, and wherein the region of complementarity is at least 15 contiguous nucleotides in length.

In yet other aspects, the disclosure provides an RNAi oligonucleotide for reducing LPA expression, the oligonucleotide comprising a sense strand of 15 to 50 nucleotides in length and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In further aspects, the disclosure provides an RNAi oligonucleotide for reducing LPA expression, the oligonucleotide comprising a sense strand of 18 to 36 nucleotides in length and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In other aspects, the disclosure provides an RNAi oligonucleotide for reducing LPA expression, the oligonucleotide comprising a sense strand of 18 to 36 nucleotides in length and an antisense strand of 22 nucleotides in length, wherein the sense strand and the antisense strand form a duplex region, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In some aspects, the disclosure provides an RNAi oligonucleotide for reducing LPA expression, the oligonucleotide comprising a sense strand of 18 to 36 nucleotides in length and an antisense strand of 22 nucleotides in length, wherein the sense strand and the antisense strand form a duplex region, wherein the 3' end of the sense strand comprises a stem-loop set forth as S1-L-S2, wherein S1 is complementary to S2, and wherein L forms a loop between S1 and S2 of 3-5 nucleotides in length, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In other aspects, the disclosure provides an RNAi oligonucleotide for reducing LPA expression, the oligonucleotide comprising a sense strand of 36 nucleotides in length and an antisense strand of 22 nucleotides in length, wherein the sense strand and the antisense strand form a duplex region, wherein the 3' end of the sense strand comprises a stem-loop set forth as S1-L-S2, wherein S1 is complementary to S2, and wherein L forms a loop between S1 and S2 of 3-5 nucleotides in length, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In yet other aspects, the disclosure provides an RNAi oligonucleotide for reducing LPA expression, the oligonucleotide comprising a sense strand of 36 nucleotides in length and an antisense strand of 22 nucleotides in length, wherein the sense strand and the antisense strand form a duplex region of at least 19 nucleotides in length, optionally 20 nucleotides in length, wherein the 3' end of the sense strand comprises a stem-loop set forth as S1-L-S2, wherein S1 is complementary to S2, and wherein L forms a loop between S1 and S2 of 3-5 nucleotides in length, wherein the antisense strand comprises a region of complementarity to a LPA mRNA target sequence of any one of SEQ ID NOs: 4-387, and wherein the region of complementarity is 19 contiguous nucleotides in length, optionally 20 nucleotides in length.

In any of the foregoing or related aspects, L is a triloop or a tetraloop. In some embodiments, L is a tetraloop. In some embodiments, the tetraloop comprises the sequence 5'-GAAA-3'.

In any of the foregoing or related embodiments, the S1 and S2 are 1-10 nucleotides in length and have the same length. In some embodiments, S1 and S2 are 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length. In some embodiments, S1 and S2 are 6 nucleotides in length. In some embodiments, the stem-loop comprises the sequence 5'-GCAGCCGAAAGGCUGC-3' (SEQ ID NO: 1197).

In any of the foregoing or related embodiments, the antisense strand comprises a 3' overhang sequence of one or more nucleotides in length. In some embodiments, the 3' overhang sequence is 2 nucleotides in length, optionally wherein the 3' overhang sequence is GG.

In any of the foregoing or related embodiments, the oligonucleotide comprises at least one modified nucleotide. In some embodiments, the modified nucleotide comprises a 2'-modification. In some embodiments, the 2'-modification is a modification selected from 2'-aminoethyl, 2'-fluoro, 2'-O-methyl, 2'-O-methoxyethyl, and 2'-deoxy-2'-fluoro-β-d-arabinonucleic acid. In some embodiments, all nucleotides comprising the oligonucleotide are modified, optionally wherein the modification is a 2'-modification selected from 2'-fluoro and 2'-O-methyl.

In any of the foregoing or related embodiments, the oligonucleotide comprises at least one modified internucleotide linkage. In some embodiments, the at least one modified internucleotide linkage is a phosphorothioate linkage.

In any of the foregoing or related embodiments, the 4'-carbon of the sugar of the 5'-nucleotide of the antisense strand comprises a phosphate analog. In some embodiments, the phosphate analog is oxymethylphosphonate, vinylphosphonate or malonyl phosphonate, optionally wherein the phosphate analog is a 4'-phosphate analog comprising 5'-methoxyphosphonate-4'-oxy.

In any of the foregoing or related embodiments, at least one nucleotide of the oligonucleotide is conjugated to one or more targeting ligands. In some embodiments, each targeting ligand comprises a carbohydrate, amino sugar, cholesterol, polypeptide, or lipid. In some embodiments, each targeting ligand comprises a N-acetylgalactosamine (GalNAc) moiety. In some embodiments, the GalNAc moiety is a monovalent GalNAc moiety, a bivalent GalNAc moiety, a trivalent GalNAc moiety or a tetravalent GalNAc moiety. In some embodiments, up to 4 nucleotides of L of the stem-loop are each conjugated to a monovalent GalNAc moiety.

In any of the foregoing or related embodiments, the sense strand comprises a nucleotide sequence of any one of SEQ ID NOs: 388, 389, 390, 391, 392, 393, 394, 395, 396, 397, 398, 399, 400, 401, 402, and 403.

In any of the foregoing or related embodiments, the antisense strand comprises a nucleotide sequence of any one of SEQ ID NOs: 788, 789, 790, 791, 792, 793, 794, 795, 796, 797, 798, 799, 800, 801, 802, and 803.

In any of the foregoing or related embodiments, the sense strand and antisense strands comprise nucleotide sequences selected from the group consisting of:
  (a) SEQ ID NOs: 393 and 793, respectively;
  (b) SEQ ID NOs: 388 and 788, respectively;
  (c) SEQ ID NOs: 389 and 789, respectively;
  (d) SEQ ID NOs: 390 and 790, respectively;
  (e) SEQ ID NOs: 391 and 791, respectively;
  (f) SEQ ID NOs: 392 and 792, respectively;
  (g) SEQ ID NOs: 394 and 794, respectively;
  (h) SEQ ID NOs: 395 and 795, respectively;
  (i) SEQ ID NOs: 396 and 796, respectively;
  (j) SEQ ID NOs: 397 and 797, respectively;
  (k) SEQ ID NOs: 398 and 798, respectively;
  (l) SEQ ID NOs: 399 and 799, respectively;

(m) SEQ ID NOs: 400 and 800, respectively;
(n) SEQ ID NOs: 401 and 801, respectively;
(o) SEQ ID NOs: 402 and 802, respectively; and
(p) SEQ ID NOs: 403 and 803, respectively.

In some embodiments, the sense strand comprises a nucleotide sequence as set forth in SEQ ID NO: 393, wherein the antisense strand comprises a nucleotide sequence as set forth in SEQ ID NO: 793. In some embodiments, the sense strand comprises a nucleotide sequence as set forth in SEQ ID NO: 388, wherein the antisense strand comprises a nucleotide sequence as set forth in SEQ ID NO: 788. In some embodiments, the sense strand comprises a nucleotide sequence as set forth in SEQ ID NO: 389, wherein the antisense strand comprises a nucleotide sequence as set forth in SEQ ID NO: 789. In some embodiments, the sense strand comprises a nucleotide sequence as set forth in SEQ ID NO: 390, wherein the antisense strand comprises a nucleotide sequence as set forth in SEQ ID NO: 790. In some embodiments, the sense strand comprises a nucleotide sequence as set forth in SEQ ID NO: 391, wherein the antisense strand comprises a nucleotide sequence as set forth in SEQ ID NO: 791. In some embodiments, the sense strand comprises a nucleotide sequence as set forth in SEQ ID NO: 392, wherein the antisense strand comprises a nucleotide sequence as set forth in SEQ ID NO: 792. In some embodiments, the sense strand comprises a nucleotide sequence as set forth in SEQ ID NO: 394, wherein the antisense strand comprises a nucleotide sequence as set forth in SEQ ID NO: 794. In some embodiments, the sense strand comprises a nucleotide sequence as set forth in SEQ ID NO: 395, wherein the antisense strand comprises a nucleotide sequence as set forth in SEQ ID NO: 795. In some embodiments, the sense strand comprises a nucleotide sequence as set forth in SEQ ID NO: 396, wherein the antisense strand comprises a nucleotide sequence as set forth in SEQ ID NO: 796. In some embodiments, the sense strand comprises a nucleotide sequence as set forth in SEQ ID NO: 397, wherein the antisense strand comprises a nucleotide sequence as set forth in SEQ ID NO: 797. In some embodiments, the sense strand comprises a nucleotide sequence as set forth in SEQ ID NO: 398, wherein the antisense strand comprises a nucleotide sequence as set forth in SEQ ID NO: 798. In some embodiments, the sense strand comprises a nucleotide sequence as set forth in SEQ ID NO: 399, wherein the antisense strand comprises a nucleotide sequence as set forth in SEQ ID NO: 799. In some embodiments, the sense strand comprises a nucleotide sequence as set forth in SEQ ID NO: 400, wherein the antisense strand comprises a nucleotide sequence as set forth in SEQ ID NO: 800. In some embodiments, the sense strand comprises a nucleotide sequence as set forth in SEQ ID NO: 401, wherein the antisense strand comprises a nucleotide sequence as set forth in SEQ ID NO: 801. In some embodiments, the sense strand comprises a nucleotide sequence as set forth in SEQ ID NO: 402, wherein the antisense strand comprises a nucleotide sequence as set forth in SEQ ID NO: 802. In some embodiments, the sense strand comprises a nucleotide sequence as set forth in SEQ ID NO: 403, wherein the antisense strand comprises a nucleotide sequence as set forth in SEQ ID NO: 803.

In some embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and antisense strand are modified, wherein the antisense strand comprises a region of complementarity to a LPA mRNA target sequence of any one of SEQ ID NOs: 4-387, and wherein the region of complementarity is at least 15 contiguous nucleotides in length.

In further embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and antisense strand are modified, wherein the 4'-carbon of the sugar of the 5'-nucleotide of the antisense strand comprises a phosphate analog, wherein the antisense strand comprises a region of complementarity to a LPA mRNA target sequence of any one of SEQ ID NOs: 4-387, and wherein the region of complementarity is at least 15 contiguous nucleotides in length.

In other embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and antisense strand are modified, wherein the 4'-carbon of the sugar of the 5'-nucleotide of the antisense strand comprises a phosphate analog, wherein the antisense strand comprises a region of complementarity to a LPA mRNA target sequence of any one of SEQ ID NOs: 4-387, and wherein the region of complementarity is at least 15 contiguous nucleotides in length.

In some embodiments, the disclosure provides an RNAi oligonucleotide for reducing LPA expression, the oligonucleotide comprising a sense strand and an antisense strand, wherein the sense strand and the antisense strand form a duplex region, wherein all nucleotides comprising the sense strand and the antisense strand are modified, wherein the antisense strand and the sense strand comprise one or more 2'-fluoro and 2'-O-methyl modified nucleotides and at least one phosphorothioate linkage, wherein the 4'-carbon of the sugar of the 5'-nucleotide of the antisense strand comprises a phosphate analog, wherein the antisense strand comprises a region of complementarity to a LPA mRNA target sequence of any one of SEQ ID NOs: 4-387, and wherein the region of complementarity is at least 15 contiguous nucleotides in length.

In some embodiments, the disclosure provides a method for treating a subject having a disease, disorder or condition associated with LPA expression, the method comprising administering to the subject a therapeutically effective amount of the RNAi oligonucleotide of any one of the preceding claims, or pharmaceutical composition thereof, thereby treating the subject.

In other embodiments, the disclosure provides a pharmaceutical composition comprising a RNAi oligonucleotide described herein, and a pharmaceutically acceptable carrier, delivery agent or excipient.

In other embodiments, the disclosure provides a method of delivering an oligonucleotide to a subject, the method comprising administering a pharmaceutical composition described herein to the subject.

In another embodiments, the disclosure provides a method for reducing LPA expression in a cell, a population of cells or a subject, the method comprising the step of:
  i. contacting the cell or the population of cells with a RNAi oligonucleotide or pharmaceutical composition described herein; or
  ii. administering to the subject a RNAi oligonucleotide or pharmaceutical composition described herein. In some embodiments, reducing LPA expression comprises reducing an amount or level of LPA mRNA, an amount or level of LPA protein, or both. In some embodiments, the subject has a disease, disorder or condition associated with LPA expression. In some embodiments, the disease, disorder, or condition associated with LPA expression is a cardiometabolic disease, optionally atherosclerosis, dyslipidemia, NAFLD and NASH. In some embodiments, the RNAi oligonucleotide, or pharmaceutical composition, is administered in combination with a second composition or therapeutic agent.

In another aspect, the disclosure provides a method for treating a subject having a disease, disorder or condition associated with LPA expression, the method comprising administering to the subject a therapeutically effective amount of an RNAi oligonucleotide comprising a sense strand and an antisense strand, wherein the sense strand and the antisense strand form a duplex region, wherein the antisense strand comprises a region of complementarity to a LPA mRNA target sequence of any one of SEQ ID NOs: 4-387, and wherein the region of complementarity is at least 15 contiguous nucleotides in length.

In another aspect, the disclosure provides a method for treating a subject having a disease, disorder or condition associated with LPA expression, the method comprising administering to the subject a therapeutically effective amount of an RNAi oligonucleotide comprising a sense strand and an antisense strand selected from a row set forth in Table 5, or pharmaceutical composition thereof, thereby treating the subject.

In other embodiments, the disclosure provides a method for treating a subject having a disease, disorder or condition associated with LPA expression, the method comprising administering to the subject a therapeutically effective amount of an RNAi oligonucleotide comprising a sense strand and an antisense strand, wherein the sense strand and antisense strands comprise nucleotide sequences selected from the group consisting of:
  (a) SEQ ID NOs: 393 and 793, respectively;
  (b) SEQ ID NOs: 388 and 788, respectively;
  (c) SEQ ID NOs: 389 and 789, respectively;
  (d) SEQ ID NOs: 390 and 790, respectively;
  (e) SEQ ID NOs: 391 and 791, respectively;
  (f) SEQ ID NOs: 392 and 792, respectively;
  (g) SEQ ID NOs: 394 and 794, respectively;
  (h) SEQ ID NOs: 395 and 795, respectively;
  (i) SEQ ID NOs: 396 and 796, respectively;
  (j) SEQ ID NOs: 397 and 797, respectively;
  (k) SEQ ID NOs: 398 and 798, respectively;
  (l) SEQ ID NOs: 399 and 799, respectively;
  (m) SEQ ID NOs: 400 and 800, respectively;
  (n) SEQ ID NOs: 401 and 801, respectively;
  (o) SEQ ID NOs: 402 and 802, respectively; and
  (p) SEQ ID NOs: 403 and 803, respectively.

In some embodiments, the sense strand comprises a nucleotide sequence as set forth in SEQ ID NO: 393, wherein the antisense strand comprises a nucleotide sequence as set forth in SEQ ID NO: 793. In some embodiments, the sense strand comprises a nucleotide sequence as set forth in SEQ ID NO: 388, wherein the antisense strand comprises a nucleotide sequence as set forth in SEQ ID NO: 788. In some embodiments, the sense strand comprises a nucleotide sequence as set forth in SEQ ID NO: 389, wherein the antisense strand comprises a nucleotide sequence as set forth in SEQ ID NO: 789. In some embodiments, the sense strand comprises a nucleotide sequence as set forth in SEQ ID NO: 390, wherein the antisense strand comprises a nucleotide sequence as set forth in SEQ ID NO: 790. In some embodiments, the sense strand comprises a nucleotide sequence as set forth in SEQ ID NO: 391, wherein the antisense strand comprises a nucleotide sequence as set forth in SEQ ID NO: 791. In some embodiments, the sense strand comprises a nucleotide sequence as set forth in SEQ ID NO: 392, wherein the antisense strand comprises a nucleotide sequence as set forth in SEQ ID NO: 792. In some embodiments, the sense strand comprises a nucleotide sequence as set forth in SEQ ID NO: 394, wherein the antisense strand comprises a nucleotide sequence as set forth in SEQ ID NO: 794. In some embodiments, the sense strand comprises a nucleotide sequence as set forth in SEQ ID NO: 395, wherein the antisense strand comprises a nucleotide sequence as set forth in SEQ ID NO: 795. In some embodiments, the sense strand comprises a nucleotide sequence as set forth in SEQ ID NO: 396, wherein the antisense strand comprises a nucleotide sequence as set forth in SEQ ID NO: 796. In some embodiments, the sense strand comprises a nucleotide sequence as set forth in SEQ ID NO: 397, wherein the antisense strand comprises a nucleotide sequence as set forth in SEQ ID NO: 797. In some embodiments, the sense strand comprises a nucleotide sequence as set forth in SEQ ID NO: 398, wherein the antisense strand comprises a nucleotide sequence as set forth in SEQ ID NO: 798. In some embodiments, the sense strand comprises a nucleotide sequence as set forth in SEQ ID NO: 399, wherein the antisense strand comprises a nucleotide sequence as set forth in SEQ ID NO: 799. In some embodiments, the sense strand comprises a nucleotide sequence as set forth in SEQ ID NO: 400, wherein the antisense strand comprises a nucleotide sequence as set forth in SEQ ID NO: 800. In some embodiments, the sense strand comprises a nucleotide sequence as set forth in SEQ ID NO: 401, wherein the antisense strand comprises a nucleotide sequence as set forth in SEQ ID NO: 801. In some embodiments, the sense strand comprises a nucleotide sequence as set forth in SEQ ID NO: 402, wherein the antisense strand comprises a nucleotide sequence as set forth in SEQ ID NO: 802. In some embodiments, the sense strand comprises a nucleotide sequence as set forth in SEQ ID NO: 403, wherein the antisense strand comprises a nucleotide sequence as set forth in SEQ ID NO: 803.

In some embodiments, the disease, disorder, or condition associated with LPA expression is a cardiometabolic disease, optionally atherosclerosis, dyslipidemia, NAFLD and NASH.

In some embodiments, the disclosure provides use of an RNAi oligonucleotide or pharmaceutical composition described herein, in the manufacture of a medicament for the treatment of a disease, disorder or condition associated with LPA expression, optionally for the treatment of a cardiometabolic disease, optionally atherosclerosis, dyslipidemia, NAFLD and NASH.

In some embodiments, the disclosure provides use of an RNAi oligonucleotide or pharmaceutical composition described herein, for use, or adaptable for use, in the treatment of a disease, disorder or condition associated with LPA expression, optionally for the treatment of a cardiometabolic disease, optionally atherosclerosis, dyslipidemia, NAFLD and NASH.

In other embodiments, the disclosure provides a kit comprising an RNAi oligonucleotide described herein, an optional pharmaceutically acceptable carrier, and a package insert comprising instructions for administration to a subject having a disease, disorder or condition associated with LPA expression.

In any of the foregoing or related embodiments, the disease, disorder, or condition associated with LPA expression is a cardiometabolic disease, optionally atherosclerosis, dyslipidemia, NAFLD and NASH.

DETAILED DESCRIPTION

I. Definitions

Figure 1:
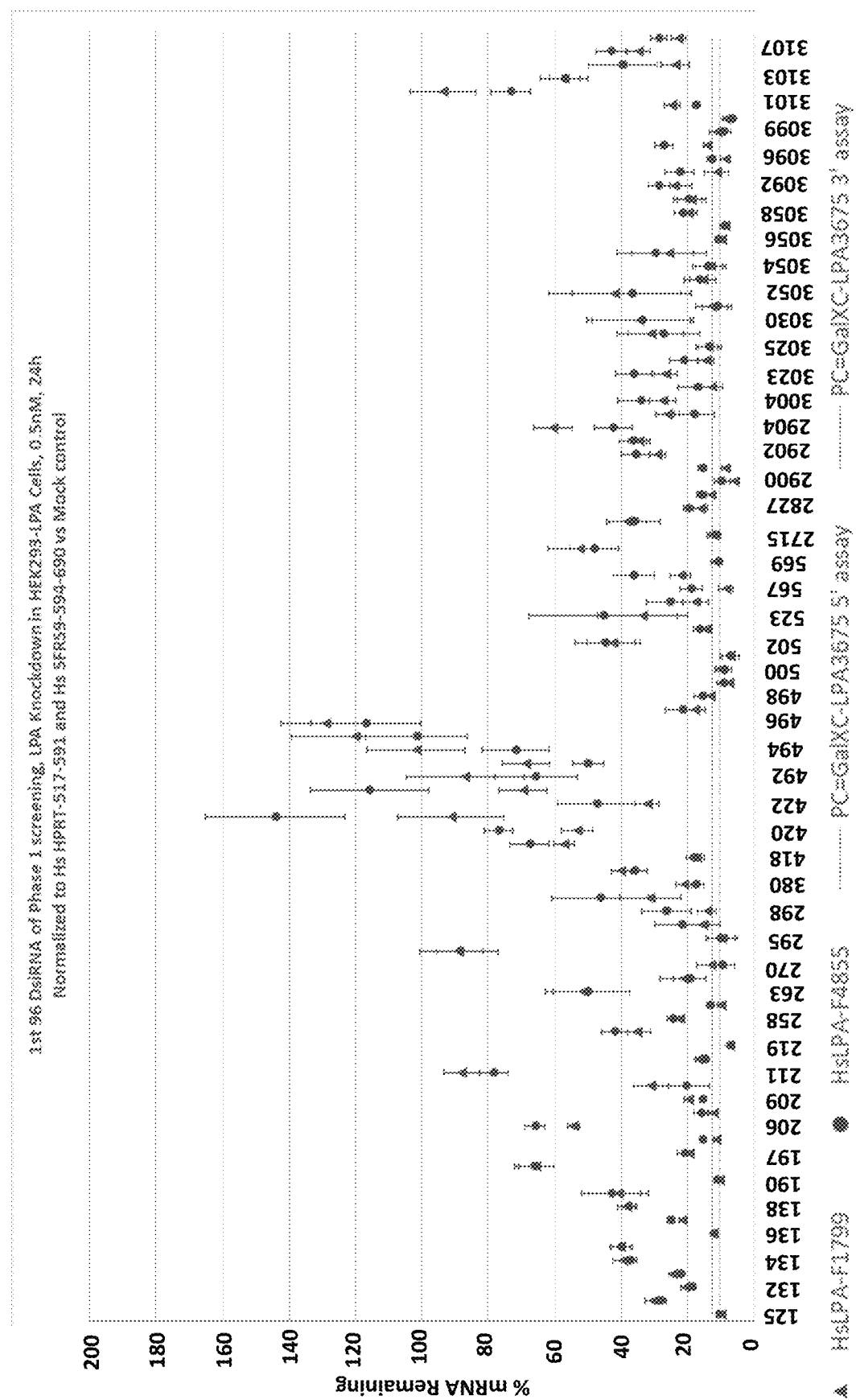
FIGS. 1-4 provide graphs depicting the percent (%) of LPA mRNA in HEK293-LPA cells transfected with the indicated DsiRNAs relative to the % of LPA mRNA control mock-treated cells.
Figure 2:
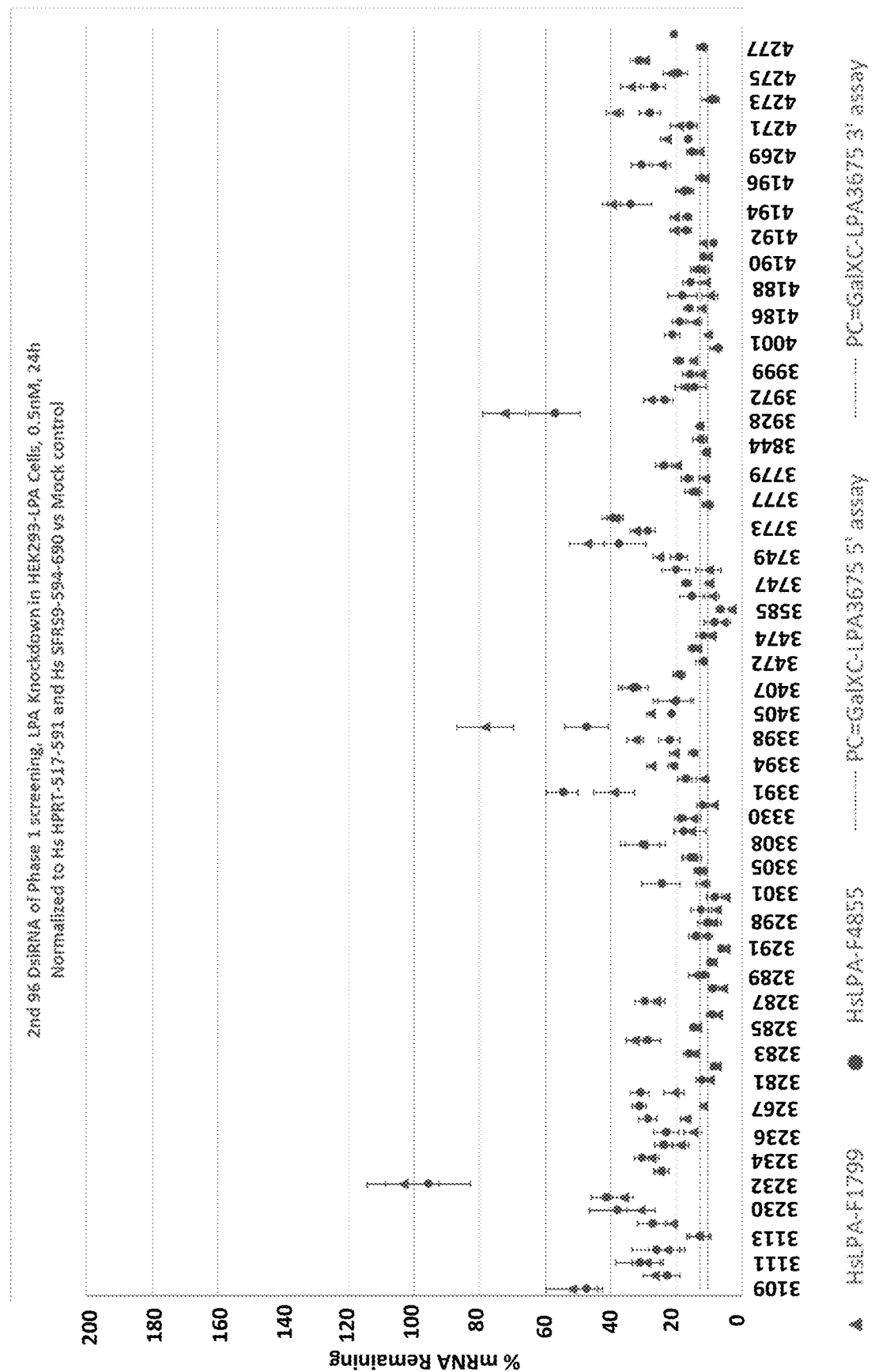

As used herein, "about," as applied to one or more values of interest, refers to a value that is similar to a stated reference value. In certain embodiments, "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1% or less in either direction (greater than or less than) of the stated reference value unless otherwise stated or otherwise evident from the context (except where such number would exceed 100% of a possible value).

As used herein, "administer," "administering," "administration" and the like refers to providing a substance (e.g., an oligonucleotide) to a subject in a manner that is pharmacologically useful (e.g., to treat a condition in the subject).

As used herein, the term "apolipoprotein(a)" and abbreviated as "apo(a)", refers to the apolipoprotein(a) polypeptide, which is a member of the apolipoprotein class of polypeptides that bind lipids to form lipoproteins. Apo(a) is a polymorphic glycoprotein encoded by the LPA gene in humans. LPA mRNA and apo(a) polypeptide are expressed predominantly in the liver. Lipoprotein (a) (abbreviated as Lp(a)) is a class of lipoprotein formed in the liver and comprises a single copy of apolipoprotein (apo) B-100 (Apo-B100) covalently tethered to apo(a). In humans, apo(a) includes at least 10 subtypes of KIV repeats, composed of 1 copy each of $KIV_1$, multiple copies of $KIV_2$, and 1 copy each of $KIV_3$-$KIV_{10}$, KV, and an inactive protease-like domain. The presence of apo(a) distinguishes Lp(a) from all other lipoprotein classes (Marcovina et al., (1995) Clin Chem. 41 (2): 246-55). For the purposes of the disclosure, "apolipoprotein(a)" or "apo(a)" refers to the apo(a) polypeptide from any vertebrate or mammal including, but not limited to, human, mouse, primate, monkey, bovine, chicken, rodent, rat, porcine, ovine and guinea pig. "Apo(a)" also refers to fragments and variants of native apo(a) that maintain at least one in vivo or in vitro activity of a native apo(a). Apo (a) encompasses full-length, unprocessed precursor forms of Apo (a), as well as mature forms resulting from post-translational processing. An exemplary sequence of a human LPA mRNA transcript is publicly available (GenBank Accession No. NM_005577.3) and disclosed herein (SEQ ID NO: 1). An exemplary sequence of cynomolgus monkey LPA mRNA is publicly available (GenBank Accession No. XM_015448517.1) and disclosed herein (SEQ ID NO: 2).

As used herein, "asialoglycoprotein receptor" or "ASGPR" refers to a bipartite C-type lectin formed by a major 48 kDa subunit (ASGPR-1) and minor 40 kDa subunit (ASGPR-2). ASGPR is primarily expressed on the sinusoidal surface of hepatocyte cells and has a major role in binding, internalizing and subsequent clearing of circulating glycoproteins that contain terminal galactose or GalNAc residues (asialoglycoproteins).

As used herein, "attenuate," "attenuating," "attenuation" and the like refers to reducing or effectively halting. As a non-limiting example, one or more of the treatments herein may reduce or effectively halt the onset or progression of cardiometabolic diseases including atherosclerosis, dyslipidemia, NAFLD and NASH in a subject. This attenuation may be exemplified by, for example, a decrease in one or more aspects (e.g., symptoms, tissue characteristics, and cellular, inflammatory or immunological activity, etc.) of cardiometabolic diseases including atherosclerosis, dyslipidemia, NAFLD and NASH, no detectable progression (worsening) of one or more aspects of cardiometabolic diseases including atherosclerosis, dyslipidemia, NAFLD and NASH, or no detectable aspects of cardiometabolic diseases including atherosclerosis, dyslipidemia, NAFLD and NASH in a subject when they might otherwise be expected.

As used herein, "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other to form regions of complementarity, as described herein.

As used herein, "deoxyribonucleotide" refers to a nucleotide having a hydrogen in place of a hydroxyl at the 2' position of its pentose sugar when compared with a ribonucleotide. A modified deoxyribonucleotide is a deoxyribonucleotide having one or more modifications or substitutions of atoms other than at the 2' position, including modifications or substitutions in or of the sugar, phosphate group or base.

As used herein, "double-stranded oligonucleotide" or "ds oligonucleotide" refers to an oligonucleotide that is substantially in a duplex form. In some embodiments, the complementary base-pairing of duplex region(s) of a ds oligonucleotide is formed between antiparallel sequences of nucleotides of covalently separate nucleic acid strands. In some embodiments, complementary base-pairing of duplex region(s) of a ds oligonucleotide is formed between antiparallel sequences of nucleotides of nucleic acid strands that are covalently linked. In some embodiments, complementary base-pairing of duplex region(s) of a ds oligonucleotide is formed from single nucleic acid strand that is folded (e.g., via a hairpin) to provide complementary antiparallel sequences of nucleotides that base pair together. In some embodiments, a ds oligonucleotide comprises two covalently separate nucleic acid strands that are fully duplexed with one another. However, in some embodiments, a ds oligonucleotide comprises two covalently separate nucleic acid strands that are partially duplexed (e.g., having overhangs at one or both ends). In some embodiments, a ds oligonucleotide comprises antiparallel sequence of nucleotides that are partially complementary, and thus, may have one or more mismatches, which may include internal mismatches or end mismatches.

As used herein, "duplex," in reference to nucleic acids (e.g., oligonucleotides), refers to a structure formed through complementary base pairing of two antiparallel sequences of nucleotides.

As used herein, "excipient" refers to a non-therapeutic agent that may be included in a composition, for example, to provide or contribute to a desired consistency or stabilizing effect.

As used herein, "hepatocyte" or "hepatocytes" refers to cells of the parenchymal tissues of the liver. These cells make up about 70%-85% of the liver's mass and manufacture serum albumin, FBN and the prothrombin group of clotting factors (except for Factors 3 and 4). Markers for hepatocyte lineage cells include, but are not limited to, transthyretin (Ttr), glutamine synthetase (Glu1), hepatocyte nuclear factor 1a (Hnf1a) and hepatocyte nuclear factor 4a (Hnf4a). Markers for mature hepatocytes may include, but are not limited to, cytochrome P450 (Cyp3al1), fumarylacetoacetate hydrolase (Fah), glucose 6-phosphate (G6p), albumin (Alb) and OC2-2F8. See, e.g., Huch et al. (2013) Nature 494:247-250.

As used herein, a "hepatotoxic agent" refers to a chemical compound, virus or other substance that is itself toxic to the liver or can be processed to form a metabolite that is toxic to the liver. Hepatotoxic agents may include, but are not limited to, carbon tetrachloride ($CCl_4$), acetaminophen (paracetamol), vinyl chloride, arsenic, chloroform, nonsteroidal anti-inflammatory drugs (such as aspirin and phenylbutazone).

As used herein, "labile linker" refers to a linker that can be cleaved (e.g., by acidic pH). A "fairly stable linker" refers to a linker that cannot be cleaved.

As used herein, "liver inflammation" or "hepatitis" refers to a physical condition in which the liver becomes swollen, dysfunctional and/or painful, especially as a result of injury or infection, as may be caused by exposure to a hepatotoxic agent. Symptoms may include jaundice (yellowing of the skin or eyes), fatigue, weakness, nausea, vomiting, appetite reduction and weight loss. Liver inflammation, if left untreated, may progress to fibrosis, cirrhosis, liver failure or liver cancer.

As used herein, "liver fibrosis" or "fibrosis of the liver" refers to an excessive accumulation in the liver of extracellular matrix proteins, which could include collagens (I, III, and IV), FBN, undulin, elastin, laminin, hyaluronan and proteoglycans resulting from inflammation and liver cell death. Liver fibrosis, if left untreated, may progress to cirrhosis, liver failure or liver cancer.

As used herein, "loop" refers to a unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

As used herein, "modified internucleotide linkage" refers to an internucleotide linkage having one or more chemical modifications when compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

As used herein, "nicked tetraloop structure" refers to a structure of a RNAi oligonucleotide that is characterized by separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

As used herein, "oligonucleotide" refers to a short nucleic acid (e.g., less than about 100 nucleotides in length). An oligonucleotide may be single-stranded (ss) or ds. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA or ss siRNA. In some embodiments, a ds oligonucleotide is an RNAi oligonucleotide.

As used herein, "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a ds oligonucleotide. In certain embodiments, the overhang is a 3' or 5' overhang on the antisense strand or sense strand of a ds oligonucleotides.

As used herein, "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include, but are not limited to, 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, e.g., U.S. Provisional Patent Application Nos. 62/383,207 (filed on 2 Sep. 2016) and 62/393,401 (filed on 12 Sep. 2016). Other modifications have been developed for the 5' end of oligonucleotides (see, e.g., Intl. Patent Application No. WO 2011/133871; U.S. Pat. No. 8,927,513; and Prakash et al. (2015) *Nucleic Acids Res.* 43:2993-3011).

As used herein, "reduced expression" of a gene (e.g., LPA) refers to a decrease in the amount or level of RNA transcript (e.g., LPA mRNA) or protein encoded by the gene and/or a decrease in the amount or level of activity of the gene in a cell, a population of cells, a sample or a subject, when compared to an appropriate reference (e.g., a reference cell, population of cells, sample or subject). For example, the act of contacting a cell with an oligonucleotide herein (e.g., an oligonucleotide comprising an antisense strand having a nucleotide sequence that is complementary to a nucleotide sequence comprising LPA mRNA) may result in a decrease in the amount or level of LPA mRNA, apo(a) protein and/or apo(a) activity (e.g., via inactivation and/or degradation of LPA mRNA by the RNAi pathway) when compared to a cell that is not treated with the ds oligonucleotide. Similarly, and as used herein, "reducing expression" refers to an act that results in reduced expression of a gene (e.g., LPA). As used herein, "reduction of LPA expression" refers to a decrease in the amount or level of LPA mRNA, apo(a) protein and/or apo(a) activity in a cell, a population of cells, a sample or a subject when compared to an appropriate reference (e.g., a reference cell, population of cells, sample, or subject).

As used herein, "region of complementarity" refers to a sequence of nucleotides of a nucleic acid (e.g., a ds oligonucleotide) that is sufficiently complementary to an antiparallel sequence of nucleotides to permit hybridization between the two sequences of nucleotides under appropriate hybridization conditions (e.g., in a phosphate buffer, in a cell, etc.). In some embodiments, an oligonucleotide herein comprises a targeting sequence having a region of complementary to a mRNA target sequence.

As used herein, "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

As used herein, "RNAi oligonucleotide" refers to either (a) a ds oligonucleotide having a sense strand (passenger) and antisense strand (guide), in which the antisense strand or part of the antisense strand is used by the Argonaute 2 (Ago2) endonuclease in the cleavage of a target mRNA (e.g., LPA mRNA) or (b) a ss oligonucleotide having a single antisense strand, where that antisense strand (or part of that antisense strand) is used by the Ago2 endonuclease in the cleavage of a target mRNA (e.g., LPA mRNA).

As used herein, "strand" refers to a single, contiguous sequence of nucleotides linked together through internucleotide linkages (e.g., phosphodiester linkages or phosphorothioate linkages). In some embodiments, a strand has two free ends (e.g., a 5' end and a 3' end).

As used herein, "subject" means any mammal, including mice, rabbits and humans. In one embodiment, the subject is a human or NHP. Moreover, "individual" or "patient" may be used interchangeably with "subject."

As used herein, "synthetic" refers to a nucleic acid or other molecule that is artificially synthesized (e.g., using a machine (e.g., a solid-state nucleic acid synthesizer)) or that is otherwise not derived from a natural source (e.g., a cell or organism) that normally produces the molecule.

As used herein, "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

As used herein, "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a $T_m$ of at least about 50° C., at least about 55° C., at least about 56° C., at least about 58° C., at least about 60° C., at least about 65° C. or at least about 75° C. in 10 mM NaHPO$_4$ to a hairpin comprising a duplex of at least 2 base pairs (bp) in length. In some embodiments, a tetraloop may stabilize a bp in an adjacent stem duplex by stacking interactions. In addition, interactions among the nucleotides in a tetraloop include, but are not limited to, non-Watson-Crick base pairing, stacking interactions, hydrogen bonding and contact interactions (Cheong et al. (1990) NATURE 346: 680-82; Heus & Pardi (1991) SCIENCE 253:191-94). In some embodiments, a tetraloop comprises or consists of 3 to 6 nucleotides and is typically 4 to 5 nucleotides. In certain embodiments, a tetraloop comprises or consists of 3, 4, 5 or 6 nucleotides, which may or may not be modified (e.g., which may or may not be conjugated to a targeting moiety). In one embodiment, a tetraloop consists of 4 nucleotides. Any nucleotide may be used in the tetraloop and standard IUPAC-IUB symbols for such nucleotides may be used as described in Cornish-Bowden (1985) *Nucleic Acids Res.* 13:3021-3030. For example, the letter "N" may be used to mean that any base may be in that position, the letter "R" may be used to show that A (adenine) or G (guanine) may be in that position, and "B" may be used to show that C (cytosine), G (guanine), T (thymine) or U (uracil) may be in that position. Examples of tetraloops include the UNCG family of tetraloops (e.g., UUCG), the GNRA family of tetraloops (e.g., GAAA), and the CUUG tetraloop (Woese et al. (1990) *Proc. Natl. Acad. Sci. USA* 87:8467-8471; Antao et al. (1991) *Nucleic Acids Res.* 19:5901-5905). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). See, e.g., Nakano et al. (2002) *Biochem.* 41:4281-14292; Shinji et al. (2000) *Nippon Kagakkai Koen Yokoshu* 78:731. In some embodiments, the tetraloop is contained within a nicked tetraloop structure.

As used herein, "treat" or "treating" refers to the act of providing care to a subject in need thereof, for example, by administering a therapeutic agent (e.g., an oligonucleotide herein) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide Inhibitors of LPA Expression

The disclosure provides, inter alia, oligonucleotides that inhibit LPA expression. In some embodiments, an oligonucleotide that inhibits LPA expression herein is targeted to an LPA mRNA.

i. LPA Target Sequences

In some embodiments, the oligonucleotide is targeted to a target sequence comprising an LPA mRNA. In some embodiments, the oligonucleotide, or a portion, fragment or strand thereof (e.g., an antisense strand or a guide strand of a ds oligonucleotide) binds or anneals to a target sequence comprising an LPA mRNA, thereby inhibiting LPA expression. In some embodiments, the oligonucleotide is targeted to an LPA target sequence for the purpose of inhibiting LPA expression in vivo. In some embodiments, the amount or extent of inhibition of LPA expression by an oligonucleotide targeted to an LPA target sequence correlates with the potency of the oligonucleotide. In some embodiments, the amount or extent of inhibition of LPA expression by an oligonucleotide targeted to an LPA target sequence correlates with the amount or extent of therapeutic benefit in a subject or patient having a disease, disorder or condition associated with the expression of LPA treated with the oligonucleotide.

Through examination and analysis of the nucleotide sequence of LPA mRNAs encoding apo(a), including mRNAs of multiple different species (e.g., human, cynomolgus monkey, and rhesus monkey; see, e.g., Example 1) and as a result of in vitro and in vivo testing (see, e.g., Example 2 and Example 3), it has been discovered that certain nucleotide sequences of LPA mRNA are more amenable than others to oligonucleotide-based inhibition of LPA expression and are thus useful as target sequences for the oligonucleotides herein. In some embodiments, a sense strand of an oligonucleotide (e.g., a ds oligonucleotide) described herein (e.g., in Table 5) comprises an LPA target sequence. In some embodiments, a portion or region of the sense strand of a ds oligonucleotide described herein (e.g., in Table 5) comprises an LPA target sequence. In some embodiments, an LPA target sequence comprises, or consists of, a sequence of any one of SEQ ID Nos: 4-387.

ii. LPA Targeting Sequences

In some embodiments, the oligonucleotides herein have regions of complementarity to LPA mRNA (e.g., within a target sequence of LPA mRNA) for purposes of targeting the LPA mRNA in cells and inhibiting LPA expression. In some embodiments, the oligonucleotides herein comprise an LPA targeting sequence (e.g., an antisense strand or a guide strand of a ds oligonucleotide) having a region of complementarity that binds or anneals to an LPA target sequence by complementary (Watson-Crick) base pairing. The targeting sequence or region of complementarity is generally of a suitable length and base content to enable binding or annealing of the oligonucleotide (or a strand thereof) to an LPA mRNA for purposes of inhibiting its expression. In some embodiments, the targeting sequence or region of complementarity is at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29 or at least about 30 nucleotides in length. In some embodiments, the targeting sequence or region of complementarity is about 12 to about 30 (e.g., 12 to 30, 12 to 22, 15 to 25, 17 to 21, 18 to 27, 19 to 27, or 15 to 30) nucleotides in length. In some embodiments, the targeting sequence or region of complementarity is about 12, 13, 14, 15, 16, 17, 18, 19, 20, 21, 22, 23, 24, 25, 26, 27, 28, 29 or 30 nucleotides in length. In some embodiments, the targeting sequence or region of complementarity is 18 nucleotides in length. In some embodiments, the targeting sequence or region of complementarity is 19 nucleotides in length. In some embodiments, the targeting sequence or region of complementarity is 20 nucleotides in length. In some embodiments, the targeting sequence or region of complementarity is 21 nucleotides in length. In some embodiments, the targeting sequence or region of complementarity is 22 nucleotides in length. In some embodiments, the targeting sequence or region of complementarity is 23 nucleotides in length. In some embodiments, the targeting sequence or region of complementarity is 24 nucleotides in length.

In some embodiments, an oligonucleotide herein comprises a targeting sequence or a region of complementarity (e.g., an antisense strand or a guide strand of a double-stranded oligonucleotide) that is fully complementary to an LPA target sequence. In some embodiments, the targeting sequence or region of complementarity is partially complementary to an LPA target sequence. In some embodiments, the oligonucleotide comprises a targeting sequence or region of complementarity that is fully complementary to a sequence of any one of SEQ ID NOs: 4-387. In some embodiments, the oligonucleotide comprises a targeting sequence or region of complementarity that is partially complementary to a sequence of any one of SEQ ID NOs: 4-387.

In some embodiments, the oligonucleotide herein comprises a targeting sequence or region of complementarity that is complementary to a contiguous sequence of nucleotides comprising an LPA mRNA, wherein the contiguous sequence of nucleotides is about 12 to about 30 nucleotides in length (e.g., 12 to 30, 12 to 28, 12 to 26, 12 to 24, 12 to 20, 12 to 18, 12 to 16, 14 to 22, 16 to 20, 18 to 20 or 18 to 19 nucleotides in length). In some embodiments, the oligonucleotide comprises a targeting sequence or region of complementarity that is complementary to a contiguous sequence of nucleotides comprising an LPA mRNA, wherein the contiguous sequence of nucleotides is 10, 11, 12, 13, 14, 15, 16, 17, 18, 19 or 20 nucleotides in length. In some embodiments, the oligonucleotide comprises a targeting sequence or region of complementarity that is complementary to a contiguous sequence of nucleotides comprising an LPA mRNA, wherein the contiguous sequence of nucleotides is 19 nucleotides in length. In some embodiments, the oligonucleotide comprises a targeting sequence or region of complementarity that is complementary to a contiguous sequence of nucleotides comprising an LPA mRNA, wherein the contiguous sequence of nucleotides is 20 nucleotides in length. In some embodiments, the oligonucleotide comprises a targeting sequence or a region of complementarity that is complementary to a contiguous sequence of nucleotides of any one of SEQ ID NOs: 4-387, optionally wherein the contiguous sequence of nucleotides is 19 nucleotides in length.

In some embodiments, a targeting sequence or region of complementarity of an oligonucleotide that is complementary to contiguous nucleotides of a sequence as set forth in any one of SEQ ID NOs: 4-387 and spans the entire length of an antisense strand. In some embodiments, a region of complementarity of an oligonucleotide that is complementary to contiguous nucleotides of a sequence as set forth in any one of SEQ ID NOs: 4-387 and spans a portion of the entire length of an antisense strand. In some embodiments, an oligonucleotide herein comprises a region of complementarity (e.g., on an antisense strand of a ds oligonucleotide) that is at least partially (e.g., fully) complementary to a contiguous stretch of nucleotides spanning nucleotides 1-20 of a sequence as set forth in any one of SEQ ID NOs: 4-387.

In some embodiments, an oligonucleotide herein comprises a targeting sequence or region of complementarity having one or more base pair (bp) mismatches with the corresponding LPA target sequence. In some embodiments, the targeting sequence or region of complementarity may have up to about 1, up to about 2, up to about 3, up to about 4, up to about 5, etc. mismatches with the corresponding LPA target sequence provided that the ability of the targeting sequence or region of complementarity to bind or anneal to the LPA mRNA under appropriate hybridization conditions and/or the ability of the oligonucleotide to reduce or inhibit LPA expression is maintained. Alternatively, in some embodiments, the targeting sequence or region of complementarity comprises no more than 1, no more than 2, no more than 3, no more than 4, or no more than 5 mismatches with the corresponding LPA target sequence provided that the ability of the targeting sequence or region of complementarity to bind or anneal to the LPA mRNA under appropriate hybridization conditions and/or the ability of the oligonucleotide to reduce or inhibit LPA expression is maintained. In some embodiments, the oligonucleotide comprises a targeting sequence or region of complementarity having 1 mismatch with the corresponding target sequence. In some embodiments, the oligonucleotide comprises a targeting sequence or region of complementarity having 2 mismatches with the corresponding target sequence. In some embodiments, the oligonucleotide comprises a targeting sequence or region of complementarity having 3 mismatches with the corresponding target sequence. In some embodiments, the oligonucleotide comprises a targeting sequence or region of complementarity having 4 mismatches with the corresponding target sequence. In some embodiments, the oligonucleotide comprises a targeting sequence or region of complementarity having 5 mismatches with the corresponding target sequence. In some embodiments, the oligonucleotide comprises a targeting sequence or region of complementarity more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein the mismatches are interspersed in any position throughout the targeting sequence or region of complementarity. In some embodiments, the oligonucleotide comprises a targeting sequence or region of complementarity more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein at least one or more non-mismatched base pair is located between the mismatches, or a combination thereof.

iii. Types of Oligonucleotides

A variety of oligonucleotide types and/or structures are useful for targeting LPA mRNA in the methods herein including, but not limited to, RNAi oligonucleotides, antisense oligonucleotides, miRNAs, etc. Any of the oligonucleotide types described herein or elsewhere are contemplated for use as a framework to incorporate an LPA mRNA targeting sequence herein for the purposes of inhibiting LPA expression.

In some embodiments, the oligonucleotides herein inhibit LPA expression by engaging with RNA interference (RNAi) pathways upstream or downstream of Dicer involvement. For example, RNAi oligonucleotides have been developed with each strand having sizes of about 19-25 nucleotides with at least one 3' overhang of 1 to 5 nucleotides (see, e.g., U.S. Pat. No. 8,372,968). Longer oligonucleotides also have been developed that are processed by Dicer to generate active RNAi products (see, e.g., U.S. Pat. No. 8,883,996). Further work produced extended ds oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as Intl. Patent Application Publication No. WO 2010/033225). Such structures may include ss extensions (on one or both sides of the molecule) as well as ds extensions.

In some embodiments, the oligonucleotides herein engage with the RNAi pathway downstream of the involvement of Dicer (e.g., Dicer cleavage). In some embodiments, the oligonucleotide has an overhang (e.g., of 1, 2, or 3 nucleotides in length) in the 3' end of the sense strand. In some embodiments, the oligonucleotide (e.g., siRNA) comprises a 21-nucleotide guide strand that is antisense to a target mRNA (e.g., LPA mRNA) and a complementary passenger strand, in which both strands anneal to form a 19-bp duplex and 2 nucleotide overhangs at either or both 3' ends. Longer oligonucleotide designs also are contemplated including oligonucleotides having a guide strand of 23 nucleotides and a passenger strand of 21 nucleotides, where there is a blunt end on the right side of the molecule (3' end of passenger strand/5' end of guide strand) and a two nucleotide 3'-guide strand overhang on the left side of the molecule (5' end of the passenger strand/3' end of the guide strand). In such molecules, there is a 21 bp duplex region. See, e.g., U.S. Pat. Nos. 9,012,138; 9,012,621 and 9,193,753.

In some embodiments, the oligonucleotides herein comprise sense and antisense strands that are both in the range of about 17 to 26 (e.g., 17 to 26, 20 to 25 or 21-23) nucleotides in length. In some embodiments, an oligonucleotide herein comprises a sense and antisense strand that are both in the range of about 19-22 nucleotides in length. In some embodiments, the sense and antisense strands are of equal length. In some embodiments, an oligonucleotide comprises sense and antisense strands, such that there is a 3'-overhang on either the sense strand or the antisense strand, or both the sense and antisense strand. In some embodiments, for oligonucleotides that have sense and antisense strands that are both in the range of about 21-23 nucleotides in length, a 3' overhang on the sense, antisense, or both sense and antisense strands is 1 or 2 nucleotides in length. In some embodiments, the oligonucleotide has a guide strand of 22 nucleotides and a passenger strand of 20 nucleotides, where there is a blunt end on the right side of the molecule (3' end of passenger strand/5' end of guide strand) and a 2 nucleotide 3'-guide strand overhang on the left side of the molecule (5' end of the passenger strand/3' end of the guide strand). In such molecules, there is a 20 bp duplex region.

Other oligonucleotide designs for use with the compositions and methods herein include: 16-mer siRNAs (see, e.g., NUCLEIC ACIDS IN CHEMISTRY AND BIOLOGY, Blackburn (ed.), Royal Society of Chemistry, 2006), shRNAs (e.g., having 19 bp or shorter stems; see, e.g., Moore et al. (2010) METHODS MOL. BIOL. 629:141-58), blunt siRNAs (e.g., of 19 bps in length; see, e.g., Kraynack & Baker (2006) *RNA* 12:163-76), asymmetrical siRNAs (aiRNA; see, e.g., Sun et al. (2008) NAT. BIOTECHNOL. 26:1379-82), asymmetric shorter-duplex siRNA (see, e.g., Chang et al. (2009) MOL. THER. 17:725-32), fork siRNAs (see, e.g., Hohjoh (2004) FEBS LETT. 557:193-198), ss siRNAs (Elsner (2012) NAT. BIOTECHNOL. 30:1063), dumbbell-shaped circular siRNAs (see, e.g., Abe et al. (2007) J. AM. CHEM. SOC. 129:15108-09), and small internally segmented interfering RNA (siRNA; see, e.g., Bramsen et al. (2007) NUCLEIC ACIDS RES. 35:5886-97). Further non-limiting examples of an oligonucleotide structures that may be used in some embodiments to reduce or inhibit the expression of LPA are microRNA (miRNA), short hairpin RNA (shRNA) and short siRNA (see, e.g., Hamilton et al. (2002) EMBO J. 21:4671-79; see also, US Patent Application Publication No. 2009/0099115).

Still, in some embodiments, an oligonucleotide for reducing or inhibiting LPA expression herein is single-stranded (ss). Such structures may include but are not limited to ss RNAi molecules. Recent efforts have demonstrated the activity of ss RNAi molecules (see, e.g., Matsui et al. (2016) *Mol. Ther.* 24:946-955). However, in some embodiments, oligonucleotides herein are antisense oligonucleotides (ASOs). An antisense oligonucleotide is a ss oligonucleotide that has a nucleobase sequence which, when written or depicted in the 5' to 3' direction, comprises the reverse complement of a targeted segment of a particular nucleic acid and is suitably modified (e.g., as a gapmer) so as to induce RNaseH-mediated cleavage of its target RNA in cells or (e.g., as a mixmer) so as to inhibit translation of the target mRNA in cells. ASOs for use herein may be modified in any suitable manner known in the art including, for example, as shown in U.S. Pat. No. 9,567,587 (including, e.g., length, sugar moieties of the nucleobase (pyrimidine, purine), and alterations of the heterocyclic portion of the nucleobase). Further, ASOs have been used for decades to reduce expression of specific target genes (see, e.g., Bennett et al. (2017) *Annu. Rev. Pharmacol.* 57:81-105).

iv. Double-Stranded Oligonucleotides

The disclosure provides double-stranded (ds) oligonucleotides for targeting LPA mRNA and inhibiting LPA expression (e.g., via the RNAi pathway) comprising a sense strand (also referred to herein as a passenger strand) and an antisense strand (also referred to herein as a guide strand). In some embodiments, the sense strand and antisense strand are separate strands and are not covalently linked. In some embodiments, the sense strand and antisense strand are covalently linked.

In some embodiments, the sense strand has a first region (R1) and a second region (R2), wherein R2 comprises a first subregion (S1), a tetraloop (L) or triloop (triL), and a second subregion (S2), wherein L or triL is located between S1 and S2, and wherein S1 and S2 form a second duplex (D2). D2 may have various lengths. In some embodiments, D2 is about 1-6 bp in length. In some embodiments, D2 is 2-6, 3-6, 4-6, 5-6, 1-5, 2-5, 3-5 or 4-5 bp in length. In some embodiments, D2 is 1, 2, 3, 4, 5 or 6 bp in length. In some embodiments, D2 is 6 bp in length.

In some embodiments, R1 of the sense strand and the antisense strand form a first duplex (D1). In some embodiments, D1 is at least about 15 (e.g., at least 15, at least 16, at least 17, at least 18, at least 19, at least 20 or at least 21) nucleotides in length. In some embodiments, D1 is in the range of about 12 to 30 nucleotides in length (e.g., 12 to 30, 12 to 27, 15 to 22, 18 to 22, 18 to 25, 18 to 27, 18 to 30 or 21 to 30 nucleotides in length). In some embodiments, D1 is at least 12 nucleotides in length (e.g., at least 12, at least 15, at least 20, at least 25, or at least 30 nucleotides in length). In some embodiments, D1 is 12, 13, 14, 15, 16, 17, 18, 19, 20, 21, 22, 23, 24, 25, 26, 27, 28, 29 or 30 nucleotides in length. In some embodiments, D1 is 20 nucleotides in length. In some embodiments, D1 comprising sense strand and antisense strand does not span the entire length of the sense strand and/or antisense strand. In some embodiments, D1 comprising the sense and antisense strand spans the entire length of either the sense strand or antisense strand or both. In certain embodiments, D1 comprising the sense strand and antisense strand spans the entire length of both the sense strand and the antisense strand.

In some embodiments, a ds oligonucleotide herein comprises a sense strand having a sequence of any one of SEQ ID NOs: 388-403 and an antisense strand comprising a complementary sequence selected from SEQ ID NOs: 788-803, as is arranged Table 3. In some embodiments, the sense strand comprises the sequence of SEQ ID NO: 393 and the antisense strand comprises the sequence of SEQ ID NO: 793.

It should be appreciated that, in some embodiments, sequences presented in the Sequence Listing may be referred to in describing the structure of an oligonucleotide (e.g., a ds oligonucleotide) or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification when compared with the specified sequence while retaining essentially same or similar complementary properties as the specified sequence.

In some embodiments, a ds oligonucleotide herein comprises a 25-nucleotide sense strand and a 27-nucleotide antisense strand that when acted upon by a Dicer enzyme results in an antisense strand that is incorporated into the mature RISC. In some embodiments, the sense strand of the ds oligonucleotide is longer than 27 nucleotides (e.g., 28, 29, 30, 31, 32, 33, 34, 35, 36, 37, 38, 39 or 40 nucleotides). In some embodiments, the sense strand of the ds oligonucleotide is longer than 25 nucleotides (e.g., 26, 27, 28, 29 or 30 nucleotides).

In some embodiments, the ds oligonucleotides herein have one 5' end that is thermodynamically less stable when compared to the other 5' end. In some embodiments, an asymmetric ds oligonucleotide is provided that comprises a blunt end at the 3' end of a sense strand and a 3'-overhang at the 3' end of an antisense strand. In some embodiments, the 3'-overhang on the antisense strand is about 1-8 nucleotides in length (e.g., 1, 2, 3, 4, 5, 6, 7 or 8 nucleotides in length). Typically, a ds oligonucleotide for RNAi has a two-nucleotide overhang on the 3' end of the antisense (guide) strand. However, other overhangs are possible. In some embodiments, an overhang is a 3'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides. However, in some embodiments, the overhang is a 5'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides.

In some embodiments, two terminal nucleotides on the 3' end of an antisense strand are modified. In some embodiments, the two terminal nucleotides on the 3' end of the antisense strand are complementary with the target mRNA (e.g., LPA mRNA). In some embodiments, the two terminal nucleotides on the 3' end of the antisense strand are not complementary with the target mRNA. In some embodiments, two terminal nucleotides on each 3' end of an oligonucleotide in the nicked tetraloop structure are GG. Typically, one or both of the two terminal GG nucleotides on each 3' end of a ds oligonucleotide is not complementary with the target mRNA.

In some embodiments, there is one or more (e.g., 1, 2, 3, 4 or 5) mismatch(es) between a sense and antisense strand. If there is more than one mismatch between a sense and antisense strand, they may be positioned consecutively (e.g., 2, 3 or more in a row), or interspersed throughout the region of complementarity. In some embodiments, the 3' end of the sense strand contains one or more mismatches. In one embodiment, two mismatches are incorporated at the 3' end of the sense strand. In some embodiments, base mismatches, or destabilization of segments at the 3' end of the sense strand of the oligonucleotide improves or increases the potency of the ds oligonucleotide.

a. Antisense Strands

In some embodiments, an oligonucleotide (e.g., a ds oligonucleotide) disclosed herein for targeting LPA mRNA and inhibiting LPA expression comprises an antisense strand comprising or consisting of a sequence as set forth in any one of SEQ ID NOs: 404-803. In some embodiments, an oligonucleotide herein comprises an antisense strand comprising or consisting of at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in any one of SEQ ID NOs: 404-803.

In some embodiments, an oligonucleotide (e.g., a ds oligonucleotide) herein comprises an antisense strand of up to about 40 nucleotides in length (e.g., up to 40, up to 35, up to 30, up to 27, up to 25, up to 21, up to 19, up to 17 or up to 12 nucleotides in length). In some embodiments, an oligonucleotide may have an antisense strand of at least about 12 nucleotides in length (e.g., at least 12, at least 15, at least 19, at least 21, at least 22, at least 25, at least 27, at least 30, at least 35 or at least 38 nucleotides in length). In some embodiments, an oligonucleotide may have an antisense strand in a range of about 12 to about 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40 or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In some embodiments, an antisense strand of an oligonucleotide is referred to as a "guide strand." For example, an antisense strand that engages with RNA-induced silencing complex (RISC) and binds to an Argonaute protein such as Ago2, or engages with or binds to one or more similar factors, and directs silencing of a target gene, the antisense strand is referred to as a guide strand. In some embodiments, a sense strand complementary to a guide strand is referred to as a "passenger strand."

b. Sense Strands

In some embodiments, an oligonucleotide (e.g., a ds oligonucleotide) herein for targeting LPA mRNA and inhibiting LPA expression comprises or consists of a sense strand sequence as set forth in in any one of SEQ ID NOs: 4-403. In some embodiments, an oligonucleotide has a sense strand that comprises or consists of at least about 12 (e.g., at least 13, at least 14, at least 15, at least 16, at least 17, at least 18, at least 19, at least 20, at least 21, at least 22 or at least 23) contiguous nucleotides of a sequence as set forth in in any one of SEQ ID NOs: 4-403.

In some embodiments, an oligonucleotide (e.g., a ds oligonucleotide) herein comprises a sense strand (or passenger strand) of up to about 40 nucleotides in length (e.g., up to 40, up to 36, up to 30, up to 27, up to 25, up to 21, up to 19, up to 17 or up to 12 nucleotides in length). In some embodiments, an oligonucleotide may have a sense strand of at least about 12 nucleotides in length (e.g., at least 12, at least 15, at least 19, at least 21, at least 25, at least 27, at least 30, at least 36 or at least 38 nucleotides in length). In some embodiments, an oligonucleotide may have a sense strand in a range of about 12 to about 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40 or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

Figure 10:
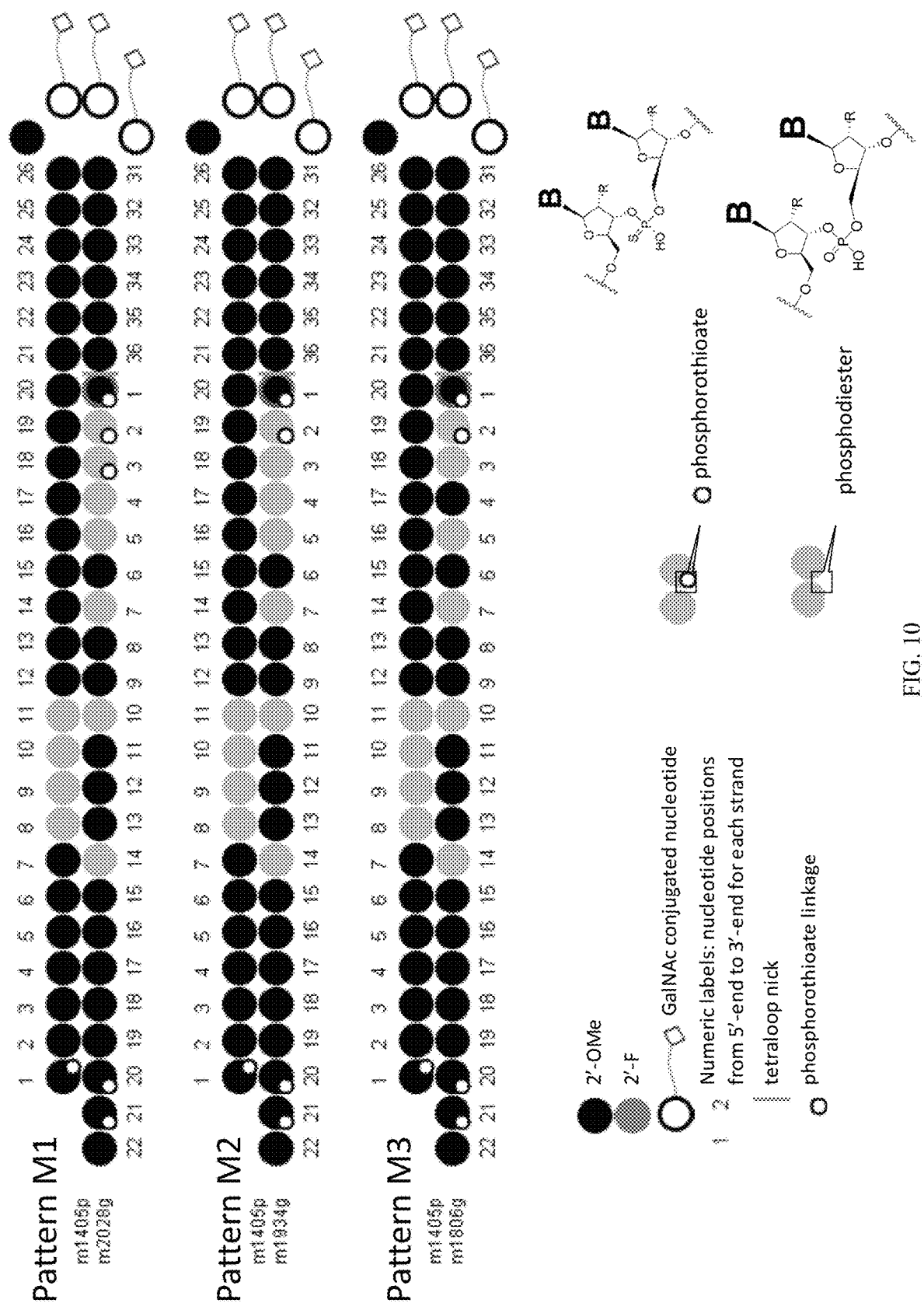
FIG. 10 provides a schematic depicting the structure and chemical modification patterns of generic N-Acetylgalactosamine (GalNAc)-conjugated LPA oligonucleotides.

In some embodiments, a sense strand comprises a stem-loop structure at its 3' end. In some embodiments, a sense strand comprises a stem-loop structure at its 5' end. In some embodiments, a stem is a duplex of 2, 3, 4, 5, 6, 7, 8, 9, 10, 11, 12, 13 or 14 bp in length. In some embodiments, a stem-loop provides the oligonucleotide protection against degradation (e.g., enzymatic degradation) and facilitates or improves targeting and/or delivery to a target cell, tissue, or organ (e.g., the liver), or both. For example, in some embodiments, the loop of a stem-loop provides nucleotides comprising one or more modifications that facilitate, improve, or increase targeting to a target mRNA (e.g., an LPA mRNA), inhibition of target gene expression (e.g., LPA expression), and/or delivery to a target cell, tissue, or organ (e.g., the liver), or both. In some embodiments, the stem-loop itself or modification(s) to the stem-loop do not substantially affect the inherent gene expression inhibition activity of the oligonucleotide, but facilitates, improves, or increases stability (e.g., provides protection against degradation) and/or delivery of the oligonucleotide to a target cell, tissue, or organ (e.g., the liver). In certain embodiments, an oligonucleotide comprises a sense strand comprising (e.g., at its 3' end) a stem-loop set forth as: S1-L-S2, in which S1 is complementary to S2, and in which L forms a single-stranded loop between S1 and S2 of up to about 10 nucleotides in length (e.g., 3, 4, 5, 6, 7, 8, 9 or 10 nucleotides in length). In some embodiments, the loop (L) is 4 nucleotides in length. FIG. 10 depicts a non-limiting example of such an oligonucleotide. In some embodiments, a loop (L) of a stem-loop having the structure S1-L-S2 as described above is a tetraloop (e.g., within a nicked tetraloop structure). In some embodiments, the tetraloop comprises ribonucleotides, deoxyribonucleotides, modified nucleotides, delivery ligands, and combinations thereof.

V. Oligonucleotide Modifications a. Sugar Modifications

In some embodiments, a modified sugar (also referred herein to a sugar analog) includes a modified deoxyribose or ribose moiety in which, for example, one or more modifications occur at the 2', 3', 4' and/or 5' carbon position of the sugar. In some embodiments, a modified sugar may also include non-natural alternative carbon structures such as those present in locked nucleic acids ("LNA"; see, e.g., Koshkin et al. (1998) TETRAHEDON 54:3607-30), unlocked nucleic acids ("UNA"; see, e.g., Snead et al. (2013) MOL. THER-NUCL. ACIDS 2: e103) and bridged nucleic acids ("BNA"; see, e.g., Imanishi & Obika (2002) CHEM COMMUN. (CAMB) 21:1653-59).

In some embodiments, a nucleotide modification in a sugar comprises a 2'-modification. In some embodiments, a 2'-modification may be 2'-O-propargyl, 2'-O-propylamin, 2'-amino, 2'-ethyl, 2'-fluoro (2'-F), 2'-aminoethyl (EA), 2'-O-methyl (2'-OMe), 2'-O-methoxyethyl (2'-MOE), 2'-O-[2-(methylamino)-2-oxoethyl](2'-O-NMA) or 2'-deoxy-2'-fluoro-β-d-arabinonucleic acid (2'-FANA). In some embodiments, the modification is 2'-F, 2'-OMe or 2'-MOE. In some embodiments, a modification in a sugar comprises a modification of the sugar ring, which may comprise modification of one or more carbons of the sugar ring. For example, a modification of a sugar of a nucleotide may comprise a 2'-oxygen of a sugar is linked to a 1'-carbon or 4'-carbon of the sugar, or a 2'-oxygen is linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the oligonucleotide described herein comprises at least about 1 modified nucleotide (e.g., at least 1, at least 5, at least 10, at least 15, at least 20, at least 25, at least 30, at least 35, at least 40, at least 45, at least 50, at least 55, at least 60, or more). In some embodiments, the sense strand of the oligonucleotide comprises at least about 1 modified nucleotide (e.g., at least 1, at least 5, at least 10, at least 15, at least 20, at least 25, at least 30, at least 35, or more). In some embodiments, the antisense strand of the oligonucleotide comprises at least about 1 modified nucleotide (e.g., at least 1, at least 5, at least 10, at least 15, at least 20, or more).

In some embodiments, all the nucleotides of the sense strand of the oligonucleotide are modified. In some embodiments, all the nucleotides of the antisense strand of the oligonucleotide are modified. In some embodiments, all the nucleotides of the oligonucleotide (i.e., both the sense strand and the antisense strand) are modified. In some embodiments, the modified nucleotide comprises a 2'-modification (e.g., a 2'-F or 2'-OMe, 2'-MOE, and 2'-deoxy-2'-fluoro-β-d-arabinonucleic acid). In some embodiments, the modified nucleotide comprises a 2'-modification (e.g., a 2'-F or 2'-OMe)

The disclosure provides oligonucleotides having different modification patterns. In some embodiments, the modified oligonucleotides comprise a sense strand sequence having a modification pattern as set forth in any one of Tables 3 and 4 (as well as FIG. 10) and an antisense strand having a modification pattern as set forth in any one of Tables 3 and 4 (as well as FIG. 10). In some embodiments, for these oligonucleotides, one or more of positions 8, 9, 10 or 11 of the sense strand is modified with a 2'-F group. In other embodiments, for these oligonucleotides, the sugar moiety at each of nucleotides at positions 1-7 and 12-20 in the sense strand is modified with a 2'-OMe.

In some embodiments, the antisense strand has 3 nucleotides that are modified at the 2'-position of the sugar moiety with a 2'-F. In some embodiments, the sugar moiety at positions 2, 5 and 14 and optionally up to 3 of the nucleotides at positions 1, 3, 7 and 10 of the antisense strand are modified with a 2'-F. In other embodiments, the sugar moiety at each of the positions at positions 2, 5 and 14 of the antisense strand is modified with the 2'-F. In other embodiments, the sugar moiety at each of the positions at positions 1, 2, 5 and 14 of the antisense strand is modified with the 2'-F. In still other embodiments, the sugar moiety at each of the positions at positions 1, 2, 3, 5, 7 and 14 of the antisense strand is modified with the 2'-F. In yet another embodiment, the sugar moiety at each of the positions at positions 1, 2, 3, 5, 10 and 14 of the antisense strand is modified with the 2'-F. In another embodiment, the sugar moiety at each of the positions at positions 2, 3, 5, 7, 10 and 14 of the antisense strand is modified with the 2'-F.

b. 5' Terminal Phosphates

In some embodiments, 5'-terminal phosphate groups of an RNAi oligonucleotide enhance the interaction with Ago2. However, oligonucleotides comprising a 5'-phosphate group may be susceptible to degradation via phosphatases or other enzymes, which can limit their bioavailability in vivo. In some embodiments, an oligonucleotide (e.g., a ds oligonucleotide) herein includes analogs of 5' phosphates that are resistant to such degradation. In some embodiments, the phosphate analog is oxymethylphosphonate, vinylphosphonate or malonyl phosphonate, or a combination thereof. In certain embodiments, the 3' end of an oligonucleotide strand is attached to chemical moiety that mimics the electrostatic and steric properties of a natural 5'-phosphate group ("phosphate mimic").

In some embodiments, an oligonucleotide has a phosphate analog at a 4'-carbon position of the sugar (referred to as a "4'-phosphate analog"). See, e.g., Intl. Patent Application Publication No. WO 2018/045317. In some embodiments, an oligonucleotide herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the amino methyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—CH$_2$—PO(OH)$_2$ or —O—CH$_2$—PO(OR)$_2$, in which R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$ or a protecting group. In certain embodiments, the alkyl group is CH$_2$CH$_3$. More typically, R is independently selected from H, CH$_3$ or CH$_2$CH$_3$.

c. Modified Internucleoside Linkages

In some embodiments, an oligonucleotide comprises a modified internucleoside linkage. In some embodiments, phosphate modifications or substitutions result in an oligonucleotide that comprises at least about 1 (e.g., at least 1, at least 2, at least 3 or at least 5) modified internucleotide linkage. In some embodiments, any one of the oligonucleotides disclosed herein comprises about 1 to about 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9 or 10 modified internucleotide linkages.

A modified internucleotide linkage may be a phosphorodithioate linkage, a phosphorothioate linkage, a phosphotriester linkage, a thionoalkylphosphonate linkage, a thionalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

In some embodiments, the oligonucleotide described herein has a phosphorothioate linkage between one or more of positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In some embodiments, the oligonucleotide described herein has a phosphorothioate linkage between each of positions 1 and 2 of the sense strand, positions 1 and 2 of the antisense strand, positions 2 and 3 of the antisense strand, positions 20 and 21 of the antisense strand, and positions 21 and 22 of the antisense strand.

d. Base Modifications

In some embodiments, oligonucleotides herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain nitrogen atom. See, e.g., US Patent Application Publication No. 2008/0274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution, that, when present in a duplex, can be positioned opposite more than one type of base without substantially altering structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower T$_m$ than a duplex formed with the complementary nucleic acid. However, in some embodiments, when compared to a reference single-stranded nucleic acid in which the universal base has been replaced with a base to generate a single mismatch, the single-stranded nucleic acid containing the universal base forms a duplex with the target nucleic acid that has a higher T$_m$ than a duplex formed with the nucleic acid comprising the mismatched base.

Non-limiting examples of universal-binding nucleotides include, but are not limited to, inosine, 1-β-D-ribofuranosyl-5-nitroindole and/or 1-β-D-ribofuranosyl-3-nitropyrrole (see, US Patent Application Publication No. 2007/0254362; Van Aerschot et al. (1995) NUCLEIC ACIDS RES. 23:4363-70; Loakes et al. (1995) NUCLEIC ACIDS RES. 23:2361-66; and Loakes & Brown (1994) NUCLEIC ACIDS RES. 22:4039-43).

c. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See US Patent Application Publication No. 2011/0294869, Intl. Patent Application Publication Nos. WO 2014/088920 and WO 2015/188197, and Meade et al. (2014) NAT. BIOTECHNOL. 32:1256-63. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (see, Dellinger et al. (2003) J. AM. CHEM. SOC. 125:940-50).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed, and the result is a cleaved oligonucleotide. Using reversible, glutathione-sensitive moieties, it is possible to introduce sterically larger chemical groups into the oligonucleotide of interest when compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of sugar, particularly when the modified nucleotide is the 3'-terminal nucleotide of the oligonucleotide. In some embodiments, the glutathione-sensitive moiety comprises a sulfonyl group. See, e.g., U.S. Provisional Patent Application No. 62/378,635, entitled *Compositions Comprising Reversibly Modified Oligonucleotides and Uses Thereof*, which was filed on Aug. 23, 2016.

vi. Targeting Ligands

In some embodiments, it is desirable to target the oligonucleotides of the disclosure to one or more cells or one or more organs. Such a strategy can help to avoid undesirable effects in other organs or avoid undue loss of the oligonucleotide to cells, tissue or organs that would not benefit from the oligonucleotide. Accordingly, in some embodiments, oligonucleotides disclosed herein are modified to facilitate targeting and/or delivery to a tissue, cell or organ (e.g., to facilitate delivery of the oligonucleotide to the liver). In certain embodiments, oligonucleotides disclosed herein are modified to facilitate delivery of the oligonucleotide to the hepatocytes of the liver. In some embodiments, an oligonucleotide comprises at least one nucleotide (e.g., 1, 2, 3, 4, 5, 6 or more nucleotides) conjugated to one or more targeting ligand(s).

In some embodiments, the targeting ligand comprises a carbohydrate, amino sugar, cholesterol, peptide, polypeptide, protein or part of a protein (e.g., an antibody or antibody fragment), or lipid. In some embodiments, the targeting ligand is an aptamer. For example, a targeting ligand may be an RGD peptide that is used to target tumor vasculature or glioma cells, CREKA peptide to target tumor vasculature or stoma, transferring, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., targeting ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a targeting ligand. In some embodiments, an oligonucleotide (e.g., a ds oligonucleotide) provided by the disclosure comprises a stem-loop at the 3' end of the sense strand, wherein the loop of the stem-loop comprises a triloop or a tetraloop, and wherein the 3 or 4 nucleotides comprising the triloop or tetraloop, respectfully, are individually conjugated to a targeting ligand.

GalNAc is a high affinity ligand for the ASGPR, which is primarily expressed on the sinusoidal surface of hepatocyte cells and has a major role in binding, internalizing and subsequent clearing circulating glycoproteins that contain terminal galactose or GalNAc residues (asialoglycoproteins). Conjugation (either indirect or direct) of GalNAc moieties to oligonucleotides of the instant disclosure can be used to target these oligonucleotides to the ASGPR expressed on cells. In some embodiments, an oligonucleotide of the instant disclosure is conjugated to at least one or more GalNAc moieties, wherein the GalNAc moieties target the oligonucleotide to an ASGPR expressed on human liver cells (e.g. human hepatocytes). In some embodiments, the GalNAc moiety target the oligonucleotide to the liver.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3 or 4 monovalent GalNAc moieties, and is typically conjugated to 3 or 4 monovalent GalNAc moieties). In some embodiments, an oligonucleotide is conjugated to one or more bivalent GalNAc, trivalent GalNAc or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of a tetraloop are each conjugated to a separate GalNAc. In some embodiments, 1 to 3 nucleotides of a triloop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. In some embodiments, GalNAc moieties are conjugated to a nucleotide of the sense strand. For example, 4 GalNAc moieties can be conjugated to nucleotides in the tetraloop of the sense strand where each GalNAc moiety is conjugated to 1 nucleotide.

In some embodiments, an oligonucleotide herein comprises a monovalent GalNAc attached to a guanine nucleotide referred to as [ademG-GalNAc] or 2'-aminodiethoxymethanol-Guanine-GalNAc, as depicted below:

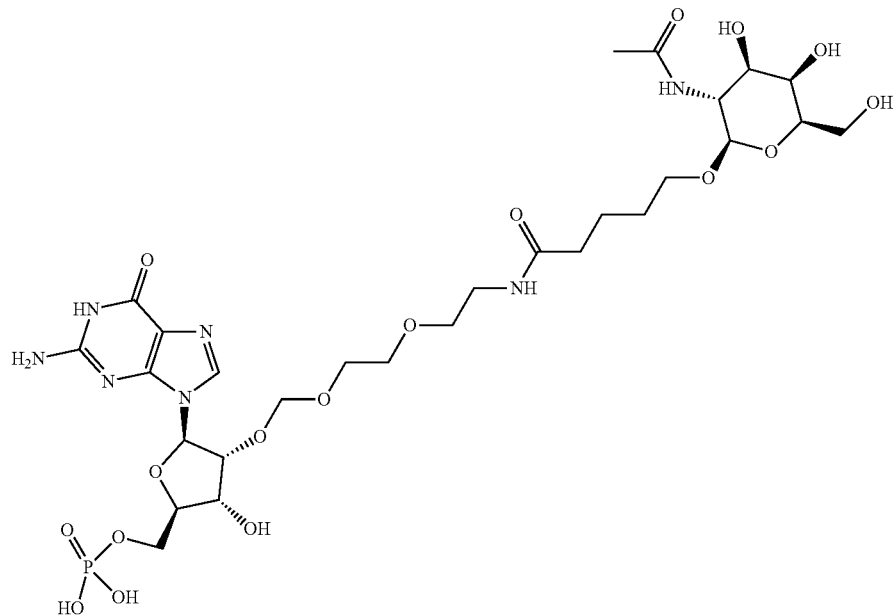 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(=O)[nH]c(N)nc32)O[C@H](CO)[C@H](O)[C@@H]1O]

In some embodiments, an oligonucleotide herein comprises a monovalent GalNAc attached to an adenine nucleotide, referred to as [ademA-GalNAc] or 2'-aminodiethoxymethanol-Adenine-GalNAc, as depicted below:

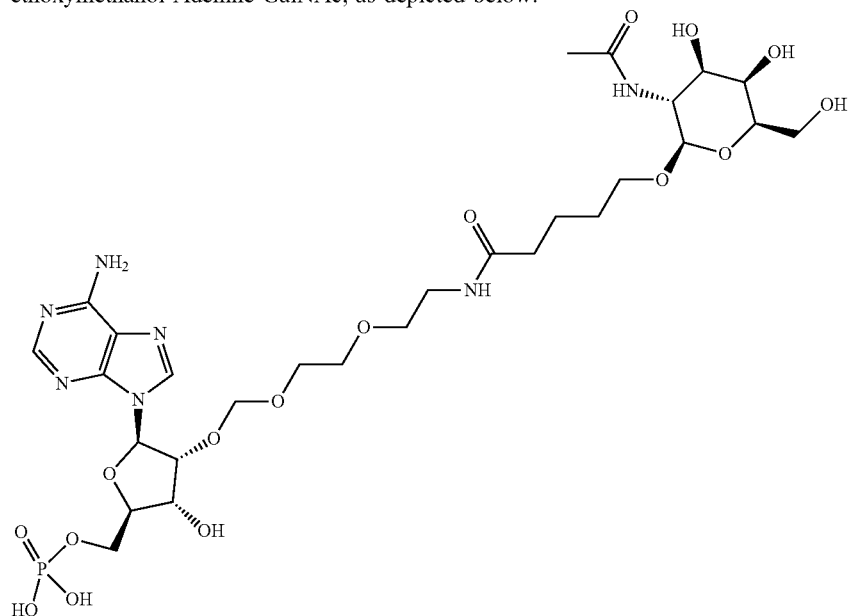

Figure 3:
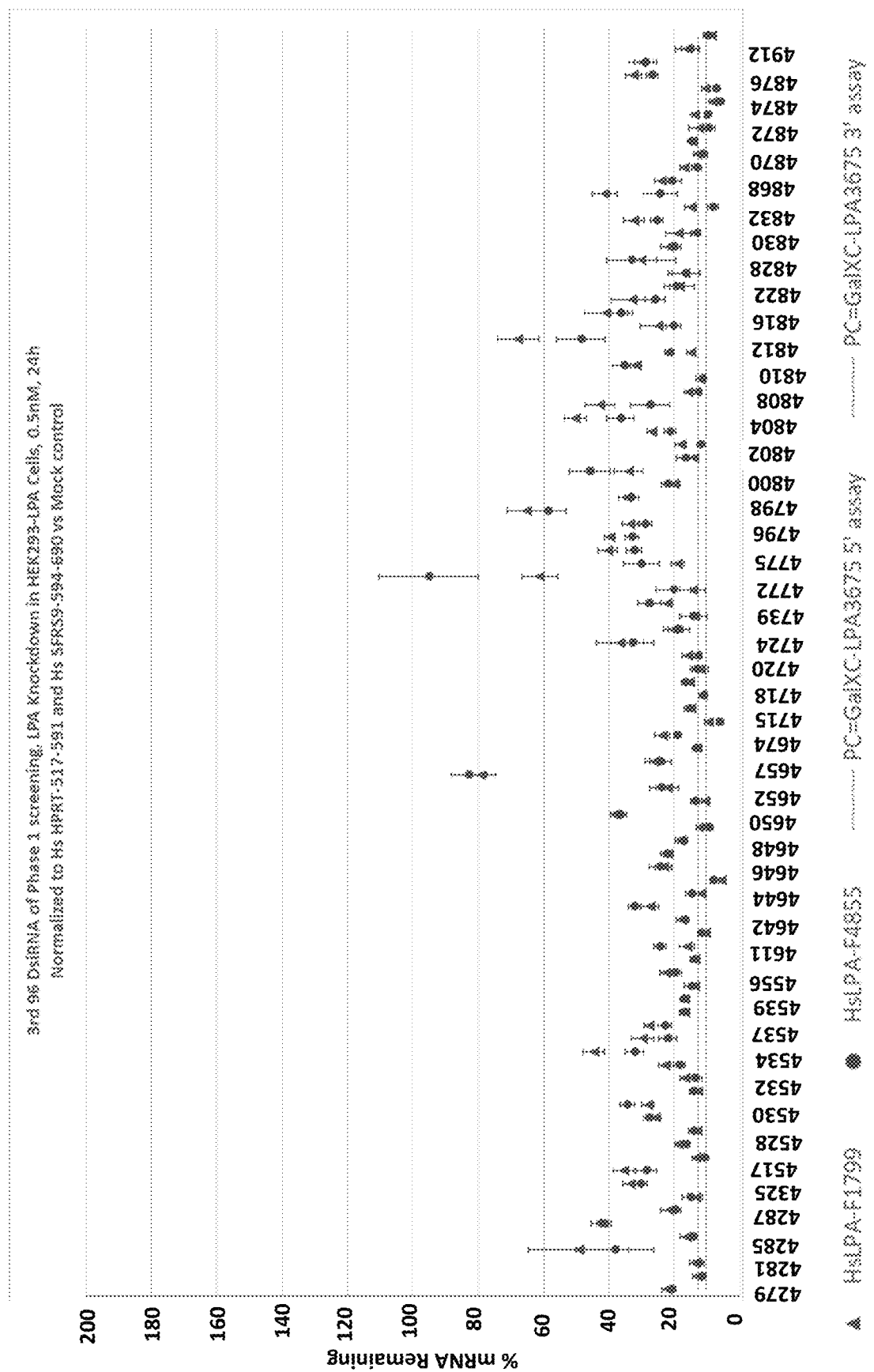
Figure 4:
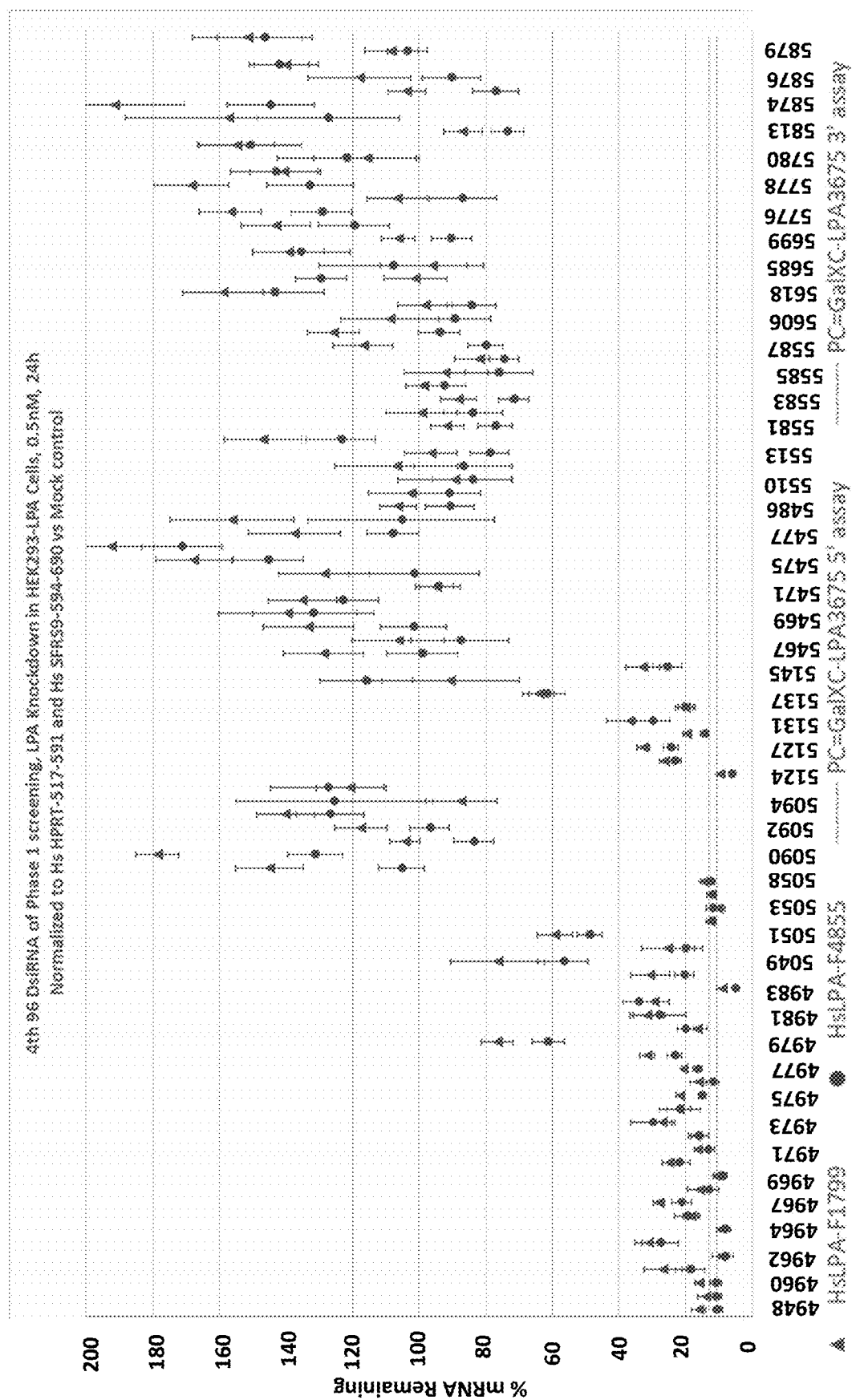
Figure 5:
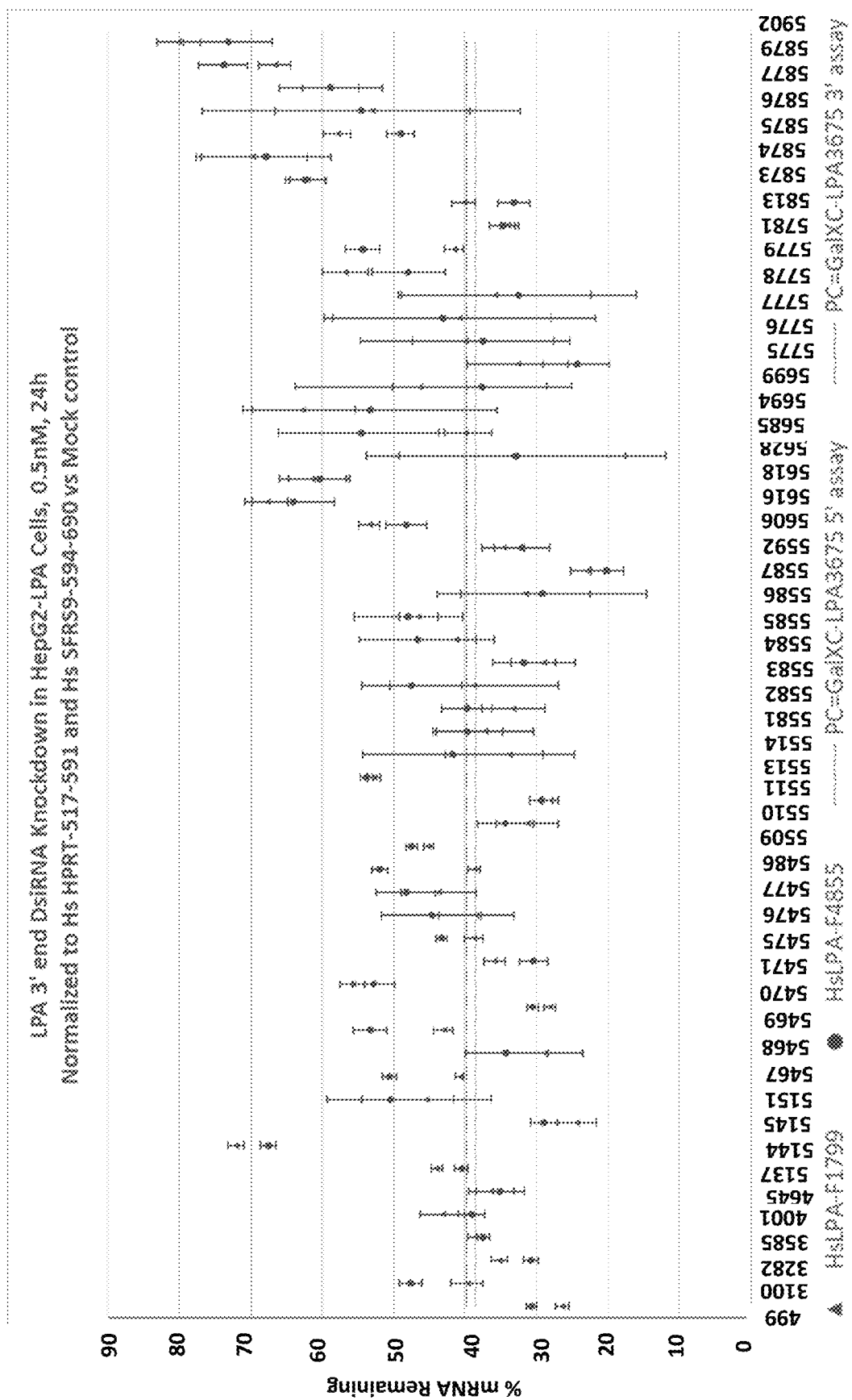
FIG. 5 provides a graph depicting the percent (%) of LPA mRNA in HepG2-LPA cells transfected with the indicated DsiRNAs relative to the % of LPA mRNA control mock-treated cells.

An example of such conjugation is shown below for a loop comprising from 5' to 3' the nucleotide sequence GAAA (L=linker, X=heteroatom) stem attachment points are shown. Such a loop may be present, for example, at positions 27-30 of the sense strand listed in Table 5 and as shown in FIG. 3. In the chemical formula,

is used to describe an attachment point to the oligonucleotide strand.

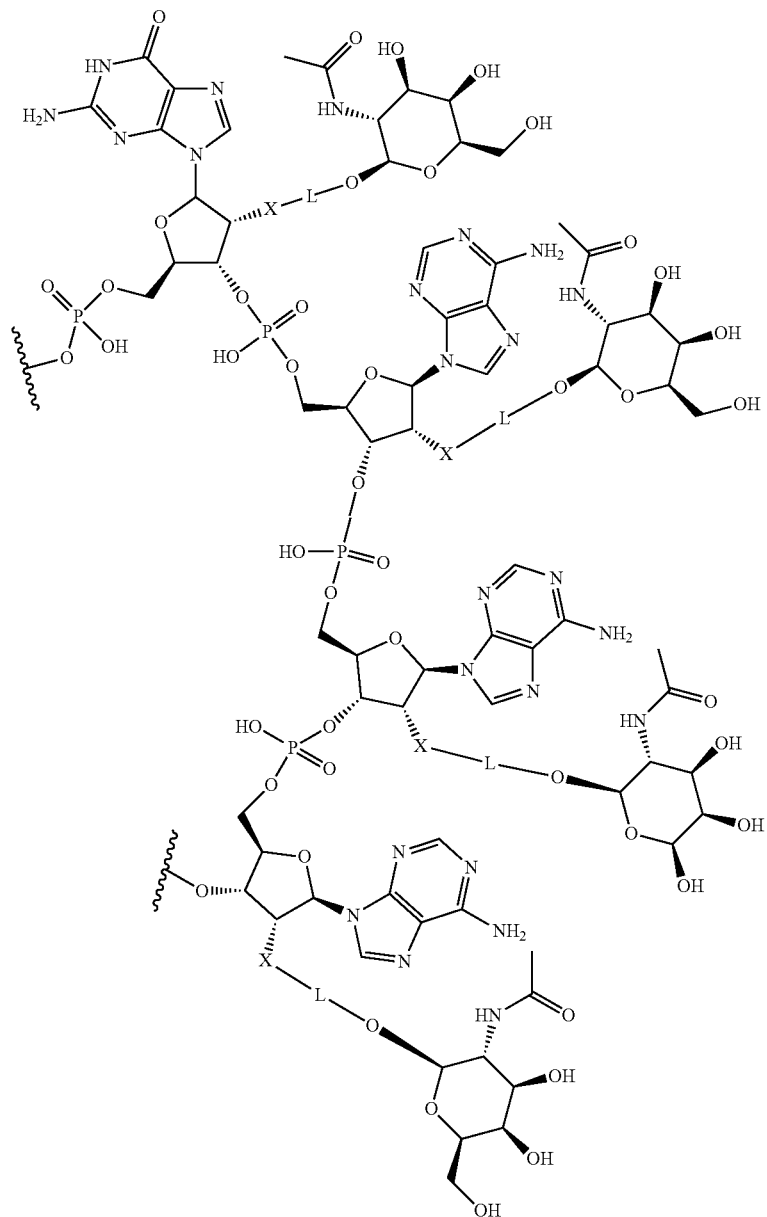

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is stable. An example is shown below for a loop comprising from 5' to 3' the nucleotides GAAA, in which GalNAc moieties are attached to nucleotides of the loop using an acetal linker. Such a loop may be present, for example, at positions 27-30 of the any one of the sense strand listed in Tables 3 or 4 and as shown in FIG. 10. In the chemical formula,

is an attachment point to the oligonucleotide strand.

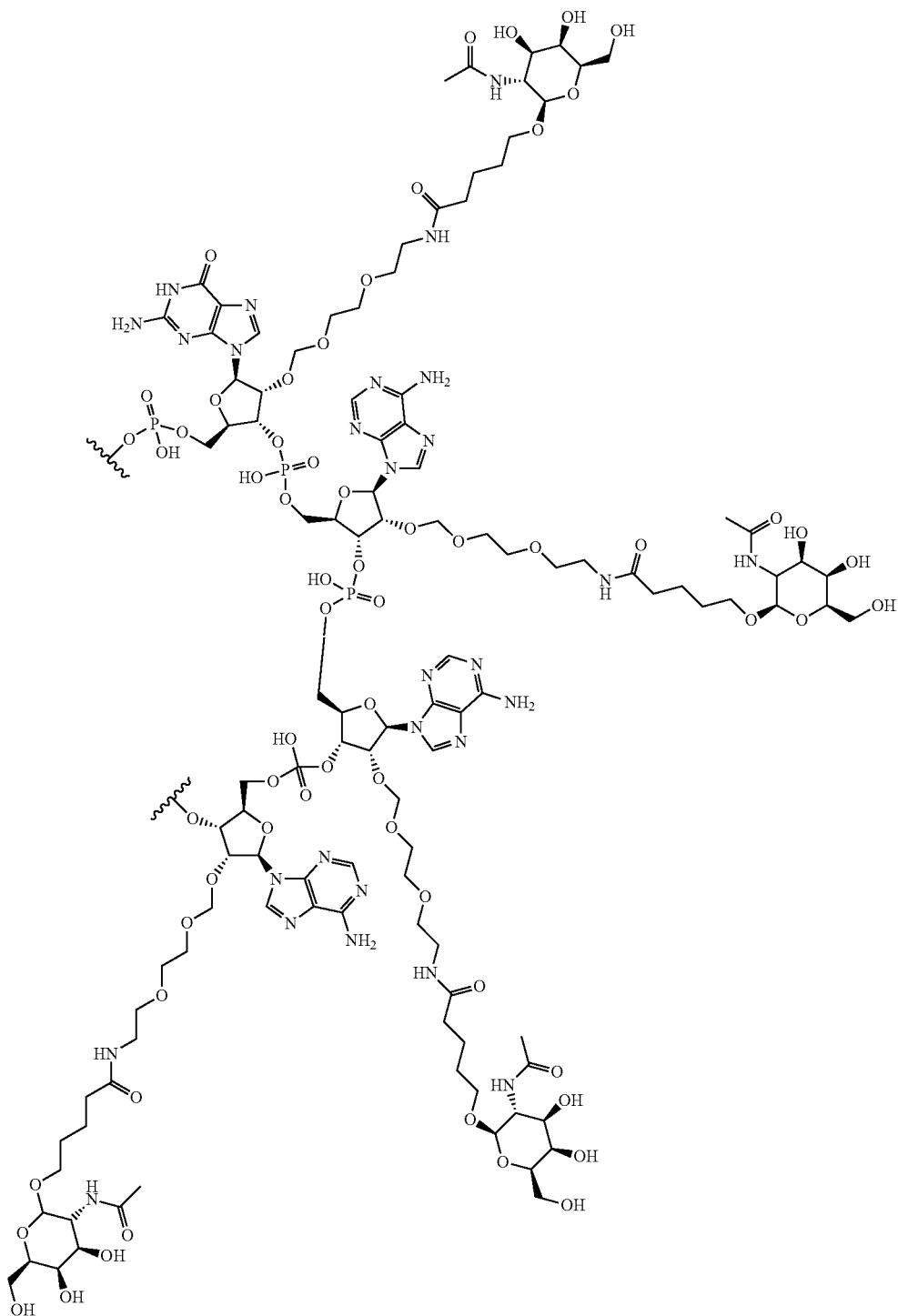

As mentioned, various appropriate methods or chemistry synthetic techniques (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is a stable linker.

In some embodiments, a duplex extension (e.g., of up to 3, 4, 5 or 6 bp in length) is provided between a targeting ligand (e.g., a GalNAc moiety) and a ds oligonucleotide. In some embodiments, the oligonucleotides herein do not have a GalNAc conjugated thereto.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, an oligonucleotide is formulated in buffer solutions such as phosphate buffered saline solutions, liposomes, micellar structures and capsids.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine, can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere or a nanoparticle, or may be otherwise formulated for administration to the cells, tissues, organs, or body of a subject in need thereof (see, e.g., Remington: THE SCIENCE AND PRACTICE OF PHARMACY, 22nd edition, Pharmaceutical Press, 2013).

In some embodiments, the formulations herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol or polyvinylpyrrolidone) or a collapse temperature modifier (e.g., dextran, Ficoll™ or gelatin).

In some embodiments, a pharmaceutical composition is formulated to be compatible with its intended route of administration. Examples of routes of administration include parenteral (e.g., intravenous, intramuscular, intraperitoneal, intradermal, subcutaneous), oral (e.g., inhalation), transdermal (e.g., topical), transmucosal and rectal administration.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and liquid polyethylene glycol, and the like), and suitable mixtures thereof. In many cases, it will be preferable to include isotonic agents, for example, sugars, polyalcohols such as mannitol, sorbitol, sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent or more, although the percentage of the active ingredient(s) may be between about 1% to about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though several embodiments are directed to liver-targeted delivery of any of the oligonucleotides herein, targeting of other tissues is also contemplated.

IV. Methods of Use i. Reducing LPA Expression in Cells

The disclosure provides methods for contacting or delivering to a cell or population of cells an effective amount any of the oligonucleotides (e.g., a ds oligonucleotide) herein for purposes of reducing LPA expression. In some embodiments, a reduction of LPA expression is determined by measuring a reduction in the amount or level of LPA mRNA, apo(a) protein, or apo(a) activity in a cell. The methods can include the steps described herein, and these may be be, but not necessarily, carried out in the sequence as described. Other sequences, however, also are conceivable. Moreover, individual or multiple steps bay be carried out either in parallel and/or overlapping in time and/or individually or in multiply repeated steps. Furthermore, the methods may include additional, unspecified steps.

Methods herein are useful in any appropriate cell type. In some embodiments, a cell is any cell that expresses mRNA (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue and skin). In some embodiments, the cell is a primary cell obtained from a subject. In some embodiments, the primary cell has undergone a limited number of passages such that the cell substantially maintains is natural phenotypic properties. In some embodiments, a cell to which the oligonucleotide is delivered is ex vivo or in vitro (i.e., can be delivered to a cell in culture or to an organism in which the cell resides).

In some embodiments, the oligonucleotides herein are delivered to a cell or population of cells using a nucleic acid delivery method known in the art including, but not limited to, injection of a solution containing the oligonucleotide, bombardment by particles covered by the oligonucleotide, exposing the cell or population of cells to a solution containing the oligonucleotide, or electroporation of cell membranes in the presence of the oligonucleotide. Other methods known in the art for delivering oligonucleotides to cells may be used, such as lipid-mediated carrier transport, chemical-mediated transport, and cationic liposome transfection such as calcium phosphate, and others.

In some embodiments, reduction of LPA expression is determined by an assay or technique that evaluates one or more molecules, properties or characteristics of a cell or population of cells associated with LPA expression (e.g., using an LPA expression biomarker) or by an assay or technique that evaluates molecules that are directly indicative of LPA expression in a cell or population of cells (e.g., LPA mRNA or apo(a) protein). In some embodiments, the extent to which an oligonucleotide herein reduces LPA expression is evaluated by comparing LPA expression in a cell or population of cells contacted with the oligonucleotide to a control cell or population of cells (e.g., a cell or population of cells not contacted with the oligonucleotide or contacted with a control oligonucleotide). In some embodiments, a control amount or level of LPA expression in a control cell or population of cells is predetermined, such that the control amount or level need not be measured in every instance the assay or technique is performed. The predetermined level or value can take a variety of forms. In some embodiments, a predetermined level or value can be single cut-off value, such as a median or mean.

In some embodiments, contacting or delivering an oligonucleotide (e.g., a ds oligonucleotide) herein to a cell or a population of cells results in a reduction in LPA expression. In some embodiments, the reduction in LPA expression is relative to a control amount or level of LPA expression in cell or population of cells not contacted with the oligonucleotide or contacted with a control oligonucleotide. In some embodiments, the reduction in LPA expression is about 1% or lower, about 5% or lower, about 10% or lower, about 15% or lower, about 20% or lower, about 25% or lower, about 30% or lower, about 35% or lower, about 40% or lower, about 45% or lower, about 50% or lower, about 55% or lower, about 60% or lower, about 70% or lower, about 80% or lower, or about 90% or lower relative to a control amount or level of LPA expression. In some embodiments, the control amount or level of LPA expression is an amount or level of LPA mRNA and/or apo(a) protein in a cell or population of cells that has not been contacted with an oligonucleotide herein. In some embodiments, the effect of delivery of an oligonucleotide to a cell or population of cells according to a method herein is assessed after any finite period or amount of time (e.g., minutes, hours, days, weeks, months). For example, in some embodiments, LPA expression is determined in a cell or population of cells at least about 4 hours, about 8 hours, about 12 hours, about 18 hours, about 24 hours; or at least about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, about 42 days, about 49 days, about 56 days, about 63 days, about 70 days, about 77 days, or about 84 days or more after contacting or delivering the oligonucleotide to the cell or population of cells. In some embodiments, LPA expression is determined in a cell or population of cells at least about 1 month, about 2 months, about 3 months, about 4 months, about 5 months, or about 6 months or more after contacting or delivering the oligonucleotide to the cell or population of cells.

In some embodiments, an oligonucleotide is delivered in the form of a transgene that is engineered to express in a cell the oligonucleotide or strands comprising the oligonucleotide (e.g., its sense and antisense strands). In some embodiments, an oligonucleotide is delivered using a transgene engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Medical Use

The disclosure also provides oligonucleotides for use, or adaptable for use, to treat a subject (e.g., a human having a disease, disorder or condition associated with LPA expression) that would benefit from reducing LPA expression. In some embodiments, the disclosure provides oligonucleotides for use, or adapted for use, to treat a subject having a disease, disorder or condition associated with expression of LPA. The disclosure also provides oligonucleotides for use, or adaptable for use, in the manufacture of a medicament or pharmaceutical composition for treating a disease, disorder or condition associated with LPA expression. In some embodiments, the oligonucleotides for use, or adaptable for use, target LPA mRNA and reduce LPA expression (e.g., via the RNAi pathway). In some embodiments, the oligonucleotides for use, or adaptable for use, target LPA mRNA and reduce the amount or level of LPA mRNA, apo(a) protein and/or apo(a) activity.

In addition, in some embodiments of the methods herein, a subject having a disease, disorder or condition associated with LPA expression or is predisposed to the same is selected for treatment with an oligonucleotide (e.g., a ds oligonucleotide) herein. In some embodiments, the method comprises selecting an individual having a marker (e.g., a biomarker) for a disease, disorder or condition associated with LPA expression, or predisposed to the same, such as, but not limited to, LPA mRNA, apo(a) protein, lipoprotein (a), or a combination thereof. Likewise, and as detailed below, some embodiments of the methods provided by the disclosure include steps such as measuring or obtaining a baseline value for a marker of LPA expression (e.g., lipoprotein (a)), and then comparing such obtained value to one or more other baseline values or values obtained after the subject is administered the oligonucleotide to assess the effectiveness of treatment.

iii. Methods of Treatment

The disclosure also provides methods of treating a subject having, suspected of having, or at risk of developing a disease, disorder or condition associated with LPA expression with an oligonucleotide herein. In some embodiments, the disclosure provides methods of treating or attenuating the onset or progression of a disease, disorder or condition associated with LPA expression using the oligonucleotides herein. In other embodiments, the disclosure provides methods to achieve one or more therapeutic benefits in a subject having a disease, disorder or condition associated with LPA expression using the oligonucleotides herein. In some embodiments of the methods herein, the subject is treated by administering a therapeutically effective amount of any one or more of the oligonucleotides herein. In some embodiments, treatment comprises reducing LPA expression. In some embodiments, the subject is treated therapeutically. In some embodiments, the subject is treated prophylactically.

In some embodiments of the methods herein, an oligonucleotide herein, or a pharmaceutical composition comprising the oligonucleotide, is administered to a subject having a disease, disorder or condition associated with LPA expression such that LPA expression is reduced in the subject, thereby treating the subject. In some embodiments, an amount or level of LPA mRNA is reduced in the subject. In some embodiments, an amount or level of apo(a) protein is reduced in the subject. In some embodiments, an amount or level of lipoprotein (a) is reduced in the subject. In some embodiments, an amount or level of apo(a) activity is reduced in the subject. In some embodiments, an amount or level of triglyceride (TG) (e.g., one or more TG(s) or total TGs) is reduced in the subject. In some embodiments, an amount or level of cholesterol (e.g., total cholesterol, LDL cholesterol, and/or HDL cholesterol) is reduced in the subject. In some embodiments, an amount or level of low-density lipoprotein (LDL) cholesterol is reduced in the subject. In some embodiments, an amount or activity of OxPL is reduced or altered in the subject. In some embodiments, an amount or activity of LDL-C is reduced or altered in the subject. In some embodiments, an amount or activity of apoB-100 is reduced or altered in the subject. In some embodiments, any combination of the following is reduced or altered in the subject: LPA expression, an amount or level of LPA mRNA, an amount or level of apo(a) protein, an amount or level of apo(a) activity, an amount or level of TG, an amount or level of cholesterol, an amount or activity of OxPL, an amount or activity of LDL-C, and/or an amount or activity of apoB-100.

In some embodiments of the methods herein, an oligonucleotide herein, or a pharmaceutical composition comprising the oligonucleotide, is administered to a subject having a disease, disorder or condition associated with LPA expression such that LPA expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to LPA expression prior to administration of the oligonucleotide or pharmaceutical composition. In some embodiments, LPA expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to LPA expression in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of LPA mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of LPA mRNA prior to administration of the oligonucleotide or pharmaceutical composition. In some embodiments, an amount or level of LPA mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of LPA mRNA in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of apo(a) protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of apo(a) protein prior to administration of the oligonucleotide or pharmaceutical composition. In some embodiments, an amount or level of apo(a) protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of apo(a) protein in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of apo(a) activity is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of apo(a) activity prior to administration of the oligonucleotide or pharmaceutical composition. In some embodiments, an amount or level of apo(a) activity is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of apo(a) activity in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with LPA expression such that an amount or level of lipoprotein (a) is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of lipoprotein (a) prior to administration of the oligonucleotide or pharmaceutical composition. In some embodiments, an amount or level of lipoprotein (a) is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of lipoprotein (a) in a subject (e.g., a reference or control subject) not receiving the oligonucleotide or pharmaceutical composition or receiving a control oligonucleotide, pharmaceutical composition or treatment.

Lipoprotein (a) levels range widely in human adults with plasma levels ranging from <0.1 mg/dL to >200 mg/dL, thus exhibiting up to three orders of magnitude difference among individuals (Schmidt et al., (2016) J Lipid Res. 57 (8): 1339-1359). Lipoprotein (a) levels<30 mg/dl are considered optimal in the United States and Canada (Anderson et al., (2016) CAN J CARDIOL 32:1263-82). The European Atherosclerosis Society (EAS) has proposed <50 mg/dL as optimal, and lipoprotein (a) levels>60 mg/dl are used as a cutoff for the reimbursement of apheresis in Germany and the United Kingdom (Tsimikas (2017) J AM COLL CARDIOL. 69 (6): 692-711). In some embodiments, a subject selected for treatment or treated with an oligonucleotide herein is identified or determined to have an amount or level of lipoprotein (a) of about 30 mg/dL or greater. In some embodiments, a subject selected for treatment or treated with an oligonucleotide herein is identified or determined to have an amount or level of lipoprotein (a) of >30 mg/dL. In some embodiments, a subject selected for treatment or treated with an oligonucleotide herein is identified or determined to have an amount or level of lipoprotein (a) of about 50 mg/dL or greater. In some embodiments, a subject selected for treatment or treated with an oligonucleotide herein is identified or determined to have an amount or level of lipoprotein (a) of about 60 mg/dL or greater. In some embodiments, a subject selected for treatment or treated with an oligonucleotide herein is identified or determined to have an amount or level of lipoprotein (a) in the range of 30 mg/dL to 300 mg/dL.

Generally, a normal or desirable TG range for a human patient is ≤150 mg/dl of blood, with <100 being considered ideal. In some embodiments, the patient selected for treatment or treated is identified or determined to have an amount or level of TG of ≥150 mg/dL. In some embodiments, the patient selected for treatment or treated is identified or determined to have an amount or level of TG in the range of 150 to 199 mg/dL, which is considered borderline high TG levels. In some embodiments, the patient selected for treatment or treated is identified or determined to have an amount or level of TG in the range of 200 to 499 mg/dl, which is considered high TG levels. In some embodiments, the patient selected for treatment or treated is identified or determined to have an amount or level of TG in the range of 500 mg/dL or higher (i.e., ≥500 mg/dL), which is considered very high TG levels. In some embodiments, the patient selected for treatment or treated is identified or determined to have an amount or level of TG which is ≥150 mg/dL, ≥200 mg/dL or ≥500 mg/dL. In some embodiments, the patient selected for treatment or treated is identified or determined to have an amount of level of TG of 200 to 499 mg/dL, or 500 mg/dL or higher. In some embodiments, the patient selected for treatment or treated is identified or determined to have an amount or level of TG which is ≥200 mg/dL.

In some embodiments of the methods herein, an oligonucleotide herein, or a pharmaceutical composition comprising the oligonucleotide, is administered to a subject having a disease, disorder or condition associated with LPA expression such that an amount or level of cholesterol (e.g., total cholesterol, LDL cholesterol, and/or HDL cholesterol) is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of cholesterol prior to administration of the oligonucleotide or pharmaceutical composition. In some embodiments, an amount or level of cholesterol is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of cholesterol in a subject (e.g., a reference or control subject) not receiving the oligonucleotide or pharmaceutical composition or receiving a control oligonucleotide, pharmaceutical composition or treatment.

Generally, a normal or desirable cholesterol range (total cholesterol) for an adult human patient is <200 mg/dL of blood. In some embodiments, the patient selected for treatment or treated is identified or determined to have an amount or level of cholesterol of ≥200 mg/dL. In some embodiments, the patient selected for treatment or treated is identified or determined to have an amount or level of cholesterol in the range of 200 to 239 mg/dL, which is considered borderline high cholesterol levels. In some embodiments, the patient selected for treatment or treated is identified or determined to have an amount or level of cholesterol in the range of 240 mg/dL and higher (i.e., ≥240 mg/dL), which is considered high cholesterol levels. In some embodiments, the patient selected from treatment or treated is identified or determined to have an amount or level of cholesterol of 200 to 239 mg/dL, or 240 mg/dL or higher. In some embodiments, the patient selected for treatment or treated is identified or determined to have an amount or level of cholesterol which is ≥200 mg/dL or ≥240 mg/dL or higher.

In some embodiments of the methods herein, an oligonucleotide herein, or a pharmaceutical composition comprising the oligonucleotide, is administered to a subject having a disease, disorder, or condition associated with LPA expression such that an amount or level of LDL cholesterol is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of LDL cholesterol prior to administration of the oligonucleotide or pharmaceutical composition. In some embodiments, an amount or level of LDL cholesterol is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of LDL cholesterol in a subject (e.g., a reference or control subject) not receiving the oligonucleotide or pharmaceutical composition or receiving a control oligonucleotide, pharmaceutical composition or treatment.

Generally, a normal or desirable LDL cholesterol range for an adult human patient is <100 mg/dL of blood. In some embodiments, the patient selected for treatment or treated is identified or determined to have an amount or level of cholesterol of ≥100 mg/dL. In some embodiments, the patient selected for treatment or treated is identified or determined to have an amount or level of LDL cholesterol in the range of 100 to 129 mg/dL, which is considered above optimal. In some embodiments, the patient selected for treatment or treated is identified or determined to have an amount or level of LDL cholesterol in the range of 130 to 159 mg/dL, which is considered borderline high levels. In some embodiments, the patient selected for treatment or treated is identified or determined to have an amount or level of LDL cholesterol in the range of 160 to 189 mg/dL, which is considered high LDL cholesterol levels. In some embodiments, the patient selected for treatment or treated is identified or determined to have an amount or level of LDL cholesterol in the range of 190 mg/dL and higher (i.e., ≥190 mg/dL), which is considered very high LDL cholesterol levels. In some embodiments, the patient selected for treatment or treated is identified or determined to have an amount or level of LDL cholesterol which is ≥100 mg/dL, ≥130 mg/dL, ≥160 mg/dL, or ≥190 mg/dL or higher, preferably ≥160 mg/dL, or ≥190 mg/dL or higher. In some embodiments, the patient selected for treatment or treated is identified or determined to have an amount or level of LDL cholesterol of 100 to 129 mg/dL, 130 to 159 mg/dL, 160 to 189 mg/dL, or 190 mg/dL and higher.

Suitable methods for determining LPA expression, an amount or level of LPA mRNA, an amount or level of apo(a) protein, an amount or level of apo(a) activity, an amount or level of lipoprotein (a), and/or an amount or level of OxPL, LDL-C, apoB-100, TG and/or LDL cholesterol in the subject, or in a sample from the subject, are known in the art.

Further, the Examples set forth herein illustrate exemplary methods for determining LPA expression.

In some embodiments, LPA expression, the amount or level of LPA mRNA, apo(a) protein, apo(a) activity, OxPL, LDL-C, apoB-100, TG, LDL cholesterol, or any combination thereof, is reduced in a cell (e.g., a hepatocyte), a population or a group of cells (e.g., an organoid), an organ (e.g., liver), blood or a fraction thereof (e.g., plasma), a tissue (e.g., liver tissue), a sample (e.g., a liver biopsy sample), or any other biological material obtained or isolated from the subject. In some embodiments, LPA expression, the amount or level of LPA mRNA, apo(a) protein, apo(a) activity, OxPL, LDL-C, apoB-100, TG, LDL cholesterol, or any combination thereof, is reduced in more than one type of cell (e.g., a hepatocyte and one or more other type(s) of cell), more than one groups of cells, more than one organ (e.g., liver and one or more other organ(s)), more than one fraction of blood (e.g., plasma and one or more other blood fraction(s)), more than one type of tissue (e.g., liver tissue and one or more other type(s) of tissue), more than one type of sample (e.g., a liver biopsy sample and one or more other type(s) of biopsy sample) obtained or isolated from the subject.

Examples of a disease, disorder or condition associated with LPA expression include, but are not limited to, Berger's disease, peripheral artery disease, coronary artery disease, metabolic syndrome, acute coronary syndrome, aortic valve stenosis, aortic valve regurgitation, aortic dissection, retinal artery occlusion, cerebrovascular disease, mesenteric ischemia, superior mesenteric artery occlusion, renal artery stenosis, stable/unstable angina, acute coronary syndrome, heterozygous or homozygous familial hypercholesterolemia, hyperapobetalipoproteinemia, cerebrovascular atherosclerosis, cerebrovascular disease, and venous thrombosis, or a combination thereof.

Because of their high specificity, the oligonucleotides herein specifically target mRNAs of target genes of cells, tissues, or organs (e.g., liver). In preventing disease, the target gene may be one which is required for initiation or maintenance of the disease or which has been identified as being associated with a higher risk of contracting the disease. In treating disease, the oligonucleotide can be brought into contact with the cells or tissue exhibiting or responsible for mediating the disease. For example, an oligonucleotide substantially identical to all or part of a wild-type (i.e., native) or mutated gene associated with a disorder or condition associated with LPA expression may be brought into contact with or introduced into a cell or tissue type of interest such as a hepatocyte or other liver cell.

In some embodiments, the target gene may be a target gene from any mammal, such as a human. Any gene may be silenced according to the method described herein.

Methods described herein are typically involve administering to a subject a therapeutically effective amount of an oligonucleotide herein, that is, an amount capable of producing a desirable therapeutic result. A therapeutically acceptable amount may be an amount that can therapeutically treat a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides herein are administered intravenously or subcutaneously.

As a non-limiting set of examples, the oligonucleotides herein would typically be administered quarterly (once every three months), bi-monthly (once every two months), monthly or weekly. For example, the oligonucleotides may be administered every week or at intervals of two, or three weeks. Alternatively, the oligonucleotides may be administered daily. In some embodiments, a subject is administered one or more loading doses of the oligonucleotide followed by one or more maintenance doses of the oligonucleotide.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

V. Kits

In some embodiments, the disclosure provides a kit comprising an oligonucleotide herein, and instructions for use. In some embodiments, the kit comprises an oligonucleotide herein, and a package insert containing instructions for use of the kit and/or any component thereof. In some embodiments, the kit comprises, in a suitable container, an oligonucleotide herein, one or more controls, and various buffers, reagents, enzymes and other standard ingredients well known in the art. In some embodiments, the container comprises at least one vial, well, test tube, flask, bottle, syringe or other container means, into which the oligonucleotide is placed, and in some instances, suitably aliquoted. In some embodiments where an additional component is provided, the kit contains additional containers into which this component is placed. The kits can also include a means for containing the oligonucleotide and any other reagent in close confinement for commercial sale. Such containers may include injection or blow-molded plastic containers into which the desired vials are retained. Containers and/or kits can include labeling with instructions for use and/or warnings.

In some embodiments, a kit comprises an oligonucleotide herein, and a pharmaceutically acceptable carrier, or a pharmaceutical composition comprising the oligonucleotide and instructions for treating or delaying progression of a disease, disorder or condition associated with LPA expression in a subject in need thereof.

EXAMPLES

While the disclosure has been described with reference to the specific embodiments set forth in the following Examples, it should be understood by those skilled in the art that various changes may be made, and equivalents may be substituted without departing from the true spirit and scope of the disclosure. Further, the following Examples are offered by way of illustration and are not intended to limit the scope of the disclosure in any manner. In addition, modifications may be made to adapt to a situation, material, composition of matter, process, process step or steps, to the objective, spirit and scope of the disclosure. All such modifications are intended to be within the scope of the disclosure. Standard techniques well known in the art or the techniques specifically described below are utilized.

Example 1: Preparation of Double-Stranded RNAi Oligonucleotides

Oligonucleotide Synthesis and Purification

The ds RNAi oligonucleotides described in the foregoing Examples are chemically synthesized using methods described herein. Generally, ds RNAi oligonucleotides are synthesized using solid phase oligonucleotide synthesis methods as described for 19-23mer siRNAs (see, e.g., Scaringe et al. (1990) NUCLEIC ACIDS RES. 18:5433-41 and Usman et al. (1987) J. AM. CHEM. SOC. 109:7845-45; see also, U.S. Pat. Nos. 5,804,683; 5,831,071; 5,998,203; 6,008,400; 6,111,086; 6,117,657; 6,353,098; 6,362,323; 6,437,117 and 6,469,158).

Individual RNA strands are synthesized and HPLC purified according to standard methods (Integrated DNA Technologies; Coralville, IA). For example, RNA oligonucleotides are synthesized using solid phase phosphoramidite chemistry, deprotected and desalted on NAP-5 columns (Amersham Pharmacia Biotech; Piscataway, NJ) using standard techniques (Damha & Olgivie (1993) METHODS MOL. BIOL. 20:81-114; Wincott et al. (1995) NUCLEIC ACIDS RES. 23:2677-84). The oligomers are purified using ion-exchange high performance liquid chromatography (IE-HPLC) on an Amersham Source 15Q column (1.0 cm×25 cm; Amersham Pharmacia Biotech) using a 15 min step-linear gradient. The gradient varies from 90:10 Buffers A:B to 52:48 Buffers A:B, where Buffer A is 100 mM Tris pH 8.5 and Buffer B is 100 mM Tris pH 8.5, 1 M NaCl. Samples are monitored at 260 nm and peaks corresponding to the full-length oligonucleotide species are collected, pooled, desalted on NAP-5 columns, and lyophilized.

The purity of each oligomer is determined by capillary electrophoresis (CE) on a Beckman PACE 5000 (Beckman Coulter, Inc.; Fullerton, CA). The CE capillaries have a 100 μm inner diameter and contain ssDNA 100R Gel (Beckman-Coulter). Typically, about 0.6 nmole of oligonucleotide is injected into a capillary, is run in an electric field of 444 V/cm and is detected by UV absorbance at 260 nm. Denaturing Tris-Borate-7 M-urea running buffer is purchased from Beckman-Coulter. Oligoribonucleotides are obtained that are at least 90% pure as assessed by CE for use in experiments described below. Compound identity is verified by matrix-assisted laser desorption ionization time-of-flight (MALDI-TOF) mass spectroscopy on a Voyager DE™ Biospectometry Work Station (Applied Biosystems; Foster City, CA) following the manufacturer's recommended protocol. Relative molecular masses of all oligomers are obtained, often within 0.2% of expected molecular mass.

Preparation of Duplexes ssRNA oligomers are resuspended (e.g., at 100 μM concentration) in duplex buffer consisting of 100 mM potassium acetate, 30 mM HEPES, pH 7.5. Complementary sense and antisense strands are mixed in equal molar amounts to yield a final solution of, for example, 50 μM duplex. Samples are heated to 100° ° C. for 5' in RNA buffer (IDT) and are allowed to cool to room temperature before use. The ds RNA oligonucleotides are stored at −20° C. ss RNA oligomers are stored lyophilized or in nuclease-free water at −80° C.

Example 2: RNAi Oligonucleotide Inhibition of LPA Expression In Vitro

LPA mRNA Target Sequence Identification

To identify RNAi oligonucleotide inhibitors of LPA expression, a computer-based algorithm was used to computationally identify LPA mRNA target sequences suitable for assaying inhibition of LPA expression by the RNAi pathway. The algorithm provides RNAi oligonucleotide guide (antisense) strand sequences each having a region of complementarity to a suitable LPA target sequence of human LPA mRNA (e.g., SEQ ID NO: 1; Table 1). Some of the guide strand sequences identified by the algorithm are also complementary to the corresponding LPA target sequence of monkey LPA mRNA (SEQ ID NO: 2; Table 1). RNAi oligonucleotides (formatted as DsiRNA oligonucleotides) were generated (Table 2), each with a unique guide strand having a region of complementarity to an LPA target sequence identified by the algorithm. The passenger (sense) strands of the DsiRNAs provided in Table 2 comprise a unique human LPA mRNA target sequence identified by the algorithm.

TABLE 1

Sequences of Human and NHP (Monkey) mRNA

| Species | GenBank Ref Seq # | SEQ ID NO: |
|---|---|---|
| Human (Hs) | NM_005577.3 | 1 |
| Cynomolgus monkey (Mf) | XM_015448517.1 | 2 |
| Rhesus monkey | XM_028847001.1 | 3 |

TABLE 2

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| DsiRNA | | | | | | |
| LPA-125 | CUGAGCAAAGCCAUGUGGU ACAGGA | 4 | UCCUGUACCACAUG GCUUUGCUCAGGU | 404 | CUGAGCAAAG CCAUGUGGU | 804 |
| LPA-128 | AGCAAAGCCAUGUGGUCCA AGAUTG | 5 | CAAUCUUGGACCAC AUGGCUUUGCUCA | 405 | AGCAAAGCCA UGUGGUCCA | 805 |
| LPA-132 | AAGCCAUGUGGUCCAGGAU AGCUAC | 6 | GUAGCUAUCCUGGA CCACAUGGCUUUG | 406 | AAGCCAUGUG GUCCAGGAU | 806 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-133 | AGCCAUGUGGUCCAGGAUU ACUACC | 7 | GGUAGUAAUCCUGG ACCACAUGGCUUU | 407 | AGCCAUGUGG UCCAGGAUU | 807 |
| LPA-134 | GCCAUGUGGUCCAGGAUUG AUACCA | 8 | UGGUAUCAAUCCUG GACCACAUGGCUU | 408 | GCCAUGUGGU CCAGGAUUG | 808 |
| LPA-135 | CCAUGUGGUCCAGGAUUGC AACCAT | 9 | AUGGUUGCAAUCCU GGACCACAUGGCU | 409 | CCAUGUGGUC CAGGAUUGC | 809 |
| LPA-136 | CAUGUGGUCCAGGAUUGCU ACCATG | 10 | CAUGGUAGCAAUCC UGGACCACAUGGC | 410 | CAUGUGGUCC AGGAUUGCU | 810 |
| LPA-137 | AUGUGGUCCAGGAUUGCUA ACAUGG | 11 | CCAUGUUAGCAAUC CUGGACCACAUGG | 411 | AUGUGGUCCA GGAUUGCUA | 811 |
| LPA-138 | UGUGGUCCAGGAUUGCUAC AAUGGT | 12 | ACCAUUGUAGCAAU CCUGGACCACAUG | 412 | UGUGGUCCAG GAUUGCUAC | 812 |
| LPA-160 | GGUGAUGGACAGAGUUAUC AAGGCA | 13 | UGCCUUGAUAACUC UGUCCAUCACCAU | 413 | GGUGAUGGAC AGAGUUAUC | 813 |
| LPA-190 | UCCACCACUGUCACAGGAA AGACCT | 14 | AGGUCUUUCCUGUG ACAGUGGUGGAGU | 414 | UCCACCACUG UCACAGGAA | 814 |
| LPA-191 | CCACCACUGUCACAGGAAG AACCTG | 15 | CAGGUUCUUCCUGU GACAGUGGUGGAG | 415 | CCACCACUGU CACAGGAAG | 815 |
| LPA-197 | CUGUCACAGGAAGGACCUG ACAAGC | 16 | GCUUGUCAGGUCCU UCCUGUGACAGUG | 416 | CUGUCACAGG AAGGACCUG | 816 |
| LPA-205 | GGAAGGACCUGCCAAGCUU AGUCAT | 17 | AUGACUAAGCUUGG CAGGUCCUUCCUG | 417 | GGAAGGACCU GCCAAGCUU | 817 |
| LPA-206 | GAAGGACCUGCCAAGCUUG AUCATC | 18 | GAUGAUCAAGCUUG GCAGGUCCUUCCU | 418 | GAAGGACCUG CCAAGCUUG | 818 |
| LPA-208 | AGGACCUGCCAAGCUUGGU AAUCTA | 19 | UAGAUUACCAAGCU UGGCAGGUCCUUC | 419 | AGGACCUGCC AAGCUUGGU | 819 |
| LPA-209 | GGACCUGCCAAGCUUGGUC AUCTAT | 20 | AUAGAUGACCAAGC UUGGCAGGUCCUU | 420 | GGACCUGCCA AGCUUGGUC | 820 |
| LPA-210 | GACCUGCCAAGCUUGGUCA ACTATG | 21 | CAUAGUUGACCAAG CUUGGCAGGUCCU | 421 | GACCUGCCAA GCUUGGUCA | 821 |
| LPA-211 | ACCUGCCAAGCUUGGUCAU AUAUGA | 22 | UCAUAUAUGACCAA GCUUGGCAGGUCC | 422 | ACCUGCCAAG CUUGGUCAU | 822 |
| LPA-212 | CCUGCCAAGCUUGGUCAUC AAUGAC | 23 | GUCAUUGAUGACCA AGCUUGGCAGGUC | 423 | CCUGCCAAGC UUGGUCAUC | 823 |
| LPA-219 | AGCUUGGUCAUCUAUGACA ACACAT | 24 | AUGUGUUGUCAUAG AUGACCAAGCUUG | 424 | AGCUUGGUCA UCUAUGACA | 824 |
| LPA-225 | GUCAUCUAUGACACCACAU AAACAT | 25 | AUGUUUAUGUGGUG UCAUAGAUGACCA | 425 | GUCAUCUAUG ACACCACAU | 825 |
| LPA-258 | CACAGAAAACUACCCAAAU ACUGGC | 26 | GCCAGUAUUUGGGU AGUUUUCUGUGGU | 426 | CACAGAAAAC UACCCAAAU | 826 |
| LPA-261 | AGAAAACUACCCAAAUGCU AGCUTG | 27 | CAAGCUAGCAUUUG GGUAGUUUUCUGU | 427 | AGAAAACUAC CCAAAUGCU | 827 |
| LPA-263 | AAAACUACCCAAAUGCUGG AUUGAT | 28 | AUCAAUCCAGCAUU UGGGUAGUUUUCU | 428 | AAAACUACCC AAAUGCUGG | 828 |
| LPA-269 | ACCCAAAUGCUGGCUUGAU AAUGAA | 29 | UUCAUUAUCAAGCC AGCAUUUGGGUAG | 429 | ACCCAAAUGC UGGCUUGAU | 829 |

TABLE 2-continued

DsiRNAs Targeting Human LPA mRNA and
Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-270 | CCCAAAUGCUGGCUUGAUC AUGAAC | 30 | GUUCAUGAUCAAGC CAGCAUUUGGGUA | 430 | CCCAAAUGCU GGCUUGAUC | 830 |
| LPA-291 | GAACUACUGCAGGAAUCCA AAUGCT | 31 | AGCAUUUGGAUUCC UGCAGUAGUUCAU | 431 | GAACUACUGC AGGAAUCCA | 831 |
| LPA-295 | UACUGCAGGAAUCCAGAUG AUGUGG | 32 | CCACAUCAUCUGGA UUCCUGCAGUAGU | 432 | UACUGCAGGA AUCCAGAUG | 832 |
| LPA-296 | ACUGCAGGAAUCCAGAUGC AGUGGC | 33 | GCCACUGCAUCUGG AUUCCUGCAGUAG | 433 | ACUGCAGGAA UCCAGAUGC | 833 |
| LPA-298 | UGCAGGAAUCCAGAUGCUG AGGCAG | 34 | CUGCCUCAGCAUCU GGAUUCCUGCAGU | 434 | UGCAGGAAUC CAGAUGCUG | 834 |
| LPA-355 | AGGUGGGAGUACUGCAACC AGACGC | 35 | GCGUCUGGUUGCAG UACUCCCACCUGA | 435 | AGGUGGGAGU ACUGCAACC | 835 |
| LPA-380 | AAUGCUCAGACGCAGAAGG AACUGC | 36 | GCAGUUCCUUCUGC GUCUGAGCAUUGC | 436 | AAUGCUCAGA CGCAGAAGG | 836 |
| LPA-417 | GACUGUUACCCCGGUUCCA AGCCTA | 37 | UAGGCUUGGAACCG GGGUAACAGUCGG | 437 | GACUGUUACC CCGGUUCCA | 837 |
| LPA-418 | ACUGUUACCCCGGUUCCAA ACCUAG | 38 | CUAGGUUUGGAACC GGGGUAACAGUCG | 438 | ACUGUUACCC CGGUUCCAA | 838 |
| LPA-419 | CUGUUACCCCGGUUCCAAG ACUAGA | 39 | UCUAGUCUUGGAAC CGGGGUAACAGUC | 439 | CUGUUACCCC GGUUCCAAG | 839 |
| LPA-420 | UGUUACCCCGGUUCCAAGC AUAGAG | 40 | CUCUAUGCUUGGAA CCGGGGUAACAGU | 440 | UGUUACCCCG GUUCCAAGC | 840 |
| LPA-421 | GUUACCCCGGUUCCAAGCC AAGAGG | 41 | CCUCUUGGCUUGGA ACCGGGGUAACAG | 441 | GUUACCCCGG UUCCAAGCC | 841 |
| LPA-422 | UUACCCCGGUUCCAAGCCU AGAGGC | 42 | GCCUCUAGGCUUGG AACCGGGGUAACA | 442 | UUACCCCGGU UCCAAGCCU | 842 |
| LPA-423 | UACCCCGGUUCCAAGCCUA AAGGCT | 43 | AGCCUUUAGGCUUG GAACCGGGGUAAC | 443 | UACCCCGGUU CCAAGCCUA | 843 |
| LPA-492 | GUGCUACCAUGGUAAUGGA AAGAGT | 44 | ACUCUUUCCAUUAC CAUGGUAGCACUC | 444 | GUGCUACCAU GGUAAUGGA | 844 |
| LPA-493 | UGCUACCAUGGUAAUGGAC AGAGTT | 45 | AACUCUGUCCAUUA CCAUGGUAGCACU | 445 | UGCUACCAUG GUAAUGGAC | 845 |
| LPA-494 | GCUACCAUGGUAAUGGACA AAGUTA | 46 | UAACUUUGUCCAUU ACCAUGGUAGCAC | 446 | GCUACCAUGG UAAUGGACA | 846 |
| LPA-495 | CUACCAUGGUAAUGGACAG AGUUAT | 47 | AUAACUCUGUCCAU UACCAUGGUAGCA | 447 | CUACCAUGGU AAUGGACAG | 847 |
| LPA-496 | UACCAUGGUAAUGGACAGA AUUATC | 48 | GAUAAUUCUGUCCA UUACCAUGGUAGC | 448 | UACCAUGGUA AUGGACAGA | 848 |
| LPA-497 | ACCAUGGUAAUGGACAGAG AUAUCG | 49 | CGAUAUCUCUGUCC AUUACCAUGGUAG | 449 | ACCAUGGUAA UGGACAGAG | 849 |
| LPA-498 | CCAUGGUAAUGGACAGAGU AAUCGA | 50 | UCGAUUACUCUGUC CAUUACCAUGGUA | 450 | CCAUGGUAAU GGACAGAGU | 850 |
| LPA-499 | CAUGGUAAUGGACAGAGUU AUCGAG | 51 | CUCGAUAACUCUGU CCAUUACCAUGGU | 451 | CAUGGUAAUG GACAGAGUU | 851 |
| LPA-500 | AUGGUAAUGGACAGAGUUA ACGAGG | 52 | CCUCGUUAACUCUG UCCAUUACCAUGG | 452 | AUGGUAAUGG ACAGAGUUA | 852 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-501 | UGGUAAUGGACAGAGUUAUAGAGGC | 53 | GCCUCUAUAACUCUGUCCAUUACCAUG | 453 | UGGUAAUGGACAGAGUUAU | 853 |
| LPA-502 | GGUAAUGGACAGAGUUAUCAAGGCA | 54 | UGCCUUGAUAACUCUGUCCAUUACCAU | 454 | GGUAAUGGACAGAGUUAUC | 854 |
| LPA-503 | GUAAUGGACAGAGUUAUCGAGGCAC | 55 | GUGCCUCGAUAACUCUGUCCAUUACCA | 455 | GUAAUGGACAGAGUUAUCG | 855 |
| LPA-523 | GGCACAUACUCCACCACUGACACAG | 56 | CUGUGUCAGUGGUGGAGUAUGUGCCUC | 456 | GGCACAUACUCCACCACUG | 856 |
| LPA-563 | CUUGGUCAUCUAUGACACCACACTC | 57 | GAGUGUGGUGUCAUAGAUGACCAAGCU | 457 | CUUGGUCAUCUAUGACACC | 857 |
| LPA-567 | GUCAUCUAUGACACCACACACGCAT | 58 | AUGCGUGUGUGGUGUCAUAGAUGACCA | 458 | GUCAUCUAUGACACCACAC | 858 |
| LPA-568 | UCAUCUAUGACACCACACUAGCATA | 59 | UAUGCUAGUGUGGUGUCAUAGAUGACC | 459 | UCAUCUAUGACACCACACU | 859 |
| LPA-569 | CAUCUAUGACACCACACUCACAUAG | 60 | CUAUGUGAGUGUGGUGUCAUAGAUGAC | 460 | CAUCUAUGACACCACACUC | 860 |
| LPA-1208 | GCACAUACUCCACCACUGUAACUGG | 61 | CCAGUUACAGUGGUGGAGUAUGUGCCU | 461 | GCACAUACUCCACCACUGU | 861 |
| LPA-2715 | AGCCCUUAUUGUUAUACGAGGGAT | 62 | AUCCCUCGUAUAACAAUAAGGGCUGC | 462 | AGCCCUUAUUGUUAUACG | 862 |
| LPA-2716 | GCCCCUUAUUGUUAUACGAAGGATC | 63 | GAUCCUUCGUAUAACAAUAAGGGCUG | 463 | GCCCCUUAUUGUUAUACGA | 863 |
| LPA-2827 | CCAAGCCUAGAGGCUCCUUAUGAAC | 64 | GUUCAUAAGGAGCCUCUAGGCUUGGAA | 464 | CCAAGCCUAGAGGCUCCUU | 864 |
| LPA-2837 | AGGCUCCUUCUGAACAAGCACCAAC | 65 | GUUGGUGCUUGUUCAGAAGGAGCCUCU | 465 | AGGCUCCUUCUGAACAAGC | 865 |
| LPA-2900 | AUGGACAGAGUUAUCAAGGAACATA | 66 | UAUGUUCCUUGAUAACUCUGUCCAUUU | 466 | AUGGACAGAGUUAUCAAGG | 866 |
| LPA-2901 | UGGACAGAGUUAUCAAGGCACAUAC | 67 | GUAUGUGCCUUGAUAACUCUGUCCAUU | 467 | UGGACAGAGUUAUCAAGGC | 867 |
| LPA-2902 | GGACAGAGUUAUCAAGGCAAAUACT | 68 | AGUAUUGCCUUGAUAACUCUGUCCAU | 468 | GGACAGAGUUAUCAAGGCA | 868 |
| LPA-2903 | GACAGAGUUAUCAAGGCACAUACTT | 69 | AAGUAUGUGCCUUGAUAACUCUGUCCA | 469 | GACAGAGUUAUCAAGGCAC | 869 |
| LPA-2904 | ACAGAGUUAUCAAGGCACAAACUTC | 70 | GAAGUUUGUGCCUUGAUAACUCUGUCC | 470 | ACAGAGUUAUCAAGGCACA | 870 |
| LPA-2905 | CAGAGUUAUCAAGGCACAUACUUCA | 71 | UGAAGUAUGUGCCUUGAUAACUCUGUC | 471 | CAGAGUUAUCAAGGCACAU | 871 |
| LPA-3004 | UACCCAAAUGCUGGCUUGAACAAGA | 72 | UCUUGUUCAAGCCAGCAUUUGGGUAGU | 472 | UACCCAAAUGCUGGCUUGA | 872 |
| LPA-3007 | CCAAAUGCUGGCUUGAUCAAGAACT | 73 | AGUUCUUGAUCAAGCCAGCAUUUGGGU | 473 | CCAAAUGCUGGCUUGAUCA | 873 |
| LPA-3023 | UCAAGAACUACUGCCGAAAACCAGA | 74 | UCUGGUUUUCGGCAGUAGUUCUUGAUC | 474 | UCAAGAACUACUGCCGAAA | 874 |
| LPA-3024 | CAAGAACUACUGCCGAAAUACAGAT | 75 | AUCUGUAUUUCGGCAGUAGUUCUUGAU | 475 | CAAGAACUACUGCCGAAAU | 875 |
| LPA-3025 | AAGAACUACUGCCGAAAUCAAGATC | 76 | GAUCUUGAUUUCGGCAGUAGUUCUUGA | 476 | AAGAACUACUGCCGAAAUC | 876 |

TABLE 2-continued

DsiRNAs Targeting Human LPA mRNA and
Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3027 | GAACUACUGCCGAAAUCCA AAUCCT | 77 | AGGAUUUGGAUUUC GGCAGUAGUUCUU | 477 | GAACUACUGC CGAAAUCCA | 877 |
| LPA-3030 | CUACUGCCGAAAUCCAGAU ACUGTG | 78 | CACAGUAUCUGGAU UUCGGCAGUAGUU | 478 | CUACUGCCGA AAUCCAGAU | 878 |
| LPA-3051 | UGUGGCAGCCCCUUGGUGU AAUACA | 79 | UGUAUUACACCAAG GGCUGCCACAGG | 479 | UGUGGCAGCC CCUUGGUGU | 879 |
| LPA-3052 | GUGGCAGCCCCUUGGUGUU AUACAA | 80 | UUGUAUAACACCAA GGGGCUGCCACAG | 480 | GUGGCAGCCC CUUGGUGUU | 880 |
| LPA-3053 | UGGCAGCCCCUUGGUGUUA AACAAC | 81 | GUUGUUUAACACCA AGGGGCUGCCACA | 481 | UGGCAGCCCC UUGGUGUUA | 881 |
| LPA-3054 | GGCAGCCCCUUGGUGUUAU ACAACA | 82 | UGUUGUAUAACACC AAGGGGCUGCCAC | 482 | GGCAGCCCCU UGGUGUUAU | 882 |
| LPA-3055 | GCAGCCCCUUGGUGUUAUA AAACAG | 83 | CUGUUUUAUAACAC CAAGGGGCUGCCA | 483 | GCAGCCCCUU GGUGUUAUA | 883 |
| LPA-3056 | CAGCCCCUUGGUGUUAUAC AACAGA | 84 | UCUGUUGUAUAACA CCAAGGGGCUGCC | 484 | CAGCCCCUUG GUGUUAUAC | 884 |
| LPA-3057 | AGCCCCUUGGUGUUAUACA ACAGAT | 85 | AUCUGUUGUAUAAC ACCAAGGGGCUGC | 485 | AGCCCCUUGG UGUUAUACA | 885 |
| LPA-3058 | GCCCCUUGGUGUUAUACAA AAGATC | 86 | GAUCUUUGUAUAA CACCAAGGGGCUG | 486 | GCCCCUUGGU GUUAUACAA | 886 |
| LPA-3059 | CCCCUUGGUGUUAUACAAC AGAUCC | 87 | GGAUCUGUUGUAUA ACACCAAGGGGCU | 487 | CCCCUUGGUG UUAUACAAC | 887 |
| LPA-3092 | GGUGGGAGUACUGCAACCU AACACG | 88 | CGUGUUAGGUUGCA GUACUCCCACCUG | 488 | GGUGGGAGUA CUGCAACCU | 888 |
| LPA-3093 | GUGGGAGUACUGCAACCUG ACACGA | 89 | UCGUGUCAGGUUGC AGUACUCCCACCU | 489 | GUGGGAGUAC UGCAACCUG | 889 |
| LPA-3096 | GGAGUACUGCAACCUGACA AGAUGC | 90 | GCAUCUUGUCAGGU UGCAGUACUCCCA | 490 | GGAGUACUGC AACCUGACA | 890 |
| LPA-3097 | GAGUACUGCAACCUGACAC AAUGCT | 91 | AGCAUUGUGUCAGG UUGCAGUACUCCC | 491 | GAGUACUGCA ACCUGACAC | 891 |
| LPA-3099 | GUACUGCAACCUGACACGA AGCUCA | 92 | UGAGCUUCGUGUCA GGUUGCAGUACUC | 492 | GUACUGCAAC CUGACACGA | 892 |
| LPA-3100 | UACUGCAACCUGACACGAU ACUCAG | 93 | CUGAGUAUCGUGUC AGGUUGCAGUACU | 493 | UACUGCAACC UGACACGAU | 893 |
| LPA-3101 | ACUGCAACCUGACACGAUG AUCAGA | 94 | UCUGAUCAUCGUGU CAGGUUGCAGUAC | 494 | ACUGCAACCU GACACGAUG | 894 |
| LPA-3102 | CUGCAACCUGACACGAUGC ACAGAT | 95 | AUCUGUGCAUCGUG UCAGGUUGCAGUA | 495 | CUGCAACCUG ACACGAUGC | 895 |
| LPA-3103 | UGCAACCUGACACGAUGCU AAGATG | 96 | CAUCUUAGCAUCGU GUCAGGUUGCAGU | 496 | UGCAACCUGA CACGAUGCU | 896 |
| LPA-3105 | CAACCUGACACGAUGCUCA AAUGCA | 97 | UGCAUUUGAGCAUC GUGUCAGGUUGCA | 497 | CAACCUGACA CGAUGCUCA | 897 |
| LPA-3107 | ACCUGACACGAUGCUCAGA AGCAGA | 98 | UCUGCUUCUGAGCA UCGUGUCAGGUUG | 498 | ACCUGACACG AUGCUCAGA | 898 |
| LPA-3108 | CCUGACACGAUGCUCAGAU ACAGAA | 99 | UUCUGUAUCUGAGC AUCGUGUCAGGUU | 499 | CCUGACACGA UGCUCAGAU | 899 |
| LPA-3109 | CUGACACGAUGCUCAGAUG AAGAAT | 100 | AUUCUUCAUCUGAG CAUCGUGUCAGGU | 500 | CUGACACGAU GCUCAGAUG | 900 |

TABLE 2-continued

DsiRNAs Targeting Human LPA mRNA and
Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3110 | UGACACGAUGCUCAGAUGCAGAATG | 101 | CAUUCUGCAUCUGAGCAUCGUGUCAGG | 501 | UGACACGAUGCUCAGAUGC | 901 |
| LPA-3111 | GACACGAUGCUCAGAUGCAAAAUGG | 102 | CCAUUUUGCAUCUGAGCAUCGUGUCAG | 502 | GACACGAUGCUCAGAUGCA | 902 |
| LPA-3112 | ACACGAUGCUCAGAUGCAGAAUGGA | 103 | UCCAUUCUGCAUCUGAGCAUCGUGUCA | 503 | ACACGAUGCUCAGAUGCAG | 903 |
| LPA-3113 | CACGAUGCUCAGAUGCAGAAUGGAC | 104 | GUCCAUUCUGCAUCUGAGCAUCGUGUC | 504 | CACGAUGCUCAGAUGCAGA | 904 |
| LPA-3229 | UGCUACUACCAUUAUGGACAGAGTT | 105 | AACUCUGUCCAUAAUGGUAGUAGCAGU | 505 | UGCUACUACCAUUAUGGAC | 905 |
| LPA-3230 | GCUACUACCAUUAUGGACAAAGUTA | 106 | UAACUUUGUCCAUAAUGGUAGUAGCAG | 506 | GCUACUACCAUUAUGGACA | 906 |
| LPA-3231 | CUACUACCAUUAUGGACAGAGUUAC | 107 | GUAACUCUGUCCAUAAUGGUAGUAGCA | 507 | CUACUACCAUUAUGGACAG | 907 |
| LPA-3232 | UACUACCAUUAUGGACAGAAUUACC | 108 | GGUAAUUCUGUCCAUAAUGGUAGUAGC | 508 | UACUACCAUUAUGGACAGA | 908 |
| LPA-3233 | ACUACCAUUAUGGACAGAGAUACCG | 109 | CGGUAUCUCUGUCCAUAAUGGUAGUAG | 509 | ACUACCAUUAUGGACAGAG | 909 |
| LPA-3234 | CUACCAUUAUGGACAGAGUAACCGA | 110 | UCGGUUACUCUGUCCAUAAUGGUAGUA | 510 | CUACCAUUAUGGACAGAGU | 910 |
| LPA-3235 | UACCAUUAUGGACAGAGUUACCGAG | 111 | CUCGGUAACUCUGUCCAUAAUGGUAGU | 511 | UACCAUUAUGGACAGAGUU | 911 |
| LPA-3236 | ACCAUUAUGGACAGAGUUAACGAGG | 112 | CCUCGUUAACUCUGUCCAUAAUGGUAG | 512 | ACCAUUAUGGACAGAGUUA | 912 |
| LPA-3257 | GAGGCACAUACUCCACCACAGUCAC | 113 | GUGACUGUGGUGGAGUAUGUGCCUCGG | 513 | GAGGCACAUACUCCACCAC | 913 |
| LPA-3267 | CUCCACCACUGUCACAGGAAGAACT | 114 | AGUUCUUCCUGUGACAGUGGUGGAGUA | 514 | CUCCACCACUGUCACAGGA | 914 |
| LPA-3280 | ACAGGAAGAACUUGCCAAGAUUGGT | 115 | ACCAAUCUUGGCAAGUUCUUCCUGUGA | 515 | ACAGGAAGAACUUGCCAAG | 915 |
| LPA-3281 | CAGGAAGAACUUGCCAAGCAUGGTC | 116 | GACCAUGCUUGGCAAGUUCUUCCUGUG | 516 | CAGGAAGAACUUGCCAAGC | 916 |
| LPA-3282 | AGGAAGAACUUGCCAAGCUAGGUCA | 117 | UGACCUAGCUUGGCAAGUUCUUCCUGU | 517 | AGGAAGAACUUGCCAAGCU | 917 |
| LPA-3283 | GGAAGAACUUGCCAAGCUUAGUCAT | 118 | AUGACUAAGCUUGGCAAGUUCUUCCUG | 518 | GGAAGAACUUGCCAAGCUU | 918 |
| LPA-3284 | GAAGAACUUGCCAAGCUUGAUCATC | 119 | GAUGAUCAAGCUUGGCAAGUUCUUCCU | 519 | GAAGAACUUGCCAAGCUUG | 919 |
| LPA-3285 | AAGAACUUGCCAAGCUUGGACAUCT | 120 | AGAUGUCCAAGCUUGGCAAGUUCUUCC | 520 | AAGAACUUGCCAAGCUUGG | 920 |
| LPA-3286 | AGAACUUGCCAAGCUUGGUAAUCTA | 121 | UAGAUUACCAAGCUUGGCAAGUUCUUC | 521 | AGAACUUGCCAAGCUUGGU | 921 |
| LPA-3287 | GAACUUGCCAAGCUUGGUCAUCUAT | 122 | AUAGAUGACCAAGCUUGGCAAGUUCUU | 522 | GAACUUGCCAAGCUUGGUC | 922 |
| LPA-3288 | AACUUGCCAAGCUUGGUCAACUATG | 123 | CAUAGUUGACCAAGCUUGGCAAGUUCU | 523 | AACUUGCCAAGCUUGGUCA | 923 |

TABLE 2-continued

DsiRNAs Targeting Human LPA mRNA and
Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-3289 | ACUUGCCAAGCUUGGUCAUAUAUGA | 124 | UCAUAUAUGACCAAGCUUGGCAAGUUC | 524 | ACUUGCCAAGCUUGGUCAU | 924 |
| LPA-3290 | CUUGCCAAGCUUGGUCAUCAAUGAC | 125 | GUCAUUGAUGACCAAGCUUGGCAAGUU | 525 | CUUGCCAAGCUUGGUCAUC | 925 |
| LPA-3291 | UUGCCAAGCUUGGUCAUCUAUGACA | 126 | UGUCAUAGAUGACCAAGCUUGGCAAGU | 526 | UUGCCAAGCUUGGUCAUCU | 926 |
| LPA-3292 | UGCCAAGCUUGGUCAUCUAAGACAC | 127 | GUGUCUUAGAUGACCAAGCUUGGCAAG | 527 | UGCCAAGCUUGGUCAUCUA | 927 |
| LPA-3298 | GCUUGGUCAUCUAUGACACAACACC | 128 | GGUGUUGUGUCAUAGAUGACCAAGCUU | 528 | GCUUGGUCAUCUAUGACAC | 928 |
| LPA-3300 | UUGGUCAUCUAUGACACCAAACCAG | 129 | CUGGUUUGGUGUCAUAGAUGACCAAGC | 529 | UUGGUCAUCUAUGACACCA | 929 |
| LPA-3301 | UGGUCAUCUAUGACACCACACCAGC | 130 | GCUGGUGUGGUGUCAUAGAUGACCAAG | 530 | UGGUCAUCUAUGACACCAC | 930 |
| LPA-3303 | GUCAUCUAUGACACCACACAAGCAT | 131 | AUGCUUGUGUGGUGUCAUAGAUGACCA | 531 | GUCAUCUAUGACACCACAC | 931 |
| LPA-3305 | CAUCUAUGACACCACACCAACAUAG | 132 | CUAUGUUGGUGUGGUGUCAUAGAUGAC | 532 | CAUCUAUGACACCACACCA | 932 |
| LPA-3306 | AUCUAUGACACCACACCAGAAUAGT | 133 | ACUAUUCUGGUGUGGUGUCAUAGAUGA | 533 | AUCUAUGACACCACACCAG | 933 |
| LPA-3308 | CUAUGACACCACACCAGCAAAGUCG | 134 | CGACUUUGCUGGUGUGGUGUCAUAGAU | 534 | CUAUGACACCACACCAGCA | 934 |
| LPA-3329 | GUCGGACCCCAGAAAACUAACCAAA | 135 | UUUGGUUAGUUUUCUGGGGUCCGACUA | 535 | GUCGGACCCCAGAAAACUA | 935 |
| LPA-3330 | UCGGACCCCAGAAAACUACACAAAT | 136 | AUUUGUGUAGUUUUCUGGGGUCCGACU | 536 | UCGGACCCCAGAAAACUAC | 936 |
| LPA-3340 | GAAAACUACCCAAAUGCUGACCUGA | 137 | UCAGGUCAGCAUUUGGGUAGUUUUCUG | 537 | GAAAACUACCCAAAUGCUG | 937 |
| LPA-3391 | GCUGAGAUUCGCCCUUGGUAUUACA | 138 | UGUAAUACCAAGGGCGAAUCUCAGCAU | 538 | GCUGAGAUUCGCCCUUGGU | 938 |
| LPA-3392 | CUGAGAUUCGCCCUUGGUGAUACAC | 139 | GUGUAUCACCAAGGGCGAAUCUCAGCA | 539 | CUGAGAUUCGCCCUUGGUG | 939 |
| LPA-3394 | GAGAUUCGCCCUUGGUGUUACACCA | 140 | UGGUGUAACACCAAGGGCGAAUCUCAG | 540 | GAGAUUCGCCCUUGGUGUU | 940 |
| LPA-3395 | AGAUUCGCCCUUGGUGUUAAACCAT | 141 | AUGGUUUAACACCAAGGGCGAAUCUCA | 541 | AGAUUCGCCCUUGGUGUUA | 941 |
| LPA-3398 | UUCGCCCUUGGUGUUACACAAUGGA | 142 | UCCAUUGUGUAACACCAAGGGCGAAUC | 542 | UUCGCCCUUGGUGUUACAC | 942 |
| LPA-3404 | CUUGGUGUUACACCAUGGAACCCAG | 143 | CUGGGUUCCAUGGUGUAACACCAAGGG | 543 | CUUGGUGUUACACCAUGGA | 943 |
| LPA-3405 | UUGGUGUUACACCAUGGAUACCAGT | 144 | ACUGGUAUCCAUGGUGUAACACCAAGG | 544 | UUGGUGUUACACCAUGGAU | 944 |
| LPA-3406 | UGGUGUUACACCAUGGAUCACAGTG | 145 | CACUGUGAUCCAUGGUGUAACACCAAG | 545 | UGGUGUUACACCAUGGAUC | 945 |
| LPA-3407 | GGUGUUACACCAUGGAUCCAAGUGT | 146 | ACACUUGGAUCCAUGGUGUAACACCAA | 546 | GGUGUUACACCAUGGAUCC | 946 |
| LPA-3409 | UGUUACACCAUGGAUCCCAAUGUCA | 147 | UGACAUUGGGAUCCAUGGUGUAACACC | 547 | UGUUACACCAUGGAUCCCA | 947 |

TABLE 2-continued

DsiRNAs Targeting Human LPA mRNA and
Controls Evaluated in Cells

| Passenger (Sense) | SEQ ID NO: | Guide (Antisense) | SEQ ID NO: | Target Sequence | SEQ ID NO: |
|---|---|---|---|---|---|
| LPA-3472 | GAAUCAAGUGUCCUUGCAA AUCUCA | 148 | UGAGAUUUGCAAGG ACACUUGAUUCUG | 548 | GAAUCAAGUG UCCUUGCAA | 948 |
| LPA-3473 | AAUCAAGUGUCCUUGCAAC ACUCAC | 149 | GUGAGUGUUGCAAG GACACUUGAUUCU | 549 | AAUCAAGUGU CCUUGCAAC | 949 |
| LPA-3474 | AUCAAGUGUCCUUGCAACU AUCACG | 150 | CGUGAUAGUUGCAA GGACACUUGAUUC | 550 | AUCAAGUGUC CUUGCAACU | 950 |
| LPA-3584 | AUGGACAGAGUUAUCGAGG AUCAUU | 151 | AAUGAUCCUCGAUA ACUCUGUCCAUCA | 551 | AUGGACAGAG UUAUCGAGG | 951 |
| LPA-3585 | UGGACAGAGUUAUCGAGGC ACAUUC | 152 | GAAUGUGCCUCGAU AACUCUGUCCAUC | 552 | UGGACAGAGU UAUCGAGGC | 952 |
| LPA-3655 | ACACCACACUGGCAUCAGA AGACAA | 153 | UUGUCUUCUGAUGC CAGUGUGGUGUCA | 553 | ACACCACACU GGCAUCAGA | 953 |
| LPA-3747 | UUGGUGUUAUACCAUGGAU ACCAAU | 154 | AUUGGUAUCCAUGG UAUAACACCAAGG | 554 | UUGGUGUUAU ACCAUGGAU | 954 |
| LPA-3748 | UGGUGUUAUACCAUGGAUC ACAAUG | 155 | CAUUGUGAUCCAUG GUAUAACACCAAG | 555 | UGGUGUUAUA CCAUGGAUC | 955 |
| LPA-3749 | GGUGUUAUACCAUGGAUCC AAAUGT | 156 | ACAUUUGGAUCCAU GGUAUAACACCAA | 556 | GGUGUUAUAC CAUGGAUCC | 956 |
| LPA-3750 | GUGUUAUACCAUGGAUCCC AAUGTC | 157 | GACAUUGGGAUCCA UGGUAUAACACCA | 557 | GUGUUAUACC AUGGAUCCC | 957 |
| LPA-3773 | UCAGAUGGGAGUACUGCAA ACUGAC | 158 | GUCAGUUUGCAGUA CUCCCAUCUGACA | 558 | UCAGAUGGGA GUACUGCAA | 958 |
| LPA-3776 | GAUGGGAGUACUGCAACCU AACACA | 159 | UGUGUUAGGUUGCA GUACUCCCAUCUG | 559 | GAUGGGAGUA CUGCAACCU | 959 |
| LPA-3777 | AUGGGAGUACUGCAACCUG ACACAA | 160 | UUGUGUCAGGUUGC AGUACUCCCAUCU | 560 | AUGGGAGUAC UGCAACCUG | 960 |
| LPA-3778 | UGGGAGUACUGCAACCUGA AACAAU | 161 | AUUGUUUCAGGUUG CAGUACUCCCAUC | 561 | UGGGAGUACU GCAACCUGA | 961 |
| LPA-3779 | GGGAGUACUGCAACCUGAC ACAAUG | 162 | CAUUGUGUCAGGUU GCAGUACUCCCAU | 562 | GGGAGUACUG CAACCUGAC | 962 |
| LPA-3840 | GGCUGUUUCUGAACAAGCA ACAACG | 163 | CGUGUUGCUUGUU CAGAAACAGCCGU | 563 | GGCUGUUUCU GAACAAGCA | 963 |
| LPA-3844 | GUUUCUGAACAAGCACCAA AGGAGC | 164 | GCUCCUUUGGUGCU UGUUCAGAAACAG | 564 | GUUUCUGAAC AAGCACCAA | 964 |
| LPA-3927 | CUCCACCACUGUUACAGGA AGGACA | 165 | UGUCCUUCCUGUAA CAGUGGUGGAGAA | 565 | CUCCACCACU GUUACAGGA | 965 |
| LPA-3928 | UCCACCACUGUUACAGGAA AGACAT | 166 | AUGUCUUUCCUGUA ACAGUGGUGGAGA | 566 | UCCACCACUG UUACAGGAA | 966 |
| LPA-3929 | CCACCACUGUUACAGGAAG AACATG | 167 | CAUGUUCUUCCUGU AACAGUGGUGGAG | 567 | CCACCACUGU UACAGGAAG | 967 |
| LPA-3972 | GACACCACACUGGCAUCAG AGAACC | 168 | GGUUCUCUGAUGCC AGUGUGGUGUCAU | 568 | GACACCACAC UGGCAUCAG | 968 |
| LPA-3973 | ACACCACACUGGCAUCAGA AAACCA | 169 | UGGUUUUCUGAUGC CAGUGUGGUGUCA | 569 | ACACCACACU GGCAUCAGA | 969 |
| LPA-3999 | AGAAUACUACCCAAAUGGU AGCCTG | 170 | CAGGCUACCAUUUG GGUAGUAUUCUGU | 570 | AGAAUACUAC CCAAAUGGU | 970 |
| LPA-4000 | GAAUACUACCCAAAUGGUG ACCUGA | 171 | UCAGGUCACCAUUU GGGUAGUAUUCUG | 571 | GAAUACUACC CAAAUGGUG | 971 |

TABLE 2-continued

DsiRNAs Targeting Human LPA mRNA and Controls Evaluated in Cells

| Passenger (Sense) | SEQ ID NO: | Guide (Antisense) | SEQ ID NO: | Target Sequence | SEQ ID NO: |
|---|---|---|---|---|---|
| LPA-4001 | AAUACUACCCAAAUGGUGG ACUGAC | 172 | GUCAGUCCACCAUU UGGGUAGUAUUCU | 572 | AAUACUACCC AAAUGGUGG | 972 |
| LPA-4185 | UCCUUCUGAAGAAGCACCA ACUGAA | 173 | UUCAGUUGGUGCUU CUUCAGAAGGAAG | 573 | UCCUUCUGAA GAAGCACCA | 973 |
| LPA-4186 | CCUUCUGAAGAAGCACCAA AUGAAA | 174 | UUUCAUUUGGUGCU UCUUCAGAAGGAA | 574 | CCUUCUGAAG AAGCACCAA | 974 |
| LPA-4187 | CUUCUGAAGAAGCACCAAC AGAAAA | 175 | UUUUCUGUUGGUGC UUCUUCAGAAGGA | 575 | CUUCUGAAGA AGCACCAAC | 975 |
| LPA-4188 | UUCUGAAGAAGCACCAACU AAAAAC | 176 | GUUUUUAGUUGGUG CUUCUUCAGAAGG | 576 | UUCUGAAGAA GCACCAACU | 976 |
| LPA-4189 | UCUGAAGAAGCACCAACUG AAAACA | 177 | UGUUUUCAGUUGGU GCUUCUUCAGAAG | 577 | UCUGAAGAAG CACCAACUG | 977 |
| LPA-4190 | CUGAAGAAGCACCAACUGA AAACAG | 178 | CUGUUUUCAGUUGG UGCUUCUUCAGAA | 578 | CUGAAGAAGC ACCAACUGA | 978 |
| LPA-4191 | UGAAGAAGCACCAACUGAA AACAGC | 179 | GCUGUUUUCAGUUG GUGCUUCUUCAGA | 579 | UGAAGAAGCA CCAACUGAA | 979 |
| LPA-4192 | GAAGAAGCACCAACUGAAA ACAGCA | 180 | UGCUGUUUUCAGUU GGUGCUUCUUCAG | 580 | GAAGAAGCAC CAACUGAAA | 980 |
| LPA-4193 | AAGAAGCACCAACUGAAAA AAGCAC | 181 | GUGCUUUUUUCAGU UGGUGCUUCUUCA | 581 | AAGAAGCACC AACUGAAAA | 981 |
| LPA-4194 | AGAAGCACCAACUGAAAAC AGCACT | 182 | AGUGCUGUUUUCAG UUGGUGCUUCUUC | 582 | AGAAGCACCA ACUGAAAAC | 982 |
| LPA-4195 | GAAGCACCAACUGAAAACA ACACTG | 183 | CAGUGUUGUUUUCA GUUGGUGCUUCUU | 583 | GAAGCACCAA CUGAAAACA | 983 |
| LPA-4196 | AAGCACCAACUGAAAACAG AACUGG | 184 | CCAGUUCUGUUUUC AGUUGGUGCUUCU | 584 | AAGCACCAAC UGAAAACAG | 984 |
| LPA-4239 | AGGUGAUGGACAGAGUUAU AGAGGC | 185 | GCCUCUAUAACUCU GUCCAUCACCUCG | 585 | AGGUGAUGGA CAGAGUUAU | 985 |
| LPA-4269 | CUCCACCACUAUCACAGGA AGAACA | 186 | UGUUCUUCCUGUGA UAGUGGUGGAGAG | 586 | CUCCACCACU AUCACAGGA | 986 |
| LPA-4270 | UCCACCACUAUCACAGGAA AAACAT | 187 | AUGUUUUUCCUGUG AUAGUGGUGGAGA | 587 | UCCACCACUA UCACAGGAA | 987 |
| LPA-4271 | CCACCACUAUCACAGGAAG AACATG | 188 | CAUGUUCUUCCUGU GAUAGUGGUGGAG | 588 | CCACCACUAU CACAGGAAG | 988 |
| LPA-4272 | CACCACUAUCACAGGAAGA ACAUGT | 189 | ACAUGUUCUUCCUG UGAUAGUGGUGGA | 589 | CACCACUAUC ACAGGAAGA | 989 |
| LPA-4273 | ACCACUAUCACAGGAAGAA AAUGTC | 190 | GACAUUUCUUCCU GUGAUAGUGGUGG | 590 | ACCACUAUCA CAGGAAGAA | 990 |
| LPA-4274 | CCACUAUCACAGGAAGAAC AUGUCA | 191 | UGACAUGUUCUUCC UGUGAUAGUGGUG | 591 | CCACUAUCAC AGGAAGAAC | 991 |
| LPA-4275 | CACUAUCACAGGAAGAACA AGUCAG | 192 | CUGACUUGUUCUUC CUGUGAUAGUGGU | 592 | CACUAUCACA GGAAGAACA | 992 |
| LPA-4276 | ACUAUCACAGGAAGAACAU AUCAGT | 193 | ACUGAUAUGUUCUU CCUGUGAUAGUGG | 593 | ACUAUCACAG GAAGAACAU | 993 |
| LPA-4277 | CUAUCACAGGAAGAACAUG ACAGTC | 194 | GACUGUCAUGUUCU UCCUGUGAUAGUG | 594 | CUAUCACAGG AAGAACAUG | 994 |
| LPA-4278 | UAUCACAGGAAGAACAUGU AAGUCT | 195 | AGACUUACAUGUUC UUCCUGUGAUAGU | 595 | UAUCACAGGA AGAACAUGU | 995 |

TABLE 2-continued

DsiRNAs Targeting Human LPA mRNA and Controls Evaluated in Cells

| Passenger (Sense) | | SEQ ID NO: | Guide (Antisense) | SEQ ID NO: | Target Sequence | SEQ ID NO: |
|---|---|---|---|---|---|---|
| LPA-4279 | AUCACAGGAAGAACAUGUCAGUCTT | 196 | AAGACUGACAUGUUCUUCCUGUGAUAG | 596 | AUCACAGGAAGAACAUGUC | 996 |
| LPA-4280 | UCACAGGAAGAACAUGUCAAUCUTG | 197 | CAAGAUUGACAUGUUCUUCCUGUGAUA | 597 | UCACAGGAAGAACAUGUCA | 997 |
| LPA-4281 | CACAGGAAGAACAUGUCAGACUUGG | 198 | CCAAGUCUGACAUGUUCUUCCUGUGAU | 598 | CACAGGAAGAACAUGUCAG | 998 |
| LPA-4282 | ACAGGAAGAACAUGUCAGUAUUGGT | 199 | ACCAAUACUGACAUGUUCUUCCUGUGA | 599 | ACAGGAAGAACAUGUCAGU | 999 |
| LPA-4285 | GGAAGAACAUGUCAGUCUUAGUCGT | 200 | ACGACUAAGACUGACAUGUUCUUCCUG | 600 | GGAAGAACAUGUCAGUCUU | 1000 |
| LPA-4286 | GAAGAACAUGUCAGUCUUGAUCGTC | 201 | GACGAUCAAGACUGACAUGUUCUUCCU | 601 | GAAGAACAUGUCAGUCUUG | 1001 |
| LPA-4287 | AAGAACAUGUCAGUCUUGGACGUCT | 202 | AGACGUCCAAGACUGACAUGUUCUUCC | 602 | AAGAACAUGUCAGUCUUGG | 1002 |
| LPA-4288 | AGAACAUGUCAGUCUUGGUAGUCTA | 203 | UAGACUACCAAGACUGACAUGUUCUUC | 603 | AGAACAUGUCAGUCUUGGU | 1003 |
| LPA-4325 | GGCAUCGGAGGAUCCCAUUAUACTA | 204 | UAGUAUAAUGGGAUCCUCCGAUGCCAA | 604 | GGCAUCGGAGGAUCCCAUU | 1004 |
| LPA-4346 | ACUAUCCAAAUGCUGGCCUAACCAG | 205 | CUGGUUAGGCCAGCAUUUGGAUAGUAU | 605 | ACUAUCCAAAUGCUGGCCU | 1005 |
| LPA-4517 | GCACAGAGGCUCCUUCUGAACAAGC | 206 | GCUUGUUCAGAAGGAGCCUCUGUGCUU | 606 | GCACAGAGGCUCCUUCUGA | 1006 |
| LPA-4527 | UCCUUCUGAACAAGCACCAACUGAG | 207 | CUCAGUUGGUGCUUGUUCAGAAGGAGC | 607 | UCCUUCUGAACAAGCACCA | 1007 |
| LPA-4528 | CCUUCUGAACAAGCACCACAUGAGA | 208 | UCUCAUGUGGUGCUUGUUCAGAAGGAG | 608 | CCUUCUGAACAAGCACCAC | 1008 |
| LPA-4529 | CUUCUGAACAAGCACCACCAGAGAA | 209 | UUCUCUGGUGGUGCUUGUUCAGAAGGA | 609 | CUUCUGAACAAGCACCACC | 1009 |
| LPA-4530 | UUCUGAACAAGCACCACCUAAGAAA | 210 | UUUCUUAGGUGGUGCUUGUUCAGAAGG | 610 | UUCUGAACAAGCACCACCU | 1010 |
| LPA-4531 | UCUGAACAAGCACCACCUGAGAAAA | 211 | UUUUCUCAGGUGGUGCUUGUUCAGAAG | 611 | UCUGAACAAGCACCACCUG | 1011 |
| LPA-4532 | CUGAACAAGCACCACCUGAAAAAAG | 212 | CUUUUUUCAGGUGGUGCUUGUUCAGAA | 612 | CUGAACAAGCACCACCUGA | 1012 |
| LPA-4533 | UGAACAAGCACCACCUGAGAAAAGC | 213 | GCUUUUCUCAGGUGGUGCUUGUUCAGA | 613 | UGAACAAGCACCACCUGAG | 1013 |
| LPA-4531 | GAACAAGCACCACCUGAGAAAAGCC | 214 | GGCUUUUCUCAGGUGGUGCUUGUUCAG | 614 | GAACAAGCACCACCUGAGA | 1014 |
| LPA-4535 | AACAAGCACCACCUGAGAAAAGCCC | 215 | GGGCUUUUCUCAGGUGGUGCUUGUUCA | 615 | AACAAGCACCACCUGAGAA | 1015 |
| LPA-4537 | CAAGCACCACCUGAGAAAAACCCTG | 216 | CAGGGUUUUUCUCAGGUGGUGCUUGUU | 616 | CAAGCACCACCUGAGAAAA | 1016 |
| LPA-4538 | AAGCACCACCUGAGAAAAGACCUGT | 217 | ACAGGUCUUUUCUCAGGUGGUGCUUGU | 617 | AAGCACCACCUGAGAAAAG | 1017 |
| LPA-4539 | AGCACCACCUGAGAAAAGCACUGTG | 218 | CACAGUGCUUUUCUCAGGUGGUGCUUG | 618 | AGCACCACCUGAGAAAAGC | 1018 |
| LPA-4547 | CUGAGAAAAGCCCUGUGGUACAGGA | 219 | UCCUGUACCACAGGGCUUUUCUCAGGU | 619 | CUGAGAAAAGCCCUGUGGU | 1019 |

TABLE 2-continued

DsiRNAs Targeting Human LPA mRNA and Controls Evaluated in Cells

| Passenger (Sense) | | SEQ ID NO: | Guide (Antisense) | SEQ ID NO: | Target Sequence | SEQ ID NO: |
|---|---|---|---|---|---|---|
| LPA-4556 | GCCCUGUGGUCCAGGAUUGAUACCA | 220 | UGGUAUCAAUCCUGGACCACAGGGCUU | 620 | GCCCUGUGGUCCAGGAUUG | 1020 |
| LPA-4559 | CUGUGGUCCAGGAUUGCUAACAUGG | 221 | CCAUGUUAGCAAUCCUGGACCACAGGG | 621 | CUGUGGUCCAGGAUUGCUA | 1021 |
| LPA-4611 | CUCCACCACUGUCACAGGAAGGACC | 222 | GGUCCUUCCUGUGACAGUGGUGGAGGA | 622 | CUCCACCACUGUCACAGGA | 1022 |
| LPA-4612 | UCCACCACUGUCACAGGAAAGACCT | 223 | AGGUCUUUCCUGUGACAGUGGUGGAGG | 623 | UCCACCACUGUCACAGGAA | 1023 |
| LPA-4642 | UCUUGGUCAUCUAUGAUACAACACT | 224 | AGUGUUGUAUCAUAGAUGACCAAGAUU | 624 | UCUUGGUCAUCUAUGAUAC | 1024 |
| LPA-4643 | CUUGGUCAUCUAUGAUACCACACTG | 225 | CAGUGUGGUAUCAUAGAUGACCAAGAU | 625 | CUUGGUCAUCUAUGAUACC | 1025 |
| LPA-4644 | UUGGUCAUCUAUGAUACCAAACUGG | 226 | CCAGUUUGGUAUCAUAGAUGACCAAGA | 626 | UUGGUCAUCUAUGAUACCA | 1026 |
| LPA-4645 | UGGUCAUCUAUGAUACCACACUGGC | 227 | GCCAGUGUGGUAUCAUAGAUGACCAAG | 627 | UGGUCAUCUAUGAUACCAC | 1027 |
| LPA-4646 | GGUCAUCUAUGAUACCACAAUGGCA | 228 | UGCCAUUGUGGUAUCAUAGAUGACCAA | 628 | GGUCAUCUAUGAUACCACA | 1028 |
| LPA-4647 | GUCAUCUAUGAUACCACACAGGCAT | 229 | AUGCCUGUGUGGUAUCAUAGAUGACCA | 629 | GUCAUCUAUGAUACCACAC | 1029 |
| LPA-4648 | UCAUCUAUGAUACCACACUAGCATC | 230 | GAUGCUAGUGUGGUAUCAUAGAUGACC | 630 | UCAUCUAUGAUACCACACU | 1030 |
| LPA-4649 | CAUCUAUGAUACCACACUGACAUCA | 231 | UGAUGUCAGUGUGGUAUCAUAGAUGAC | 631 | CAUCUAUGAUACCACACUG | 1031 |
| LPA-4650 | AUCUAUGAUACCACACUGGAAUCAG | 232 | CUGAUUCCAGUGUGGUAUCAUAGAUGA | 632 | AUCUAUGAUACCACACUGG | 1032 |
| LPA-4651 | UCUAUGAUACCACACUGGCAUCAGA | 233 | UCUGAUGCCAGUGUGGUAUCAUAGAUG | 633 | UCUAUGAUACCACACUGGC | 1033 |
| LPA-4652 | CUAUGAUACCACACUGGCAACAGAG | 234 | CUCUGUUGCCAGUGUGGUAUCAUAGAU | 634 | CUAUGAUACCACACUGGCA | 1034 |
| LPA-4655 | UGAUACCACACUGGCAUCAAAGGAC | 235 | GUCCUUUGAUGCCAGUGUGGUAUCAUA | 635 | UGAUACCACACUGGCAUCA | 1035 |
| LPA-4657 | AUACCACACUGGCAUCAGAAGACCC | 236 | GGGUCUUCUGAUGCCAGUGUGGUAUCA | 636 | AUACCACACUGGCAUCAGA | 1036 |
| LPA-4673 | AGAGGACCCCAGAAAACUAACCAAA | 237 | UUUGGUUAGUUUUCUGGGGUCCUCUGA | 637 | AGAGGACCCCAGAAAACUA | 1037 |
| LPA-4674 | GAGGACCCCAGAAAACUACACAAAT | 238 | AUUUGUGUAGUUUUCUGGGGUCCUCUG | 638 | GAGGACCCCAGAAAACUAC | 1038 |
| LPA-4712 | AGAACUACUGCAGGAAUCCAGAUTC | 239 | GAAUCGGAUUCCUGCAGUAGUUCUCG | 639 | AGAACUACUGCAGGAAUCC | 1039 |
| LPA-4715 | ACUACUGCAGGAAUCCAGAAUCUGG | 240 | CCAGAUUCGGAUUCCUGCAGUAGUUC | 640 | ACUACUGCAGGAAUCCAGA | 1040 |
| LPA-4717 | UACUGCAGGAAUCCAGAUUAUGGGA | 241 | UCCCAUAAUCUGGAUUCCUGCAGUAGU | 641 | UACUGCAGGAAUCCAGAUU | 1041 |
| LPA-4718 | ACUGCAGGAAUCCAGAUUCAGGGAA | 242 | UUCCCUGAAUCUGGAUUCCUGCAGUAG | 642 | ACUGCAGGAAUCCAGAUUC | 1042 |
| LPA-4719 | CUGCAGGAAUCCAGAUUCUAGGAAA | 243 | UUUCCUAGAAUCUGGAUUCCUGCAGUA | 643 | CUGCAGGAAUCCAGAUUCU | 1043 |
| LPA-4720 | UGCAGGAAUCCAGAUUCUGAGAAAC | 244 | GUUUCUCAGAAUCUGGAUUCCUGCAGU | 644 | UGCAGGAAUCCAGAUUCUG | 1044 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-4721 | GCAGGAAUCCAGAUUCUGG AAAACA | 245 | UGUUUUCCAGAAUC UGGAUUCCUGCAG | 645 | GCAGGAAUCC AGAUUCUGG | 1045 |
| LPA-4724 | GGAAUCCAGAUUCUGGGAA ACAACC | 246 | GGUUGUUUCCCAGA AUCUGGAUUCCUG | 646 | GGAAUCCAGA UUCUGGGAA | 1046 |
| LPA-4738 | GGGAAACAACCCUGGUGUU ACACAA | 247 | UUGUGUAACACCAG GGUUGUUUCCCAG | 647 | GGGAAACAAC CCUGGUGUU | 1047 |
| LPA-4739 | GGAAACAACCCUGGUGUUA AACAAC | 248 | GUUGUUUAACACCA GGGUUGUUUCCCA | 648 | GGAAACAACC CUGGUGUUA | 1048 |
| LPA-4771 | UGUGUGAGGUGGGAGUACU ACAAUC | 249 | GAUUGUAGUACUCC CACCUCACACACG | 649 | UGUGUGAGGU GGGAGUACU | 1049 |
| LPA-4772 | GUGUGAGGUGGGAGUACUG AAAUCT | 250 | AGAUUUCAGUACUC CCACCUCACACAC | 650 | GUGUGAGGUG GGAGUACUG | 1050 |
| LPA-4774 | GUGAGGUGGGAGUACUGCA AUCUGA | 251 | UCAGAUUGCAGUAC UCCCACCUCACAC | 651 | GUGAGGUGGG AGUACUGCA | 1051 |
| LPA-4775 | UGAGGUGGGAGUACUGCAA ACUGAC | 252 | GUCAGUUUGCAGUA CUCCCACCUCACA | 652 | UGAGGUGGGA GUACUGCAA | 1052 |
| LPA-4795 | CUGACACAAUGCUCAGAAA AAGAAT | 253 | AUUCUUUUCUGAG CAUUGUGUCAGAU | 653 | CUGACACAAU GCUCAGAAA | 1053 |
| LPA-4796 | UGACACAAUGCUCAGAAAC AGAATC | 254 | GAUUCUGUUUCUGA GCAUUGUGUCAGA | 654 | UGACACAAUG CUCAGAAAC | 1054 |
| LPA-4797 | GACACAAUGCUCAGAAACA AAAUCA | 255 | UGAUUUUGUUUCUG AGCAUUGUGUCAG | 655 | GACACAAUGC UCAGAAACA | 1055 |
| LPA-4798 | ACACAAUGCUCAGAAACAG AAUCAG | 256 | CUGAUUCUGUUUCU GAGCAUUGUGUCA | 656 | ACACAAUGCU CAGAAACAG | 1056 |
| LPA-4799 | CACAAUGCUCAGAAACAGA AUCAGG | 257 | CCUGAUUCUGUUUC UGAGCAUUGUGUC | 657 | CACAAUGCUC AGAAACAGA | 1057 |
| LPA-4800 | ACAAUGCUCAGAAACAGAA ACAGGT | 258 | ACCUGUUUCUGUUU CUGAGCAUUGUGU | 658 | ACAAUGCUCA GAAACAGAA | 1058 |
| LPA-4801 | CAAUGCUCAGAAACAGAAU AAGGTG | 259 | CACCUUAUUCUGUU UCUGAGCAUUGUG | 659 | CAAUGCUCAG AAACAGAAU | 1059 |
| LPA-4802 | AAUGCUCAGAAACAGAAUC AGGUGT | 260 | ACACCUGAUUCUGU UUCUGAGCAUUGU | 660 | AAUGCUCAGA AACAGAAUC | 1060 |
| LPA-4803 | AUGCUCAGAAACAGAAUCA AGUGTC | 261 | GACACUUGAUUCUG UUUCUGAGCAUUG | 661 | AUGCUCAGAA ACAGAAUCA | 1061 |
| LPA-4804 | UGCUCAGAAACAGAAUCAG AUGUCC | 262 | GGACAUCUGAUUCU GUUUCUGAGCAUU | 662 | UGCUCAGAAA CAGAAUCAG | 1062 |
| LPA-4806 | CUCAGAAACAGAAUCAGGU AUCCTA | 263 | UAGGAUACCUGAUU CUGUUUCUGAGCA | 663 | CUCAGAAACA GAAUCAGGU | 1063 |
| LPA-4808 | CAGAAACAGAAUCAGGUGU ACUAGA | 264 | UCUAGUACACCUGA UUCUGUUUCUGAG | 664 | CAGAAACAGA AUCAGGUGU | 1064 |
| LPA-4809 | AGAAACAGAAUCAGGUGUC AUAGAG | 265 | CUCUAUGACACCUG AUUCUGUUUCUGA | 665 | AGAAACAGAA UCAGGUGUC | 1065 |
| LPA-4810 | GAAACAGAAUCAGGUGUCC AAGAGA | 266 | UCUCUUGGACACCU GAUUCUGUUUCUG | 666 | GAAACAGAAU CAGGUGUCC | 1066 |
| LPA-4811 | AAACAGAAUCAGGUGUCCU AGAGAC | 267 | GUCUCUAGGACACC UGAUUCUGUUUCU | 667 | AAACAGAAUC AGGUGUCCU | 1067 |
| LPA-4812 | AACAGAAUCAGGUGUCCUA AAGACT | 268 | AGUCUUUAGGACAC CUGAUUCUGUUUC | 668 | AACAGAAUCA GGUGUCCUA | 1068 |

TABLE 2-continued

DsiRNAs Targeting Human LPA mRNA and
Controls Evaluated in Cells

| Passenger (Sense) | | SEQ ID NO: | Guide (Antisense) | SEQ ID NO: | Target Sequence | SEQ ID NO: |
|---|---|---|---|---|---|---|
| LPA-4814 | CAGAAUCAGGUGUCCUAGA AACUCC | 269 | GGAGUUUCUAGGAC ACCUGAUUCUGUU | 669 | CAGAAUCAGG UGUCCUAGA | 1069 |
| LPA-4816 | GAAUCAGGUGUCCUAGAGA AUCCCA | 270 | UGGGAUUCUCUAGG ACACCUGAUUCUG | 670 | GAAUCAGGUG UCCUAGAGA | 1070 |
| LPA-4818 | AUCAGGUGUCCUAGAGACU ACCACT | 271 | AGUGGUAGUCUCUA GGACACCUGAUUC | 671 | AUCAGGUGUC CUAGAGACU | 1071 |
| LPA-4822 | GGUGUCCUAGAGACUCCCA AUGUTG | 272 | CAACAUUGGGAGUC UCUAGGACACCUG | 672 | GGUGUCCUAG AGACUCCCA | 1072 |
| LPA-4827 | CCUAGAGACUCCCACUGUU AUUCCA | 273 | UGGAAUAACAGUGG GAGUCUCUAGGAC | 673 | CCUAGAGACU CCCACUGUU | 1073 |
| LPA-4828 | CUAGAGACUCCCACUGUUG AUCCAG | 274 | CUGGAUCAACAGUG GGAGUCUCUAGGA | 674 | CUAGAGACUC CCACUGUUG | 1074 |
| LPA-4829 | UAGAGACUCCCACUGUUGU ACCAGT | 275 | ACUGGUACAACAGU GGGAGUCUCUAGG | 675 | UAGAGACUCC CACUGUUGU | 1075 |
| LPA-4830 | AGAGACUCCCACUGUUGUU ACAGTT | 276 | AACUGUAACAACAG UGGGAGUCUCUAG | 676 | AGAGACUCCC ACUGUUGUU | 1076 |
| LPA-4831 | GAGACUCCCACUGUUGUUC AAGUTC | 277 | GAACUUGAACAACA GUGGGAGUCUCUA | 677 | GAGACUCCCA CUGUUGUUC | 1077 |
| LPA-4832 | AGACUCCCACUGUUGUUCC AGUUCC | 278 | GGAACUGGAACAAC AGUGGGAGUCUCU | 678 | AGACUCCCAC UGUUGUUCC | 1078 |
| LPA-4867 | GCUCAUUCUGAAGCAGCAC AAACTG | 279 | CAGUUUGUGCUGCU UCAGAAUGAGCCU | 679 | GCUCAUUCUG AAGCAGCAC | 1079 |
| LPA-4868 | CUCAUUCUGAAGCAGCACC AACUGA | 280 | UCAGUUGGUGCUGC UUCAGAAUGAGCC | 680 | CUCAUUCUGA AGCAGCACC | 1080 |
| LPA-4869 | UCAUUCUGAAGCAGCACCA ACUGAG | 281 | CUCAGUUGGUGCUG CUUCAGAAUGAGC | 681 | UCAUUCUGAA GCAGCACCA | 1081 |
| LPA-4870 | CAUUCUGAAGCAGCACCAA AUGAGC | 282 | GCUCAUUUGGUGCU GCUUCAGAAUGAG | 682 | CAUUCUGAAG CAGCACCAA | 1082 |
| LPA-4871 | AUUCUGAAGCAGCACCAAC AGAGCA | 283 | UGCUCUGUUGGUGC UGCUUCAGAAUGA | 683 | AUUCUGAAGC AGCACCAAC | 1083 |
| LPA-4872 | UUCUGAAGCAGCACCAACU AAGCAA | 284 | UUGCUUAGUUGGUG CUGCUUCAGAAUG | 684 | UUCUGAAGCA GCACCAACU | 1084 |
| LPA-4873 | UCUGAAGCAGCACCAACUG AGCAAA | 285 | UUUGCUCAGUUGGU GCUGCUUCAGAAU | 685 | UCUGAAGCAG CACCAACUG | 1085 |
| LPA-4874 | CUGAAGCAGCACCAACUGA ACAAAC | 286 | GUUUGUUCAGUUGG UGCUGCUUCAGAA | 686 | CUGAAGCAGC ACCAACUGA | 1086 |
| LPA-4875 | UGAAGCAGCACCAACUGAG AAAACC | 287 | GGUUUUCUCAGUUG GUGCUGCUUCAGA | 687 | UGAAGCAGCA CCAACUGAG | 1087 |
| LPA-4876 | GAAGCAGCACCAACUGAGC AAACCC | 288 | GGGUUUGCUCAGUU GGUGCUGCUUCAG | 688 | GAAGCAGCAC CAACUGAGC | 1088 |
| LPA-4877 | AAGCAGCACCAACUGAGCA AACCCC | 289 | GGGGUUUGCUCAGU UGGUGCUGCUUCA | 689 | AAGCAGCACC AACUGAGCA | 1089 |
| LPA-4912 | CAGUGCUACCAUGGUAAUG ACCAGA | 290 | UCUGGUCAUUACCA UGGUAGCACUGCC | 690 | CAGUGCUACC AUGGUAAUG | 1090 |
| LPA-4913 | AGUGCUACCAUGGUAAUGG ACAGAG | 291 | CUCUGUCCAUUACC AUGGUAGCACUGC | 691 | AGUGCUACCA UGGUAAUGG | 1091 |
| LPA-4948 | ACAUUCUCCACCACUGUCA AAGGAA | 292 | UUCCUUUGACAGUG GUGGAGAAUGUGC | 692 | ACAUUCUCCA CCACUGUCA | 1092 |

TABLE 2-continued

DsiRNAs Targeting Human LPA mRNA and
Controls Evaluated in Cells

| Passenger (Sense) | SEQ ID NO: | Guide (Antisense) | SEQ ID NO: | Target Sequence | SEQ ID NO: |
|---|---|---|---|---|---|
| LPA-4959 | CACUGUCACAGGAAGGACAAGUCAA | 293 | UUGACUUGUCCUUCCUGUGACAGUGGU | 693 | CACUGUCACAGGAAGGACA | 1093 |
| LPA-4960 | ACUGUCACAGGAAGGACAUAUCAAT | 294 | AUUGAUAUGUCCUUCCUGUGACAGUGG | 694 | ACUGUCACAGGAAGGACAU | 1094 |
| LPA-4961 | CUGUCACAGGAAGGACAUGACAATC | 295 | GAUUGUCAUGUCCUUCCUGUGACAGUG | 695 | CUGUCACAGGAAGGACAUG | 1095 |
| LPA-4962 | UGUCACAGGAAGGACAUGUAAAUCT | 296 | AGAUUUACAUGUCCUUCCUGUGACAGU | 696 | UGUCACAGGAAGGACAUGU | 1096 |
| LPA-4963 | GUCACAGGAAGGACAUGUCAAUCTT | 297 | AAGAUUGACAUGUCCUUCCUGUGACAG | 697 | GUCACAGGAAGGACAUGUC | 1097 |
| LPA-4964 | UCACAGGAAGGACAUGUCAAUCUTG | 298 | CAAGAUUGACAUGUCCUUCCUGUGACA | 698 | UCACAGGAAGGACAUGUCA | 1098 |
| LPA-4966 | ACAGGAAGGACAUGUCAAUAUUGGT | 299 | ACCAAUAUUGACAUGUCCUUCCUGUGA | 699 | ACAGGAAGGACAUGUCAAU | 1099 |
| LPA-4967 | CAGGAAGGACAUGUCAAUCAUGGTC | 300 | GACCAUGAUUGACAUGUCCUUCCUGUG | 700 | CAGGAAGGACAUGUCAAUC | 1100 |
| LPA-4968 | AGGAAGGACAUGUCAAUCUAGGUCA | 301 | UGACCUAGAUUGACAUGUCCUUCCUGU | 701 | AGGAAGGACAUGUCAAUCU | 1101 |
| LPA-4969 | GGAAGGACAUGUCAAUCUUAGUCAT | 302 | AUGACUAAGAUUGACAUGUCCUUCCUG | 702 | GGAAGGACAUGUCAAUCUU | 1102 |
| LPA-4970 | GAAGGACAUGUCAAUCUUGAUCATC | 303 | GAUGAUCAAGAUUGACAUGUCCUUCCU | 703 | GAAGGACAUGUCAAUCUUG | 1103 |
| LPA-4971 | AAGGACAUGUCAAUCUUGGACAUCC | 304 | GGAUGUCCAAGAUUGACAUGUCCUUCC | 704 | AAGGACAUGUCAAUCUUGG | 1104 |
| LPA-4972 | AGGACAUGUCAAUCUUGGUAAUCCA | 305 | UGGAUUACCAAGAUUGACAUGUCCUUC | 705 | AGGACAUGUCAAUCUUGGU | 1105 |
| LPA-4973 | GGACAUGUCAAUCUUGGUCAUCCAT | 306 | AUGGAUGACCAAGAUUGACAUGUCCUU | 706 | GGACAUGUCAAUCUUGGUC | 1106 |
| LPA-4974 | GACAUGUCAAUCUUGGUCAACCATG | 307 | CAUGGUUGACCAAGAUUGACAUGUCCU | 707 | GACAUGUCAAUCUUGGUCA | 1107 |
| LPA-4975 | ACAUGUCAAUCUUGGUCAUACAUGA | 308 | UCAUGUAUGACCAAGAUUGACAUGUCC | 708 | ACAUGUCAAUCUUGGUCAU | 1108 |
| LPA-4976 | CAUGUCAAUCUUGGUCAUCAAUGAC | 309 | GUCAUUGAUGACCAAGAUUGACAUGUC | 709 | CAUGUCAAUCUUGGUCAUC | 1109 |
| LPA-4977 | AUGUCAAUCUUGGUCAUCCAUGACA | 310 | UGUCAUGGAUGACCAAGAUUGACAUGU | 710 | AUGUCAAUCUUGGUCAUCC | 1110 |
| LPA-4978 | UGUCAAUCUUGGUCAUCCAAGACAC | 311 | GUGUCUUGGAUGACCAAGAUUGACAUG | 711 | UGUCAAUCUUGGUCAUCCA | 1111 |
| LPA-4979 | GUCAAUCUUGGUCAUCCAUAACACC | 312 | GGUGUUAUGGAUGACCAAGAUUGACAU | 712 | GUCAAUCUUGUGUCAUCCAU | 1112 |
| LPA-4980 | UCAAUCUUGGUCAUCCAUGACACCA | 313 | UGGUGUCAUGGAUGACCAAGAUUGACA | 713 | UCAAUCUUGGUCAUCCAUG | 1113 |
| LPA-4981 | CAAUCUUGGUCAUCCAUGAAACCAC | 314 | GUGGUUUCAUGGAUGACCAAGAUUGAC | 714 | CAAUCUUGGUCAUCCAUGA | 1114 |
| LPA-4982 | AAUCUUGGUCAUCCAUGACACCACA | 315 | UGUGGUGUCAUGGAUGACCAAGAUUGA | 715 | AAUCUUGGUCAUCCAUGAC | 1115 |
| LPA-4983 | AUCUUGGUCAUCCAUGACAACACAC | 316 | GUGUGUUGUCAUGGAUGACCAAGAUUG | 716 | AUCUUGGUCAUCCAUGACA | 1116 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-5048 | UGACAAUGAACUACUGCAGAAAUCC | 317 | GGAUUUCUGCAGUAGUUCAUUGUCAGG | 717 | UGACAAUGAACUACUGCAG | 1117 |
| LPA-5049 | GACAAUGAACUACUGCAGGAAUCCA | 318 | UGGAUUCCUGCAGUAGUUCAUUGUCAG | 718 | GACAAUGAACUACUGCAGG | 1118 |
| LPA-5050 | ACAAUGAACUACUGCAGGAAUCCAG | 319 | CUGGAUUCCUGCAGUAGUUCAUUGUCA | 719 | ACAAUGAACUACUGCAGGA | 1119 |
| LPA-5051 | CAAUGAACUACUGCAGGAAACCAGA | 320 | UCUGGUUUCCUGCAGUAGUUCAUUGUC | 720 | CAAUGAACUACUGCAGGAA | 1120 |
| LPA-5052 | AAUGAACUACUGCAGGAAUACAGAT | 321 | AUCUGUAUUCCUGCAGUAGUUCAUUGU | 721 | AAUGAACUACUGCAGGAAU | 1121 |
| LPA-5053 | AUGAACUACUGCAGGAAUCAAGATG | 322 | CAUCUUGAUUCCUGCAGUAGUUCAUUG | 722 | AUGAACUACUGCAGGAAUC | 1122 |
| LPA-5054 | UGAACUACUGCAGGAAUCCAGAUGC | 323 | GCAUCUGGAUUCCUGCAGUAGUUCAUU | 723 | UGAACUACUGCAGGAAUCC | 1123 |
| LPA-5058 | CUACUGCAGGAAUCCAGAUACCGAT | 324 | AUCGGUAUCUGGAUUCCUGCAGUAGUU | 724 | CUACUGCAGGAAUCCAGAU | 1124 |
| LPA-5084 | CAGGCCCUUGGUGUUUUACAAUGGA | 325 | UCCAUUGUAAAACACCAAGGGCCUGUA | 725 | CAGGCCCUUGGUGUUUUAC | 1125 |
| LPA-5090 | CUUGGUGUUUUACCAUGGAACCCAG | 326 | CUGGGUUCCAUGGUAAAACACCAAGGG | 726 | CUUGGUGUUUUACCAUGGA | 1126 |
| LPA-5091 | UUGGUGUUUUACCAUGGACACCAGC | 327 | GCUGGUGUCCAUGGUAAAACACCAAGG | 727 | UUGGUGUUUUACCAUGGAC | 1127 |
| LPA-5092 | UGGUGUUUUACCAUGGACCACAGCA | 328 | UGCUGUGGUCCAUGGUAAAACACCAAG | 728 | UGGUGUUUUACCAUGGACC | 1128 |
| LPA-5093 | GGUGUUUUACCAUGGACCCCAAGCAT | 329 | AUGCUUGGGUCCAUGGUAAAACACCAA | 729 | GGUGUUUUACCAUGGACCC | 1129 |
| LPA-5094 | GUGUUUUACCAUGGACCCCAGCATC | 330 | GAUGCUGGGGUCCAUGGUAAAACACCA | 730 | GUGUUUUACCAUGGACCCC | 1130 |
| LPA-5096 | GUUUUACCAUGGACCCCAGAAUCAG | 331 | CUGAUUCGGGGUCCAUGGUAAAACAC | 731 | GUUUUACCAUGGACCCCAG | 1131 |
| LPA-5124 | GGAGUACUGCAACCUGACGAGAUGC | 332 | GCAUCUCGUCAGGUUGCAGUACUCCCA | 732 | GGAGUACUGCAACCUGACG | 1132 |
| LPA-5125 | GAGUACUGCAACCUGACGCAAUGCT | 333 | AGCAUUGCGUCAGGUUGCAGUACUCCC | 733 | GAGUACUGCAACCUGACGC | 1133 |
| LPA-5127 | GUACUGCAACCUGACGCGAAGCUCA | 334 | UGAGCUUCGCGUCAGGUUGCAGUACUC | 734 | GUACUGCAACCUGACGCGA | 1134 |
| LPA-5128 | UACUGCAACCUGACGCGAUACUCAG | 335 | CUGAGUAUCGCGUCAGGUUGCAGUACU | 735 | UACUGCAACCUGACGCGAU | 1135 |
| LPA-5131 | UGCAACCUGACGCGAUGCUAAGACA | 336 | UGUCUUAGCAUCGCGUCAGGUUGCAGU | 736 | UGCAACCUGACGCGAUGCU | 1136 |
| LPA-5136 | CCUGACGCGAUGCUCAGACACAGAA | 337 | UUCUGUGUCUGAGCAUCGCGUCAGGUU | 737 | CCUGACGCGAUGCUCAGAC | 1137 |
| LPA-5137 | CUGACGCGAUGCUCAGACAAAGAAG | 338 | CUUCUUUGUCUGAGCAUCGCGUCAGGU | 738 | CUGACGCGAUGCUCAGACA | 1138 |
| LPA-5144 | GAUGCUCAGACACAGAAGGAACUGT | 339 | ACAGUUCCUUCUGUGUCUGAGCAUCGC | 739 | GAUGCUCAGACACAGAAGG | 1139 |
| LPA-5145 | AUGCUCAGACACAGAAGGGACUGTG | 340 | CACAGUCCCUUCUGUGUCUGAGCAUCG | 740 | AUGCUCAGACACAGAAGGG | 1140 |

TABLE 2-continued

DsiRNAs Targeting Human LPA mRNA and Controls Evaluated in Cells

| | Passenger (Sense) | SEQ ID NO: | Guide (Antisense) | SEQ ID NO: | Target Sequence | SEQ ID NO: |
|---|---|---|---|---|---|---|
| LPA-5151 | AGACACAGAAGGGACUGUGAUCGCT | 341 | AGCGAUCACAGUCCCUUCUGUGUCUGA | 741 | AGACACAGAAGGGACUGUG | 1141 |
| LPA-5467 | GCAUCCUCUUCAUUUGAUUAUGGGA | 342 | UCCCAUAAUCAAAUGAAGAGGAUGCAC | 742 | GCAUCCUCUUCAUUUGAUU | 1142 |
| LPA-5468 | CAUCCUCUUCAUUUGAUUGAGGGAA | 343 | UUCCCUCAAUCAAAUGAAGAGGAUGCA | 743 | CAUCCUCUUCAUUUGAUUG | 1143 |
| LPA-5469 | AUCCUCUUCAUUUGAUUGUAGGAAG | 344 | CUUCCUACAAUCAAAUGAAGAGGAUGC | 744 | AUCCUCUUCAUUUGAUUGU | 1144 |
| LPA-5470 | UCCUCUUCAUUUGAUUGUGAGAAGC | 345 | GCUUCUCACAAUCAAAUGAAGAGGAUG | 745 | UCCUCUUCAUUUGAUUGUG | 1145 |
| LPA-5471 | CCUCUUCAUUUGAUUGUGGAAAGCC | 346 | GGCUUUCCACAAUCAAAUGAAGAGGAU | 746 | CCUCUUCAUUUGAUUGUGG | 1146 |
| LPA-5474 | CUUCAUUUGAUUGUGGGAAACCUCA | 347 | UGAGGUUUCCACAAUCAAAUGAAGAG | 747 | CUUCAUUUGAUUGUGGGAA | 1147 |
| LPA-5475 | UUCAUUUGAUUGUGGGAAGACUCAA | 348 | UUGAGUCUUCCCACAAUCAAAUGAAGA | 748 | UUCAUUUGAUUGUGGGAAG | 1148 |
| LPA-5476 | UCAUUUGAUUGUGGGAAGCAUCAAG | 349 | CUUGAUGCUUCCCACAAUCAAAUGAAG | 749 | UCAUUUGAUUGUGGGAAGC | 1149 |
| LPA-5477 | CAUUUGAUUGUGGGAAGCCACAAGT | 350 | ACUUGUGGCUUCCCACAAUCAAAUGAA | 750 | CAUUUGAUUGUGGGAAGCC | 1150 |
| LPA-5478 | AUUUGAUUGUGGGAAGCCUAAAGTG | 351 | CACUUUAGGCUUCCCACAAUCAAAUGA | 751 | AUUUGAUUGUGGGAAGCCU | 1151 |
| LPA-5486 | GUGGGAAGCCUCAAGUGGAACCGAA | 352 | UUCGGUUCCACUUGAGGCUUCCCACAA | 752 | GUGGGAAGCCUCAAGUGGA | 1152 |
| LPA-5509 | AAGAAAUGUCCUGGAAGCAAUGUAG | 353 | CUACAUUGCUUCCAGGACAUUUCUUCG | 753 | AAGAAAUGUCCUGGAAGCA | 1153 |
| LPA-5510 | AGAAAUGUCCUGGAAGCAUAGUAGG | 354 | CCUACUAUGCUUCCAGGACAUUUCUUC | 754 | AGAAAUGUCCUGGAAGCAU | 1154 |
| LPA-5511 | GAAAUGUCCUGGAAGCAUUAUAGGG | 355 | CCCUAUAAUGCUUCCAGGACAUUUCUU | 755 | GAAAUGUCCUGGAAGCAUU | 1155 |
| LPA-5513 | AAUGUCCUGGAAGCAUUGUAGGGGG | 356 | CCCCCUACAAUGCUUCCAGGACAUUUC | 756 | AAUGUCCUGGAAGCAUUGU | 1156 |
| LPA-5514 | AUGUCCUGGAAGCAUUGUAAGGGGG | 357 | CCCCCUUACAAUGCUUCCAGGACAUUU | 757 | AUGUCCUGGAAGCAUUGUA | 1157 |
| LPA-5581 | AGAACAAGGUUUGGAAAGCACUUCT | 358 | AGAAGUGCUUUCCAAACCUUGUUCUGA | 758 | AGAACAAGGUUUGGAAAGC | 1158 |
| LPA-5582 | GAACAAGGUUUGGAAAGCAAUUCTG | 359 | CAGAAUUGCUUUCCAAACCUUGUUCUG | 759 | GAACAAGGUUUGGAAAGCA | 1159 |
| LPA-5583 | AACAAGGUUUGGAAAGCACAUCUGT | 360 | ACAGAUGUGCUUUCAAACCUUGUUCU | 760 | AACAAGGUUUGGAAAGCAC | 1160 |
| LPA-5584 | ACAAGGUUUGGAAAGCACUACUGTG | 361 | CACAGUAGUGCUUUCCAAACCUUGUUC | 761 | ACAAGGUUUGGAAAGCACU | 1161 |
| LPA-5585 | CAAGGUUUGGAAAGCACUUAUGUGG | 362 | CCACAUAAGUGCUUUCCAAACCUUGUU | 762 | CAAGGUUUGGAAAGCACUU | 1162 |
| LPA-5586 | AAGGUUUGGAAAGCACUUCAGUGGA | 363 | UCCACUGAAGUGCUUUCCAAACCUUGU | 763 | AAGGUUUGGAAAGCACUUC | 1163 |
| LPA-5587 | AGGUUUGGAAAGCACUUCUAUGGAG | 364 | CUCCAUAGAAGUGCUUUCCAAACCUUG | 764 | AGGUUUGGAAAGCACUUCU | 1164 |

TABLE 2-continued

DsiRNAs Targeting Human LPA mRNA and
Controls Evaluated in Cells

| Passenger (Sense) | SEQ ID NO: | Guide (Antisense) | SEQ ID NO: | Target Sequence | SEQ ID NO: |
|---|---|---|---|---|---|
| LPA-5592 | UGGAAAGCACUUCUGUGGA AGCACC | 365 | GGUGCUUCCACAGA AGUGCUUUCCAAA | 765 | UGGAAAGCAC UUCUGUGGA | 1165 |
| LPA-5606 | GUGGAGGCACCUUAAUAUC ACCAGA | 366 | UCUGGUGAUAUUAA GGUGCCUCCACAG | 766 | GUGGAGGCAC CUUAAUAUC | 1166 |
| LPA-5616 | CUUAAUAUCCCCAGAGUGG AUGCUG | 367 | CAGCAUCCACUCUG GGGAUAUUAAGGU | 767 | CUUAAUAUCC CCAGAGUGG | 1167 |
| LPA-5618 | UAAUAUCCCCAGAGUGGGU ACUGAC | 36 | GUCAGUACCCACUC UGGGGAUAUUAAG | 768 | UAAUAUCCCC AGAGUGGGU | 1168 |
| LPA-5628 | AGAGUGGGUGCUGACUGCU ACUCAC | 369 | GUGAGUAGCAGUCA GCACCCACUCUGG | 769 | AGAGUGGGUG CUGACUGCU | 1169 |
| LPA-5685 | CAAGGUCAUCCUGGGUGCA AACCAA | 370 | UUGGUUUGCACCCA GGAUGACCUUGUA | 770 | CAAGGUCAUC CUGGGUGCA | 1170 |
| LPA-5694 | CCUGGGUGCACACCAAGAA AUGAAC | 371 | GUUCAUUUCUUGGU GUGCACCCAGGAU | 771 | CCUGGGUGCA CACCAAGAA | 1171 |
| LPA-5699 | GUGCACACCAAGAAGUGAA ACUCGA | 372 | UCGAGUUUCACUUC UUGGUGUGCACCC | 772 | GUGCACACCA AGAAGUGAA | 1172 |
| LPA-5775 | AGCAGAUAUUGCCUUGCUA AAGCUA | 373 | UAGCUUUAGCAAGG CAAUAUCUGCUUG | 773 | AGCAGAUAUU GCCUUGCUA | 1173 |
| LPA-5776 | GCAGAUAUUGCCUUGCUAA AGCUAA | 374 | UUAGCUUUAGCAAG GCAAUAUCUGCUU | 774 | GCAGAUAUUG CCUUGCUAA | 1174 |
| LPA-5777 | CAGAUAUUGCCUUGCUAAA ACUAAG | 375 | CUUAGUUUUAGCAA GGCAAUAUCUGCU | 775 | CAGAUAUUGC CUUGCUAAA | 1175 |
| LPA-5778 | AGAUAUUGCCUUGCUAAAG AUAAGC | 376 | GCUUAUCUUUAGCA AGGCAAUAUCUGC | 776 | AGAUAUUGCC UUGCUAAAG | 1176 |
| LPA-5779 | GAUAUUGCCUUGCUAAAGC AAAGCA | 377 | UGCUUUGCUUUAGC AAGGCAAUAUCUG | 777 | GAUAUUGCCU UGCUAAAGC | 1177 |
| LPA-5780 | AUAUUGCCUUGCUAAAGCU AAGCAG | 378 | CUGCUUAGCUUUAG CAAGGCAAUAUCU | 778 | AUAUUGCCUU GCUAAAGCU | 1178 |
| LPA-5781 | UAUUGCCUUGCUAAAGCUA AGCAGG | 379 | CCUGCUUAGCUUUA GCAAGGCAAUAUC | 779 | UAUUGCCUUG CUAAAGCUA | 1179 |
| LPA-5813 | UCAUCACUGACAAAGUAAU ACCAGC | 380 | GCUGGUAUUACUUU GUCAGUGAUGACG | 780 | UCAUCACUGA CAAAGUAAU | 1180 |
| LPA-5873 | GGACUGAAUGUUACAUCAC AGGCUG | 381 | CAGCCUGUGAUGUA ACAUUCAGUCCUG | 781 | GGACUGAAUG UUACAUCAC | 1181 |
| LPA-5874 | GACUGAAUGUUACAUCACU AGCUGG | 382 | CCAGCUAGUGAUGU AACAUUCAGUCCU | 782 | GACUGAAUGU UACAUCACU | 1182 |
| LPA-5875 | ACUGAAUGUUACAUCACUG ACUGGG | 383 | CCCAGUCAGUGAUG UAACAUUCAGUCC | 783 | ACUGAAUGUU ACAUCACUG | 1183 |
| LPA-5876 | CUGAAUGUUACAUCACUGG AUGGGG | 384 | CCCCAUCCAGUGAU GUAACAUUCAGUC | 784 | CUGAAUGUUA CAUCACUGG | 1184 |
| LPA-5877 | UGAAUGUUACAUCACUGGC AGGGGA | 385 | UCCCCUGCCAGUGA UGUAACAUUCAGU | 785 | UGAAUGUUAC AUCACUGGC | 1185 |
| LPA-5879 | AAUGUUACAUCACUGGCUG AGGAGA | 386 | UCUCCUCAGCCAGU GAUGUAACAUUCA | 786 | AAUGUUACAU CACUGGCUG | 1186 |
| LPA-5902 | GAAACCCAAGGUACCUUUG AGACUG | 387 | CAGUCUCAAAGGUA CCUUGGGUUUCUC | 787 | GAAACCCAAG GUACCUUUG | 1187 |

TABLE 2-continued

DsiRNAs Targeting Human LPA mRNA and Controls Evaluated in Cells

| Passenger (Sense) | | SEQ ID NO: | Guide (Antisense) | SEQ ID NO: | Target Sequence | SEQ ID NO: |
|---|---|---|---|---|---|---|
| Control | | | | | | |
| Gal XC-LPA-3675 | GACAACAGAAUAUUAUCCA AGCAGCCGAAAGGCUGC | 1188 | UUGGAUAAUAUUCU GUUGUCGG | 1189 | GACAACAGAA UAUUAUCCA | 1190 |
| NC1 | CGUUAAUCGCGUAUAAUAC GCGUAT | 1191 | AUACGCGUAUUAUA CGCGAUUAACGAC | 1192 | N/A | |
| NC5 | CAUAUUGCGCGUAUAGUCG CGUUAG | 1193 | CUAACGCGACUAUA CGCGCAAUAUGGU | 1194 | N/A | |
| NC7 | GGCGCGUAUAGUCGCGCGU AUAGTC | 1195 | GACUAUACGCGCGA CUAUACGCGCCUC | 1196 | N/A | |

In Vitro Cell-Based Assays

The ability of each of the DsiRNAs listed in Table 2 to inhibit LPA expression was determined using in vitro cell-based assays. Briefly, human embryonic kidney 293 (HEK293) or HepG2 cells stably expressing a human LPA gene were transfected with each of the DsiRNAs listed in Table 2 at 0.5 nM in separate wells of a multi-well cell-culture plate. Cells were maintained for 24 hours following transfection, and then the amount of remaining LPA mRNA from the transfected cells was determined using TAQMAN®-based qPCR assays. Two qPCR assays, a 3' assay and a 5' assay, were used to determine LPA mRNA levels as measured using PCR probes conjugated to 6-carboxyfluorescein (6-FAM).

The results of the HEK293 and HepG2 cell-based assays to evaluate the ability of the DsiRNAs listed in Table 2 to inhibit LPA expression are shown in FIGS. 1-4 and FIG. 5, respectively. Cells transfected with a GalNAc-conjugated LPA oligonucleotide (GalXC-LPA-3675 SEQ ID NO: 1188 and 1189) were used as a positive control. DsiRNAs that resulted in less than or equal to about 15%-20% LPA mRNA remaining in DsiRNA-transfected cells when compared to mock-transfected cells were generally considered to comprise sequences that provide a suitable amount of knock-down or reduction of target mRNA expression for further evaluation. In FIGS. 1-5, the percent of LPA mRNA remaining in cells transfected with DsiRNAs, as indicated, relative to time-matched control cells is shown (3' assay=circle shapes; 5' assay=triangle shapes).

Figure 6:
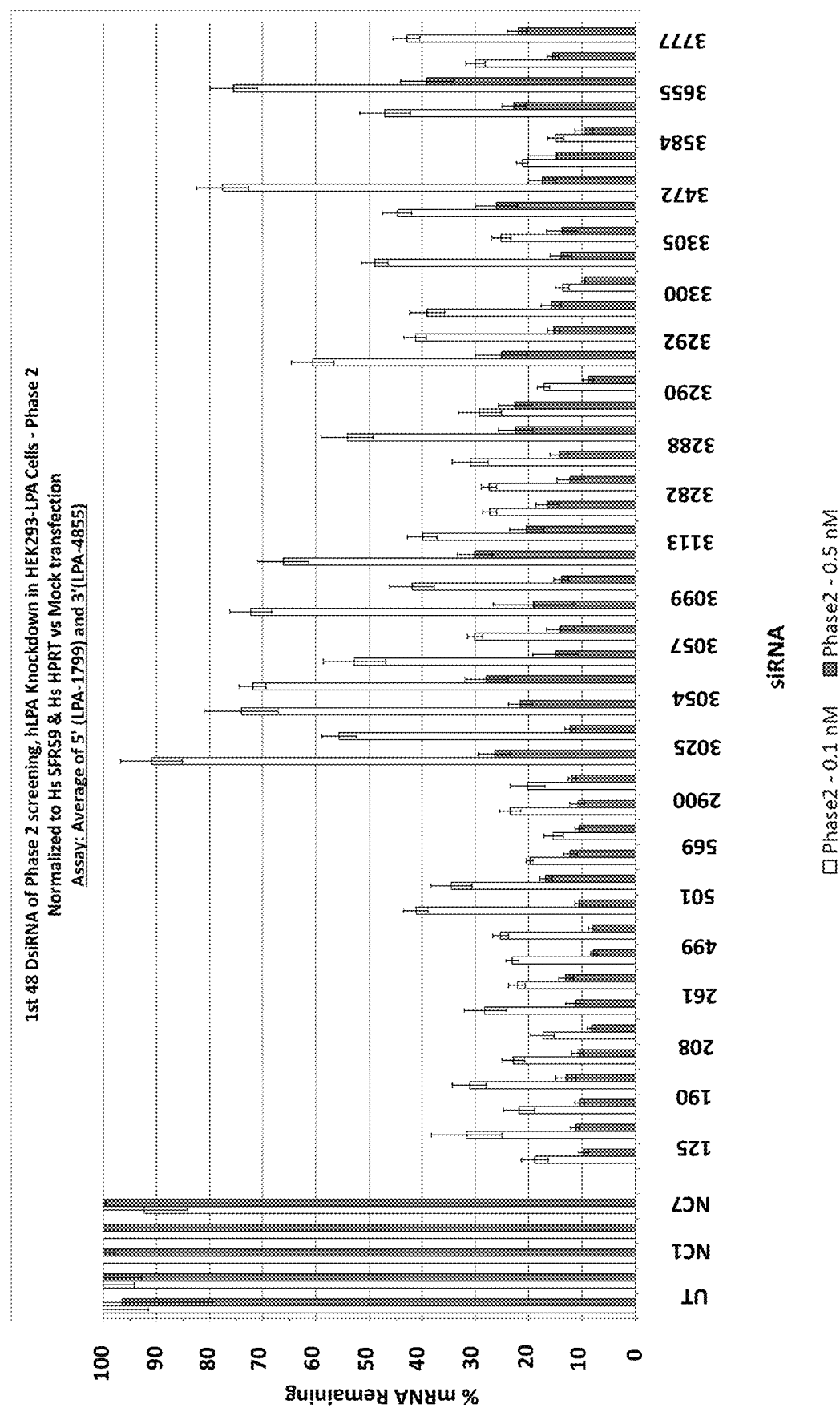
FIGS. 6-7 provide graphs depicting the percent (%) of LPA mRNA in HEK293-LPA cells transfected with the indicated DsiRNAs relative to the % of LPA mRNA control mock-treated cells.
Figure 7:
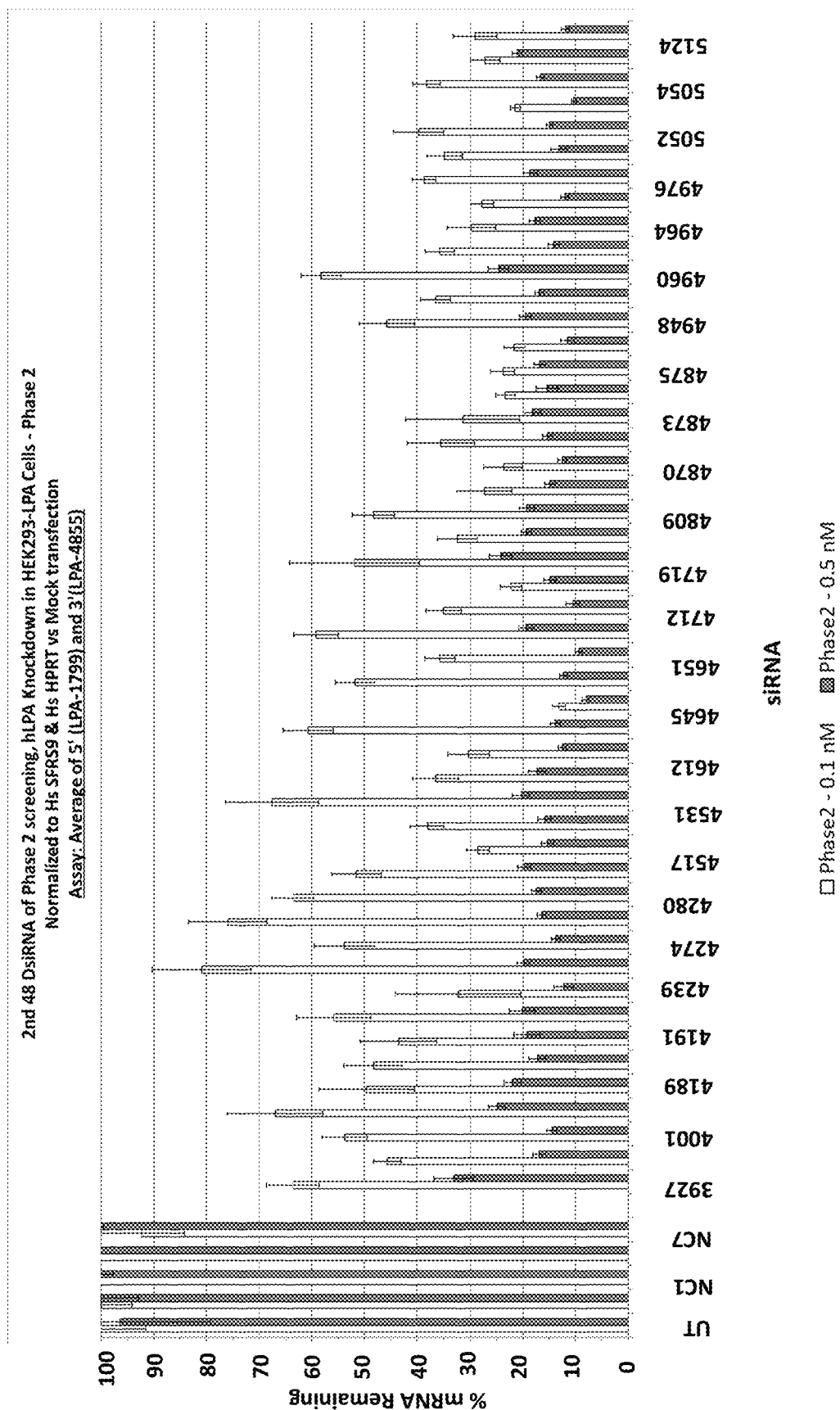

To further evaluate the DsiRNA hits, a subset of the DsiRNAs listed in Table 2 were tested to determine their ability to inhibit LPA expression using in vitro cell-based assays at two different DsiRNA concentrations (FIG. 6 and FIG. 7). Briefly, HEK293 cells stably expressing a human LPA gene were transfected with DsiRNAs at 0.1 nM and 0.5 nM in separate wells of a multi-well cell-culture plate. Cells were maintained for 24 hr. following transfection, and then the amount of remaining LPA mRNA from the transfected cells was determined using TAQMAN®-based qPCR assays. Two qPCR assays, a 3' assay and a 5' assay, were used to determine LPA mRNA levels as measured using PCR probes conjugated to hexachloro-fluorescein (HEX). Untransfected cells (UT), mock-transfected cells (Mock), and cells transfected with control oligonucleotides (NC1, SEQ ID NOs: 1191 and 1192; NC5, SEQ ID NO: 1193 and 1194; and NC7, SEQ ID NO: 1195 and 1196) were used as negative controls. As shown in FIGS. 6 and 7, the percent of LPA mRNA remaining in HEK293 cells transfected with the indicated DsiRNAs is an average of the LPA mRNA levels from the 3' assay and 5' assay and is normalized to time-matched, mock-transfected control HEK293 cells.

Taken together, these results show that DsiRNAs designed to target human LPA mRNA inhibit LPA expression in cells, as determined by a reduced amount of LPA mRNA in DsiRNA-transfected cells relative to control cells. These results demonstrate that the nucleotide sequences comprising the DsiRNA are useful for generating RNAi oligonucleotides to inhibit LPA expression. Further, these results demonstrate that multiple LPA mRNA target sequences are suitable for the RNAi-mediated inhibition of LPA expression.

Example 3: RNAi Oligonucleotide Inhibition of LPA Expression In Vivo

Of the DsiRNAs screened in the cell-based assays described in Example 2, the nucleotide sequences of 14 DsiRNAs were selected for further evaluation in vivo. Briefly, the nucleotide sequences of the 14 selected DsiRNAs were used to generate 14 corresponding double-stranded RNAi oligonucleotides comprising a nicked tetraloop GalNAc-conjugated structure (referred to herein as "GalNAc-conjugated LPA oligonucleotides") having a 36-mer passenger strand and a 22-mer guide strand (Table 3). Further, the nucleotide sequences comprising the passenger strand and guide strand of the GalNAc-conjugated LPA oligonucleotides have a distinct pattern of modified nucleotides and phosphorothioate linkages (e.g., see FIG. 10 for a schematic of the generic structure and chemical modification patterns (M1, M2, and M3) of the GalNAc-conjugated LPA oligonucleotides). The three adenosine nucleotides comprising the tetraloop are each conjugated to a GalNAc moiety (CAS #: 14131-60-3).

TABLE 3

GalNAc-Conjugated LPA Oligonucleotides Evaluated in Mice

| Oligonucleotide | DP # | SEQ ID NO (Sense) | SEQ ID NO (Antisense) |
|---|---|---|---|
| LPA-0190-M1 | DP15791P: DP15790G | 388 | 788 |
| LPA-0501-M1 | DP15634P: DP15633G | 389 | 789 |
| LPA-3100-M1 | DP15639P: DP15638G | 390 | 790 |

TABLE 3-continued

GalNAc-Conjugated LPA Oligonucleotides Evaluated in Mice

| Oligonucleotide | DP # | SEQ ID NO (Sense) | SEQ ID NO (Antisense) |
|---|---|---|---|
| LPA-3286-M1 | DP15643P: DP15642G | 391 | 791 |
| LPA-3288-M1 | DP15645P: DP15644G | 392 | 792 |
| LPA-3291-M1 | DP15647P: DP15646G | 393 | 793 |
| LPA-3584-M1 | DP15651P: DP15650G | 394 | 794 |
| LPA-3585-M1 | DP15653P: DP15652G | 395 | 795 |
| LPA-4645-M1 | DP15657P: DP15656G | 396 | 796 |
| LPA-4717-M1 | DP15801P: DP15800G | 397 | 797 |
| LPA-5510-M1 | DP15815P: DP15814G | 398 | 798 |
| LPA-3750-M1 | DP13346P: DP13385G | 399 | 799 |
| LPA-2900-M2 | DP13351P: DP14623G | 400 | 800 |
| LPA-3675-M2 | DP13346P: DP14624G | 401 | 801 |
| LPA-2900-M3 | DP13351P: DP13387G | 402 | 802 |
| LPA-3675-M3 | DP13346P: DP13385G | 403 | 803 |

Mouse Studies

The GalNAc-conjugated LPA oligonucleotides listed in Table 3 were evaluated in an HDI mouse model, wherein HDI mice were engineered to transiently express human LPA mRNA in hepatocytes. The GalNAc-conjugated LPA oligonucleotide LPA-3675-M2 was used as a benchmark control. Briefly, 6-8-week-old female CD-1 mice (n=5) were treated subcutaneously with the indicated GalNAc-conjugated LPA oligonucleotides at a dose level of 0.5 mg/kg (FIG. 8) or at a dose level of 0.25 mg/kg, 0.5 mg/kg, and 1 mg/kg (FIG. 9). Three days later (72 h), the mice were hydrodynamically injected (HDI) with a DNA plasmid encoding the full human LPA gene under control of a ubiquitous cytomegalovirus (CMV) promoter sequence. One day after introduction of the DNA plasmid, liver samples from mice were collected. Total RNA derived from these mice were subjected to qRT-PCR analysis for LPA mRNA, relative to mice treated only with an identical volume of PBS. The values were normalized for transfection efficiency using the NeoR gene included on the plasmid.

Figure 8:
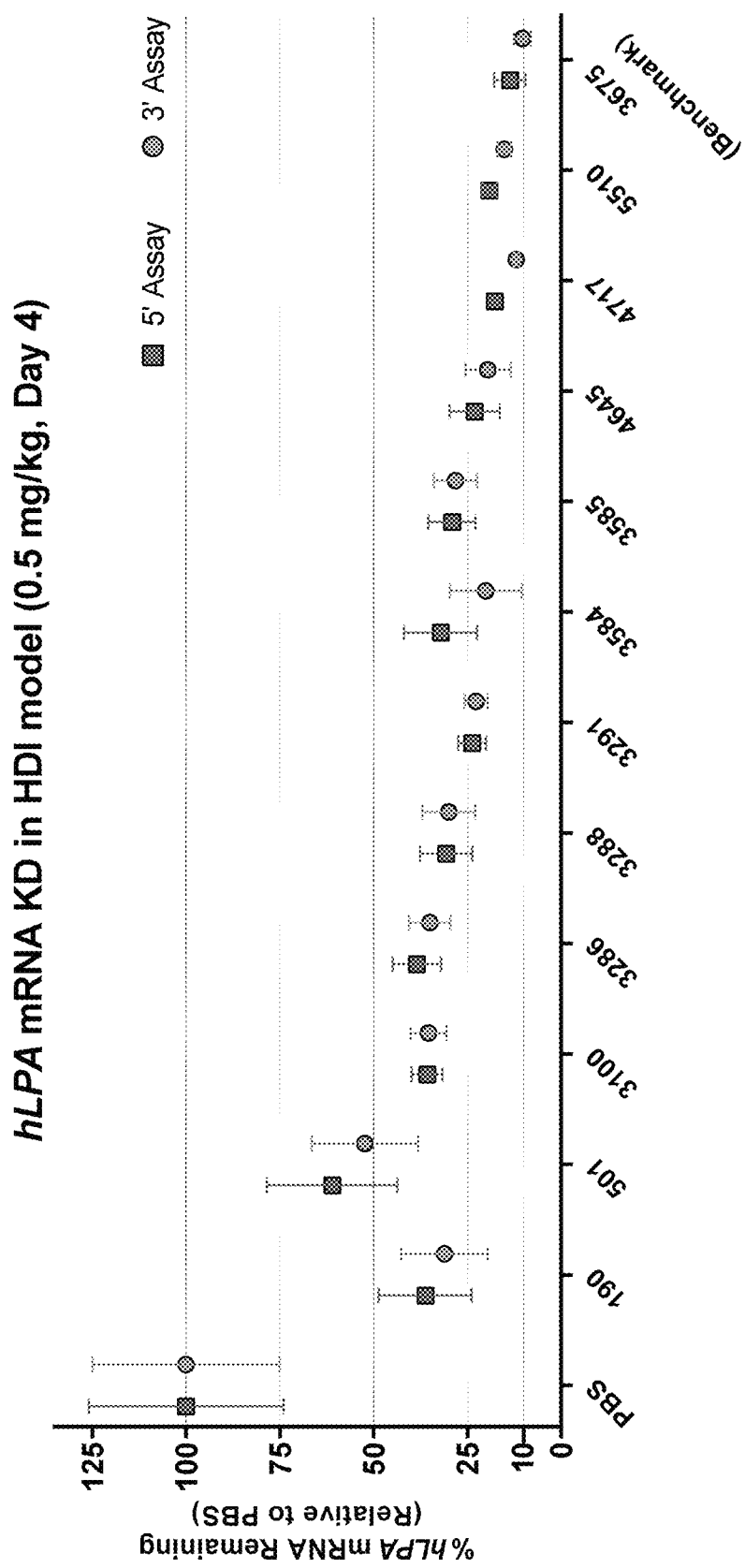
FIGS. 8-9 provide graphs depicting the percent (%) of LPA mRNA in liver samples from mice treated with the indicated GalNAc-conjugated LPA oligonucleotides relative to mice treated with phosphate buffered saline (PBS).
Figure 9:
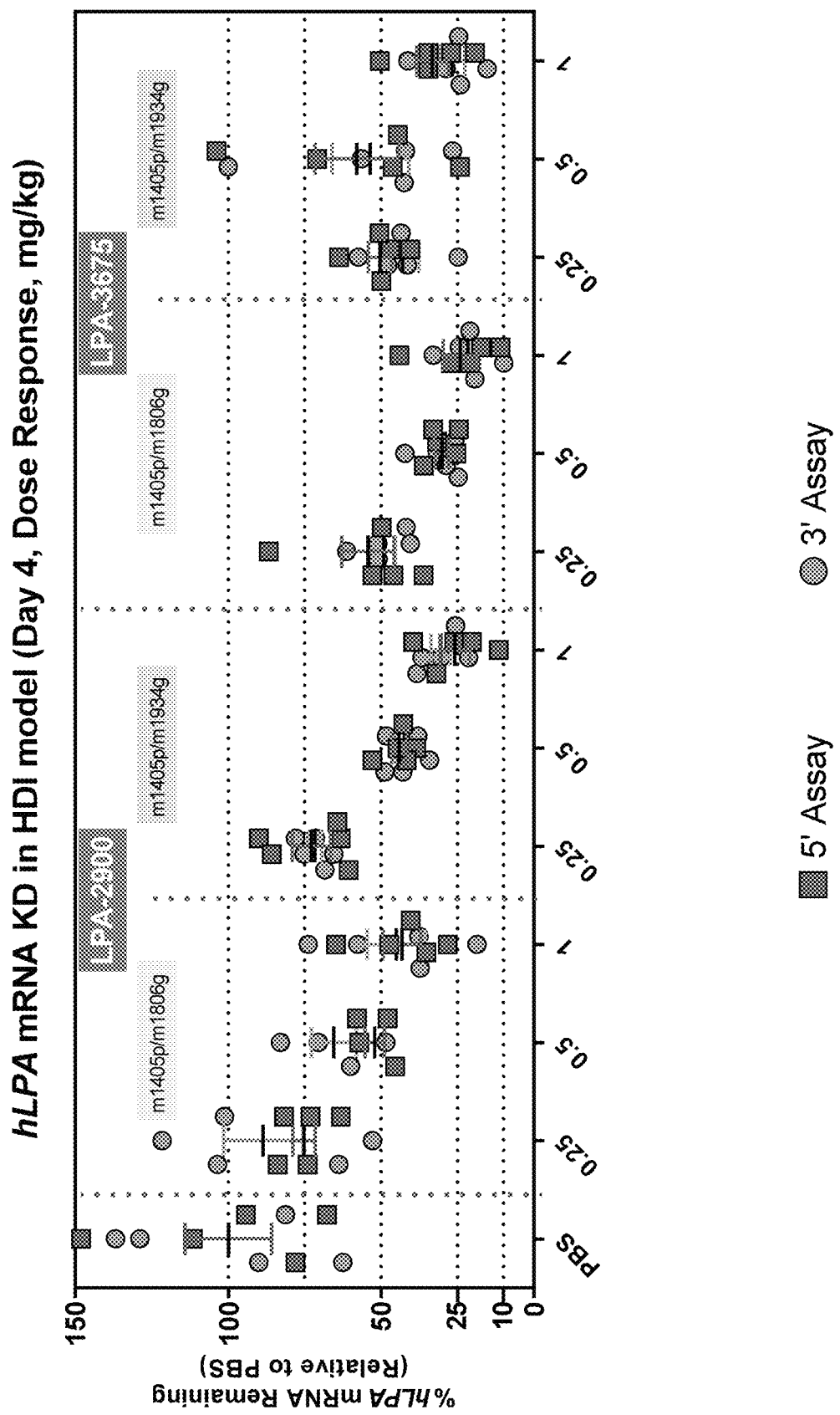

As shown in FIG. 8, the indicated GalNAc-conjugated LPA oligonucleotides inhibited LPA expression, as determined by a reduction in the amount of LPA mRNA in liver samples from oligonucleotide-treated HDI mice relative to mice treated with PBS. To further evaluate the ability of GalNAc-conjugated LPA oligonucleotides to inhibit LPA expression, two of the GalNAc-conjugated LPA oligonucleotide sequences (LPA-2900 and LPA-3675) each having a different chemical modification pattern (M2 and M3) were tested for their ability to inhibit LPA expression in the HDI mice described above at three different concentrations (0.25 mg/kg, 0.5 mg/kg, and 1.0 mg/kg). As shown in FIG. 9, the indicated GalNAc-conjugated LPA oligonucleotides inhibited LPA expression in HDI mice in a dose-dependent manner.

Taken together, these results show that GalNAc-conjugated LPA oligonucleotides designed to target human LPA mRNA inhibit LPA expression in mice, as determined by a reduction in the amount of LPA mRNA in HDI mouse livers relative to control mice treated with PBS. Based on these results, 10 of the 14 GalNAc-conjugated LPA oligonucleotides evaluated in HDI mice were selected for evaluation of their ability to inhibit LPA expression in non-human primates (NHPs). The 10 GalNAc-conjugated LPA oligonucleotides listed in Table 4 comprise chemically modified nucleotides having pattern M1, M2, or M3 as described in FIG. 10.

TABLE 4

GalNAc-Conjugated LPA Oligonucleotides Evaluated in NHPs

| Oligonucleotide | DP # | SEQ ID NO (Sense) | SEQ ID NO (Antisense) |
|---|---|---|---|
| LPA-0190-M1 | DP15791P: DP15790G | 388 | 788 |
| LPA-3100-M1 | DP15639P: DP15638G | 390 | 790 |
| LPA-3288-M1 | DP15645P: DP15644G | 392 | 792 |
| LPA-3291-M1 | DP15647P: DP15646G | 393 | 793 |
| LPA-3585-M1 | DP15653P: DP15652G | 395 | 795 |
| LPA-4645-M1 | DP15657P: DP15656G | 396 | 796 |
| LPA-4717-M1 | DP15801P: DP15800G | 397 | 797 |
| LPA-5510-M1 | DP15815P: DP15814G | 398 | 798 |
| LPA-2900-M2 | DP13351P: DP14623G | 400 | 800 |
| LPA-3675-M3 | DP13346P: DP13385G | 403 | 803 |

Non-Human Primate (NHP) Studies

Figure 11A:
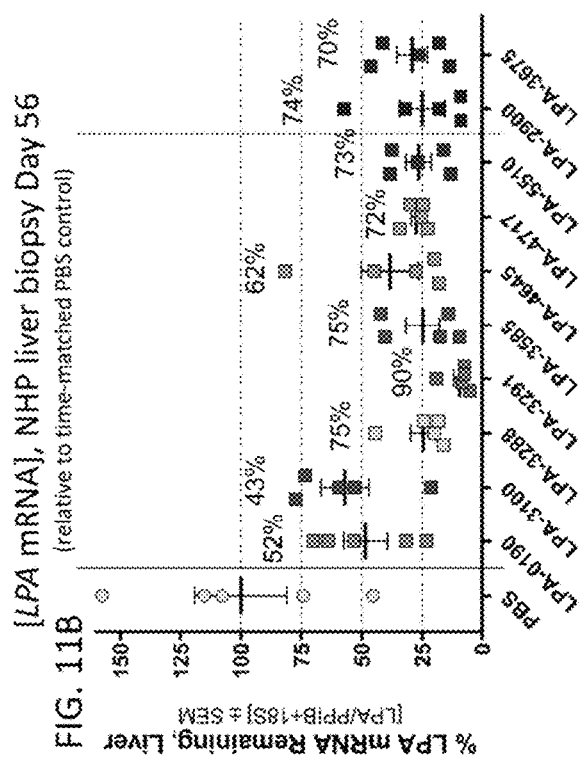
FIGS. 11A-11C provide graphs depicting the percent (%) of LPA mRNA in liver samples from non-human primates (NHPs) treated with the indicated GalNAc-conjugated LPA oligonucleotides relative to NHPs treated with PBS on day 28 (FIG. 11A), day 56 (FIG. 11B) and day 84 (FIG. 11C) following treatment.
Figure 11B:
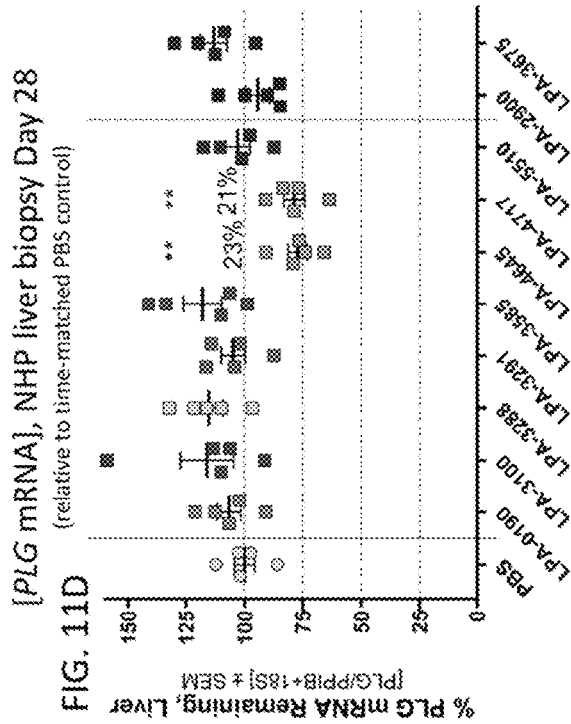
Figure 11C:
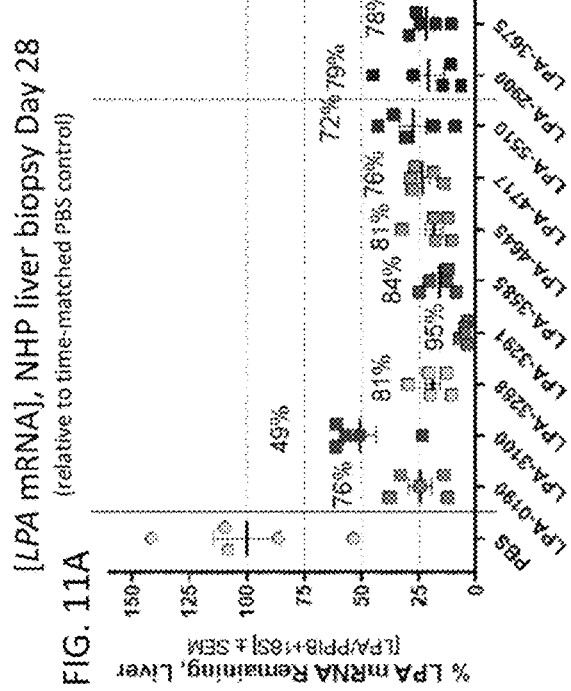
Figure 11D:
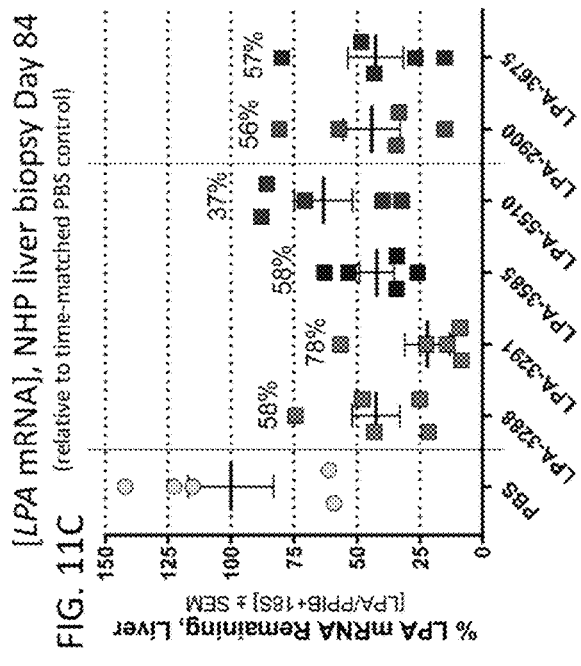
FIG. 11D provides a graph depicting the percent (%) of PLG mRNA in liver samples from NHPs treated with the indicated GalNAc-conjugated LPA oligonucleotides relative to NHPs treated with PBS on day 28.
Figure 12:
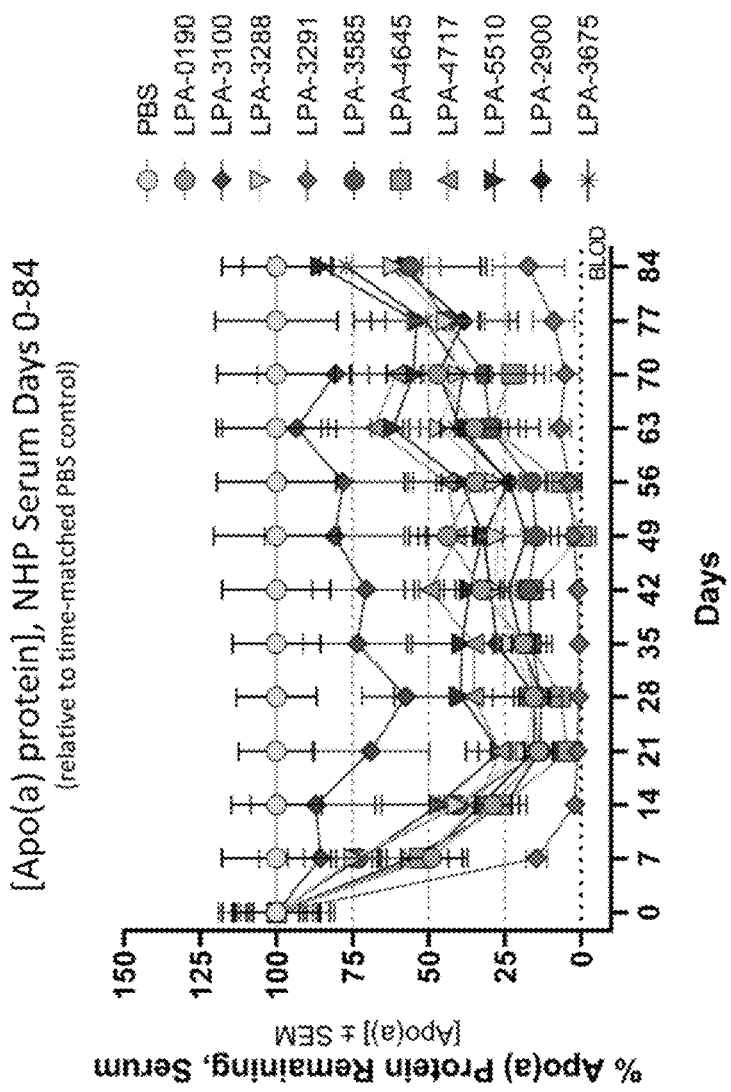
FIG. 12 provides a graph depicting the mean percent (%) of apo(a) protein in serum from NHPs treated with the indicated GalNAc-conjugated LPA oligonucleotides relative to NHPs treated with PBS over time.

The GalNAc-conjugated LPA oligonucleotides listed in Table 4 were evaluated in cynomolgus monkeys (*Macaca fascicularis*). In this study, the monkeys are grouped so that their mean body weights (about 5.4 kg) are comparable between the control and experimental groups. Each cohort contains two male and three female subjects. The GalNAc-conjugated LPA oligonucleotides were administered subcutaneously on Study Day 0. Blood samples were collected on Study Days -8, -5 and 0, and weekly after dosing. Ultrasound-guided core needle liver biopsies were collected on Study Days 28, 56 and 84. At each time point, total RNA derived from the liver biopsy samples was subjected to qRT-PCR analysis to measure LPA mRNA in oligonucleotide-treated monkeys relative to monkeys treated with a comparable volume of PBS. To normalize the data, the measurements were made relative to the geometric mean of two reference genes, PPIB and 18S rRNA. As shown in FIG. 11A (Day 28), FIG. 11B (Day 56), and FIG. 11C (Day 84), treatment of NHPs with the GalNAc-conjugated LPA oligonucleotides listed in Table 4 inhibited LPA expression in the liver, as determined by a reduction in the amount of LPA mRNA in liver samples from oligonucleotide-treated NHPs relative to NHPs treated with PBS. The amount of plasminogen (PLG) mRNA in the liver samples of treated NHPs was also determined and is shown in FIG. 11D. From the same NHP study, inhibition of LPA expression was also determined by measuring apo(a) protein serum from treated NHPs by ELISA. As shown in FIG. 12, a significant reduction in serum apo(a) protein was observed in NHPs treated with GalNAc-conjugated LPA oligonucleotides compared to NHPs treated with PBS. Values from three pre-dose samples are averaged and set to 100%, and data are reported as relative values compared to the pre-dose average. Taken together, these results demonstrate that treatment of NHPs with GalNAc-conjugated LPA oligonucleotides reduced the amount of LPA mRNA in the liver and reduced the amount of apo(a) protein in the serum.

Taken together, these results show that GalNAc-conjugated LPA oligonucleotides designed to target human LPA mRNA inhibit LPA expression in vivo (as determined by the reduction of the amount of LPA mRNA and apo(a) protein in treated animals).

SEQUENCE LISTING

The following nucleic and/or amino acid sequences are referred to in the disclosure above and are provided below for reference.

TABLE 5

| Oligonucleotide | Sequence (Sense Strand) | SEQ ID NO: | Sequence (Antisense Strand) | SEQ ID NO: |
|---|---|---|---|---|
| LPA-125 | CUGAGCAAAGCCAUGUGGUACAGGA | 4 | UCCUGUACCACAUGGCUUUGCUCAGGU | 404 |
| LPA-128 | AGCAAAGCCAUGUGGUCCAAGAUTG | 5 | CAAUCUUGGACCACAUGGCUUUGCUCA | 405 |
| LPA-132 | AAGCCAUGUGGUCCAGGAUAGCUAC | 6 | GUAGCUAUCCUGGACCACAUGGCUUUG | 406 |
| LPA-133 | AGCCAUGUGGUCCAGGAUUACUACC | 7 | GGUAGUAAUCCUGGACCACAUGGCUUU | 407 |
| LPA-134 | GCCAUGUGGUCCAGGAUUGAUACCA | 8 | UGGUAUCAAUCCUGGACCACAUGGCUU | 408 |
| LPA-135 | CCAUGUGGUCCAGGAUUGCAACCAT | 9 | AUGGUUGCAAUCCUGGACCACAUGGCU | 409 |
| LPA-136 | CAUGUGGUCCAGGAUUGCUACCATG | 10 | CAUGGUAGCAAUCCUGGACCACAUGGC | 410 |
| LPA-137 | AUGUGGUCCAGGAUUGCUACAUGG | 11 | CCAUGUUAGCAAUCCUGGACCACAUGG | 411 |
| LPA-138 | UGUGGUCCAGGAUUGCUACAAUGGT | 12 | ACCAUUGUAGCAAUCCUGGACCACAUG | 412 |
| LPA-160 | GGUGAUGGACAGAGUUAUCAAGGCA | 13 | UGCCUUGAUAACUCUGUCCAUCACCAU | 413 |
| LPA-190 | UCCACCACUGUCACAGGAAAGACCT | 14 | AGGUCUUUCCUGUGACAGUGGUGGAGU | 414 |
| LPA-191 | CCACCACUGUCACAGGAAGAACCTG | 15 | CAGGUUCUUCCUGUGACAGUGGUGGAG | 415 |
| LPA-197 | CUGUCACAGGAAGGACCUGACAAGC | 16 | GCUUGUCAGGUCCUUCCUGUGACAGUG | 416 |
| LPA-205 | GGAAGGACCUGCCAAGCUUAGUCAT | 17 | AUGACUAAGCUUGGCAGGUCCUUCCUG | 417 |
| LPA-206 | GAAGGACCUGCCAAGCUUGAUCATC | 18 | GAUGAUCAAGCUUGGCAGGUCCUUCCU | 418 |
| LPA-208 | AGGACCUGCCAAGCUUGGUAAUCTA | 19 | UAGAUUACCAAGCUUGGCAGGUCCUUC | 419 |
| LPA-209 | GGACCUGCCAAGCUUGGUCAUCUAT | 20 | AUAGAUGACCAAGCUUGGCAGGUCCUU | 420 |
| LPA-210 | GACCUGCCAAGCUUGGUCAACUATG | 21 | CAUAGUUGACCAAGCUUGGCAGGUCCU | 421 |
| LPA-211 | ACCUGCCAAGCUUGGUCAUAUAUGA | 22 | UCAUAUAUGACCAAGCUUGGCAGGUCC | 422 |
| LPA-212 | CCUGCCAAGCUUGGUCAUCAAUGAC | 23 | GUCAUUGAUGACCAAGCUUGGCAGGUC | 423 |
| LPA-219 | AGCUUGGUCAUCUAUGACAACACAT | 24 | AUGUGUUGUCAUAGAUGACCAAGCUUG | 424 |
| LPA-225 | GUCAUCUAUGACACCACAUAAACAT | 25 | AUGUUUAUGUGGUGUCAUAGAUGACCA | 425 |
| LPA-258 | CACAGAAAACUACCCAAAUACUGGC | 26 | GCCAGUAUUUGGGUAGUUUUCUGUGGU | 426 |
| LPA-261 | AGAAAACUACCCAAAUGCUAGCUTG | 27 | CAAGCUAGCAUUUGGGUAGUUUUCUGU | 427 |
| LPA-263 | AAAACUACCCAAAUGCUGGAUUGAT | 28 | AUCAAUCCAGCAUUUGGGUAGUUUUCU | 428 |

TABLE 5-continued

LPA Oligonucleotide Sequences (Unmodified)

| | | | | |
|---|---|---|---|---|
| LPA-269 | ACCCAAAUGCUGGCUUGAUAAUGAA | 29 | UUCAUUAUCAAGCCAGCAUUUGGGUAG | 429 |
| LPA-270 | CCCAAAUGCUGGCUUGAUCAUGAAC | 30 | GUUCAUGAUCAAGCCAGCAUUUGGGUA | 430 |
| LPA-291 | GAACUACUGCAGGAAUCCAAAUGCT | 31 | AGCAUUUGGAUUCCUGCAGUAGUUCAU | 431 |
| LPA-295 | UACUGCAGGAAUCCAGAUGAUGUGG | 32 | CCACAUCAUCUGGAUUCCUGCAGAGU | 432 |
| LPA-296 | ACUGCAGGAAUCCAGAUGCAGUGGC | 33 | GCCACUGCAUCUGGAUUCCUGCAGUAG | 433 |
| LPA-298 | UGCAGGAAUCCAGAUGCUGAGGCAG | 34 | CUGCCUCAGCAUCUGGAUUCCUGCAGU | 434 |
| LPA-355 | AGGUGGGAGUACUGCAACCAGACGC | 35 | GCGUCUGGUUGCAGUACUCCCACCUGA | 435 |
| LPA-380 | AAUGCUCAGACGCAGAAGGAACUGC | 36 | GCAGUUCCUUCUGCGUCUGAGCAUUGC | 436 |
| LPA-417 | GACUGUUACCCCGGUUCCAAGCCTA | 37 | UAGGCUUGGAACCGGGGUAACAGUCGG | 437 |
| LPA-418 | ACUGUUACCCCGGUUCCAAACCUAG | 38 | CUAGGUUUGGAACCGGGGUAACAGUCG | 438 |
| LPA-419 | CUGUUACCCCGGUUCCAAGACUAGA | 39 | UCUAGUCUUGGAACCGGGGUAACAGUC | 439 |
| LPA-420 | UGUUACCCCGGUUCCAAGCAUAGAG | 40 | CUCUAUGCUUGGAACCGGGGUAACAGU | 440 |
| LPA-421 | GUUACCCCGGUUCCAAGCCAAGAGG | 41 | CCUCUUGGCUUGGAACCGGGGUAACAG | 441 |
| LPA-422 | UUACCCCGGUUCCAAGCCUAGAGGC | 42 | GCCUCUAGGCUUGGAACCGGGGUAACA | 442 |
| LPA-423 | UACCCCGGUUCCAAGCCUAAAGGCT | 43 | AGCCUUUAGGCUUGGAACCGGGGUAAC | 443 |
| LPA-492 | GUGCUACCAUGGUAAUGGAAAGAGT | 44 | ACUCUUUCCAUUACCAUGGUAGCACUC | 444 |
| LPA-493 | UGCUACCAUGGUAAUGGACAGAGTT | 45 | AACUCUGUCCAUUACCAUGGUAGCACU | 445 |
| LPA-494 | GCUACCAUGGUAAUGGACAAAGUTA | 46 | UAACUUUGUCCAUUACCAUGGUAGCAC | 446 |
| LPA-495 | CUACCAUGGUAAUGGACAGAGUUAT | 47 | AUAACUCUGUCCAUUACCAUGGUAGCA | 447 |
| LPA-496 | UACCAUGGUAAUGGACAGAAUUAUC | 48 | GAUAAUUCUGUCCAUUACCAUGGUAGC | 448 |
| LPA-497 | ACCAUGGUAAUGGACAGAGAUAUCG | 49 | CGAUAUCUCUGUCCAUUACCAUGGUAG | 449 |
| LPA-498 | CCAUGGUAAUGGACAGAGUAAUCGA | 50 | UCGAUUACUCUGUCCAUUACCAUGGUA | 450 |
| LPA-499 | CAUGGUAAUGGACAGAGUUAUCGAG | 51 | CUCGAUAACUCUGUCCAUUACCAUGGU | 451 |
| LPA-500 | AUGGUAAUGGACAGAGUUACGAGG | 52 | CCUCGUUAACUCUGUCCAUUACCAUGG | 452 |
| LPA-501 | UGGUAAUGGACAGAGUUAUAGAGGC | 53 | GCCUCUAUAACUCUGUCCAUUACCAUG | 453 |
| LPA-502 | GGUAAUGGACAGAGUUAUCAAGGCA | 54 | UGCCUUGAUAACUCUGUCCAUUACCAU | 454 |

TABLE 5-continued

LPA Oligonucleotide Sequences (Unmodified)

| | | | | |
|---|---|---|---|---|
| LPA-503 | GUAAUGGACAGAGUUAUCGAGGCAC | 55 | GUGCCUCGAUAACUCUGUCCAUUACCA | 455 |
| LPA-523 | GGCACAUACUCCACCACUGACACAG | 56 | CUGUGUCAGUGGUGGAGUAUGUGCCUC | 456 |
| LPA-563 | CUUGGUCAUCUAUGACACCACACUC | 57 | GAGUGUGGUGUCAUAGAUGACCAAGCU | 457 |
| LPA-567 | GUCAUCUAUGACACCACACACGCAT | 58 | AUGCGUGUGGUGUCAUAGAUGACCA | 458 |
| LPA-568 | UCAUCUAUGACACCACACUAGCATA | 59 | UAUGCUAGUGUGGUGUCAUAGAUGACC | 459 |
| LPA-569 | CAUCUAUGACACCACACUCACAUAG | 60 | CUAUGUGAGUGUGGUGUCAUAGAUGAC | 460 |
| LPA-1208 | GCACAUACUCCACCACUGUAACUGG | 61 | CCAGUUACAGUGGUGGAGUAUGUGCCU | 461 |
| LPA-2715 | AGCCCCUUAUUGUUAUACGAGGGAT | 62 | AUCCCUCGUAUAACAAUAAGGGGCUGC | 462 |
| LPA-2716 | GCCCCUUAUUGUUAUACGAAGGATC | 63 | GAUCCUUCGUAUAACAAUAAGGGGCUG | 463 |
| LPA-2827 | CCAAGCCUAGAGGCUCCUUAUGAAC | 64 | GUUCAUAAGGAGCCUCUAGGCUUGGAA | 464 |
| LPA-2837 | AGGCUCCUUCUGAACAAGCACCAAC | 65 | GUUGGUGCUUGUUCAGAAGGAGCCUCU | 465 |
| LPA-2900 | AUGGACAGAGUUAUCAAGGAACATA | 66 | UAUGUUCCUUGAUAACUCUGUCCAUUU | 466 |
| LPA-2901 | UGGACAGAGUUAUCAAGGCACAUAC | 67 | GUAUGUGCCUUGAUAACUCUGUCCAUU | 467 |
| LPA-2902 | GGACAGAGUUAUCAAGGCAAAUACT | 68 | AGUAUUUGCCUUGAUAACUCUGUCCAU | 468 |
| LPA-2903 | GACAGAGUUAUCAAGGCACAUACTT | 69 | AAGUAUGUGCCUUGAUAACUCUGUCCA | 469 |
| LPA-2904 | ACAGAGUUAUCAAGGCACAAACUTC | 70 | GAAGUUUGUGCCUUGAUAACUCUGUCC | 470 |
| LPA-2905 | CAGAGUUAUCAAGGCACAUACUUCA | 71 | UGAAGUAUGUGCCUUGAUAACUCUGUC | 471 |
| LPA-3004 | UACCCAAAUGCUGGCUUGAACAAGA | 72 | UCUUGUUCAAGCCAGCAUUUGGGUAGU | 472 |
| LPA-3007 | CCAAAUGCUGGCUUGAUCAAGAACT | 73 | AGUUCUUGAUCAAGCCAGCAUUUGGGU | 473 |
| LPA-3023 | UCAAGAACUACUGCCGAAAACCAGA | 74 | UCUGGUUUUCGGCAGUAGUUCUUGAUC | 474 |
| LPA-3024 | CAAGAACUACUGCCGAAAUACAGAT | 75 | AUCUGUAUUUCGGCAGUAGUUCUUGAU | 475 |
| LPA-3025 | AAGAACUACUGCCGAAAUCAAGATC | 76 | GAUCUUGAUUUCGGCAGUAGUUCUUGA | 476 |
| LPA-3027 | GAACUACUGCCGAAAUCCAAAUCCT | 77 | AGGAUUUGGAUUUCGGCAGUAGUUCUU | 477 |
| LPA-3030 | CUACUGCCGAAAUCCAGAUACUGTG | 78 | CACAGUAUCGGAUUUCGGCAGUAGUU | 478 |
| LPA-3051 | UGUGGCAGCCCCUUGGUGUAAUACA | 79 | UGUAUUACACCAAGGGGCUGCCACAGG | 479 |
| LPA-3052 | GUGGCAGCCCCUUGGUGUUAUACAA | 80 | UUGUAUAACACCAAGGGGCUGCCACAG | 480 |

TABLE 5-continued

LPA Oligonucleotide Sequences (Unmodified)

| | | | | |
|---|---|---|---|---|
| LPA-3053 | UGGCAGCCCCUUGGUGUUAAA CAAC | 81 | GUUGUUUAACACCAAGGGGCUGCC ACA | 481 |
| LPA-3054 | GGCAGCCCCUUGGUGUUAUAC AACA | 82 | UGUUGUAUAACACCAAGGGGCUGC CAC | 482 |
| LPA-3055 | GCAGCCCCUUGGUGUUAUAAA ACAG | 83 | CUGUUUAUAACACCAAGGGGCUG CCA | 483 |
| LPA-3056 | CAGCCCCUUGGUGUUAUACAA CAGA | 84 | UCUGUUGUAUAACACCAAGGGGCU GCC | 484 |
| LPA-3057 | AGCCCCUUGGUGUUAUACAAC AGAT | 85 | AUCUGUUGUAUAACACCAAGGGGC UGC | 485 |
| LPA-3058 | GCCCCUUGGUGUUAUACAAAA GATC | 86 | GAUCUUUUGUAUAACACCAAGGGG CUG | 486 |
| LPA-3059 | CCCCUUGGUGUUAUACAACAG AUCC | 87 | GGAUCUGUUGUAUAACACCAAGGG GCU | 487 |
| LPA-3092 | GGUGGGAGUACUGCAACCUAA CACG | 88 | CGUGUUAGGUUGCAGUACUCCCAC CUG | 488 |
| LPA-3093 | GUGGGAGUACUGCAACCUGAC ACGA | 89 | UCGUGUCAGGUUGCAGUACUCCCA CCU | 489 |
| LPA-3096 | GGAGUACUGCAACCUGACAAG AUGC | 90 | GCAUCUUGUCAGGUUGCAGUACUC CCA | 490 |
| LPA-3097 | GAGUACUGCAACCUGACACAA UGCT | 91 | AGCAUUGUGUCAGGUUGCAGUACU CCC | 491 |
| LPA-3099 | GUACUGCAACCUGACACGAAG CUCA | 92 | UGAGCUUCGUGUCAGGUUGCAGUA CUC | 492 |
| LPA-3100 | UACUGCAACCUGACACGAUAC UCAG | 93 | CUGAGUAUCGUGUCAGGUUGCAGU ACU | 493 |
| LPA-3101 | ACUGCAACCUGACACGAUGAU CAGA | 94 | UCUGAUCAUCGUGUCAGGUUGCAG UAC | 494 |
| LPA-3102 | CUGCAACCUGACACGAUGCAC AGAT | 95 | AUCUGUGCAUCGUGUCAGGUUGCA GUA | 495 |
| LPA-3103 | UGCAACCUGACACGAUGCUAA GATG | 96 | CAUCUUAGCAUCGUGUCAGGUUGC AGU | 496 |
| LPA-3105 | CAACCUGACACGAUGCUCAAA UGCA | 97 | UGCAUUUGAGCAUCGUGUCAGGUU GCA | 497 |
| LPA-3107 | ACCUGACACGAUGCUCAGAAG CAGA | 98 | UCUGCUUCUGAGCAUCGUGUCAGG UUG | 498 |
| LPA-3108 | CCUGACACGAUGCUCAGAUAC AGAA | 99 | UUCUGUAUCUGAGCAUCGUGUCAG GUU | 499 |
| LPA-3109 | CUGACACGAUGCUCAGAUGAA GAAT | 100 | AUUCUUCAUCUGAGCAUCGUGUCA GGU | 500 |
| LPA-3110 | UGACACGAUGCUCAGAUGCAG AATG | 101 | CAUUCUGCAUCUGAGCAUCGUGUC AGG | 501 |
| LPA-3111 | GACACGAUGCUCAGAUGCAAA AUGG | 102 | CCAUUUUGCAUCUGAGCAUCGUGU CAG | 502 |
| LPA-3112 | ACACGAUGCUCAGAUGCAGAA UGGA | 103 | UCCAUUCUGCAUCUGAGCAUCGUG UCA | 503 |
| LPA-3113 | CACGAUGCUCAGAUGCAGAAU GGAC | 104 | GUCCAUUCUGCAUCUGAGCAUCGU GUC | 504 |
| LPA-3229 | UGCUACUACCAUUAUGGACAG AGTT | 105 | AACUCUGUCCAUAAUGGUAGUAGC AGU | 505 |
| LPA-3230 | GCUACUACCAUUAUGGACAAA GUTA | 106 | UAACUUUGUCCAUAAUGGUAGUAG CAG | 506 |

TABLE 5-continued

LPA Oligonucleotide Sequences (Unmodified)

| | | | | |
|---|---|---|---|---|
| LPA-3231 | CUACUACCAUUAUGGACAGAGUUAC | 107 | GUAACUCUGUCCAUAAUGGUAGUAGCA | 507 |
| LPA-3232 | UACUACCAUUAUGGACAGAAUUACC | 108 | GGUAAUUCUGUCCAUAAUGGUAGUAGC | 508 |
| LPA-3233 | ACUACCAUUAUGGACAGAGAUACCG | 109 | CGGUAUCUCUGUCCAUAAUGGUAG | 509 |
| LPA-3234 | CUACCAUUAUGGACAGAGUAACCGA | 110 | UCGGUUACUCUGUCCAUAAUGGUAGUA | 510 |
| LPA-3235 | UACCAUUAUGGACAGAGUUACCGAG | 111 | CUCGGUAACUCUGUCCAUAAUGGUAGU | 511 |
| LPA-3236 | ACCAUUAUGGACAGAGUUACGAGG | 112 | CCUCGUUAACUCUGUCCAUAAUGGUAG | 512 |
| LPA-3257 | GAGGCACAUACUCCACCACAGUCAC | 113 | GUGACUGUGGUGGAGUAUGUGCCUCGG | 513 |
| LPA-3267 | CUCCACCACUGUCACAGGAAGAACT | 114 | AGUUCUUCCUGUGACAGUGGUGGAGUA | 514 |
| LPA-3280 | ACAGGAAGAACUUGCCAAGAUUGGT | 115 | ACCAAUCUUGGCAAGUUCUUCCUGUGA | 515 |
| LPA-3281 | CAGGAAGAACUUGCCAAGCAUGGTC | 116 | GACCAUGCUUGGCAAGUUCUUCCUGUG | 516 |
| LPA-3282 | AGGAAGAACUUGCCAAGCUAGGUCA | 117 | UGACCUAGCUUGGCAAGUUCUUCCUGU | 517 |
| LPA-3283 | GGAAGAACUUGCCAAGCUUAGUCAT | 118 | AUGACUAAGCUUGGCAAGUUCUUCCUG | 518 |
| LPA-3284 | GAAGAACUUGCCAAGCUUGAUCATC | 119 | GAUGAUCAAGCUUGGCAAGUUCUUCCU | 519 |
| LPA-3285 | AAGAACUUGCCAAGCUUGGACAUCT | 120 | AGAUGUCCAAGCUUGGCAAGUUCUUCC | 520 |
| LPA-3286 | AGAACUUGCCAAGCUUGGUAAUCTA | 121 | UAGAUUACCAAGCUUGGCAAGUUCUUC | 521 |
| LPA-3287 | GAACUUGCCAAGCUUGGUCAUCUAT | 122 | AUAGAUGACCAAGCUUGGCAAGUUCUU | 522 |
| LPA-3288 | AACUUGCCAAGCUUGGUCAACUATG | 123 | CAUAGUUGACCAAGCUUGGCAAGUUCU | 523 |
| LPA-3289 | ACUUGCCAAGCUUGGUCAUAUAUGA | 124 | UCAUAUAUGACCAAGCUUGGCAAGUUC | 524 |
| LPA-3290 | CUUGCCAAGCUUGGUCAUCAAUGAC | 125 | GUCAUUGAUGACCAAGCUUGGCAAGUU | 525 |
| LPA-3291 | UUGCCAAGCUUGGUCAUCUAUGACA | 126 | UGCAUAGAUGACCAAGCUUGGCAAGU | 526 |
| LPA-3292 | UGCCAAGCUUGGUCAUCUAAGACAC | 127 | GUGUCUUAGAUGACCAAGCUUGGCAAG | 527 |
| LPA-3298 | GCUUGGUCAUCUAUGACACAACACC | 128 | GGUGUUGUGUCAUAGAUGACCAAGCUU | 528 |
| LPA-3300 | UUGGUCAUCUAUGACACCAAACCAG | 129 | CUGGUUUGGUGUCAUAGAUGACCAAGC | 529 |
| LPA-3301 | UGGUCAUCUAUGACACCACACAGC | 130 | GCUGGUGGUGUCAUAGAUGACCAAG | 530 |
| LPA-3303 | GUCAUCUAUGACACCACACAAGCAT | 131 | AUGCUUGUGUGGUGUCAUAGAUGACCA | 531 |
| LPA-3305 | CAUCUAUGACACCACACCAACAUAG | 132 | CUAUGUUGGUGUGGUGUCAUAGAUGAC | 532 |

TABLE 5-continued

LPA Oligonucleotide Sequences (Unmodified)

| | | | | |
|---|---|---|---|---|
| LPA-3306 | AUCUAUGACACCACACCAGAAUAGT | 133 | ACUAUUCUGGUGUGGUGUCAUAGAUGA | 533 |
| LPA-3308 | CUAUGACACCACACCAGCAAAGUCG | 134 | CGACUUUGCUGGUGUGGUGUCAUAGAU | 534 |
| LPA-3329 | GUCGGACCCCAGAAAACUAACCAAA | 135 | UUUGGUUAGUUUUCUGGGGUCCGACUA | 535 |
| LPA-3330 | UCGGACCCCAGAAAACUACACAAAT | 136 | AUUUGUGUAGUUUUCUGGGGUCCGACU | 536 |
| LPA-3340 | GAAAACUACCCAAAUGCUGACCUGA | 137 | UCAGGUCAGCAUUUGGGUAGUUUUCUG | 537 |
| LPA-3391 | GCUGAGAUUCGCCCUUGGUAUUACA | 138 | UGUAAUACCAAGGGCGAAUCUCAGCAU | 538 |
| LPA-3392 | CUGAGAUUCGCCCUUGGUGAUACAC | 139 | GUGUAUCACCAAGGGCGAAUCUCAGCA | 539 |
| LPA-3394 | GAGAUUCGCCCUUGGUGUUACACCA | 140 | UGGUGUAACACCAAGGGCGAAUCUCAG | 540 |
| LPA-3395 | AGAUUCGCCCUUGGUGUUAAACCAT | 141 | AUGGUUUAACACCAAGGGCGAAUCUCA | 541 |
| LPA-3398 | UUCGCCCUUGGUGUUACACAAUGGA | 142 | UCCAUUGUGUAACACCAAGGGCGAAUC | 542 |
| LPA-3404 | CUUGGUGUUACACCAUGGAACCCAG | 143 | CUGGGUUCCAUGGUGUAACACCAAGGG | 543 |
| LPA-3405 | UUGGUGUUACACCAUGGAUACCAGT | 144 | ACUGGUAUCCAUGGUGUAACACCAAGG | 544 |
| LPA-3406 | UGGUGUUACACCAUGGAUCACAGTG | 145 | CACUGUGAUCCAUGGUGUAACACCAAG | 545 |
| LPA-3407 | GGUGUUACACCAUGGAUCCAAGUGT | 146 | ACACUUGGAUCCAUGGUGUAACACCAA | 546 |
| LPA-3409 | UGUUACACCAUGGAUCCCAAUGUCA | 147 | UGACAUUGGGAUCCAUGGUGUAACACC | 547 |
| LPA-3472 | GAAUCAAGUGUCCUUGCAAAUCUCA | 148 | UGAGAUUUGCAAGGACACUUGAUUCUG | 548 |
| LPA-3473 | AAUCAAGUGUCCUUGCAACACUCAC | 149 | GUGAGUGUUGCAAGGACACUUGAUUCU | 549 |
| LPA-3474 | AUCAAGUGUCCUUGCAACUAUCACG | 150 | CGUGAUAGUUGCAAGGACACUUGAUUC | 550 |
| LPA-3584 | AUGGACAGAGUUAUCGAGGAUCATT | 151 | AAUGAUCCUCGAUAACUCUGUCCAUCA | 551 |
| LPA-3585 | UGGACAGAGUUAUCGAGGCACAUTC | 152 | GAAUGUGCCUCGAUAACUCUGUCCAUC | 552 |
| LPA-3655 | ACACCACACUGGCAUCAGAAGACAA | 153 | UUGUCUUCUGAUGCCAGUGUGGUGUCA | 553 |
| LPA-3747 | UUGGUGUUAUACCAUGGAUACCAAT | 154 | AUUGGUAUCCAUGGUAUAACACCAAGG | 554 |
| LPA-3748 | UGGUGUUAUACCAUGGAUCACAATG | 155 | CAUUGUGAUCCAUGGUAUAACACCAAG | 555 |
| LPA-3749 | GGUGUUAUACCAUGGAUCCAAUGT | 156 | ACAUUUGGAUCCAUGGUAUAACACCAA | 556 |
| LPA-3750 | GUGUUAUACCAUGGAUCCCAAUGTC | 157 | GACAUUGGGAUCCAUGGUAUAACACCA | 557 |
| LPA-3773 | UCAGAUGGGAGUACUGCAAACUGAC | 158 | GUCAGUUUGCAGUACUCCCAUCUGACA | 558 |

TABLE 5-continued

LPA Oligonucleotide Sequences (Unmodified)

| | | | | |
|---|---|---|---|---|
| LPA-3776 | GAUGGGAGUACUGCAACCUAACACA | 159 | UGUGUUAGGUUGCAGUACUCCCAUCUG | 559 |
| LPA-3777 | AUGGGAGUACUGCAACCUGACACAA | 160 | UUGUGUCAGGUUGCAGUACUCCCAUCU | 560 |
| LPA-3778 | UGGGAGUACUGCAACCUGAAACAAT | 161 | AUUGUUUCAGGUUGCAGUACUCCCAUC | 561 |
| LPA-3779 | GGGAGUACUGCAACCUGACACAAUG | 162 | CAUUGUGUCAGGUUGCAGUACUCCCAU | 562 |
| LPA-3840 | GGCUGUUUCUGAACAAGCAACAACG | 163 | CGUUGUUGCUUGUUCAGAAACAGCCGU | 563 |
| LPA-3844 | GUUUCUGAACAAGCACCAAGGAGC | 164 | GCUCCUUUGGUGCUUGUUCAGAAACAG | 564 |
| LPA-3927 | CUCCACCACUGUUACAGGAAGACA | 165 | UGUCCUUCCUGUAACAGUGGUGGAGAA | 565 |
| LPA-3928 | UCCACCACUGUUACAGGAAGACAT | 166 | AUGUCUUUCCUGUAACAGUGGUGGAGA | 566 |
| LPA-3929 | CCACCACUGUUACAGGAAGACATG | 167 | CAUGUUCUUCCUGUAACAGUGGUGGAG | 567 |
| LPA-3972 | GACACCACUGGCAUCAGAGAACC | 168 | GGUUCUCUGAUGCCAGUGUGGUGUCAU | 568 |
| LPA-3973 | ACACCACUGGCAUCAGAAAACCA | 169 | UGGUUUUCUGAUGCCAGUGUGGUGUCA | 569 |
| LPA-3999 | AGAAUACUACCCAAAUGGUAGCCTG | 170 | CAGGCUACCAUUUGGGUAGUAUUCUGU | 570 |
| LPA-4000 | GAAUACUACCCAAAUGGUGACCUGA | 171 | UCAGGUCACCAUUUGGGUAGUAUUCUG | 571 |
| LPA-4001 | AAUACUACCCAAAUGGUGGACUGAC | 172 | GUCAGUCCACCAUUUGGGUAGUAUUCU | 572 |
| LPA-4185 | UCCUUCUGAAGAAGCACCAACUGAA | 173 | UUCAGUUGGUGCUUCUUCAGAAGGAAG | 573 |
| LPA-4186 | CCUUCUGAAGAAGCACCAAAUGAAA | 174 | UUUCAUUUGGUGCUUCUUCAGAAGGAA | 574 |
| LPA-4187 | CUUCUGAAGAAGCACCAACAGAAAA | 175 | UUUUCUGUUGGUGCUUCUUCAGAAGGA | 575 |
| LPA-4188 | UUCUGAAGAAGCACCAACUAAAAAC | 176 | GUUUUUAGUUGGUGCUUCUUCAGAAGG | 576 |
| LPA-4189 | UCUGAAGAAGCACCAACUGAAAACA | 177 | UGUUUUCAGUUGGUGCUUCUUCAGAAG | 577 |
| LPA-4190 | CUGAAGAAGCACCAACUGAAACAG | 178 | CUGUUUUCAGUUGGUGCUUCUUCAGAA | 578 |
| LPA-4191 | UGAAGAAGCACCAACUGAAAACAGC | 179 | GCUGUUUUCAGUUGGUGCUUCUUCAGA | 579 |
| LPA-4192 | GAAGAAGCACCAACUGAAAACAGCA | 180 | UGCUGUUUUCAGUUGGUGCUUCUUCAG | 580 |
| LPA-4193 | AAGAAGCACCAACUGAAAAAAGCAC | 181 | GUGCUUUUUUCAGUUGGUGCUUCUUCA | 581 |
| LPA-4194 | AGAAGCACCAACUGAAAACAGCACT | 182 | AGUGCUGUUUUCAGUUGGUGCUUCUUC | 582 |
| LPA-4195 | GAAGCACCAACUGAAAACAACACTG | 183 | CAGUGUUGUUUUCAGUUGGUGCUUCUU | 583 |
| LPA-4196 | AAGCACCAACUGAAAACAGAACUGG | 184 | CCAGUUCUGUUUUCAGUUGGUGCUUCU | 584 |

TABLE 5-continued

LPA Oligonucleotide Sequences (Unmodified)

| | | | | |
|---|---|---|---|---|
| LPA-4239 | AGGUGAUGGACAGAGUUAUAGAGGC | 185 | GCCUCUAUAACUCUGUCCAUCACCUCG | 585 |
| LPA-4269 | CUCCACCACUAUCACAGGAAGAACA | 186 | UGUUCUUCCUGUGAUAGUGGUGGAGAG | 586 |
| LPA-4270 | UCCACCACUAUCACAGGAAAAACAT | 187 | AUGUUUUUCCUGUGAUAGUGGUGGAGA | 587 |
| LPA-4271 | CCACCACUAUCACAGGAAGAACATG | 188 | CAUGUUCUUCCUGUGAUAGUGGUGGAG | 588 |
| LPA-4272 | CACCACUAUCACAGGAAGAACAUGT | 189 | ACAUGUUCUUCCUGUGAUAGUGGUGGA | 589 |
| LPA-4273 | ACCACUAUCACAGGAAGAAAAUGTC | 190 | GACAUUUUCUUCCUGUGAUAGUGGUGG | 590 |
| LPA-4274 | CCACUAUCACAGGAAGAACAUGUCA | 191 | UGACAUGUUCUUCCUGUGAUAGUGGUG | 591 |
| LPA-4275 | CACUAUCACAGGAAGAACAAGUCAG | 192 | CUGACUUGUUCUUCCUGUGAUAGUGGU | 592 |
| LPA-4276 | ACUAUCACAGGAAGAACAUAUCAGT | 193 | ACUGAUAUGUUCUUCCUGUGAUAGUGG | 593 |
| LPA-4277 | CUAUCACAGGAAGAACAUGACAGTC | 194 | GACUGUCAUGUUCUUCCUGUGAUAGUG | 594 |
| LPA-4278 | UAUCACAGGAAGAACAUGUAAGUCT | 195 | AGACUUACAUGUUCUUCCUGUGAUAGU | 595 |
| LPA-4279 | AUCACAGGAAGAACAUGUCAGUCTT | 196 | AAGACUGACAUGUUCUUCCUGUGAUAG | 596 |
| LPA-4280 | UCACAGGAAGAACAUGUCAAUCUTG | 197 | CAAGAUUGACAUGUUCUUCCUGUGAUA | 597 |
| LPA-4281 | CACAGGAAGAACAUGUCAGACUUGG | 198 | CCAAGUCUGACAUGUUCUUCCUGUGAU | 598 |
| LPA-4282 | ACAGGAAGAACAUGUCAGUAUUGGT | 199 | ACCAAUACUGACAUGUUCUUCCUGUGA | 599 |
| LPA-4285 | GGAAGAACAUGUCAGUCUUAGUCGT | 200 | ACGACUAAGACUGACAUGUUCUUCCUG | 600 |
| LPA-4286 | GAAGAACAUGUCAGUCUUGAUCGTC | 201 | GACGAUCAAGACUGACAUGUUCUUCCU | 601 |
| LPA-4287 | AAGAACAUGUCAGUCUUGGACGUCT | 202 | AGACGUCCAAGACUGACAUGUUCUUCC | 602 |
| LPA-4288 | AGAACAUGUCAGUCUUGGUAGUCTA | 203 | UAGACUACCAAGACUGACAUGUUCUUC | 603 |
| LPA-4325 | GGCAUCGGAGGAUCCCAUUAUACTA | 204 | UAGUAUAAUGGGAUCCUCCGAUGCCAA | 604 |
| LPA-4346 | ACUAUCCAAAUGCUGGCCUAACCAG | 205 | CUGGUUAGGCCAGCAUUUGGAUAGUAU | 605 |
| LPA-4517 | GCACAGAGGCUCCUUCUGAACAAGC | 206 | GCUUGUUCAGAAGGAGCCUCUGUGCUU | 606 |
| LPA-4527 | UCCUUCUGAACAAGCACCAACUGAG | 207 | CUCAGUUGGUGCUUGUUCAGAAGGAGC | 607 |
| LPA-4528 | CCUUCUGAACAAGCACCACAUGAGA | 208 | UCUCAUGUGGUGCUUGUUCAGAAGGAG | 608 |
| LPA-4529 | CUUCUGAACAAGCACCACCAGAGAA | 209 | UUCUCUGGUGGUGCUUGUUCAGAAGGA | 609 |
| LPA-4530 | UUCUGAACAAGCACCACCUAAGAAA | 210 | UUUCUUAGGUGGUGCUUGUUCAGAAGG | 610 |

TABLE 5-continued

LPA Oligonucleotide Sequences (Unmodified)

| | | | | |
|---|---|---|---|---|
| LPA-4531 | UCUGAACAAGCACCACCUGAGAAAA | 211 | UUUUCUCAGGUGGUGCUUGUUCAGAAG | 611 |
| LPA-4532 | CUGAACAAGCACCACCUGAAAAAAG | 212 | CUUUUUUCAGGUGGUGCUUGUUCAGAA | 612 |
| LPA-4533 | UGAACAAGCACCACCUGAGAAAAGC | 213 | GCUUUUCUCAGGUGGUGCUUGUUCAGA | 613 |
| LPA-4534 | GAACAAGCACCACCUGAGAAAAGCC | 214 | GGCUUUUCUCAGGUGGUGCUUGUUCAG | 614 |
| LPA-4535 | AACAAGCACCACCUGAGAAAAGCCC | 215 | GGGCUUUUCUCAGGUGGUGCUUGUUCA | 615 |
| LPA-4537 | CAAGCACCACCUGAGAAAAACCCTG | 216 | CAGGGUUUUCUCAGGUGGUGCUUGUU | 616 |
| LPA-4538 | AAGCACCACCUGAGAAAAGACCUGT | 217 | ACAGGUCUUUUCUCAGGUGGUGCUUGU | 617 |
| LPA-4539 | AGCACCACCUGAGAAAAGCACUGTG | 218 | CACAGUGCUUUUCUCAGGUGGUGCUUG | 618 |
| LPA-4547 | CUGAGAAAAGCCCUGUGGUACAGGA | 219 | UCCUGUACCACAGGGCUUUUCUCAGGU | 619 |
| LPA-4556 | GCCCUGUGGUCCAGGAUUGAUACCA | 220 | UGGUAUCAAUCCUGGACCACAGGGCUU | 620 |
| LPA-4559 | CUGUGGUCCAGGAUUGCUAACAUGG | 221 | CCAUGUUAGCAAUCCUGGACCACAGGG | 621 |
| LPA-4611 | CUCCACCACUGUCACAGGAAGGACC | 222 | GGUCCUUCCUGUGACAGUGGUGGAGGA | 622 |
| LPA-4612 | UCCACCACUGUCACAGGAAAGACCT | 223 | AGGUCUUUCCUGUGACAGUGGUGGAGG | 623 |
| LPA-4642 | UCUUGGUCAUCUAUGAUACAACACT | 224 | AGUGUUGUAUCAUAGAUGACCAAGAUU | 624 |
| LPA-4643 | CUUGGUCAUCUAUGAUACCACACTG | 225 | CAGUGUGGUAUCAUAGAUGACCAAGAU | 625 |
| LPA-4644 | UUGGUCAUCUAUGAUACCAAACUGG | 226 | CCAGUUUGGUAUCAUAGAUGACCAAGA | 626 |
| LPA-4645 | UGGUCAUCUAUGAUACCACACUGGC | 227 | GCCAGUGUGGUAUCAUAGAUGACCAAG | 627 |
| LPA-4646 | GGUCAUCUAUGAUACCACAAUGGCA | 228 | UGCCAUUGUGGUAUCAUAGAUGACCAA | 628 |
| LPA-4647 | GUCAUCUAUGAUACCACACAGGCAT | 229 | AUGCCUGUGUGGUAUCAUAGAUGACCA | 629 |
| LPA-4648 | UCAUCUAUGAUACCACACUAGCATC | 230 | GAUGCUAGUGUGGUAUCAUAGAUGACC | 630 |
| LPA-4649 | CAUCUAUGAUACCACACUGACAUCA | 231 | UGAUGUCAGUGUGGUAUCAUAGAUGAC | 631 |
| LPA-4650 | AUCUAUGAUACCACACUGGAAUCAG | 232 | CUGAUUCCAGUGUGGUAUCAUAGAUGA | 632 |
| LPA-4651 | UCUAUGAUACCACACUGGCAUCAGA | 233 | UCUGAUGCCAGUGUGGUAUCAUAGAUG | 633 |
| LPA-4652 | CUAUGAUACCACACUGGCAACAGAG | 234 | CUCUGUUGCCAGUGUGGUAUCAUAGAU | 634 |
| LPA-4655 | UGAUACCACACUGGCAUCAAAGGAC | 235 | GUCCUUUGAUGCCAGUGUGGUAUCAUA | 635 |
| LPA-4657 | AUACCACACUGGCAUCAGAAGACCC | 236 | GGGUCUUCUGAUGCCAGUGUGGUAUCA | 636 |

TABLE 5-continued

LPA Oligonucleotide Sequences (Unmodified)

| | | | | |
|---|---|---|---|---|
| LPA-4673 | AGAGGACCCCAGAAAACUAACCAAA | 237 | UUUGGUUAGUUUUCUGGGGUCCUCUGA | 637 |
| LPA-4674 | GAGGACCCCAGAAAACUACACAAAT | 238 | AUUUGUGUAGUUUUCUGGGGUCCUCUG | 638 |
| LPA-4712 | AGAACUACUGCAGGAAUCCAGAUC | 239 | GAAUCUGGAUUCCUGCAGUAGUUCUCG | 639 |
| LPA-4715 | ACUACUGCAGGAAUCCAGAAUCUGG | 240 | CCAGAUUCUGGAUUCCUGCAGUAGUUC | 640 |
| LPA-4717 | UACUGCAGGAAUCCAGAUUAUGGGA | 241 | UCCCAUAAUCUGGAUUCCUGCAGUAGU | 641 |
| LPA-4718 | ACUGCAGGAAUCCAGAUUCAGGGAA | 242 | UUCCCUGAAUCUGGAUUCCUGCAGUAG | 642 |
| LPA-4719 | CUGCAGGAAUCCAGAUUCUAGGAAA | 243 | UUUCCUAGAAUCUGGAUUCCUGCAGUA | 643 |
| LPA-4720 | UGCAGGAAUCCAGAUUCUGAGAAAC | 244 | GUUUCUCAGAAUCUGGAUUCCUGCAGU | 644 |
| LPA-4721 | GCAGGAAUCCAGAUUCUGGAAACA | 245 | UGUUUUCCAGAAUCUGGAUUCCUGCAG | 645 |
| LPA-4724 | GGAAUCCAGAUUCUGGGAAACAACC | 246 | GGUUGUUUCCCAGAAUCUGGAUUCCUG | 646 |
| LPA-4738 | GGGAAACAACCCUGGUGUUACACAA | 247 | UUGUGUAACACCAGGGUUGUUUCCCAG | 647 |
| LPA-4739 | GGAAACAACCCUGGUGUUAAACAAC | 248 | GUUGUUUAACACCAGGGUUGUUUCCCA | 648 |
| LPA-4771 | UGUGUGAGGUGGGAGUACUACAAUC | 249 | GAUUGUAGUACUCCCACCUCACACACG | 649 |
| LPA-4772 | GUGUGAGGUGGGAGUACUGAAAUCT | 250 | AGAUUUCAGUACUCCCACCUCACACAC | 650 |
| LPA-4774 | GUGAGGUGGGAGUACUGCAAUCUGA | 251 | UCAGAUUGCAGUACUCCCACCUCACAC | 651 |
| LPA-4775 | UGAGGUGGGAGUACUGCAAACUGAC | 252 | GUCAGUUUGCAGUACUCCCACCUCACA | 652 |
| LPA-4795 | CUGACACAAUGCUCAGAAAAGAAT | 253 | AUUCUUUUCUGAGCAUUGUGUCAGAU | 653 |
| LPA-4796 | UGACACAAUGCUCAGAAACAGAATC | 254 | GAUUCUGUUUCUGAGCAUUGUGUCAGA | 654 |
| LPA-4797 | GACACAAUGCUCAGAAACAAAAUCA | 255 | UGAUUUUGUUUCUGAGCAUUGUGUCAG | 655 |
| LPA-4798 | ACACAAUGCUCAGAAACAGAAUCAG | 256 | CUGAUUCUGUUUCUGAGCAUUGUGUCA | 656 |
| LPA-4799 | CACAAUGCUCAGAAACAGAAUCAGG | 257 | CCUGAUUCUGUUUCUGAGCAUUGUGUC | 657 |
| LPA-4800 | ACAAUGCUCAGAAACAGAAACAGGT | 258 | ACCUGUUUCUGUUUCUGAGCAUUGUGU | 658 |
| LPA-4801 | CAAUGCUCAGAAACAGAAUAAGGTG | 259 | CACCUUAUUCUGUUUCUGAGCAUUGUG | 659 |
| LPA-4802 | AAUGCUCAGAAACAGAAUCAGGUGT | 260 | ACACCUGAUUCUGUUUCUGAGCAUUGU | 660 |
| LPA-4803 | AUGCUCAGAAACAGAAUCAAGUGUC | 261 | GACACUUGAUUCUGUUUCUGAGCAUUG | 661 |
| LPA-4804 | UGCUCAGAAACAGAAUCAGAUGUCC | 262 | GGACAUCUGAUUCUGUUUCUGAGCAUU | 662 |

TABLE 5-continued

LPA Oligonucleotide Sequences (Unmodified)

| | | | | |
|---|---|---|---|---|
| LPA-4806 | CUCAGAAACAGAAUCAGGUAU CCTA | 263 | UAGGAUACCUGAUUCUGUUUCUGA GCA | 663 |
| LPA-4808 | CAGAAACAGAAUCAGGUGUAC UAGA | 264 | UCUAGUACACCUGAUUCUGUUUCU GAG | 664 |
| LPA-4809 | AGAAACAGAAUCAGGUGUCAU AGAG | 265 | CUCUAUGACACCUGAUUCUGUUUC UGA | 665 |
| LPA-4810 | GAAACAGAAUCAGGUGUCCAA GAGA | 266 | UCUCUUGGACACCUGAUUCUGUUU CUG | 666 |
| LPA-4811 | AAACAGAAUCAGGUGUCCUAG AGAC | 267 | GUCUCUAGGACACCUGAUUCUGUU UCU | 667 |
| LPA-4812 | AACAGAAUCAGGUGUCCUAAA GACT | 268 | AGUCUUUAGGACACCUGAUUCUGU UUC | 668 |
| LPA-4814 | CAGAAUCAGGUGUCCUAGAAA CUCC | 269 | GGAGUUUCUAGGACACCUGAUUCU GUU | 669 |
| LPA-4816 | GAAUCAGGUGUCCUAGAGAAU CCCA | 270 | UGGGAUUCUCUAGGACACCUGAUU CUG | 670 |
| LPA-4818 | AUCAGGUGUCCUAGAGACUAC CACT | 271 | AGUGGUAGUCUCUAGGACACCUGA UUC | 671 |
| LPA-4822 | GGUGUCCUAGAGACUCCCAAU GUTG | 272 | CAACAUUGGGAGUCUCUAGGACAC CUG | 672 |
| LPA-4827 | CCUAGAGACUCCCACUGUUAU UCCA | 273 | UGGAAUAACAGUGGGAGUCUCUAG GAC | 673 |
| LPA-4828 | CUAGAGACUCCCACUGUUGAU CCAG | 274 | CUGGAUCAACAGUGGGAGUCUCUA GGA | 674 |
| LPA-4829 | UAGAGACUCCCACUGUUGUAC CAGT | 275 | ACUGGUACAACAGUGGGAGUCUCU AGG | 675 |
| LPA-4830 | AGAGACUCCCACUGUUGUUAC AGTT | 276 | AACUGUAACAACAGUGGGAGUCUC UAG | 676 |
| LPA-4831 | GAGACUCCCACUGUUGUUCAA GUTC | 277 | GAACUUGAACAACAGUGGGAGUCU CUA | 677 |
| LPA-4832 | AGACUCCCACUGUUGUUCCAG UUCC | 278 | GGAACUGGAACAACAGUGGGAGUC UCU | 678 |
| LPA-4867 | GCUCAUUCUGAAGCAGCACAA ACTG | 279 | CAGUUUGUGCUGCUUCAGAAUGAG CCU | 679 |
| LPA-4868 | CUCAUUCUGAAGCAGCACCAA CUGA | 280 | UCAGUUGGUGCUGCUUCAGAAUGA GCC | 680 |
| LPA-4869 | UCAUUCUGAAGCAGCACCAAC UGAG | 281 | CUCAGUUGGUGCUGCUUCAGAAUG AGC | 681 |
| LPA-4870 | CAUUCUGAAGCAGCACCAAAU GAGC | 282 | GCUCAUUUGGUGCUGCUUCAGAAU GAG | 682 |
| LPA-4871 | AUUCUGAAGCAGCACCAACAG AGCA | 283 | UGCUCUGUUGGUGCUGCUUCAGAA UGA | 683 |
| LPA-4872 | UUCUGAAGCAGCACCAACUAA GCAA | 284 | UUGCUUAGUUGGUGCUGCUUCAGA AUG | 684 |
| LPA-4873 | UCUGAAGCAGCACCAACUGAG CAAA | 285 | UUUGCUCAGUUGGUGCUGCUUCAG AAU | 685 |
| LPA-4874 | CUGAAGCAGCACCAACUGAAC AAAC | 286 | GUUUGUUCAGUUGGUGCUGCUUCA GAA | 686 |
| LPA-4875 | UGAAGCAGCACCAACUGAGAA AACC | 287 | GGUUUUCUCAGUUGGUGCUGCUUC AGA | 687 |
| LPA-4876 | GAAGCAGCACCAACUGAGCAA ACCC | 288 | GGGUUUGCUCAGUUGGUGCUGCUU CAG | 688 |

TABLE 5-continued

LPA Oligonucleotide Sequences (Unmodified)

| | | | | |
|---|---|---|---|---|
| LPA-4877 | AAGCAGCACCAACUGAGCAAA CCCC | 289 | GGGGUUUGCUCAGUUGGUGCUGCU UCA | 689 |
| LPA-4912 | CAGUGCUACCAUGGUAAUGAC CAGA | 290 | UCUGGUCAUUACCAUGGUAGCACU GCC | 690 |
| LPA-4913 | AGUGCUACCAUGGUAAUGGAC AGAG | 291 | CUCUGUCCAUUACCAUGGUAGCAC UGC | 691 |
| LPA-4948 | ACAUUCUCCACCACUGUCAAA GGAA | 292 | UUCCUUUGACAGUGGUGGAGAAUG UGC | 692 |
| LPA-4959 | CACUGUCACAGGAAGGACAAG UCAA | 293 | UUGACUUGUCCUUCCUGUGACAGU GGU | 693 |
| LPA-4960 | ACUGUCACAGGAAGGACAUAU CAAT | 294 | AUUGAUAUGUCCUUCCUGUGACAG UGG | 694 |
| LPA-4961 | CUGUCACAGGAAGGACAUGAC AATC | 295 | GAUUGUCAUGUCCUUCCUGUGACA GUG | 695 |
| LPA-4962 | UGUCACAGGAAGGACAUGUAA AUCT | 296 | AGAUUUACAUGUCCUUCCUGUGAC AGU | 696 |
| LPA-4963 | GUCACAGGAAGGACAUGUCAA UCTT | 297 | AAGAUUGACAUGUCCUUCCUGUGA CAG | 697 |
| LPA-4964 | UCACAGGAAGGACAUGUCAAU CUTG | 298 | CAAGAUUGACAUGUCCUUCCUGUG ACA | 698 |
| LPA-4966 | ACAGGAAGGACAUGUCAAUAU UGGT | 299 | ACCAAUAUUGACAUGUCCUUCCUG UGA | 699 |
| LPA-4967 | CAGGAAGGACAUGUCAAUCAU GGTC | 300 | GACCAUGAUUGACAUGUCCUUCCU GUG | 700 |
| LPA-4968 | AGGAAGGACAUGUCAAUCUAG GUCA | 301 | UGACCUAGAUUGACAUGUCCUUCC UGU | 701 |
| LPA-4969 | GGAAGGACAUGUCAAUCUUAG UCAT | 302 | AUGACUAAGAUUGACAUGUCCUUC CUG | 702 |
| LPA-4970 | GAAGGACAUGUCAAUCUUGAU CATC | 303 | GAUGAUCAAGAUUGACAUGUCCUU CCU | 703 |
| LPA-4971 | AAGGACAUGUCAAUCUUGGAC AUCC | 304 | GGAUGUCCAAGAUUGACAUGUCCU UCC | 704 |
| LPA-4972 | AGGACAUGUCAAUCUUGGUAA UCCA | 305 | UGGAUUACCAAGAUUGACAUGUCC UUC | 705 |
| LPA-4973 | GGACAUGUCAAUCUUGGUCAU CCAT | 306 | AUGGAUGACCAAGAUUGACAUGUC CUU | 706 |
| LPA-4974 | GACAUGUCAAUCUUGGUCAAC CATG | 307 | CAUGGUUGACCAAGAUUGACAUGU CCU | 707 |
| LPA-4975 | ACAUGUCAAUCUUGGUCAUAC AUGA | 308 | UCAUGUAUGACCAAGAUUGACAUG UCC | 708 |
| LPA-4976 | CAUGUCAAUCUUGGUCAUCAA UGAC | 309 | GUCAUUGAUGACCAAGAUUGACAU GUC | 709 |
| LPA-4977 | AUGUCAAUCUUGGUCAUCCAU GACA | 310 | UGUCAUGGAUGACCAAGAUUGACA UGU | 710 |
| LPA-4978 | UGUCAAUCUUGGUCAUCCAAG ACAC | 311 | GUGUCUUGGAUGACCAAGAUUGAC AUG | 711 |
| LPA-4979 | GUCAAUCUUGGUCAUCCAUAA CACC | 312 | GGUGUUAUGGAUGACCAAGAUUGA CAU | 712 |
| LPA-4980 | UCAAUCUUGGUCAUCCAUGAC ACCA | 313 | UGGUGUCAUGGAUGACCAAGAUUG ACA | 713 |
| LPA-4981 | CAAUCUUGGUCAUCCAUGAAA CCAC | 314 | GUGGUUUCAUGGAUGACCAAGAUU GAC | 714 |

TABLE 5-continued

LPA Oligonucleotide Sequences (Unmodified)

| LPA-4982 | AAUCUUGGUCAUCCAUGACAC CACA | 315 | UGUGGUGUCAUGGAUGACCAAGAU UGA | 715 |
|---|---|---|---|---|
| LPA-4983 | AUCUUGGUCAUCCAUGACAAC ACAC | 316 | GUGUGUUGUCAUGGAUGACCAAGA UUG | 716 |
| LPA-5048 | UGACAAUGAACUACUGCAGAA AUCC | 317 | GGAUUUCUGCAGUAGUUCAUUGUC AGG | 717 |
| LPA-5049 | GACAAUGAACUACUGCAGGAA UCCA | 318 | UGGAUUCCUGCAGUAGUUCAUUGU CAG | 718 |
| LPA-5050 | ACAAUGAACUACUGCAGGAAU CCAG | 319 | CUGGAUUCCUGCAGUAGUUCAUUG UCA | 719 |
| LPA-5051 | CAAUGAACUACUGCAGGAAAC CAGA | 320 | UCUGGUUUCCUGCAGUAGUUCAUU GUC | 720 |
| LPA-5052 | AAUGAACUACUGCAGGAAUAC AGAT | 321 | AUCUGUAUUCCUGCAGUAGUUCAU UGU | 721 |
| LPA-5053 | AUGAACUACUGCAGGAAUCAA GATG | 322 | CAUCUUGAUUCCUGCAGUAGUUCA UUG | 722 |
| LPA-5054 | UGAACUACUGCAGGAAUCCAG AUGC | 323 | GCAUCUGGAUUCCUGCAGUAGUUC AUU | 723 |
| LPA-5058 | CUACUGCAGGAAUCCAGAUAC CGAT | 324 | AUCGGUAUCUGGAUUCCUGCAGUA GUU | 724 |
| LPA-5084 | CAGGCCCUUGGUGUUUUACAA UGGA | 325 | UCCAUUGUAAAACACCAAGGGCCU GUA | 725 |
| LPA-5090 | CUUGGUGUUUUACCAUGGAAC CCAG | 326 | CUGGGUUCCAUGGUAAAACACCAA GGG | 726 |
| LPA-5091 | UUGGUGUUUUACCAUGGACAC CAGC | 327 | GCUGGUGUCCAUGGUAAAACACCA AGG | 727 |
| LPA-5092 | UGGUGUUUUACCAUGGACCAC AGCA | 328 | UGCUGUGGUCCAUGGUAAAACACC AAG | 728 |
| LPA-5093 | GGUGUUUUACCAUGGACCCAA GCAT | 329 | AUGCUUGGGUCCAUGGUAAAACAC CAA | 729 |
| LPA-5094 | GUGUUUUACCAUGGACCCCAG CATC | 330 | GAUGCUGGGGUCCAUGGUAAAACA CCA | 730 |
| LPA-5096 | GUUUUACCAUGGACCCCAGAA UCAG | 331 | CUGAUUCUGGGGUCCAUGGUAAAA CAC | 731 |
| LPA-5124 | GGAGUACUGCAACCUGACGAG AUGC | 332 | GCAUCUCGUCAGGUUGCAGUACUC CCA | 732 |
| LPA-5125 | GAGUACUGCAACCUGACGCAA UGCT | 333 | AGCAUUGCGUCAGGUUGCAGUACU CCC | 733 |
| LPA-5127 | GUACUGCAACCUGACGCGAAG CUCA | 334 | UGAGCUUCGCGUCAGGUUGCAGUA CUC | 734 |
| LPA-5128 | UACUGCAACCUGACGCGAUAC UCAG | 335 | CUGAGUAUCGCGUCAGGUUGCAGU ACU | 735 |
| LPA-5131 | UGCAACCUGACGCGAUGCUAA GACA | 336 | UGUCUUAGCAUCGCGUCAGGUUGC AGU | 736 |
| LPA-5136 | CCUGACGCGAUGCUCAGACAC AGAA | 337 | UUCUGUGUCUGAGCAUCGCGUCAG GUU | 737 |
| LPA-5137 | CUGACGCGAUGCUCAGACAAA GAAG | 338 | CUUCUUUGUCUGAGCAUCGCGUCA GGU | 738 |
| LPA-5144 | GAUGCUCAGACACAGAAGGAA CUGT | 339 | ACAGUUCCUUCUGUGUCUGAGCAU CGC | 739 |
| LPA-5145 | AUGCUCAGACACAGAAGGGAC UGTG | 340 | CACAGUCCCUUCUGUGUCUGAGCA UCG | 740 |

TABLE 5-continued

LPA Oligonucleotide Sequences (Unmodified)

| | | | | |
|---|---|---|---|---|
| LPA-5151 | AGACACAGAAGGGACUGUGAU CGCT | 341 | AGCGAUCACAGUCCCUUCUGUGUC UGA | 741 |
| LPA-5467 | GCAUCCUCUUCAUUUGAUUAU GGGA | 342 | UCCCAUAAUCAAAUGAAGAGGAUG CAC | 742 |
| LPA-5468 | CAUCCUCUUCAUUUGAUUGAG GAA | 343 | UUCCCUCAAUCAAAUGAAGAGGAU GCA | 743 |
| LPA-5469 | AUCCUCUUCAUUUGAUUGUAG GAAG | 344 | CUUCCUACAAUCAAAUGAAGAGGA UGC | 744 |
| LPA-5470 | UCCUCUUCAUUUGAUUGUGAG AAGC | 345 | GCUUCUCACAAUCAAAUGAAGAGG AUG | 745 |
| LPA-5471 | CCUCUUCAUUUGAUUGUGGAA AGCC | 346 | GGCUUUCCACAAUCAAAUGAAGAG GAU | 746 |
| LPA-5474 | CUUCAUUUGAUUGUGGGAAAC CUCA | 347 | UGAGGUUUCCCACAAUCAAAUGAA GAG | 747 |
| LPA-5475 | UUCAUUUGAUUGUGGGAAGAC UCAA | 348 | UUGAGUCUUCCCACAAUCAAAUGA AGA | 748 |
| LPA-5476 | UCAUUUGAUUGUGGGAAGCAU CAAG | 349 | CUUGAUGCUUCCCACAAUCAAAUG AAG | 749 |
| LPA-5477 | CAUUUGAUUGUGGGAAGCCAC AAGT | 350 | ACUUGUGGCUUCCCACAAUCAAAU GAA | 750 |
| LPA-5478 | AUUUGAUUGUGGGAAGCCUAA AGTG | 351 | CACUUUAGGCUUCCCACAAUCAAA UGA | 751 |
| LPA-5486 | GUGGGAAGCCUCAAGUGGAAC CGAA | 352 | UUCGGUUCCACUUGAGGCUUCCCA CAA | 752 |
| LPA-5509 | AAGAAAUGUCCUGGAAGCAAU GUAG | 353 | CUACAUUGCUUCCAGGACAUUUCU UCG | 753 |
| LPA-5510 | AGAAAUGUCCUGGAAGCAUAG UAGG | 354 | CCUACUAUGCUUCCAGGACAUUUC UUC | 754 |
| LPA-5511 | GAAAUGUCCUGGAAGCAUUAU AGGG | 355 | CCCUAUAAUGCUUCCAGGACAUUU CUU | 755 |
| LPA-5513 | AAUGUCCUGGAAGCAUUGUAG GGGG | 356 | CCCCUACAAUGCUUCCAGGACAU UUC | 756 |
| LPA-5514 | AUGUCCUGGAAGCAUUGUAAG GGGG | 357 | CCCCCUUACAAUGCUUCCAGGACA UUU | 757 |
| LPA-5581 | AGAACAAGGUUUGGAAAGCAC UUCT | 358 | AGAAGUGCUUUCCAAACCUUGUUC UGA | 758 |
| LPA-5582 | GAACAAGGUUUGGAAAGCAAU UCTG | 359 | CAGAAUUGCUUUCCAAACCUUGUU CUG | 759 |
| LPA-5583 | AACAAGGUUUGGAAAGCACAU CUGT | 360 | ACAGAUGUGCUUUCCAAACCUUGU UCU | 760 |
| LPA-5584 | ACAAGGUUUGGAAAGCACUAC UGTG | 361 | CACAGUAGUGCUUUCCAAACCUUG UUC | 761 |
| LPA-5585 | CAAGGUUUGGAAAGCACUUAU GUGG | 362 | CCACAUAAGUGCUUUCCAAACCUU GUU | 762 |
| LPA-5586 | AAGGUUUGGAAAGCACUUCAG UGGA | 363 | UCCACUGAAGUGCUUUCCAAACCU UGU | 763 |
| LPA-5587 | AGGUUUGGAAAGCACUUCUAU GGAG | 364 | CUCCAUAGAAGUGCUUUCCAAACC UUG | 764 |
| LPA-5592 | UGGAAAGCACUUCUGUGGAAG CACC | 365 | GGUGCUUCCACAGAAGUGCUUUCC AAA | 765 |
| LPA-5606 | GUGGAGGCACCUUAAUAUCAC CAGA | 366 | UCUGGUGAUAUUAAGGUGCCUCCA CAG | 766 |

TABLE 5-continued

LPA Oligonucleotide Sequences (Unmodified)

| | | | | |
|---|---|---|---|---|
| LPA-5616 | CUUAAUAUCCCCAGAGUGGAUGCTG | 367 | CAGCAUCCACUCUGGGGAUAUUAAGGU | 767 |
| LPA-5618 | UAAUAUCCCCAGAGUGGGUACUGAC | 368 | GUCAGUACCCACUCUGGGGAUAUUAAG | 768 |
| LPA-5628 | AGAGUGGGUGCUGACUGCUACUCAC | 369 | GUGAGUAGCAGUCAGCACCCACUCUGG | 769 |
| LPA-5685 | CAAGGUCAUCCUGGGUGCAAACCAA | 370 | UUGGUUUGCACCCAGGAUGACCUUGUA | 770 |
| LPA-5694 | CCUGGGUGCACACCAAGAAAUGAAC | 371 | GUUCAUUUCUUGGUGUGCACCCAGGAU | 771 |
| LPA-5699 | GUGCACACCAAGAAGUGAAACUCGA | 372 | UCGAGUUUCACUUCUUGGUGUGCACCC | 772 |
| LPA-5775 | AGCAGAUAUUGCCUUGCUAAAGCTA | 373 | UAGCUUUAGCAAGGCAAUAUCUGCUUG | 773 |
| LPA-5776 | GCAGAUAUUGCCUUGCUAAAGCUAA | 374 | UUAGCUUUAGCAAGGCAAUAUCUGCUU | 774 |
| LPA-5777 | CAGAUAUUGCCUUGCUAAAACUAAG | 375 | CUUAGUUUUAGCAAGGCAAUAUCUGCU | 775 |
| LPA-5778 | AGAUAUUGCCUUGCUAAAGAUAAGC | 376 | GCUUAUCUUUAGCAAGGCAAUAUCUGC | 776 |
| LPA-5779 | GAUAUUGCCUUGCUAAAGCAAAGCA | 377 | UGCUUUGCUUUAGCAAGGCAAUAUCUG | 777 |
| LPA-5780 | AUAUUGCCUUGCUAAAGCUAAGCAG | 378 | CUGCUUAGCUUUAGCAAGGCAAUAUCU | 778 |
| LPA-5781 | UAUUGCCUUGCUAAAGCUAAGCAGG | 379 | CCUGCUUAGCUUUAGCAAGGCAAUAUC | 779 |
| LPA-5813 | UCAUCACUGACAAAGUAAUACCAGC | 380 | GCUGGUAUUACUUUGUCAGUGAUGACG | 780 |
| LPA-5873 | GGACUGAAUGUUACAUCACAGGCTG | 381 | CAGCCUGUGAUGUAACAUUCAGUCCUG | 781 |
| LPA-5874 | GACUGAAUGUUACAUCACUAGCUGG | 382 | CCAGCUAGUGAUGUAACAUUCAGUCCU | 782 |
| LPA-5875 | ACUGAAUGUUACAUCACUGACUGGG | 383 | CCCAGUCAGUGAUGUAACAUUCAGUCC | 783 |
| LPA-5876 | CUGAAUGUUACAUCACUGGAUGGGG | 384 | CCCCAUCCAGUGAUGUAACAUUCAGUC | 784 |
| LPA-5877 | UGAAUGUUACAUCACUGGCAGGGGA | 385 | UCCCCUGCCAGUGAUGUAACAUUCAGU | 785 |
| LPA-5879 | AAUGUUACAUCACUGGCUGAGAGA | 386 | UCUCCUCAGCCAGUGAUGUAACAUUCA | 786 |
| LPA-5902 | GAAACCCAAGGUACCUUUGAGACTG | 387 | CAGUCUCAAAGGUACCUUGGGUUUCUC | 787 |
| LPA-0190-M1 | UCCACCACUGUCACAGGAAAGCAGCCGAAAGGCUGC | 388 | UUUCCUGUGACAGUGGUGGAGG | 788 |
| LPA-0501-M1 | UGGUAAUGGACAGAGUUAUAGCAGCCGAAAGGCUGC | 389 | UAUAACUCUGUCCAUUACCAGG | 789 |
| LPA-3100-M1 | UACUGCAACCUGACACGAUAGCAGCCGAAAGGCUGC | 390 | UAUCGUGUCAGGUUGCAGUAGG | 790 |
| LPA-3286-M1 | AGAACUUGCCAAGCUUGGUAGCAGCCGAAAGGCUGC | 391 | UACCAAGCUUGGCAAGUUCUGG | 791 |
| LPA-3288-M1 | AACUUGCCAAGCUUGGUCAAGCAGCCGAAAGGCUGC | 392 | UUGACCAAGCUUGGCAAGUUGG | 792 |

TABLE 5-continued

| LPA Oligonucleotide Sequences (Unmodified) | | | | |
|---|---|---|---|---|
| LPA-3291-M1 | UUGCCAAGCUUGGUCAUCUAG CAGCCGAAAGGCUGC | 393 | UAGAUGACCAAGCUUGGCAAGG | 793 |
| LPA-3584-M1 | AUGGACAGAGUUAUCGAGGAG CAGCCGAAAGGCUGC | 394 | UCCUCGAUAACUCUGUCCAUGG | 794 |
| LPA-3585-M1 | UGGACAGAGUUAUCGAGGCAG CAGCCGAAAGGCUGC | 395 | UGCCUCGAUAACUCUGUCCAGG | 795 |
| LPA-4645-M1 | UGGUCAUCUAUGAUACCACAG CAGCCGAAAGGCUGC | 396 | UGUGGUAUCAUAGAUGACCAGG | 796 |
| LPA-4717-M1 | UACUGCAGGAAUCCAGAUUAG CAGCCGAAAGGCUGC | 397 | UAAUCUGGAUUCCUGCAGUAGG | 797 |
| LPA-5510-M1 | AGAAAUGUCCUGGAAGCAUAG CAGCCGAAAGGCUGC | 398 | UAUGCUUCCAGGACAUUUCUGG | 798 |
| LPA-3750-M1 | GACAACAGAAUAUUAUCCAAG CAGCCGAAAGGCUGC | 399 | UUGGAUAAUAUUCUGUUGUCGG | 799 |
| LPA-2900-M2 | AUGGACAGAGUUAUCAAGGAG CAGCCGAAAGGCUGC | 400 | UCCUUGAUAACUCUGUCCAUGG | 800 |
| LPA-3675-M2 | GACAACAGAAUAUUAUCCAAG CAGCCGAAAGGCUGC | 401 | UUGGAUAAUAUUCUGUUGUCGG | 801 |
| LPA-2900-M3 | AUGGACAGAGUUAUCAAGGAG CAGCCGAAAGGCUGC | 402 | UCCUUGAUAACUCUGUCCAUGG | 802 |
| LPA-3675-M3 | GACAACAGAAUAUUAUCCAAG CAGCCGAAAGGCUGC | 403 | UUGGAUAAUAUUCUGUUGUCGG | 803 |

Human (Hs): NM_005577.3 (SEQ ID NO: 1)

```
CTGGGATTGG GACACACTTT CTGGGCACTG CTGGCCAGTC CCAAAATGGA ACATAAGGAA
GTGGTTCTTC TACTTCTTTT ATTTCTGAAA TCAGCAGCAC CTGAGCAAAG CCATGTGGTC
CAGGATTGCT ACCATGGTGA TGGACAGAGT TATCGAGGCA CGTACTCCAC CACTGTCACA
GGAAGGACCT GCCAAGCTTG GTCATCTATG ACACCACATC AACATAATAG GACCACAGAA
AACTACCCAA ATGCTGGCTT GATCATGAAC TACTGCAGGA ATCCAGATGC TGTGGCAGCT
CCTTATTGTT ATACGAGGGA TCCCGGTGTC AGGTGGGAGT ACTGCAACCT GACGCAATGC
TCAGACGCAG AAGGGACTGC CGTCGCGCCT CCGACTGTTA CCCCGGTTCC AAGCCTAGAG
GCTCCTTCCG AACAAGCACC GACTGAGCAA AGGCCTGGGG TGCAGGAGTG CTACCATGGT
AATGGACAGA GTTATCGAGG CACATACTCC ACCACTGTCA CAGGAAGAAC CTGCCAAGCT
TGGTCATCTA TGACACCACA CTCGCATAGT CGGACCCCAG AATACTACCC AAATGCTGGC
TTGATCATGA ACTACTGCAG GAATCCAGAT GCTGTGGCAG CTCCTTATTG TTATACGAGG
GATCCCGGTG TCAGGTGGGA GTACTGCAAC CTGACGCAAT GCTCAGACGC AGAAGGGACT
GCCGTCGCGC CTCCGACTGT TACCCCGGTT CCAAGCCTAG AGGCTCCTTC CGAACAAGCA
CCGACTGAGC AAAGGCCTGG GGTGCAGGAG TGCTACCATG GTAATGGACA GAGTTATCGA
GGCACATACT CCACCACTGT CACAGGAAGA ACCTGCCAAG CTTGGTCATC TATGACACCA
CACTCGCATA GTCGGACCCC AGAATACTAC CCAAATGCTG CTTGATCAT GAACTACTGC
AGGAATCCAG ATGCTGTGGC AGCTCCTTAT TGTTATACGA GGGATCCCGG TGTCAGGTGG
GAGTACTGCA ACCTGACGCA ATGCTCAGAC GCAGAAGGGA CTGCCGTCGC GCCTCCGACT
GTTACCCCGG TTCCAAGCCT AGAGGCTCCT TCCGAACAAG CACCGACTGA GCAGAGGCCT
GGGGTGCAGG AGTGCTACCA CGGTAATGGA CAGAGTTATC GAGGCACATA CTCCACCACT
GTCACTGGAA GAACCTGCCA AGCTTGGTCA TCTATGACAC CACACTCGCA TAGTCGGACC
CCAGAATACT ACCCAAATGC TGGCTTGATC ATGAACTACT GCAGGAATCC AGATGCTGTG
GCAGCTCCTT ATTGTTATAC GAGGGATCCC GGTGTCAGGT GGGAGTACTG CAACCTGACG
CAATGCTCAG ACGCAGAAGG GACTGCCGTC GCGCCTCCGA CTGTTACCCC GGTTCCAAGC
CTAGAGGCTC CTTCCGAACA AGCACCGACT GAGCAAAGGC CTGGGGTGCA GGAGTGCTAC
CATGGTAATG GACAGAGTTA TCGAGGCACA TACTCCACCA CTGTCACAGG AAGAACCTGC
CAAGCTTGGT CATCTATGAC ACCACACTCG CATAGTCGGA CCCCAGAATA CTACCCAAAT
GCTGGCTTGA TCATGAACTA CTGCAGGAAT CCAGATGCTG TGGCAGCTCC TTATTGTTAT
ACGAGGGATC CCGGTGTCAG GTGGGAGTAC TGCAACCTGA CGCAATGCAGAGAA
GGGACTGCCG TCGCGCCTCC GACTGTTACC CCGGTTCCAA GCCTAGAGGC TCCTTCCGAA
CAAGCACCGA CTGAGCAAAG GCCTGGGGTG CAGGAGTGCT ACCATGGTAA TGGACAGAGT
TATCGAGGCA CATACTCCAC CACTGTCACA GGAAGAACCT GCCAAGCTTG GTCATCTATG
ACACCACACT CGCATAGTCG GACCCCAGAA TACTACCCAA ATGCTGGCTT GATCATGAAC
TACTGCAGGA ATCCAGATGC TGTGGCAGCT CCTTATTGTT ATACGAGGGA TCCCGGTGTC
AGGTGGGAGT ACTGCAACCT GACGCAATGC TCAGACGCAG AAGGGACTGC CGTCGCGCCT
CCGACTGTTA CCCCGGTTCC AAGCCTAGAG GCTCCTTCCG AACAAGCACC GACTGAGCAA
AGGCCTGGGG TGCAGGAGTG CTACCATGGT AATGGACAGA GTTATCGAGG CACATACTCC
ACCACTGTCA CAGGAAGAAC CTGCCAAGCT TGGTCATCTA TGACACCACA CTCGCATAGT
CGGACCCCAG AATACTACCC AAATGCTGGC TTGATCATGA ACTACTGCAG GAATCCAGAT
GCTGTGGCAG CTCCTTATTG TTATACGAGG GATCCCGGTG TCAGGTGGGA GTACTGCAAC
CTGACGCAAT GCTCAGACGC AGAAGGGACT GCCGTCGCGC CTCCGACTGT TACCCCGGTT
CCAAGCCTAG AGGCTCCTTC CGAACAAGCA CCGACTGAGC AGAGGCCTGG GGTGCAGGAG
```

TABLE 5-continued

LPA Oligonucleotide Sequences (Unmodified)

```
TGCTACCACG GTAATGGACA GAGTTATCGA GGCACATACT CCACCACTGT CACTGGAAGA
ACCTGCCAAG CTTGGTCATC TATGACACCA CACTCGCATA GTCGGACCCC AGAATACTAC
CCAAATGCTG GCTTGATCAT GAACTACTGC AGGAATCCAG ATCCTGTGGC AGCCCCTTAT
TGTTATACGA GGGATCCCAG TGTCAGGTGG GAGTACTGCA ACCTGACACA ATGCTCAGAC
GCAGAAGGGA CTGCCGTCGC GCCTCCAACT ATTACCCCGA TTCCAAGCCT AGAGGCTCCT
TCTGAACAAG CACCAACTGA GCAAAGGCCT GGGGTGCAGG AGTGCTACCA CGGAAATGGA
CAGAGTTATC AAGGCACATA CTTCATTACT GTCACAGGAA GAACCTGCCA AGCTTGGTCA
TCTATGACAC CACACTCGCA TAGTCGGACC CCAGCATACT ACCCAAATGC TGGCTTGATC
AAGAACTACT GCCGAAATCC AGATCCTGTG GCAGCCCCTT GGTGTTATAC AACAGATCCC
AGTGTCAGGT GGGAGTACTG CAACCTGACA CGATGCTCAG ATGCAGAATG GACTGCCTTC
GTCCCTCCGA ATGTTATTCT GGCTCCAAGC CTAGAGGCTT TTTTTGAACA AGCACTGACT
GAGGAAACCC CCGGGGTACA GGACTGCTAC TACCATTATG ACAGAGTTA CCGAGGCACA
TACTCCACCA CTGTCACAGG AAGAACTTGC AAGCTTGGT CATCTATGAC ACCACACCAG
CATAGTCGGA CCCCAGAAAA CTACCCAAAT GCTGGCCTGA CCAGGAACTA CTGCAGGAAT
CCAGATGCTG AGATTCGCCC TTGGTGTTAC ACCATGGATC CCAGTGTCAG GTGGGAGTAC
TGCAACCTGA CACAATGCCT GGTGACAGAA TCAAGTGTCC TTGCAACTCT CACGGTGGTC
CCAGATCCAA GCACAGAGGC TTCTTCTGAA GAAGCACCAA CGGAGCAAAG CCCCGGGGTC
CAGGATTGCT ACCATGGTGA TGGACAGAGT TATCGAGGCT CATTCTCTAC CACTGTCACA
GGAAGGACAT GTCAGTCTTG GTCCTCTATG ACACCACACT GGCATCAGAG GACAACAGAA
TATTATCCAA ATGGTGGCCT GACCAGGAAC TACTGCAGGA ATCCAGATGC TGAGATTAGT
CCTTGGTGTT ATACCATGGA TCCCAATGTC AGATGGGAGT ACTGCAACCT GACACAATGT
CCAGTGACAG AATCAAGTGT CCTTGCGACG TCCACGGCTG TTTCTGAACA AGCACCAACG
GAGCAAAGCC CCACAGTCCA GGACTGCTAC CATGGTGATG GACAGAGTTA TCGAGGCTCA
TTCTCCACCA CTGTTACAGG AAGGACATGT CAGTCTTGGT CCTCTATGAC ACCACACTGG
CATCAGAGAA CCACAGAATA CTACCCAAAT GGTGGCCTGA CCAGGAACTA CTGCAGGAAT
CCAGATGCTG AGATTCGCCC TTGGTGTTAT ACCATGGATC CCAGTGTCAG ATGGGAGTAC
TGCAACCTGA CGCAATGTCC AGTGATGGAA TCAACTCTCC TCACAACTCC CACGGTGGTC
CCAGTTCCAA GCACAGAGCT TCCTTCTGAA GAAGCACCAA CTGAAAACAG CACTGGGGTC
CAGGACTGCT ACCGAGGTGA TGGACAGAGT TATCGAGGCA CACTCTCCAC CACTATCACA
GGAAGAACAT GTCAGTCTTG GTCGTCTATG ACACCACATT GGCATCGGAG GATCCCATTA
TACTATCCAA ATGCTGGCCT GACCAGGAAC TACTGCAGGA ATCCAGATGC TGAGATTCGC
CCTTGGTGTT ACACCATGGA TCCCAGTGTC AGGTGGGAGT ACTGCAACCT GACACGATGT
CCAGTGACAG AATCGAGTGT CCTCACAACT CCCACAGTGG CCCCGGTTCC AAGCACAGAG
GCTCCTTCTG AACAAGCACC ACCTGAGAAA AGCCCTGTGG TCCAGGATTG CTACCATGGT
GATGGACGGA GTTATCGAGG CATATCCTCC ACCACTGTCA CAGGAAGGAC CTGTCAATCT
TGGTCATCTA TGATACCACA CTGGCATCAG AGGACCCCAG AAAACTACCC AAATGCTGGC
CTGACCGAGA ACTACTGCAG GAATCCAGAT TCTGGGAAAC AACCCTGGTG TTACACAACC
GATCCGTGTG TGAGGTGGGA GTACTGCAAT CTGACACAAT GCTCAGAAAC AGAATCAGGT
GTCCTAGAGA CTCCCACTGT TGTTCCAGTT CCAAGCATGG AGGCTCATTC TGAAGCAGCA
CCAACTGAGC AAACCCCTGT GGTCCGGCAG TGCTACCATG GTAATGGCCA GAGTTATCGA
GGCACATTCT CCACCACTGT CACAGGAAGG ACATGTCAAT CTTGGTCATC CATGACACCA
CACCGGCATC AGAGGACCCC AGAAAACTAC CCAAATGATG GCCTGACAAT GAACTACTGC
AGGAATCCAG ATGCCGATAC AGGCCCTTGG TGTTTTACCA TGGACCCCAG CATCAGGTGG
GAGTACTGCA ACCTGACGCG ATGCTCAGAC ACAGAAGGGA CTGTGGTCGC TCCTCCGATA
GTCATCCAGG TTCCAAGCCT AGGGCCTCCT TCTGAACAAG ACTGTATGTT TGGGAATGGG
AAAGGATACC GGGGCAAGAA GGCAACCACT GTTACTGGGA CGCCATGCCA GGAATGGGCT
GCCCAGGAGC CCCATAGACA CAGCACGTTC ATTCCAGGGA CAAATAAATG GCAGGTCTG
GAAAAAAATT ACTGCCGTAA CCCTGATGGT GACATCAATG GTCCCTGGTG CTACACAATG
AATCCAAGAA AACTTTTTGA CTACTGTGAT ATCCCTCTCT GTGCATCCTC TTCATTTGAT
TGTGGGAAGC TCAAGTGGA GCCGAAGAAA TGTCCTGGAA GCATTGTAGG GGGTGTGTG
GCCCACCCAC ATTCCTGGCC CTGGCAAGTC AGTCTCAGAA CAAGGTTTGG AAAGCACTTC
TGTGGAGGCA CCTTAATATC CCCAGAGTGG GTGCTGACTG CTGCTCACTG CTTGAAGAAG
TCCTCAAGGC CTTCATCCTA CAAGGTCATC CTGGGTGCAC ACCAAGAAGT GAACCTCGAA
TCTCATGTTC AGGAAATAGA AGTGTCTAGG CTGTTCTTGG AGCCCACACA AGCAGATATT
GCCTTGCTAA AGCTAAGCAG GCCTGCCGTC ATCACTGACA AAGTAATGCC AGCTTGTCTG
CCATCCCCAG ACTACATGGT CACCGCCAGG ACTGAATGTT ACATCACTGG CTGGGGAGAA
ACCCAAGGTA CCTTTGGGAC TGGCCTTCTC AAGGAAGCCC AGCTCCTTGT TATTGAGAAT
GAAGTGTGCA ATCACTATAA GTATATTTGT GCTGAGCATT TGGCCAGAGG CACTGACAGT
TGCCAGGGTG ACAGTGGAGG GCCTCTGGTT TGCTTCGAGA AGGACAAATA CATTTTACAA
GGAGTCACTT CTTGGGGTCT TGGCTGTGCA CGCCCCAATA AGCCTGGTGT CTATGCTCGT
GTTTCAAGGT TTGTTACTTG GATTGAGGGA ATGATGAGAA ATAATTAGT GGACGGGAGA
CAGAGTGAAG CATCAACCTA CTTAGAAGCT GAAACGTGGG TAAGGATTTA GCATGCTGGA
AATAATAGAC AGCAATCAAA CGAAGACACT GTTCCCAGCT ACCAGCTATG CCAAACCTTG
GCATTTTTGG TATTTTGTG TATAAGCTTT TAAGGTCTGA CTGACAAATT CTGTATTAAG
GTGTCATAGC TATGACATTT GTTAAAAATA AACTCTGCAC TTATTTTGAT TTGA
```

Cynomolgus monkey (Mf): XM_015448517. 1 (SEQ ID NO: 2)

```
GATGCTGCAT ACTTAATGTC GAAAGGTTGC TTCATCCAAG AGCCTGGAGT TTTCAGAGAC
ACTGTCCTGA AACTATGTCC TGAAACTATG TCATTGAAAC TGAAACATTG TCCTGAAGCT
GGTATTGGGC AATACCAGCG CCTGCAGGCA ACAGCTCGGA TGCACTTAAG ATTTAAATAT
TACCCACAGA AGTTCTGGCT TGTCTGGAA ACCTTTTGC TAAACAGAAG AGCAACATTT
TTTTTTTTT CTTTTCTGGA ATTTGTAAAC AGCATTTATT CTCAGCCTTA CCTTCCAAAC
GTTGCACTTG GAACATTGCT GGGCCCCGTG GAAACAGAAG CGAACGTCAG CCAGGCCGGC
AGGGGGCGGC AGACCCCACA CTTCGCCGGG CGCCCTCACC TCCCTGGGAG GGAGTGTGCA
GCTGCCAAAA TCTTCGGCGG GGTTCAGTCC AAGCGACTTC AGCCAGCAGA TGGTCATTCT
CCTGTGACCG TGTGTACTAC AGACTGTTTC AAAACCGGGC AGGCAATTAA CAATGGGAAT
TCTGCCATCA TCGCTGACAA AGTCATCCCA GTTTGTCTGC CATCCCCAAA TTATGTGGTC
```

TABLE 5-continued

LPA Oligonucleotide Sequences (Unmodified)

```
GCCAACCAGA CTGAATGTTA TGTCACTGGC TGGGGAGAAA CCCAAGCACT ACCTGAGCAA
AGCCATGTGG TCCAGGATTG CTACCATGGT GATGGACAGA GTTATCAAGG CACATCCTCC
ACCACTGTCA CAGGAAGGAC CTGCCAAGCT TGGTCATCTA TGGAACCACA TCAGCATAAT
AGAACCACAG AAAACTACCC AAATGCTGGC TTGATCAGGA ACTACTGCAG GAATCCAGAT
CCTGTGGCAG CCCCTTATTG TTATACGATG GATCCCAATG TCAGGTGGGA GTACTGCAAC
CTGACACAAT GCTCAGACGC AGAAGGGACT GCCGTCGCAC CTCCGAATGT CACCCCGGTT
CCAAGCCTAG AGGCTCCTTC CGAACAAGCA CCGACTGAGC AAAGGCCTGG GGTGCAGGAG
TGCTACCACG GTAATGGACA GAGTTATCGA GGCACATACT TCACCACTGT GACAGGAAGA
ACCTGCCAAG CTTGGTCATC TATGACACCG CACTCTCATA GTCGGACCCC GGAAAACTAC
CCAAATGGTG GCTTGATCAG GAACTACTGC AGGAATCCAG ATCCTGTGGC AGCCCCTTAT
TGTTATACCA TGGATCCCAA TGTCAGGTGG GAGTACTGCA ACCTGACACA ATGCTCAGAC
GCAGAAGGGA TTGCCGTCAC ACCTCTGACT GTTACCCCGG TTCCAAGCCT AGAGGCTCCT
TCCAAGCAAG CACCAACTGA GCAAAGGCCT GGTGTCCAGG AGTGCTACCA CGGTAATGGA
CAGAGTTATC GAGGCACATA CTTCACCACT GTGACAGGAA GAACCTGCCA AGCTTGGTCA
TCTATGACAC CACATTCTCA TAGTCGTACC CCAGAAAACT ACCCAAATGG TGGCTTGATC
AGGAACTACT GCAGGAATCC AGATCCTGTG GCAGCCCCTT ATTGTTATAC CATGGATCCC
AATGTCAGGT GGGAGTACTG CAACCTGACA CAATGCTCAG ACGCAGAAGG GACTGCCGTC
GCACCTCCGA CTGTCACCCC GGTTCCAAGC CTAGAGGCTC CTTCCGAACA AGCACCGACT
GAGCAAAGGC CTGGGGTGCA GGAGTGCTAC CACGGTAATG GACAGAGTTA TCGAGGCACA
TACTTCACCA CTGTGACAGG AAGAACCTGC CAAGCTTGGT CATCTATGAC ACCGCACTCT
CATAGTCGGA CCCCGGAAAA CTACCCAAAT GGTGGCTTGA TCAGGAACTA CTGCAGGAAT
CCAGATCCTG TGGCAGCCCC TTATTGTTAT ACCATGGATC CCAATGTCAG GTGGGAGTAC
TGCAACCTGA CACAATGCTC AGACGCAGAA GGGACTGCCG TCGCACCTCC GAATGTCACC
CCGGTTCCAA GCCTAGAGGC TCCTTCTGAG CAAGCACCAA CTGAGCAAAG GCTTGGGGTG
CAGGAGTGCT ACCACGGTAA TGGACAGAGT TATCGAGGCA CATACTTCAC CACTGTGACA
GGAAGAACCT GCCAAGCTTG GTCATCTATG ACACCACACT CTCATAGTCG GACCCCAGAA
AACTACCCAA ATGCTGGCTT GGTCAAGAAC TACTGCCGAA ATCCAGATCC TGTGGCAGCC
CCTTGGTGTT ATACAACGGA TCCCAGTGTC AGGTGGGAGT ACTGCAACCT GACACGATGC
TCAGATGCAG AAGGGACTGC TGTTGTGCCT CCAAATATTA TTCCGGTTCC AAGCCTAGAG
GCTTTTCTTG AACAAGAACC GACTGAGGAA ACCCCCGGGG TACAGGAGTG CTACTACCAT
TATGGACAGA GTTATAGAGG CACATACTCC ACCACTGTTA CAGGAAGAAC TTGCCAAGCT
TGGTCATCTA TGACACCACA CCAGCATAGT CGGACCCCAA AAAACTATCC AAATGCTGGC
CTGACCAGGA ACTACTGCAG GAATCCAGAT GCTGAGATTC GCCCTTGGTG TTATACCATG
GATCCCAGTG TCAGGTGGGA GTACTGCAAC CTGACACAAT GTCTGGTGAC AGAATCAAGT
GTCCTTGAAA CTCTCACAGT GGTCCCAGAT CCAAGCACAC AGGCTTCTTC TGAAGAAGCA
CCAACGGAGC AAAGTCCCGA GGTCCAGGAC TGCTACCATG GTGATGGACA GAGTTATCGA
GGCTCATTCT CCACCACTGT CACAGGAAGG ACATGTCAGT CTTGGTCCTC TATGACACCA
CACTGGCATC AGAGGACAAC AGAATATTAT CCAGATGGTG GCCTGACCAG GAACTACTGC
AGGAATCCAG ATGCTGAGAT CGCCCTTGG TGTTATACCA TGGATCCCAG TGTCAGGTGG
GAGTACTGCA ACCTGACACA ATGTCCAGTG ACAGAATCAA GTGTCCTCGC AACGTCCATG
GCTGTTTCTG AACAAGCACC AATGGAGCAA AGCCCCGGGG TCCAGGACTG CTACCATGGT
GATGGACAGA GTTATCGAGG TTCATTCTCC ACCACTGTCA CAGGAAGGAC ATGTCAGTCT
TGGTCCTCTA TGACACCACA CTGGCATCAG AGGACCATAG AATACTACCC AAATGGTGGC
CTGACCAAGA ACTACTGCAG GAATCCAGAT GCTGAGATTC GCCCTTGGTG TTATACCATG
GATCCCAGAG TCAGATGGGA GTACTGCAAC CTGACACAAT GTGTGGTGAT GGAATCAAGT
GTCCTTGCAA CTCCCATGGT GGTCCCAGTT CCAAGCAGAG AGGTTCCTTC TGAAGAAGCA
CCAACTGAAA CAGCCCTGG GGTCCAGGAC TGCTACCAAG GTGATGGACA GAGTTATCGA
GGCACATTCT CCACCACTAT CACAGGAAGA ACATGTCAGT CTTGGTTGTC TATGACACCA
CATCGGCATC GGAGGATCCC ATTACGCTAT CCAAATGCTG GCCTGACCAG GAACTATTGC
AGAAATCCAG ATGCTGAGAT CGCCCTTGG TGTTACACCA TGGATCCCAG TGTCAGGTGG
GAGTACTGCA ACCTGACACA ATGTCCAGTG ACAGAATCAA GTGTCCTCAC AACTCCCACG
GTGGTCCCGG TTCCAAGCAC AGAGGCTCCT TCTGAACAAG CACCACCTGA GAAAAGCCCT
GTGGTCCAGG ATTGCTACCA TGGTGATGGA CAGAGTTATC GAGGCACATC CTCCACCACT
GTCACAGGAA GGAACTGTCA GTCTTGGTCA TCTATGATAC CACACTGGCA TCAGAGGACC
CCAGAAAACT ACCCAAATGC TGGCCTGACC AGGAACTACT GCAGGAATCC AGATTCTGGG
AAACAACCCT GGTGTTACAC GACTGATCCA TGTGTGAGGT GGGAGTACTG CAACCTGACA
CAATGCTCAG AAACAGAATC AGGTGTCCTA GAGACTCCCA CTGTTGTTCC GGTTCCAAGC
ATGGAAGCTC ATTCTGAAGC AGCACCAACT GAGCAAACTC CTGTGGTCCA GCAGTGCTAC
CATGGTAATG GACAGAGTTA TCGAGGCACA TTCTCCACCA CTGTCACAGG AAGGACATGT
CAATCTTGGT CATCCATGAC ACCACACCAG CATAAGAGGA CCCCGGAAAA CCACCCAAAT
GATGACTTGA CAATGAACTA CTGCAGGAAT CCAGATGCTG ACACAGGCCC TTGGTGTTTT
ACCATGGACC CCAGCGTCAG GCGGGAGTAC TGCAACCTGA CGCGATGCTC AGACACAGAA
GGGACTGTGG TCACACCTCC GACTGTTATC CCGTTCCAA GCCTAGAGGC TCCTTCTGAA
CAAGCATCCT CTTCATTTGA TTGTGGGAAG CCTCAAGTGG AGCCAAAGAA ATGTCCTGGA
AGCATTGTAG GTGGGTGTGT GGCCCACCCA CATTCCTGGC CCTGGCAAGT CAGTCTTAGA
ACAAGGTTTG GAAAGCACTT CTGTGGAGGC ACCTTAATAT CCCCAGAGTG GTGCTGACT
GCTGCTTGCT GCTTGGAGAC GTTCTCAAGG CCTTCCTTCT ACAAGGTCAT CCTGGGTGCA
CACCAAGAAG TGAATCTCGA ATCTCACGTT CAAGAAATAG AAGTGTCTAG GTTGTTCTTG
GAGCCCATAG GAGCAGATAT TGCCTTGCTA AAGCTAAGCA GGCTGCCAT CATCACTGAC
AAAGTAATCC CAGCCTGTCT GCCGTCTCCA AATTACGTGA TCACCGTCTG GACTGAATGT
TACATCACTG GCTGGGGAGA AACCCAAGGT ACCTTTGGGG CTGGCCTTCT CAAGGAAGCC
CAGCTTCATG TGATTGAGAA TACAGTGTGC AATCACTACG AGTTTCTGAA TGGAAGAGTC
AAATCCACCG AGCTCTGTGC TGGGCATTTG GCCGGAGGCA CTGACAGATG CCAGGGTGAC
AGTGGAGGGC CTGTGGTTTG CTTCGACAAG GACAAATACA TTTTACGAGG AATAACTTCT
TGGGGTCCTG GCTGTGCATG CCCCAATAAG CCTGGTGTCT ATGTTCGTGT TTCAAGCTTT
GTCACTTGGA TTGAGGGAGT GATGAGAAAT AATTAATTGA ACAAGAGACA GAGTGAAGCA
TTGACTCACC TAGAGGCTAG AATGGGGGTA GGGATTTAGC ACGCTGGAAA TAACGGACAG
TAATCAAACG AAGACACTGT CCCCAGCTAC CAACTATGCC AAACCTCAGC ATTTTTGGTA
```

TABLE 5-continued

LPA Oligonucleotide Sequences (Unmodified)

TTATTGTGTA TAAGCTTTTC CCGTCTGACT GCTGGGTTCT CCAATAAGGT GACATAGCTA
TGCCATTTGT TAAAAATAAA CTCTGTACTT ATTTTGATTT GAGTAAA

Rhesus monkey: XM_028847001.1 (SEQ ID NO: 3)

AGCCTTGCCT TTGAAATGTT CCAGTTGGAA CATTGCTGGG CAGCGTGCAA ACAGGAGCGA
ACGTCAGCCG GGGCGGCAGG GGGCAGCAGA CCCCACACTT TGTCCATGCC TCAGGTGGGA
GGAAGTGTCC GGCTCCAGAA ACCTGCCGCG GGCTTTATCC CAAGCGACTT CAGCCAGCAG
ACGGTTCATG TCCTGAGGCT GCAAAATACG AGTTCTGCCA TCATCGCTGA CAAAGTCATC
CCAGTTTGTC TGCCATCCCC AAATTATGCG ATCGCCAACC AGACTGAATG TTATGTCACT
GGCTGGGGAG AAACCCAAGC ACTACCTGAG CAAAGCCATG TGGTCCAGGA TTGCTACCAT
GGTGATGGAC AGAGTTATCA AGGCACATCC TCCACCACTG TCACAGGAAG GACCTGCCAA
GCTTGGTCAT CTATGGAACC ACATCAGCAT AATAGAACCA CAGAAAACTA CCCAAATGCT
GGCTTGATCA GGAACTACTG CAGGAATCCA GATCCTGTGG CAGCCCCTTA TTGTTATACG
ATGGATCCCA ATGTCAGGTG GGAGTACTGC AACCTGACAA AATGCTCAGA CGCAGAAGGG
ACTGCCGTCG CACCTCCGAA TGTCACCCCG GTTCCAAGCC TAGAGGCTCT TTCCGAACAA
GCACCGACTG AGCAAAGGCC TGGGGTGCAG GAGTGCTACC ACGGTAATGG ACAGAGTTAT
CGAGGCACAT ACTTCACCAC TGTGACAGGA AGAACCTGCC AAGCTTGGTC ATCTATGACA
CCACATTCTC ATAGTCGTAC CCCAGAAAAC TACCCAAATG GTGGCTTGAT CAGGAACTAC
TGCAGGAATC CAGATCCTGT GGCAGCCCCT TATTGTTATA CCATGGATCC CAATGTCAGG
TGGGAGTACT GCAACCTGAC ACAATGCTCA GACGCAGAAG GGACTGCCGT CGCACCTCCG
AATGTCACCC CGGTTCCAAG CCTAGAGGCT CCTTCCGAAC AAGCACCGAC TGAGCAAAGG
CCTGGGGTGC AGGAGTGCTA CCACGGTAAT GGACAGAGTT ATCGAGGCAC ATACTTCACC
ACTGTGACAG GAAGAACCTG CCAAGCTTGG TCATCTATGA CACCACATTC TCATAGTCGT
ACCCCAGAAA ACTACCCAAA TGGTGGCTTG ATCAGGAACT ACTGCAGGAA TCCAGATCCT
GTGGCAGCCC CTTATTGTTA TACCATGGAT CCCAATGTCA GGTGGGAGTA CTGCAACCTG
ACACAATGCT CAGACGCAGA GGGGACTGCC GTCGCACCTC CGACTGTCAC CCCGGTTCCA
AGCCTAGAGG CTCCTTCTGA GCAAGCACCG ACTGAGCAAA GGCCTGGGGT GCAGGAGTGC
TACCACGGTA ATGGACAGAG TTATGAGGC ACATACTTCA CCACTGTGAC AGGAAGAACC
TGCCAAGCTT GGTCATCTAT GACACCGCAC TCTCATAGTC GGACCCCGGA AAACTACCCA
AATGGTGGCT TGATCAGGAA CTACTGCAGG AATCCAGATC CTGTGGCAGC CCCTTATTGT
TATACGATGG ATCCCAATGT CAGGTGGGAG TACTGCAACC TGACACAATG CTCAGACGCA
GAAGGGACTG CCGTCGCACC TCCGAATGTC ACCCCGGTTC CAAGCCTAGA GGCTCCTTCC
GAACAAGCAC CGACTGAGCA AAGGCCTGGG GTGCAGGAGT GCTACCACGG TAATGGACAG
AGTTATCGAG GCACATACTT CACCACTGTG ACAGGAAGAA CCTGCCAAGC TTGGTCATCT
ATGACACCGC ACTCTCATAG TCGGACCCCG GAAAACTACC CAAATGGTGG CTTGATCAGG
AACTACTGCA GGAATCCAGA TCCTGTGGCA GCCCCTTATT GTTATACGAT GGATCCCAAT
GTCAGGTGGG AGTACTGCAA CCTGACACAA TGCTCAGACG CAGAAGGGAC TGCCGTCGCA
CCTCCGAATG TCACCCCGGT TCCAAGCCTA GAGGCTCCTT CCGAACAAGC ACCAACTGAG
CAAAGGCCTG GGNTGCAGGA GTGCTACCAT GGTAATGGAC AGAGTTATCG AGGCACATAC
TTCACCACTG TGACAGGAAG AACCTGCCAA GCTTGGTCAT CTATGACACC GCACTCTCAT
AGTCGGACCC CGGAAAACTA CCCAAATGGT GGCTTGATCA GGAACTACTG CAGGAATCCA
GATCCTGTGG CAGCCCCTTA TTGTTATACC ATGGATCCCA ATGTCAGGTG GNAGTACTGC
AACCTGACAC AATGCTCAGA CGCAGAAGGG ACTGCCGTCG CACCTCCGAC TGTCACCCCG
GTTCCAAGCC TAGAGGCTCC TTCGAGCAAG GCACCGACTG AGCAAAGGCC TGGGNTGCAG
GAGTGCTACC ACGGTAATGG ACAGAGTTAT CGAGGCACAT ACTTCACCAC TGTGACAGGA
AGAACCTGCC AAGCTTGGTC ATCTATGACA CCGCACTCTC ATAGTCGGAC CCCGGAAAAC
TACCCAAATG GTGGCTTGAT CAGGAACTAC TGCAGGAATC CAGATCCTGT GGCAGCCCCT
TATTGTTATA CGATGGATCC CAATGTCAGG TGGGAGTACT GCAACCTGAC ACAATGCTCA
GACGCAGAAG GGACTGCCGT CGCACCTCCG AATGTCACCC CGGTTCCAAG CCTAGAGGCT
CCTTCCGAAC AAGCACCGAC TGAGCAAAGG CCTGGGGTGC AGGAGTGCTA CCACGGTAAT
GGACAGAGTT ATCGAGGCAC ATACTTCACC ACTGTGACAG GAAGAACCTG CCAAGCTTGG
TCATCTATGA CACCGCACTC TCATAGTCGG ACCCCGGAAA ACTACCCAAA TGGTGGCTTG
ATCAGGAACT ACTGCAGGAA TCCAGATCCT GTGGCAGCCC CTTATTGTTA TACCATGGAT
CCCAATGTCA GGTGGGAGTA CTGCAACCTG ACACAATGCT CAGACGCAGA AGGGACTGCC
GTCGCACCTC CGAATGTCAC CCCGGTTCCA AGCCTAGAGG CTCCTTCTGA GCAAGCACCA
ACTGAGCAAA GCCTTGGGGT GCAGGAGTGC TACCACAGTA ATGGACAGAG TTATCGAGGC
ACATACTTCA CCACTGTGAC AGGAAGAACC TGCCAAGCTT GGTCATCTAT GACACCACAC
TCTCATAGTC GGACCCCAGA AAACTACCCA AATGCTGGCT TGGTCAAGAA CTACTGCCGA
AATCCAGATC CTGTGGCAGC CCCTTGGTGT TATACAACGG ATCCCAGTGT CAGGTGGGAG
TACTGCAACC TGACACGATG CTCAGATGCA GAAGGGACTG CTGTCATGCC TCCAAATATT
ATTCCGGTTC CAAGCCTAGA GGCTTTTCTT GAACAAGAAC CTACTGAGGA AACCCCCGGG
GTACAGGAGT GCTACTACCA TTATGGACAG AGTTATCGAG GCACATACTC CACCACTGTT
ACAGGAAGAA CTTGCCAAGC TTGGTCATCT ATGACACCAC ACCAGCATAG TCGGACCCCA
AAAACTATC CAAATGCTGG CCTGACCAGG AACTACTGCA GGAATCCAGA TGCTGAGATT
CGCCCTTGGT GTTATACCAT GGATCCCAGT GTCAGGTGGG AGTACTGCAA CCTGACACAA
TGTCTGGTGA CAGAATCAAG TGTCCTTGAA ACTCTCACAG TGGTCCCAGA TCCAAGCACA
CAGGCTTCTT CTGAAGAAGC ACCAACGGAG CAAAGTCCCG AGGTCCAGGA CTGCTACCAT
GGTGATGGAC AGAGTTATCG AGGCTCATTC TCCACCACTG TCACAGGAAG GACATGTCAG
TCTTGGTCCT CTATGACACC ACACTGGCAT CAGAGGACAA CAGAATATTA TCCAGATGGT
GGCCTGACCA GGAACTACTG CAGGAATCCA GATGCTGAGA TTCGCCCTTG TGTTATACC
ATGGATCCCA GTGTCAGGTG GGAGTACTGC AACCTGACAC AATGTCCAGT GACAGAATCA
AGTGTCCTCG CAACGTCCAT GGCTGTTTCT GAACAAGCAC CAATGGAGCA AAGCCCCGGG
GTCCAGGACT GCTACCATGG TGATGGACAG AGTTATCGAG GTTCATTCTC CACCACTGTC
ACAGGAAGGA CATGTCAGTC TTGGTCCTCT ATGACACCAC ACTGGCATCA GAGGACCATA
GAATACTACC CAAATGGTGG CCTGACCAAG AACTACTGCA GGAATCCAGA TGCTGAGATT
CGCCCTTGGT GTTATACCAT GGATCCCAGA GTCAGATGGG AGTACTGCAA CCTGACACAA
TGTGTGGTGA TGGAATCAAG TGTCCTTGCA ACTCCCATGG TGGTCCCAGT TCCAAGCAGA

TABLE 5-continued

LPA Oligonucleotide Sequences (Unmodified)

```
GAGGTTCCTT CTGAAGAAGC ACCAACTGAA AACAGCCCTG GGGTCCAGGA CTGCTACCAA
GGTGATGGAC AGAGTTATCG AGGCACATTC TCCACCACTA TCACAGGAAG AACATGTCAG
TCTTGGTTGT CTATGACACC ACATCGGCAT CGGAGGATCC CATTACGCTA TCCAAATGCT
GGCCTGACCA GGAACTATTG CAGAAATCCA GATGCTGAGA TTCGCCCTTG GTGTTACACC
ATGGATCCCA GTGTCAGGTG GGAGTACTGC AACCTGACAC AATGTCCAGT GACAGAATCA
AGTGTCCTCA CAACTCCCAC GGTGGTCCCG GTTCCAAGCA CAGAGGCTCC TTCTGAACAA
GCACCACCTG AGAAAAGCCC TGTGGTCCAG GATTGCTACC ATGGTGATGG ACAGAGTTAT
CGAGGCACAT CCTCCACCAC TGTCACAGGA AGGAACTGTC AATCTTGGTC ATCTATGATA
CCACACTGGC ATCAGAGGAC CCCAGAAAAC TACCCAAATG CTGGCCTGAC CAGGAACTAC
TGCAGGAATC CAGATTCTGG GAAACAACCC TGGTGTTACA CGACTGATCC ATGTGTGAGG
TGGGAGTACT GCAACCTGAC ACAATGCTCA GAAACAGAAT CAGGTGTCCT AGAGACTCCC
ACTGTTGTTC CGGTTCCAAG CATGGAAGCT CATTCTGAAG CAGCACCAAC TGAGCAAACC
CCTGTGGTCC AGCAGTGCTA CCATGGTAAT GGACAGAGTT ATCGAGGCAC ATTCTCCACC
ACTGTCACAG GAAGGACATG TCAATCTTGG TCATCCATGA CACCACACCA GCATAAGAGG
ACCCCGGAAA ACCACCCAAA TGATGACTTG ACAATGAACT ACTGCAGGAA TCCAGATGCT
GACACAGGCC CTTGGTGTTT TACCATGGAC CCCAGCGTCA GGCGGGAGTA CTGCAACCTG
ACGCGATGCT CAGACACAGA AGGGACTGTG GTCACACCTC CGACTGTTAT CCCGGTTCCA
AGCCTAGAGG CTCCTTCTGA ACAAGCATCC TCTTCATTTG ATTGTGGGAA GCCTCAAGTG
GAGCCAAAGA AATGTCCTGG AAGCATTGTA GGTGGGTGTG TGGCCCACCC ACATTCCTGG
CCCTGGCAAG TCAGTCTTAG AACAAGGTTT GGAAAGCACT TCTGTGGAGG CACCTTAATA
TCCCCAGAGT GGGTGCTGAC TGCTGCTTGC TGCTTGGAGA CGTTCTCAAG GCCTTCCTTC
TACAAGGTCA TCCTGGGTGC ACACCAAGAA GTGAATCTCG AATCTCATGT TCAAGAAATA
GAAGTGTCTA GGTTGTTCTT GGAGCCCATA GGAGCAGATA TTGCCTTGCT AAAGCTAAGC
AGGCCTGCCA TCATCACTGA CAAAGTAATC CCAGCCTGTC TGCCGTCTCC AAATTACGTG
ATCACCGCCT GGACTGAATG TTACATCACT GGCTGGGGAG AAACCCAAGG TACCTTTGGG
GCTGGCCTTC TCAAGGAAGC CCAGCTTCAT GTGATTGAGA ATACAGTGTG CAATCACTAC
GAGTTTCTGA ATGGAAGAGT CAAATCCACT GAGCTCTGTG CTGGGCATTT GGCCGGAGGC
ACTGACAGAT GCCAGGGTGA CAATGGAGGG CCTGTGGTTT GCTTCGACAA GGACAAATAC
ATTTTACGAG GAATAACTTC TTGGGGTCCT GGCTGTGCAT GCCCCAATAA GCCTGGTGTC
TATGTTCGTG TTTCAAGCTT TGTCACTTGG ATTGAGGGAG TGATGAGAAA TAATTAATTG
AACAAGAGAC AGAGTGAAGC ATTGACTCAC CTAGAGGCTA GAATGGGGGT AGGGATTTAG
CACGCTGGAA ATAACGGACA GTAATCAAAC GAAGACACTG TCCCCAGCTA CCAACTATGC
CAAACCTCAG CATTTTTGGT ATTATTGTGT ATAAGCTTTT CCTGTCTGAC TGCTGGGTTC
TCCAATAAGG TGACATAGCT ATGCCATTTG TTAAAAATAA ACTCTGTACT TATTTTGATT
TGAGTAAA
```

TABLE 6

LPA Oligonucleotide Sequences (modified)

| Oligonucleotide | Sequence (Sense Strand) | SEQ ID NO: | Sequence (Antisense Strand) | SEQ ID NO: |
| --- | --- | --- | --- | --- |
| LPA-0190-M1 | [mUs][mC][mC][mA][mC][mC][mA][fC][fU][fG][fU][mC][mA][mC][mA][mG][mG][mA][mA][mA][mG][mC][mA][mG][mC][mC][mG][ademA-GalNAc][ademA-GalNAc][ademA-GalNAc][mG][mG][mC][mU][mG][mC] | 388 | [Me Phosphonate-4O-mUs][fUs][fUs][fC][fC][mU][fG][mU][mG][fA][mC][mA][mG][fU][mG][mG][mU][mG][mG][mAs][mGs][mG] | 788 |
| LPA-0501-M1 | [mUs][mG][mG][mU][mA][mA][mU][fG][fG][fA][fC][mA][mG][mA][mG][mU][mU][mA][mU][mA][mG][mC][mA][mG][mC][mC][mG][ademA-GalNAc][ademA-GalNAc][ademA-GalNAc][mG][mG][mC][mU][mG][mC] | 389 | [Me Phosphonate-4O-mUs][fAs][fUs][fA][fA][mC][fU][mC][mU][fG][mU][mC][mC][fA][mU][mU][mA][mC][mC][mAs][mGs][mG] | 789 |

TABLE 6-continued

LPA Oligonucleotide Sequences (modified)

| Oligonucleotide | Sequence (Sense Strand) | SEQ ID NO: | Sequence (Antisense Strand) | SEQ ID NO: |
|---|---|---|---|---|
| LPA-3100-M1 | [mUs][mA][mC][mU][mG][mC][mA][fA][fC][fC][fU][mG][mA][mC][mA][mC][mG][mA][mU][mA][mG][mC][mA][mG][mC][mC][mG][ademA-GalNAc][ademA-GalNAc][ademA-GalNAc][mG][mG][mC][mU][mG][mC] | 390 | [Me Phosphonate-4O-mUs][fAs][fUs][fC][fG][mU][fG][mU][mC][fA][mG][mG][mU][fU][mG][mC][mA][mG][mU][mAs][mGs][mG] | 790 |
| LPA-3286-M1 | [mAs][mG][mA][mA][mC][mU][mU][fG][fC][fC][fA][mA][mG][mC][mU][mU][mG][mG][mU][mA][mG][mC][mA][mG][mC][mC][mG][ademA-GalNAc][ademA-GalNAc][ademA-GalNAc][mG][mG][mC][mU][mG][mC] | 391 | [Me Phosphonate-4O-mUs][fAs][fCs][fC][fA][mA][fG][mC][mU][fU][mG][mG][mC][fA][mA][mG][mU][mU][mC][mUs][mGs][mG] | 791 |
| LPA-3288-M1 | [mAs][mA][mC][mU][mU][mG][mC][fC][fA][fA][fG][mC][mU][mU][mG][mU][mC][mA][mA][mG][mC][mA][mG][mC][mC][mG][ademA-GalNAc][ademA-GalNAc][ademA-GalNAc][mG][mG][mC][mU][mG][mC] | 392 | [Me Phosphonate-4O-mUs][fUs][fGs][fA][fC][mC][FA][mA][mG][fC][mU][mU][mG][fG][mC][mA][mA][mG][mU][mUs][mGs][mG] | 792 |
| LPA-3291-M1 | [mUs][mU][mG][mC][mC][mA][mA][fG][fC][fU][fU][mG][mG][mU][mC][mA][mU][mC][mU][mA][mG][mC][mA][mG][mC][mC][mG][ademA-GalNAc][ademA-GalNAc][ademA-GalNAc][mG][mG][mC][mU][mG][mC] | 393 | [Me Phosphonate-4O-mUs][fAs][fGs][fA][fU][mG][fA][mC][mC][fA][mA][mG][mC][fU][mU][mG][mG][mC][mA][mAs][mGs][mG] | 793 |
| LPA-3584-M1 | [mAs][mU][mG][mG][mA][mC][mA][fG][fA][fG][fU][mU][mA][mU][mC][mG][mA][mG][mG][mA][mG][mC][mA][mG][mC][mC][mG][ademA-GalNAc][ademA-GalNAc][ademA-GalNAc][mG][mG][mC][mU][mG][mC] | 394 | [Me Phosphonate-4O-mUs][fCs][fCs][fU][fC][mG][fA][mU][mA][fA][mC][mU][mC][fU][mG][mU][mC][mC][mA][mUs][mGs][mG] | 794 |
| LPA-3585-M1 | [mUs][mG][mG][mA][mC][mA][mG][fA][fG][fU][fU][mA][mU][mC][mG][mA][mG][mG][mC][mA][mG][mC][mA][mG][mC][mC][mG][ademA-GalNAc][ademA-GalNAc][ademA-GalNAc][mG][mG][mC][mU][mG][mC] | 395 | [Me Phosphonate-4O-mUs][fGs][fCs][fC][fU][mC][fG][mA][mU][fA][mA][mC][mU][fC][mU][mG][mU][mC][mC][mAs][mGs][mG] | 795 |

TABLE 6-continued

LPA Oligonucleotide Sequences (modified)

| Oligonucleotide | Sequence (Sense Strand) | SEQ ID NO: | Sequence (Antisense Strand) | SEQ ID NO: |
|---|---|---|---|---|
| LPA-4645-M1 | [mUs][mG][mG][mU][mC][mA][mU][fC][fU][fA][fU][mG][mA][mU][mA][mC][mC][mA][mC][mA][mG][mC][mA][mG][mC][mC][mG][ademA-GalNAc][ademA-GalNAc][ademA-GalNAc][mG][mG][mC][mU][mG][mC] | 396 | [Me Phosphonate-4O-mUs][fGs][fUs][fG][fG][mU][fA][mU][mC][fA][mU][mA][mG][fA][mU][mG][mA][mC][mC][mAs][mGs][mG] | 796 |
| LPA-4717-M1 | [mUs][mA][mC][mU][mG][mC][mA][fG][fG][fA][fA][mU][mC][mC][mA][mG][mA][mU][mU][mA][mG][mC][mA][mG][mC][mC][mG][ademA-GalNAc][ademA-GalNAc][ademA-GalNAc][mG][mG][mC][mU][mG][mC] | 397 | [Me Phosphonate-4O-mUs][fAs][fAs][fU][fC][mU][fG][mG][mA][fU][mU][mC][mC][fU][mG][mC][mA][mG][mU][mAs][mGs][mG] | 797 |
| LPA-5510-M1 | [mAs][mG][mA][mA][mA][mU][mG][fU][fC][fC][fU][mG][mG][mA][mA][mG][mC][mA][mU][mA][mG][mC][mA][mG][mC][mC][mG][ademA-GalNAc][ademA-GalNAc][ademA-GalNAc][mG][mG][mC][mU][mG][mC] | 398 | [Me Phosphonate-4O-mUs][fAs][fUs][fG][fC][mU][fU][mC][mC][fA][mG][mG][mA][fC][mA][mU][mU][mU][mC][mUs][mGs][mG] | 798 |
| LPA-3750-M1 | [mGs][mA][mC][mA][mA][mC][mA][fG][fA][fA][fU][mA][mU][mU][mA][mU][mC][mC][mA][mA][mG][mC][mA][mG][mC][mC][mG][ademA-GalNAc][ademA-GalNAc][ademA-GalNAc][mG][mG][mC][mU][mG][mC] | 399 | [Me Phosphonate-4O-mUs][fUs][fGs][fG][fA][mU][fA][mA][mU][fA][mU][mU][mC][fU][mG][mU][mU][mG][mU][mCs][mGs][mG] | 799 |
| LPA-2900-M2 | [mAs][mU][mG][mG][mA][mC][mA][fG][fA][fG][fU][mU][mA][mU][mC][mA][mA][mG][mG][mA][mG][mC][mA][mG][mC][mC][mG][ademA-GalNAc][ademA-GalNAc][ademA-GalNAc][mG][mG][mC][mU][mG][mC] | 400 | [Me Phosphonate-4O-mUs][fCs][fC][fU][fU][mG][fA][mU][mA][fA][mC][mU][mC][fU][mG][mU][mC][mC][mA][mUs][mGs][mG] | 800 |
| LPA-3675-M2 | [mGs][mA][mC][mA][mA][mC][mA][fG][fA][fA][fU][mA][mU][mU][mA][mU][mC][mC][mA][mA][mG][mC][mA][mG][mC][mC][mG][ademA-GalNAc][ademA-GalNAc][ademA-GalNAc][mG][mG][mC][mU][mG][mC] | 401 | [Me Phosphonate-4O-mUs][fUs][fG][fG][fA][mU][fA][mA][mU][fA][mU][mU][mC][fU][mG][mU][mU][mG][mU][mCs][mGs][mG] | 801 |

TABLE 6-continued

LPA Oligonucleotide Sequences (modified)

| Oligonucleotide | Sequence (Sense Strand) | SEQ ID NO: | Sequence (Antisense Strand) | SEQ ID NO: |
|---|---|---|---|---|
| LPA-2900-M3 | [mAs][mU][mG][mG][mA][mC][mA][fG][fA][fG][fU][mU][mA][mU][mC][mA][mA][mG][mG][mA][mG][mC][mA][mG][mC][mC][mG][ademA-GalNAc][ademA-GalNAc][ademA-GalNAc][mG][mG][mC][mU][mG][mC] | 402 | [Me Phosphonate-4O-mUs][fCs][fC][mU][fU][mG][fA][mU][mA][fA][mC][mU][mC][fU][mG][mU][mC][mC][mA][mUs][mGs][mG] | 802 |
| LPA-3675-M3 | [mGs][mA][mC][mA][mA][mC][mA][fG][fA][fA][fU][mA][mU][mU][mA][mU][mC][mC][mA][mA][mG][mC][mA][mG][mC][mC][mG][ademA-GalNAc][ademA-GalNAc][ademA-GalNAc][mG][mG][mC][mU][mG][mC] | 403 | [Me Phosphonate-4O-mUs][fUs][fG][mG][fA][mU][fA][mA][mU][fA][mU][mU][mC][fU][mG][mU][mU][mG][mU][mCs][mGs][mG] | 803 |

Modifications in Table 6:

mC, mA, mG, mU=2'-OMe ribonucleosides; fA, fC, fG, fU=2'-F ribonucleosides; s=phosphorothioate; MePhosphonate-4O-mUs=

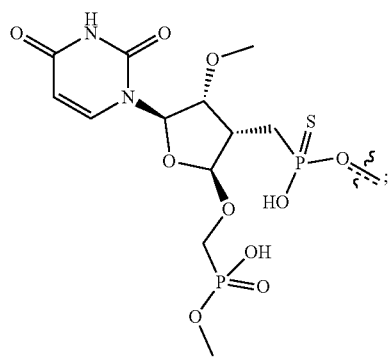

ademA-GalNAc=GalNAc attached to an adenine nucleotide:

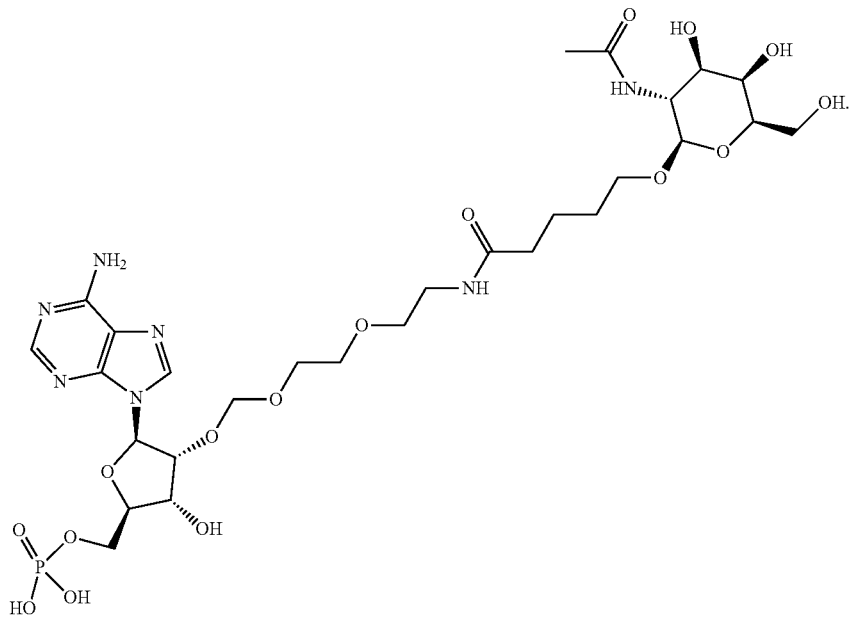 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

What is claimed is:

1. An RNAi oligonucleotide for reducing apolipoprotein (a) (LPA) expression, the oligonucleotide comprising a sense strand and an antisense strand, wherein the sense strand and the antisense strand form a duplex region, wherein the antisense strand is:

5'-[MePhosphonate-40-mUs][fAs][fGs][fA][fU][mG] [fA][mC][mC][fA][mA][mG][mC][fU][mU][mG] [mG][mC][mA][mAs][mGs][mG]-3' (SEQ ID NO: 793), and the sense strand is:

5'-[mUs][mU][mG][mC][mC][mA][mA][fG][fC][fU] [fU][mG][mG][mU][mC][mA][mU][mC][mU][mA] [mG][mC][mA][mG][mC][mC][mG][ademA-Gal-NAc][ademA-GalNAc][ademA-GalNAc][mG][mG] [mC][mU][mG][mC]-3' (SEQ ID NO: 393), wherein:

mA represents 2'-OMe adenosine;
mC represents 2'-OMe cytosine;
mG represents 2'-OMe guanosine;
mU represents 2'-OMe uridine;
fA represents 2'-F adenosine, fC represents 2'-F cytosine;
fG represents 2'-F guanosine;
fU represents 2'-F uridine;
fAs represents 2'-F adenosine with a 3'-phosphorothioate linkage;
fGs represents 2'-F guanosine with a 3'-phosphorothioate linkage;
mAs represents 2'-OMe adenosine with a 3'-phosphorothioate linkage;
mGs represents 2'-OMe guanosine with a 3'-phosphorothioate linkage;
mUs represents 2'-OMe uridine with a 3'-phosphorothioate linkage;

417 ademA-GalNAc represents 2'-aminodiethoxymethanol-adenine-GalNAc:

418 and MePhosphonate-40-mUs represents

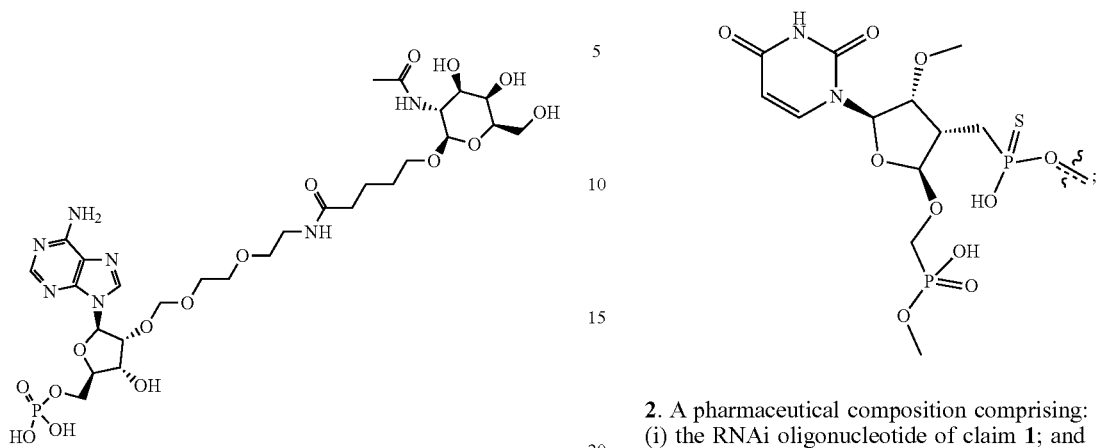

2. A pharmaceutical composition comprising:
   (i) the RNAi oligonucleotide of claim 1; and
   (ii) a pharmaceutically acceptable carrier, delivery agent or excipient.

3. The pharmaceutical composition of claim 2, wherein the carrier comprises phosphate buffered saline.

4. The pharmaceutical composition of claim 2, wherein the carrier comprises water.

\* \* \* \* \*

SEQUENCE LISTING

```
Sequence total quantity: 1197
SEQ ID NO: 1            moltype = DNA   length = 6414
FEATURE                 Location/Qualifiers
source                  1..6414
                        mol_type = unassigned DNA
                        organism = Homo sapiens
SEQUENCE: 1
ctgggattgg gacacacttt ctgggcactg ctggccagtc ccaaaatgga acataaggaa   60
gtggttcttc tacttctttt atttctgaaa tcagcagcac ctgagcaaag ccatgtggtc  120
caggattgct accatggtga tggacagagt tatcgaggca cgtactccac cactgtcaca  180
ggaaggacct gccaagcttg gtcatctatg acaccacatc aacataatag gaccacagaa  240
aactacccaa atgctggctt gatcatgaac tactgcagga atccagatgc tgtggcagct  300
ccttattgtt atacgaggga tcccggtgtc aggtgggagt actgcaacct gacgcaatgc  360
tcagacgcag aagggactgc cgtcgcgcct ccgactgtta ccccggttcc aagcctagag  420
gctccttccg aacaagcacc gactgagcaa aggcctgggg tgcaggagtg ctaccatggt  480
aatggacaga gttatcgagg cacatactcc accactgtca caggaagaac ctgccaagct  540
tggtcatcta tgacaccaca ctcgcatagt cggaccccag aatactaccc aaatgctggc  600
ttgatcatga actactgcag gaatccagat gctgtggcag ctccttattg ttatacgagg  660
gatcccggtg tcaggtggga gtactgcaac ctgacgcaat gctcagacgc agaagggact  720
gccgtcgcgc ctccgactgt taccccggtt ccaagcctag aggctccttc cgaacaagca  780
ccgactgagc aaaggcctgg ggtgcaggag tgctaccatg gtaatggaca gagttatcga  840
ggcacatact ccaccactgt cacaggaaga acctgccaag cttggtcatc tatgacacca  900
cactcgcata gtcggacccc agaatactac ccaaatgctg gcttgatcat gaactactgc  960
aggaatccag atgctgtggc agctccttat tgttatacga gggatcccgg tgtcaggtgg 1020
gagtactgca acctgacgca atgctcagac gcagaaggga ctgccgtcgc gcctccgact 1080
gttaccccgg ttccaagcct agaggctcct tccgaacaag caccgactga gcagaggcct 1140
ggggtgcagg agtgctacca cggtaatgga cagagttatc gaggcacata ctccaccact 1200
gtcactggaa gaacctgcca agcttggtca tctatgacac cacactcgca tagtcggacc 1260
ccagaatact acccaaatgc tggcttgatc atgaactact gcaggaatcc agatgctgtg 1320
gcagctcctt attgttatac gagggatccc ggtgtcaggt gggagtactg caacctgacg 1380
caatgctcag acgcagaagg gactgccgtc gcgcctccga ctgttacccc ggttccaagc 1440
ctagaggctc cttccgaaca agcaccgact gagcaaaggc ctggggtgca ggagtgctac 1500
catggtaatg gacagagtta tcgaggcaca tactccacca ctgtcacagg aagaacctgc 1560
caagcttggt catctatgac accacactcg catagtcgga ccccagaata ctacccaaat 1620
gctggcttga tcatgaacta ctgcaggaat ccagatgctg tggcagctcc ttattgttat 1680
acgagggatc ccggtgtcag gtgggagtac tgcaacctga cgcaatgctc agacgcagaa 1740
gggactgccg tcgcgcctcc gactgttacc ccggttccaa gcctagaggc tccttccgaa 1800
caagcaccga ctgagcaaag gcctggggtg caggagtgct accatggtaa tggacagagt 1860
tatcgaggca catactccac cactgtcaca ggaagaacct gccaagcttg gtcatctatg 1920
acaccacact cgcatagtcg gaccccagaa tactacccaa atgctggctt gatcatgaac 1980
tactgcagga atccagatgc tgtggcagct ccttattgtt atacgaggga tcccggtgtc 2040
aggtgggagt actgcaacct gacgcaatgc tcagacgcag aagggactgc cgtcgcgcct 2100
ccgactgtta ccccggttcc aagcctagag gctccttccg aacaagcacc gactgagcaa 2160
aggcctgggg tgcaggagtg ctaccatggt aatggacaga gttatcgagg cacatactcc 2220
accactgtca caggaagaac ctgccaagct tggtcatcta tgacaccaca ctcgcatagt 2280
```

-continued

```
cggacccag aatactaccc aaatgctggc ttgatcatga actactgcag gaatccagat    2340
gctgtggcag ctccttattg ttatacgagg gatcccggtg tcaggtggga gtactgcaac    2400
ctgacgcaat gctcagacgc agaagggact gccgtcgcgc ctccgactgt taccccggtt    2460
ccaagcctag aggctccttc cgaacaagca ccgactgagc agaggcctgg ggtgcaggag    2520
tgctaccacg gtaatggaca gagttatcga ggcacatact ccaccactgt cactggaaga    2580
acctgccaag cttggtcatc tatgacacca cactcgcata gtcggacccc agaatactac    2640
ccaaatgctg gcttgatcat gaactactgc aggaatccag atcctgtggc agccccttat    2700
tgttatacga gggatcccag tgtcaggtgg gagtactgca acctgacaca atgctcagac    2760
gcagaaggga ctgccgtcgc gcctccaact attacccgca ttccaagcct agaggctcct    2820
tctgaacaag caccaactga gcaaaggcct ggggtgcagg agtgctacca cggaaatgga    2880
cagagttatc aaggcacata cttcattact gtcacaggaa gaacctgcca agcttggtca    2940
tctatgacac cacactcgca tagtcggacc ccagcatact acccaaatgc tggcttgatc    3000
aagaactact gccgaaatcc agatcctgtg gcagcccctt ggtgttatac aacagatccc    3060
agtgtcaggt gggagtactg caacctgaca cgatgctcag atgcagaatg gactgccttc    3120
gtccctccga atgttattct ggctccaagc ctagaggctt tttttgaaca agcactgact    3180
gaggaaaccc ccggggtaca ggactgctac taccattatg gacagagtta ccgaggcaca    3240
tactccacca ctgtcacagg aagaacttgc caagcttggt catctatgac accacaccag    3300
catagtcgga ccccagaaaa ctacccaaat gctggcctga ccaggaacta ctgcaggaat    3360
ccagatgctg agattcgccc ttggtgttac accatggatc ccagtgtcag gtgggagtac    3420
tgcaacctga cacaatgcct ggtgacagaa tcaagtgtcc ttgcaactct cacggtggtc    3480
ccagatccaa gcacagaggc ttcttctgaa gaagcaccaa cggagcaaag ccccgggggtc    3540
caggattgct accatggtga tggacagagt tatcgaggct cattctctac cactgtcaca    3600
ggaaggacat gtcagtcttg gtcctctatg acaccacact ggcatcagag acaacagaa    3660
tattatccaa atggtggcct gaccaggaac tactgcagga atccagatgc tgagattagt    3720
ccttggtgtt ataccatgga tcccaatgtc agatgggagt actgcaacct gacacaatgt    3780
ccagtgacag aatcaagtgt ccttgcgacg tccacggctg tttctgaaca agcaccaacg    3840
gagcaaagcc ccacagtcca ggactgctac catggtgatg gacagagtta tcgaggctca    3900
ttctccacca ctgttacagg aaggacatgt cagtcttggt cctctatgac accacactgg    3960
catcagagaa ccacagaata ctacccaaat ggtggcctga ccaggaacta ctgcaggaat    4020
ccagatgctg agattcgccc ttggtgttat accatggatc ccagtgtcag atgggagtac    4080
tgcaacctga cgcaatgtcc agtgatggaa tcaactctcc tcacaactcc cacggtggtc    4140
ccagttccaa gcacagagct tccttctgaa gaagcaccaa ctgaaaacag cactgggggtc    4200
caggactgct accgaggtga tggacagagt tatcgaggca cactccacac tatcaca    4260
ggaagaacat gtcagtcttg gtcgtctatg acaccacatt ggcatcggag gatccatta    4320
tactatccaa atggctgcct gaccaggaac tactgcagga atccagatgc tgagattcgc    4380
ccttggtgtt acaccatgga tcccagtgtc aggtgggagt actgcaacct gacacgatgt    4440
ccagtgacag aatcgagtgt cctcacaact cccacagtgg ccccggttcc aagcacagag    4500
gctccttctg aacaagcacc acctgagaaa agccctgtgg tccaggattg ctaccatggt    4560
gatggacgga gttatcgagg catatcctcc accactgtca caggaaggac ctgtcaatct    4620
tggtcatcta tgataccaca ctggcatcag aggacccccag aaaactaccc aaatgctggc    4680
ctgaccgaga actactgcag gaatccagat tctgggaaac aacccggtgt tacacaacc    4740
gatccgtgtg tgaggtggga gtactgcaat ctgacacaat gctcagaaac agaatcaggt    4800
gtcctagaga ctcccactgt tgttccagtt ccaagcaggg aggctcattc tgaagcagca    4860
ccaactgagc aaaccctgt ggtccggcag tgctaccatg gtaatggcca gagttatcga    4920
ggcacattct ccaccactgt cacaggaagg acatgtcaat cttggtcatc catgacacca    4980
caccggcatc agaggacccc agaaaactac ccaaatgatg cctgacaat gaactactgc    5040
aggaatggac atgccgatac aggcccttgg tgttttacca tggaccccag catcaggtgg    5100
gagtactgca acctgacgcg atgctcagac acagaaggga ctgtggtcgc tcctccgact    5160
gtcatccagg ttccaagcct agggcctcct tctgaacaag actgtatgtt tgggaatggg    5220
aaaggatacc ggggcaagaa ggcaaccact gttactggga cgccatgcca ggaatgggct    5280
gcccaggacg cccatagaca cagcacgttc atttccaggga caaataaatg ggcaggtctg    5340
gaaaaaaaatt actgccgtaa ccctgatggt gacatcaatg gtccctggtg ctacacaatg    5400
aatccaagaa aacttttttga ctactgtgat atccctctct gtgcatcctc ttcatttgat    5460
tgtgggaagc ctcaagtgga gccgaagaaa tgtcctggaa gcattgtagg gggtgtgtg    5520
gcccacccac attcctggcc ctggcaagtc agtctcaaa caaggtttgg aaagcacttc    5580
tgtggaggca ccttaatatc cccagatgtg gtgctgactg ctgctcactg cttgaagaag    5640
tcctcaaggc cttcatccta caaggtcatc ctgggtgcac accaagaagt gaacctcgaa    5700
tctcatgttc aggaaataga agtgtctagg ctgttcttgg agcccacaca agcagatatt    5760
gccttgctaa agctaagcag gcctgccgtc atcactgaca agtaatgcc agcttgtctg    5820
ccatccccag actacatggt caccgccagg actgaatgtt acatcactgc ctggggagaa    5880
acccaaggta cctttgggac tggccttctc aaggaagccc agctccttgt tattgagaat    5940
gaagtgtgca atcactataa gtatatttgt gctgagcatt tggccagagg cactgacagt    6000
tgccaggtg acagtggagg gcctctgtt tgcttcgaga aggacaaata cattttacaa    6060
ggagtcactt cttgggggtct tggctgtgca cgccccaata agcctggtgt ctatgctcgt    6120
gtttcaaggt ttgttacttg gattgaggga atgatgagaa ataattaatt ggacgggaa    6180
cagagtgaag catcaaccta cttagaagct gaaacgtggg taaggattta gcatgctgga    6240
aataatagac agcaatcaaa cgaagacact gttcccagct accagctatg ccaaacctgg    6300
gcatttttgg tattttgtg tataagcttt taaggtctga ctgacaaatt ctgtattaag    6360
gtgtcatagc tatgacattt gttaaaaata aactctgcac ttattttgat ttga          6414
```

```
SEQ ID NO: 2            moltype = DNA   length = 5387
FEATURE                 Location/Qualifiers
source                  1..5387
                        mol_type = unassigned DNA
                        organism = Macaca fascicularis
SEQUENCE: 2
gatgctgcat acttaatgtc gaaaggttgc ttcatccaag agcctggagt tttcagagac     60
actgtcctga aactatgtcc tgaaactatg tcattgaaac tgaaacattg tcctgaagct    120
ggtattgggc aataccagcg cctgcaggca acagctcgga tgcacttaag atttaaatat    180
```

```
tacccacaga agttctggct tgtctgggaa aacctttttgc taaacagaag agcaacattt     240
tttttttttt cttttctgga atttgtaaac agcatttatt ctcagcctta ccttccaaac     300
gttgcacttg gaacattgct gggcccccgtg gaaacagaag cgaacgtcag ccaggccggc     360
agggggcggc agacccccaca cttcgccggg cgccctcacc tccctgggag ggagtgtgca     420
gctgccaaaa tcttcggcgg ggttcagtcc aagcgacttc agccagcaga tggtcattct     480
cctgtgaccg tgtgtactac agactgtttc aaaaccgggc aggcaattaa caatgggaat     540
tctgccatca tcgctgacaa agtcatccca gtttgtctgc catccccaaa ttatgtggtc     600
gccaaccaga ctgaatgtta tgtcactggc tggggagaaa cccaagcact acctgagcaa     660
agccatgtgg tccaggattg ctaccatggt gatggacaga gttatcaagg cacatcctcc     720
accactgtca caggaaggac ctgccaagct tggtcatcta tggaaccaca tcagcataat     780
agaaccacag aaaactaccc aaatgctggc ttgatcagga actactgcag gaatccagat     840
cctgtgcag cccccttattg ttatacgatg gatcccaatg tcaggtggga gtactgcaac     900
ctgacacaat gctcagacgc agaagggact gccgtcgcac ctccgaatgt caccccggtt     960
ccaagcctag aggctccttc cgaacaagca ccgactgagc aaaggcctgg ggtgcaggag    1020
tgctaccacg gtaatggaca gagttatcga ggcacatact tcaccactgt gacaggaaga    1080
acctgccaag cttggtcatc tatgacaccg cactctcata gtcggacccc ggaaaactac    1140
ccaaatggtg gcttgatcag gaactactgc aggaatccag atcctgtggc agcccttat    1200
tgttatacca tggatcccaa tgtcaggtgg gagtactgca acctgacaca atgctcagac    1260
gcagaaggga ttgccgtcac acctctgact gttaccccgg ttccaagcct agaggctcct    1320
tccaagcaag caccaactga gcaaaggcct ggtgtccagg agtgctacca cggtaatgga    1380
cagagttatc gaggcacata cttcaccact gtgacaggaa gaacctgcca agcttggtca    1440
tctatgacac cacattctca tagtcgtacc ccagaaaact acccaaatgg tggcttgatc    1500
aggaactact gcaggaatcc agatcctgtg gcagcccctt attgttatac catggatccc    1560
aatgtcaggt gggagtactg caacctgaca caatgctcag acgcagaagg gactgccgtc    1620
gcacctccga ctgtcacccc ggttccaagc ctagaggctc cttccgaaca agcaccgact    1680
gagcaaaggc ctggggtgca ggagtgctac cacggtaagca gacagagtta tcgaggcaca    1740
tacttcacca ctgtgacagg aagaacctgc caagcttggt catctatgac accgcactct    1800
catagtcgga ccccggaaaa ctacccaaat ggtggcttga tcaggaacta ctgcaggaat    1860
ccagatcctg tggcagcccc ttattgttat accatggatc ccaatgtcag gtgggagtac    1920
tgcaacctga cacaatgctc agacgcagaa gggactgccg tcgcacctcc gaatgtcacc    1980
ccggttccaa gcctagaggc tccttctgag caagcaccaa ctgagcaaag gcttggggtg    2040
caggagtgct accacggtaa tggacagagt tatcgaggca catacttcac cactgtgaca    2100
ggaagaacct gccaagcttg gtcatctatg acaccacact ctcatagtcg accccagaaa    2160
aactacccaa atgctggctt ggtcaagaac tactgccgaa atccagatcc tgtggcagcc    2220
ccttggtgtt atacaacgga tcccagtgtc aggtgggagt actgcaacct gacacgatgc    2280
tcagatgcag aagggactgc tgttgtgcct ccaaatatta ttccggttcc aagcctagag    2340
gcttttcttg aacaagaacc gactgaggaa acccccgggg tacaggagtg ctactaccat    2400
tatggacaga gttatagagg cacatactcc accactgtta caggaagaac ttgccaagct    2460
tggtcatcta tgacaccaca ccagcatagt cggacccccaa aaactatccc aaatgctggc    2520
ctgaccagga actactgcag gaatccagat gctgagattc gcccttggtg ttataccatg    2580
gatcccagtg tcaggtggga gtactgcaac ctgacacaat gtctggtgac agaatcaagt    2640
gtccttgaaa ctctcacagt ggtcccagat ccaagcacac aggcttcttc tgaagaagca    2700
ccaacggagc aaagtcccga ggtccaggac tgctaccatg gtgatggaca gagttatcga    2760
ggctcattct ccaccactgt cacaggaagg acatgtcagt cttggtcctc tatgacacca    2820
cactggcatc agaggacaac agaatattat ccagatggtg gcctgaccag gaactactgc    2880
aggaatccag atgctgagat cgcccttggg tgttatacca tggatcccag tgtcaggtgg    2940
gagtactgca acctgacaca atgtccagtg acagaatcaa gtgtcctcgc aacgtccatg    3000
gctgtttctg aacaagcacc aatggagcaa agccccgggg tccaggactg ctaccatggt    3060
gatggacaga gttatcgagg ttcattctcc accactgtca caggaaggac atgtcagtct    3120
tggtcctcta tgacaccaca ctggcatcag aggaccatag aatactaccc aaatggtggc    3180
ctgaccaaga actactgcag gaatccagat gctgagattc gcccttggtg ttataccatg    3240
gatcccagag tcagtgggaa gtactgcaac ctgacacaat gtgtggtgat ggaatcaagt    3300
gtcccttgcaa ctcccatggt ggtcccagtt ccaagcagag aggttccttc tgaagaagca    3360
ccaactgaaa cagccctggg ggtccaggac tgctaccaag gtgatggaca gagttatcga    3420
ggcacattct ccaccactat cacaggaaga acatgtcagt cttggttgtc tatgacacca    3480
catcggcatc ggaggatccc attacgctat ccaaatgctg gcctgaccag gaactattgc    3540
agaaatccag atgctgagat cgcccttggg tgttacacca tggatcccag tgtcaggtgg    3600
gagtactgca acctgacaca atgtccagtg acagaatcaa gtgtcctcac aactcccacg    3660
gtggtcccgg ttccaagcac agaggctcct tctgaacaag caccacctga gaaaagcct    3720
gtggtccagg attgctacca tggtgatgga cagagttatc gaggcacatc ctccaccact    3780
gtcacaggaa ggaactgtca gtcttggtca tctatgatac cacactggca tcagaggacc    3840
ccagaaaact acccaaatgc tggcctgacc aggaactact gcaggaatcc agattctggg    3900
aaacaacccct ggtgttacac gactgatcca tgtgtgaggg gggagtactg caacctgaca    3960
caatgctcag aaacagaatc aggtgtccta gactcccca ctgttgttcc ggttccagcc    4020
atggaagctc attctgaagc agcaccaact gagcaaactc ctgtggtcca gcagtgctac    4080
catggtaatg gacagagtta tcgaggcaca ttctccacca ctgtcacagg aaggacatgt    4140
caatcttggt catccatgac accaccagca taagagga ccccggaaaa ccacccaaat    4200
gatgacttga caatgaacta ctgcaggaat ccagatgctc acacaggccc ttggtgtttt    4260
accatggacc ccagcgtcag gcgggagtac tgcaacctga gcgatgctc agacacagaa    4320
gggactgtgg tcacacctcc gactgttatc ccggttccaa gcctagaggc tccttctgaa    4380
caagcatcct cttcatttga ttgtgggaag cctcaagtgg agcaaagaa atgtcctgga    4440
agcattgtag gtgggtgtgt ggcccaccca cattcctggc cctggcaagt cagtcttaga    4500
acaaggtttg gaaagcactt ctgtggaggc accttaatat cccagagtg ggtgctgact    4560
gctgcttgct gcttggagac gttctcaagg ccttcctct acaaggtcat cctgggtgca    4620
caccaagaag tgaatctcga atctcacgtt caagaaatag aagtgtctag ttgttcttg    4680
gagcccatag agcagatat tgccttgcta aagctaagca ggcctgccat catcactgac    4740
aaagtaatcc cagcctgtct gccgtctcca aattacgtga tcaccgtctg gactgaatgt    4800
tacatcactg gctggggaga aacccaaggt acctttgggg ctggccttct caaggaagcc    4860
cagcttcatg tgattgagaa tacagtgtgc aatcactacg agtttctgaa tggaagagtc    4920
```

-continued

```
aaatccaccg agctctgtgc tgggcatttg gccggaggca ctgacagatg ccagggtgac   4980
agtggagggc ctgtggtttg cttcgacaag gacaaataca ttttacgagg aataacttct   5040
tggggtcctg gctgtgcatg ccccaataag cctggtgtct atgttcgtgt ttcaagcttt   5100
gtcacttgga ttgagggagt gatgagaaat aattaattga acaagagaca gagtgaagca   5160
ttgactcacc tagaggctag aatggggta gggatttgac acgctggaaa taacggacag   5220
taatcaaacg aagacactgt ccccagctac caactatgcc aaacctcagc attttggta   5280
ttattgtgta taagctttc ccgtctgact gctgggttct ccaataaggt gacatagcta   5340
tgccatttgt taaaaataaa ctctgtactt attttgattt gagtaaa                 5387
```

| | | |
|---|---|---|
| SEQ ID NO: 3 | moltype = DNA  length = 6428 | |
| FEATURE | Location/Qualifiers | |
| source | 1..6428 | |
| | mol_type = unassigned DNA | |
| | organism = Macaca mulatta | |
| misc_difference | 2053 | |
| | note = misc_feature - a, c, g, or t | |
| misc_difference | 2272 | |
| | note = misc_feature - a, c, g, or t | |
| misc_difference | 2395 | |
| | note = misc_feature - a, c, g, or t | |

SEQUENCE: 3

```
agccttgcct ttgaaatgtt ccagttggaa cattgctggg cagcgtgcaa acaggagcga     60
acgtcagccg gggcggcagg gggcagcaga ccccacactt tgtccatgcc tcaggtggga    120
ggaagtgtcc ggctccagaa acctgccgcg ggctttatcc caagcgactt cagccagcag    180
acggttcatg tcctgaggct gcaaaatacg agttctgcca tcatcgctga caaagtcatc    240
ccagtttgtc tgccatcccc aaattatgcg atcgccaanc agactgaatg ttatgtcact    300
ggctggggag aaacccaagc actacctgag caaagccatg tggtccagga ttgctaccat    360
ggtgatggac agagttatca aggcacatcc tccaccactg tcacaggaag gacctgccaa    420
gcttggtcat ctatgaacc acatcagcat aatagaacca cagaaaacta cccaaatgct    480
ggcttgatca ggaactactg caggaatcca gatcctgtgg cagccccta ttgttatacg    540
atggatccca atgtcaggtg ggagtactgc aacctgaca aatgctcaga cgcagaaggg    600
actgccgtcg cacctccgaa tgtcaccccg gttccaagcc tagaggctct ttccgaacaa    660
gcaccgactg agcaaaggcc tggggtgcag gagtgctacc acggtaatgg acagagttat    720
cgaggcacat acttcaccac tgtgacagga agaacctgcc aagcttggtc atctatgaca    780
ccacattctc atagtcgtac cccagaaaac tacccaaatg gtggcttgat caggaactac    840
tgcaggaatc cagatcctgt ggcagcccct tattgttata ccatggatcc caatgtcagg    900
tgggagtact gcaacctgac acaatgctca gacgcagaag ggactgccgt cgcacctccg    960
aatgtcaccc cggttccaag cctagaggct ccttccgaac aagcaccgac tgagcaaagg   1020
cctggggtgc aggagtgcta ccacggtaat ggacagagtt atcgaggcac atacttcacc   1080
actgtgacag gaagaacctg ccaagcttgg tcatctatga caccacattc tcatagtcgt   1140
accccagaaa actacccaaa tggtggcttg atcaggaact actgcaggaa tccagatcct   1200
gtggcagccc cttattgtta taccatggat cccaatgtca ggtgggagta ctgcaacctg   1260
acacaatgct cagacgcaga gggactgccg tcgcacctc cgaatgtcac cccggttcca   1320
agcctagagg ctccttctga gcaagcaccg actgagcaaa ggcctggggt gcaggagtgc   1380
taccacggta atggacagag ttatcgaggc acatacttca ccactgtgac aggaagaacc   1440
tgccaagctt ggtcatctat gacaccgcac tctcatagtc ggacccgga aaactaccca   1500
aatggtggct tgatcaggaa ctactgcagg aatccagatc ctgtggcagc cccttattgt   1560
tatacgatgg atcccaatgt caggtgggag tactgcaacc tgacacaatg ctcagacgca   1620
gaagggactg ccgtcgcacc tccgaatgtc accccggttc caagcctaga ggctccttcc   1680
gaacaagcac cgactgagca aaggcctggg gtgcaggagt gctaccacgg taatggacag   1740
agttatcgag gcacatactt caccactgtg acaggaagaa cctgccaagc ttggtcatct   1800
atgacaccgc actctcatag tcggaccccg gaaaactacc caaatggtgg cttgatcagg   1860
aactactgca ggaatccaga tcctgtggca gccccttatt gttatacgat ggatcccaat   1920
gtcaggtggg agtactgcaa cctgacacaa tgctcagacg cagaagggac tgccgtcgca   1980
cctccgaatg tcaccccggt tccaagccta gaggctcctt ccgaacaagc accaactgag   2040
caaaggcctg ggntgcagga gtgctaccat ggtaatggac agagttatcg aggcacatac   2100
ttcaccactg tgacaggaag aacctgccaa gcttggtcat ctatgacacc gcactctcat   2160
agtcggaccc cggaaaacta cccaaatggt ggcttgatca ggaactactg caggaatcca   2220
gatcctgtgg cagccccta ttgttatacc atggatccca atgtcaggtg gnagtactgc   2280
aacctgacac aatgctcaga cgcagaaggg actgccgtcg cacctccgac tgtcaccccg   2340
gttccaagcc tagaggctcc ttcgagcaag caccgactg agcaaaggcc tgggntgcag   2400
gagtgctacc acggtaatgg acagagttat cgaggcacat acttcaccac tgtgacagga   2460
agaacctgcc aagcttggtc atctatgaca ccgcactctc atagtcggac cccggaaaac   2520
tacccaaatg gtggcttgat caggaactac tgcaggaatc ctgtgcagcc ctgt          2580
tattgttata cgatggatcc caatgtcagg tgggagtact gcaacctgac acaatgctca   2640
gacgcagaag ggactgccgt cgcacctccg aatgtcaccc cggttccaag cctagaggct   2700
ccttccgaac aagcaccgac tgagcaaagg cctggggtgc aggagtgcta ccacggtaat   2760
ggacagagtt atcgaggcac atacttcacc actgtgacag gaagaacctg ccaagcttgg   2820
tcatctatga caccgcactc tcatagtcgg accccgaaa actacccaaa tggtggcttg   2880
atcaggaact actgcaggaa tccagatcct gtggcagccc cttattgtta taccatggat   2940
cccaatgtca ggtgggagta ctgcaacctg acacaatgct cagacgcaga gggactgcc   3000
gtcgcacctc cgaatgtcac cccggttcca agcctagagg ctccttctga gcaagcacca   3060
actgagcaaa ggcttgggt gcaggagtgc taccacagta atggacagag ttatcgaggc   3120
acatacttca ccactgtgac aggaagaacc tgccaagctt ggtcatctat gacaccacac   3180
tctcatagtc ggaccccaga aaactaccca aatgctggct tggtcaagaa ctactgccga   3240
aatccagatc ctgtggcagc cccttggtgt tatacaacgg atcccagtgt caggtgggag   3300
tactgcaacc tgacacgatg ctcagatgca aagggactg ctgtcatgcc tccaaatatt   3360
attccggttc caagcctaga ggcttttctt gaacaagaac ctactgagga aacccccggg   3420
gtacaggagt gctactacca ttatggacag agttatcgag gcacatactc caccactgtt   3480
```

```
acaggaagaa cttgccaagc ttggtcatct atgacaccac accagcatag tcggacccca   3540
aaaaactatc caaatgctgg cctgaccagg aactactgca ggaatccaga tgctgagatt   3600
cgcccttggt gttataccat ggatcccagt gtcaggtggg agtactgcaa cctgacacaa   3660
tgtctggtga cagaatcaag tgtccttgaa actctcacag tggtcccaga tccaagcaca   3720
caggcttctt ctgaagaagc accaacggag caaagtcccg aggtccagga ctgctaccat   3780
ggtgatggac agagttatcg aggctcattc tccaccactg tcacaggaag gacatgtcag   3840
tcttggtcct ctatgacacc acactggcat cagaggacaa cagaatatta tccagatggt   3900
ggcctgacca ggaactactg caggaatcca gatgctgaga ttcgcccttg tgttatacc    3960
atggatccca gtgtcaggtg ggagtactgc aacctgacac aatgtccagt gacagaatca   4020
agtgtcctcg caacgtccat ggctgtttct gaacaagcac caatggagca aagcccccggg   4080
gtccaggact gctaccatgg tgatggacag agttatcgag gttcattctc caccactgtc   4140
acaggaagga catgtcagtc ttggtcctct atgacaccac actggcatca gaggaccata   4200
gaatactacc caaatggtgg cctgaccaag aactactgca ggaatccaga tgctgagatt   4260
cgcccttggt gttataccat ggatcccagt gtcagatgga gtactgcaa cctgacacaa   4320
tgtgtggtga tggaatcaag tgtccttgca actcccatgg tggtcccagt tccaagcaga   4380
gaggttcctt ctgaagaagc accaactgaa aacagccctg gggtccagga ctgctaccaa   4440
ggtgatggac agagttatcg aggcacattc tccaccacta tcacaggaag aacatgtcag   4500
tcttggttgt ctatgacacc acatcggcat cggaggatcc cattacgcta tccaaatgct   4560
ggcctgacca ggaactattg cagaaatcca gatgctgaga ttcgcccttg tgttacacc    4620
atggatccca gtgtcaggtg ggagtactgc aacctgacac aatgtccagt gacagaatca   4680
agtgtcctca caactcccac ggtggtcccg gttccaagca cagaggctcc ttctgaacaa   4740
gcaccacctg agaaaagccc tgtggtccag gattgctacc atggtgatgg acagagttat   4800
cgaggcacat cctccaccac tgtcacagga aggaactgtc aatcttggtc atctatgata   4860
ccacactggc atcagaggac cccagaaaac tacccaaatg ctggcctgac caggaactac   4920
tgcaggaatc cagattctgg gaaacaaccc tggtgttaca cgactgatcc atgtgtgagg   4980
tgggagtact gcaacctgac acaatgctca gaaacagaat caggtgtcct agagactccc   5040
actgttgttc cggttccaag catggaagct cattctgaag cagcaccaac tgagcaaacc   5100
cctgtggtcc agcagtgcta ccatggtaat ggacagagtt atcgaggcac attctccacc   5160
actgtcacag gaaggacatg tcaatcttgg tcatccatga caccacacca gcataaggag   5220
accccggaaa accaccccaa tgatgacttg acaatgaact actgcaggaa tccagatgct   5280
gacacaggcc cttggtgttt taccatggac cccagcgtca ggcgggagta ctgcaacctg   5340
acgcgatgct cagacacaga agggactgtg gtcacacctc cgactgttat cccggttcca   5400
agcctagagg ctccttctga acaagcatcc tcttcatttg attgtgggaa gcctcaagtg   5460
gagccaaaga aatgtcctgg aagcattgta ggtgggtgtg tggcccaccc acattcctgg   5520
ccctggcaag tcagtcttag aacaaggttt ggaaagcact tctggtggag caccttaata   5580
tccccagagt gggtgctgac tgctgcttgc tgcttggaga cgttctcaag gccttccttc   5640
tacaaggtca tcctgggtgc acaccaagaa gtgaatctcg aatctcatgt tcaagaaata   5700
gaagtgtcta ggttgttctt ggagcccata ggagcagata ttgccttgct aaagctaagc   5760
aggcctgcca tcatcactga caaagtaatc ccagcctgtc tgccgtctcc aaattacgtg   5820
atcaccgcct ggactgaatg ttacatcact ggctggggag aaacccaagg tacctttggg   5880
gctgccttc tcaaggaagc ccagcttcat gtgattgaga atacagtgtg caatcactac   5940
gagtttctga atgaaagagt caaatccact gagctctgtg ctgggcattt ggccggaggc   6000
actgacagat gccagggtga caatggaggg cctgtggttt gcttcgacaa ggacaaatac   6060
attttacgag gaataacttc ttggggtcct ggctgtgcat gccccaataa gcctggtgtc   6120
tatgttcgtg tttcaagctt tgtcacttgg attgagggag tgatgagaaa taattaattg   6180
aacaagagac agagtgaagc attgactcac ctagaggcta gaatgggggt agggatttag   6240
cacgctggaa ataacggaca gtaatcaaac gaagcacttg tccccagcta ccaactatgc   6300
caaacctcag catttttggt attattgtgt ataagctttt cctgtctgac tgctgggttc   6360
tccaataagg tgcacatagct atgccatttg ttaaaaataa actctgtact tattttgatt   6420
tgagtaaa                                                             6428
```

```
SEQ ID NO: 4            moltype = RNA   length = 25
FEATURE                 Location/Qualifiers
source                  1..25
                        mol_type = other RNA
                        organism = synthetic construct
                        note = Synthetic
SEQUENCE: 4
ctgagcaaag ccatgtggta cagga                                         25

SEQ ID NO: 5            moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 5
agcaaagcca tgtggtccaa gattg                                         25

SEQ ID NO: 6            moltype = RNA   length = 25
FEATURE                 Location/Qualifiers
source                  1..25
                        mol_type = other RNA
                        organism = synthetic construct
                        note = Synthetic
SEQUENCE: 6
```
aagccatgtg gtccaggata gctac                                                25

SEQ ID NO: 7              moltype = RNA   length = 25
FEATURE                   Location/Qualifiers
source                    1..25
                          mol_type = other RNA
                          organism = synthetic construct
                          note = Synthetic
SEQUENCE: 7
agccatgtgg tccaggatta ctacc                                                25

SEQ ID NO: 8              moltype = RNA   length = 25
FEATURE                   Location/Qualifiers
source                    1..25
                          mol_type = other RNA
                          organism = synthetic construct
                          note = Synthetic
SEQUENCE: 8
gccatgtggt ccaggattga tacca                                                25

SEQ ID NO: 9              moltype = DNA   length = 25
FEATURE                   Location/Qualifiers
source                    1..25
                          mol_type = other DNA
                          organism = synthetic construct
                          note = Synthetic
modified_base             25
                          mod_base = OTHER
                          note = thymine
SEQUENCE: 9
ccatgtggtc caggattgca accat                                                25

SEQ ID NO: 10             moltype = DNA   length = 25
FEATURE                   Location/Qualifiers
source                    1..25
                          mol_type = other DNA
                          organism = synthetic construct
                          note = Synthetic
modified_base             24
                          mod_base = OTHER
                          note = thymine
SEQUENCE: 10
catgtggtcc aggattgcta ccatg                                                25

SEQ ID NO: 11             moltype = RNA   length = 25
FEATURE                   Location/Qualifiers
source                    1..25
                          mol_type = other RNA
                          organism = synthetic construct
                          note = Synthetic
SEQUENCE: 11
atgtggtcca ggattgctaa catgg                                                25

SEQ ID NO: 12             moltype = DNA   length = 25
FEATURE                   Location/Qualifiers
source                    1..25
                          mol_type = other DNA
                          organism = synthetic construct
                          note = Synthetic
modified_base             25
                          mod_base = OTHER
                          note = thymine
SEQUENCE: 12
tgtggtccag gattgctaca atggt                                                25

SEQ ID NO: 13             moltype = RNA   length = 25
FEATURE                   Location/Qualifiers
source                    1..25
                          mol_type = other RNA
                          organism = synthetic construct
                          note = Synthetic
SEQUENCE: 13
ggtgatggac agagttatca aggca                                                25

SEQ ID NO: 14             moltype = DNA   length = 25
FEATURE                   Location/Qualifiers
source                    1..25
                          mol_type = other DNA
                          organism = synthetic construct

```
                                note = Synthetic
modified_base                   25
                                mod_base = OTHER
                                note = thymine
SEQUENCE: 14
tccaccactg tcacaggaaa gacct                                              25

SEQ ID NO: 15                   moltype = DNA   length = 25
FEATURE                         Location/Qualifiers
source                          1..25
                                mol_type = other DNA
                                organism = synthetic construct
                                note = Synthetic
modified_base                   24
                                mod_base = OTHER
                                note = thymine
SEQUENCE: 15
ccaccactgt cacaggaaga acctg                                              25

SEQ ID NO: 16                   moltype = RNA   length = 25
FEATURE                         Location/Qualifiers
source                          1..25
                                mol_type = other RNA
                                organism = synthetic construct
                                note = Synthetic
SEQUENCE: 16
ctgtcacagg aaggacctga caagc                                              25

SEQ ID NO: 17                   moltype = DNA   length = 25
FEATURE                         Location/Qualifiers
source                          1..25
                                mol_type = other DNA
                                organism = synthetic construct
                                note = Synthetic
modified_base                   25
                                mod_base = OTHER
                                note = thymine
SEQUENCE: 17
ggaaggacct gccaagctta gtcat                                              25

SEQ ID NO: 18                   moltype = DNA   length = 25
FEATURE                         Location/Qualifiers
source                          1..25
                                mol_type = other DNA
                                organism = synthetic construct
                                note = Synthetic
modified_base                   24
                                mod_base = OTHER
                                note = thymine
SEQUENCE: 18
gaaggacctg ccaagcttga tcatc                                              25

SEQ ID NO: 19                   moltype = DNA   length = 25
FEATURE                         Location/Qualifiers
source                          1..25
                                mol_type = other DNA
                                organism = synthetic construct
                                note = Synthetic
modified_base                   24
                                mod_base = OTHER
                                note = thymine
SEQUENCE: 19
aggacctgcc aagcttggta atcta                                              25

SEQ ID NO: 20                   moltype = DNA   length = 25
FEATURE                         Location/Qualifiers
source                          1..25
                                mol_type = other DNA
                                organism = synthetic construct
                                note = Synthetic
modified_base                   25
                                mod_base = OTHER
                                note = thymine
SEQUENCE: 20
ggacctgcca agcttggtca tctat                                              25

SEQ ID NO: 21                   moltype = DNA   length = 25
FEATURE                         Location/Qualifiers
source                          1..25
```

```
                              mol_type = other DNA
                              organism = synthetic construct
                              note = Synthetic
modified_base                 24
                              mod_base = OTHER
                              note = thymine
SEQUENCE: 21
gacctgccaa gcttggtcaa ctatg                                              25

SEQ ID NO: 22                 moltype = RNA  length = 25
FEATURE                       Location/Qualifiers
source                        1..25
                              mol_type = other RNA
                              organism = synthetic construct
                              note = Synthetic
SEQUENCE: 22
acctgccaag cttggtcata tatga                                              25

SEQ ID NO: 23                 moltype = RNA  length = 25
FEATURE                       Location/Qualifiers
source                        1..25
                              mol_type = other RNA
                              organism = synthetic construct
                              note = Synthetic
SEQUENCE: 23
cctgccaagc ttggtcatca atgac                                              25

SEQ ID NO: 24                 moltype = DNA  length = 25
FEATURE                       Location/Qualifiers
source                        1..25
                              mol_type = other DNA
                              organism = synthetic construct
                              note = Synthetic
modified_base                 25
                              mod_base = OTHER
                              note = thymine
SEQUENCE: 24
agcttggtca tctatgacaa cacat                                              25

SEQ ID NO: 25                 moltype = DNA  length = 25
FEATURE                       Location/Qualifiers
source                        1..25
                              mol_type = other DNA
                              organism = synthetic construct
                              note = Synthetic
modified_base                 25
                              mod_base = OTHER
                              note = thymine
SEQUENCE: 25
gtcatctatg acaccacata aacat                                              25

SEQ ID NO: 26                 moltype = RNA  length = 25
FEATURE                       Location/Qualifiers
source                        1..25
                              mol_type = other RNA
                              organism = synthetic construct
                              note = Synthetic
SEQUENCE: 26
cacagaaaac tacccaaata ctggc                                              25

SEQ ID NO: 27                 moltype = DNA  length = 25
FEATURE                       Location/Qualifiers
source                        1..25
                              mol_type = other DNA
                              organism = synthetic construct
                              note = Synthetic
modified_base                 24
                              mod_base = OTHER
                              note = thymine
SEQUENCE: 27
agaaaactac ccaaatgcta gcttg                                              25

SEQ ID NO: 28                 moltype = DNA  length = 25
FEATURE                       Location/Qualifiers
source                        1..25
                              mol_type = other DNA
                              organism = synthetic construct
                              note = Synthetic
modified_base                 25
```

```
                            mod_base = OTHER
                            note = thymine
SEQUENCE: 28
aaaactaccc aaatgctgga ttgat                                       25

SEQ ID NO: 29              moltype = RNA   length = 25
FEATURE                    Location/Qualifiers
source                     1..25
                           mol_type = other RNA
                           organism = synthetic construct
                           note = Synthetic
SEQUENCE: 29
acccaaatgc tggcttgata atgaa                                       25

SEQ ID NO: 30              moltype = RNA   length = 25
FEATURE                    Location/Qualifiers
source                     1..25
                           mol_type = other RNA
                           organism = synthetic construct
                           note = Synthetic
SEQUENCE: 30
cccaaatgct ggcttgatca tgaac                                       25

SEQ ID NO: 31              moltype = DNA   length = 25
FEATURE                    Location/Qualifiers
source                     1..25
                           mol_type = other DNA
                           organism = synthetic construct
                           note = Synthetic
modified_base              25
                           mod_base = OTHER
                           note = thymine
SEQUENCE: 31
gaactactgc aggaatccaa atgct                                       25

SEQ ID NO: 32              moltype = RNA   length = 25
FEATURE                    Location/Qualifiers
source                     1..25
                           mol_type = other RNA
                           organism = synthetic construct
                           note = Synthetic
SEQUENCE: 32
tactgcagga atccagatga tgtgg                                       25

SEQ ID NO: 33              moltype = RNA   length = 25
FEATURE                    Location/Qualifiers
source                     1..25
                           mol_type = other RNA
                           organism = synthetic construct
                           note = Synthetic
SEQUENCE: 33
actgcaggaa tccagatgca gtggc                                       25

SEQ ID NO: 34              moltype = RNA   length = 25
FEATURE                    Location/Qualifiers
source                     1..25
                           mol_type = other RNA
                           organism = synthetic construct
                           note = Synthetic
SEQUENCE: 34
tgcaggaatc cagatgctga ggcag                                       25

SEQ ID NO: 35              moltype = RNA   length = 25
FEATURE                    Location/Qualifiers
source                     1..25
                           mol_type = other RNA
                           organism = synthetic construct
                           note = Synthetic
SEQUENCE: 35
aggtgggagt actgcaacca gacgc                                       25

SEQ ID NO: 36              moltype = RNA   length = 25
FEATURE                    Location/Qualifiers
source                     1..25
                           mol_type = other RNA
                           organism = synthetic construct
                           note = Synthetic
SEQUENCE: 36
aatgctcaga cgcagaagga actgc                                       25
```

```
SEQ ID NO: 37            moltype = DNA   length = 25
FEATURE                  Location/Qualifiers
source                   1..25
                         mol_type = other DNA
                         organism = synthetic construct
                         note = Synthetic
modified_base            24
                         mod_base = OTHER
                         note = thymine
SEQUENCE: 37
gactgttacc ccggttccaa gccta                                               25

SEQ ID NO: 38            moltype = RNA   length = 25
FEATURE                  Location/Qualifiers
source                   1..25
                         mol_type = other RNA
                         organism = synthetic construct
                         note = Synthetic
SEQUENCE: 38
actgttaccc cggttccaaa cctag                                               25

SEQ ID NO: 39            moltype = RNA   length = 25
FEATURE                  Location/Qualifiers
source                   1..25
                         mol_type = other RNA
                         organism = synthetic construct
                         note = Synthetic
SEQUENCE: 39
ctgttacccc ggttccaaga ctaga                                               25

SEQ ID NO: 40            moltype = RNA   length = 25
FEATURE                  Location/Qualifiers
source                   1..25
                         mol_type = other RNA
                         organism = synthetic construct
                         note = Synthetic
SEQUENCE: 40
tgttaccccg gttccaagca tagag                                               25

SEQ ID NO: 41            moltype = RNA   length = 25
FEATURE                  Location/Qualifiers
source                   1..25
                         mol_type = other RNA
                         organism = synthetic construct
                         note = Synthetic
SEQUENCE: 41
gttaccccgg ttccaagcca agagg                                               25

SEQ ID NO: 42            moltype = RNA   length = 25
FEATURE                  Location/Qualifiers
source                   1..25
                         mol_type = other RNA
                         organism = synthetic construct
                         note = Synthetic
SEQUENCE: 42
ttaccccggt tccaagccta gaggc                                               25

SEQ ID NO: 43            moltype = DNA   length = 25
FEATURE                  Location/Qualifiers
source                   1..25
                         mol_type = other DNA
                         organism = synthetic construct
                         note = Synthetic
modified_base            25
                         mod_base = OTHER
                         note = thymine
SEQUENCE: 43
taccccggtt ccaagcctaa aggct                                               25

SEQ ID NO: 44            moltype = DNA   length = 25
FEATURE                  Location/Qualifiers
source                   1..25
                         mol_type = other DNA
                         organism = synthetic construct
                         note = Synthetic
modified_base            25
                         mod_base = OTHER
                         note = thymine
```

```
SEQUENCE: 44
gtgctaccat ggtaatggaa agagt                                              25

SEQ ID NO: 45            moltype = DNA   length = 25
FEATURE                  Location/Qualifiers
source                   1..25
                         mol_type = other DNA
                         organism = synthetic construct
                         note = Synthetic
modified_base            24
                         mod_base = OTHER
                         note = thymine
modified_base            25
                         mod_base = OTHER
                         note = thymine
SEQUENCE: 45
tgctaccatg gtaatggaca gagtt                                              25

SEQ ID NO: 46            moltype = DNA   length = 25
FEATURE                  Location/Qualifiers
source                   1..25
                         mol_type = other DNA
                         organism = synthetic construct
                         note = Synthetic
modified_base            24
                         mod_base = OTHER
                         note = thymine
SEQUENCE: 46
gctaccatgg taatggacaa agtta                                              25

SEQ ID NO: 47            moltype = DNA   length = 25
FEATURE                  Location/Qualifiers
source                   1..25
                         mol_type = other DNA
                         organism = synthetic construct
                         note = Synthetic
modified_base            25
                         mod_base = OTHER
                         note = thymine
SEQUENCE: 47
ctaccatggt aatggacaga gttat                                              25

SEQ ID NO: 48            moltype = DNA   length = 25
FEATURE                  Location/Qualifiers
source                   1..25
                         mol_type = other DNA
                         organism = synthetic construct
                         note = Synthetic
modified_base            24
                         mod_base = OTHER
                         note = thymine
SEQUENCE: 48
taccatggta atggacagaa ttatc                                              25

SEQ ID NO: 49            moltype = RNA   length = 25
FEATURE                  Location/Qualifiers
source                   1..25
                         mol_type = other RNA
                         organism = synthetic construct
                         note = Synthetic
SEQUENCE: 49
accatggtaa tggacagaga tatcg                                              25

SEQ ID NO: 50            moltype = RNA   length = 25
FEATURE                  Location/Qualifiers
source                   1..25
                         mol_type = other RNA
                         organism = synthetic construct
                         note = Synthetic
SEQUENCE: 50
ccatggtaat ggacagagta atcga                                              25

SEQ ID NO: 51            moltype = RNA   length = 25
FEATURE                  Location/Qualifiers
source                   1..25
                         mol_type = other RNA
                         organism = synthetic construct
                         note = Synthetic
SEQUENCE: 51
```

```
catggtaatg gacagagtta tcgag                                              25

SEQ ID NO: 52          moltype = RNA   length = 25
FEATURE                Location/Qualifiers
source                 1..25
                       mol_type = other RNA
                       organism = synthetic construct
                       note = Synthetic
SEQUENCE: 52
atggtaatgg acagagttaa cgagg                                              25

SEQ ID NO: 53          moltype = RNA   length = 25
FEATURE                Location/Qualifiers
source                 1..25
                       mol_type = other RNA
                       organism = synthetic construct
                       note = Synthetic
SEQUENCE: 53
tggtaatgga cagagttata gaggc                                              25

SEQ ID NO: 54          moltype = RNA   length = 25
FEATURE                Location/Qualifiers
source                 1..25
                       mol_type = other RNA
                       organism = synthetic construct
                       note = Synthetic
SEQUENCE: 54
ggtaatggac agagttatca aggca                                              25

SEQ ID NO: 55          moltype = RNA   length = 25
FEATURE                Location/Qualifiers
source                 1..25
                       mol_type = other RNA
                       organism = synthetic construct
                       note = Synthetic
SEQUENCE: 55
gtaatggaca gagttatcga ggcac                                              25

SEQ ID NO: 56          moltype = RNA   length = 25
FEATURE                Location/Qualifiers
source                 1..25
                       mol_type = other RNA
                       organism = synthetic construct
                       note = Synthetic
SEQUENCE: 56
ggcacatact ccaccactga cacag                                              25

SEQ ID NO: 57          moltype = DNA   length = 25
FEATURE                Location/Qualifiers
source                 1..25
                       mol_type = other DNA
                       organism = synthetic construct
                       note = Synthetic
modified_base          24
                       mod_base = OTHER
                       note = thymine
SEQUENCE: 57
cttggtcatc tatgacacca cactc                                              25

SEQ ID NO: 58          moltype = DNA   length = 25
FEATURE                Location/Qualifiers
source                 1..25
                       mol_type = other DNA
                       organism = synthetic construct
                       note = Synthetic
modified_base          25
                       mod_base = OTHER
                       note = thymine
SEQUENCE: 58
gtcatctatg acaccacaca cgcat                                              25

SEQ ID NO: 59          moltype = DNA   length = 25
FEATURE                Location/Qualifiers
source                 1..25
                       mol_type = other DNA
                       organism = synthetic construct
                       note = Synthetic
modified_base          24
                       mod_base = OTHER
```

```
                              note = thymine
SEQUENCE: 59
tcatctatga caccacacta gcata                                               25

SEQ ID NO: 60           moltype = RNA  length = 25
FEATURE                 Location/Qualifiers
source                  1..25
                        mol_type = other RNA
                        organism = synthetic construct
                        note = Synthetic
SEQUENCE: 60
catctatgac accacactca catag                                               25

SEQ ID NO: 61           moltype = RNA  length = 25
FEATURE                 Location/Qualifiers
source                  1..25
                        mol_type = other RNA
                        organism = synthetic construct
                        note = Synthetic
SEQUENCE: 61
gcacatactc caccactgta actgg                                               25

SEQ ID NO: 62           moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 62
agccccttat tgttatacga gggat                                               25

SEQ ID NO: 63           moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 63
gccccttatt gttatacgaa ggatc                                               25

SEQ ID NO: 64           moltype = RNA  length = 25
FEATURE                 Location/Qualifiers
source                  1..25
                        mol_type = other RNA
                        organism = synthetic construct
                        note = Synthetic
SEQUENCE: 64
ccaagcctag aggctcctta tgaac                                               25

SEQ ID NO: 65           moltype = RNA  length = 25
FEATURE                 Location/Qualifiers
source                  1..25
                        mol_type = other RNA
                        organism = synthetic construct
                        note = Synthetic
SEQUENCE: 65
aggctccttc tgaacaagca ccaac                                               25

SEQ ID NO: 66           moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 66
atggacagag ttatcaagga acata                                               25

SEQ ID NO: 67           moltype = RNA  length = 25
FEATURE                 Location/Qualifiers
source                  1..25
```

```
                        mol_type = other RNA
                        organism = synthetic construct
                        note = Synthetic
SEQUENCE: 67
tggacagagt tatcaaggca catac                                              25

SEQ ID NO: 68           moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 68
ggacagagtt atcaaggcaa atact                                              25

SEQ ID NO: 69           moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
modified_base           25
                        mod_base = OTHER
                        note = thymine
SEQUENCE: 69
gacagagtta tcaaggcaca tactt                                              25

SEQ ID NO: 70           moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 70
acagagttat caaggcacaa acttc                                              25

SEQ ID NO: 71           moltype = RNA  length = 25
FEATURE                 Location/Qualifiers
source                  1..25
                        mol_type = other RNA
                        organism = synthetic construct
                        note = Synthetic
SEQUENCE: 71
cagagttatc aaggcacata cttca                                              25

SEQ ID NO: 72           moltype = RNA  length = 25
FEATURE                 Location/Qualifiers
source                  1..25
                        mol_type = other RNA
                        organism = synthetic construct
                        note = Synthetic
SEQUENCE: 72
tacccaaatg ctggcttgaa caaga                                              25

SEQ ID NO: 73           moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 73
ccaaatgctg gcttgatcaa gaact                                              25

SEQ ID NO: 74           moltype = RNA  length = 25
FEATURE                 Location/Qualifiers
source                  1..25
                        mol_type = other RNA
```

```
                        organism = synthetic construct
                        note = Synthetic
SEQUENCE: 74
tcaagaacta ctgccgaaaa ccaga                                                 25

SEQ ID NO: 75           moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 75
caagaactac tgccgaaata cagat                                                 25

SEQ ID NO: 76           moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 76
aagaactact gccgaaatca agatc                                                 25

SEQ ID NO: 77           moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 77
gaactactgc cgaaatccaa atcct                                                 25

SEQ ID NO: 78           moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 78
ctactgccga aatccagata ctgtg                                                 25

SEQ ID NO: 79           moltype = RNA  length = 25
FEATURE                 Location/Qualifiers
source                  1..25
                        mol_type = other RNA
                        organism = synthetic construct
                        note = Synthetic
SEQUENCE: 79
tgtggcagcc ccttggtgta ataca                                                 25

SEQ ID NO: 80           moltype = RNA  length = 25
FEATURE                 Location/Qualifiers
source                  1..25
                        mol_type = other RNA
                        organism = synthetic construct
                        note = Synthetic
SEQUENCE: 80
gtggcagccc cttggtgtta tacaa                                                 25

SEQ ID NO: 81           moltype = RNA  length = 25
FEATURE                 Location/Qualifiers
source                  1..25
                        mol_type = other RNA
                        organism = synthetic construct
                        note = Synthetic
SEQUENCE: 81
tggcagcccc ttggtgttaa acaac                                                 25
```

```
SEQ ID NO: 82          moltype = RNA   length = 25
FEATURE                Location/Qualifiers
source                 1..25
                       mol_type = other RNA
                       organism = synthetic construct
                       note = Synthetic
SEQUENCE: 82
ggcagcccct tggtgttata caaca                                          25

SEQ ID NO: 83          moltype = RNA   length = 25
FEATURE                Location/Qualifiers
source                 1..25
                       mol_type = other RNA
                       organism = synthetic construct
                       note = Synthetic
SEQUENCE: 83
gcagccccct tggtgttataa aacag                                         25

SEQ ID NO: 84          moltype = RNA   length = 25
FEATURE                Location/Qualifiers
source                 1..25
                       mol_type = other RNA
                       organism = synthetic construct
                       note = Synthetic
SEQUENCE: 84
cagccccttg gtgttataca acaga                                          25

SEQ ID NO: 85          moltype = DNA   length = 25
FEATURE                Location/Qualifiers
source                 1..25
                       mol_type = other DNA
                       organism = synthetic construct
                       note = Synthetic
modified_base          25
                       mod_base = OTHER
                       note = thymine
SEQUENCE: 85
agccccttgg tgttatacaa cagat                                          25

SEQ ID NO: 86          moltype = DNA   length = 25
FEATURE                Location/Qualifiers
source                 1..25
                       mol_type = other DNA
                       organism = synthetic construct
                       note = Synthetic
modified_base          24
                       mod_base = OTHER
                       note = thymine
SEQUENCE: 86
gccccttggt gttatacaaa agatc                                          25

SEQ ID NO: 87          moltype = RNA   length = 25
FEATURE                Location/Qualifiers
source                 1..25
                       mol_type = other RNA
                       organism = synthetic construct
                       note = Synthetic
SEQUENCE: 87
ccccttggtg ttatacaaca gatcc                                          25

SEQ ID NO: 88          moltype = RNA   length = 25
FEATURE                Location/Qualifiers
source                 1..25
                       mol_type = other RNA
                       organism = synthetic construct
                       note = Synthetic
SEQUENCE: 88
ggtgggagta ctgcaaccta acacg                                          25

SEQ ID NO: 89          moltype = RNA   length = 25
FEATURE                Location/Qualifiers
source                 1..25
                       mol_type = other RNA
                       organism = synthetic construct
                       note = Synthetic
SEQUENCE: 89
gtgggagtac tgcaacctga cacga                                          25
```

```
SEQ ID NO: 90              moltype = RNA  length = 25
FEATURE                    Location/Qualifiers
source                     1..25
                           mol_type = other RNA
                           organism = synthetic construct
                           note = Synthetic
SEQUENCE: 90
ggagtactgc aacctgacaa gatgc                                              25

SEQ ID NO: 91              moltype = DNA  length = 25
FEATURE                    Location/Qualifiers
source                     1..25
                           mol_type = other DNA
                           organism = synthetic construct
                           note = Synthetic
modified_base              25
                           mod_base = OTHER
                           note = thymine
SEQUENCE: 91
gagtactgca acctgacaca atgct                                              25

SEQ ID NO: 92              moltype = RNA  length = 25
FEATURE                    Location/Qualifiers
source                     1..25
                           mol_type = other RNA
                           organism = synthetic construct
                           note = Synthetic
SEQUENCE: 92
gtactgcaac ctgacacgaa gctca                                              25

SEQ ID NO: 93              moltype = RNA  length = 25
FEATURE                    Location/Qualifiers
source                     1..25
                           mol_type = other RNA
                           organism = synthetic construct
                           note = Synthetic
SEQUENCE: 93
tactgcaacc tgacacgata ctcag                                              25

SEQ ID NO: 94              moltype = RNA  length = 25
FEATURE                    Location/Qualifiers
source                     1..25
                           mol_type = other RNA
                           organism = synthetic construct
                           note = Synthetic
SEQUENCE: 94
actgcaacct gacacgatga tcaga                                              25

SEQ ID NO: 95              moltype = DNA  length = 25
FEATURE                    Location/Qualifiers
source                     1..25
                           mol_type = other DNA
                           organism = synthetic construct
                           note = Synthetic
modified_base              25
                           mod_base = OTHER
                           note = thymine
SEQUENCE: 95
ctgcaacctg acacgatgca cagat                                              25

SEQ ID NO: 96              moltype = DNA  length = 25
FEATURE                    Location/Qualifiers
source                     1..25
                           mol_type = other DNA
                           organism = synthetic construct
                           note = Synthetic
modified_base              24
                           mod_base = OTHER
                           note = thymine
SEQUENCE: 96
tgcaacctga cacgatgcta agatg                                              25

SEQ ID NO: 97              moltype = RNA  length = 25
FEATURE                    Location/Qualifiers
source                     1..25
                           mol_type = other RNA
                           organism = synthetic construct
                           note = Synthetic
SEQUENCE: 97
```

```
caacctgaca cgatgctcaa atgca                                         25

SEQ ID NO: 98           moltype = RNA   length = 25
FEATURE                 Location/Qualifiers
source                  1..25
                        mol_type = other RNA
                        organism = synthetic construct
                        note = Synthetic
SEQUENCE: 98
acctgacacg atgctcagaa gcaga                                         25

SEQ ID NO: 99           moltype = RNA   length = 25
FEATURE                 Location/Qualifiers
source                  1..25
                        mol_type = other RNA
                        organism = synthetic construct
                        note = Synthetic
SEQUENCE: 99
cctgacacga tgctcagata cagaa                                         25

SEQ ID NO: 100          moltype = DNA   length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 100
ctgacacgat gctcagatga agaat                                         25

SEQ ID NO: 101          moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 101
tgacacgatg ctcagatgca gaatg                                         25

SEQ ID NO: 102          moltype = RNA   length = 25
FEATURE                 Location/Qualifiers
source                  1..25
                        mol_type = other RNA
                        organism = synthetic construct
                        note = Synthetic
SEQUENCE: 102
gacacgatgc tcagatgcaa aatgg                                         25

SEQ ID NO: 103          moltype = RNA   length = 25
FEATURE                 Location/Qualifiers
source                  1..25
                        mol_type = other RNA
                        organism = synthetic construct
                        note = Synthetic
SEQUENCE: 103
acacgatgct cagatgcaga atgga                                         25

SEQ ID NO: 104          moltype = RNA   length = 25
FEATURE                 Location/Qualifiers
source                  1..25
                        mol_type = other RNA
                        organism = synthetic construct
                        note = Synthetic
SEQUENCE: 104
cacgatgctc agatgcagaa tggac                                         25

SEQ ID NO: 105          moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
```

```
                              note = thymine
modified_base                 25
                              mod_base = OTHER
                              note = thymine
SEQUENCE: 105
tgctactacc attatggaca gagtt                                        25

SEQ ID NO: 106                moltype = DNA  length = 25
FEATURE                       Location/Qualifiers
source                        1..25
                              mol_type = other DNA
                              organism = synthetic construct
                              note = Synthetic
modified_base                 24
                              mod_base = OTHER
                              note = thymine
SEQUENCE: 106
gctactacca ttatggacaa agtta                                        25

SEQ ID NO: 107                moltype = RNA  length = 25
FEATURE                       Location/Qualifiers
source                        1..25
                              mol_type = other RNA
                              organism = synthetic construct
                              note = Synthetic
SEQUENCE: 107
ctactaccat tatggacaga gttac                                        25

SEQ ID NO: 108                moltype = RNA  length = 25
FEATURE                       Location/Qualifiers
source                        1..25
                              mol_type = other RNA
                              organism = synthetic construct
                              note = Synthetic
SEQUENCE: 108
tactaccatt atggacagaa ttacc                                        25

SEQ ID NO: 109                moltype = RNA  length = 25
FEATURE                       Location/Qualifiers
source                        1..25
                              mol_type = other RNA
                              organism = synthetic construct
                              note = Synthetic
SEQUENCE: 109
actaccatta tggacagaga taccg                                        25

SEQ ID NO: 110                moltype = RNA  length = 25
FEATURE                       Location/Qualifiers
source                        1..25
                              mol_type = other RNA
                              organism = synthetic construct
                              note = Synthetic
SEQUENCE: 110
ctaccattat ggacagagta accga                                        25

SEQ ID NO: 111                moltype = RNA  length = 25
FEATURE                       Location/Qualifiers
source                        1..25
                              mol_type = other RNA
                              organism = synthetic construct
                              note = Synthetic
SEQUENCE: 111
taccattatg gacagagtta ccgag                                        25

SEQ ID NO: 112                moltype = RNA  length = 25
FEATURE                       Location/Qualifiers
source                        1..25
                              mol_type = other RNA
                              organism = synthetic construct
                              note = Synthetic
SEQUENCE: 112
accattatgg acagagttaa cgagg                                        25

SEQ ID NO: 113                moltype = RNA  length = 25
FEATURE                       Location/Qualifiers
source                        1..25
                              mol_type = other RNA
                              organism = synthetic construct
                              note = Synthetic
```

-continued

```
SEQUENCE: 113
gaggcacata ctccaccaca gtcac                                            25

SEQ ID NO: 114          moltype = DNA   length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 114
ctccaccact gtcacaggaa gaact                                            25

SEQ ID NO: 115          moltype = DNA   length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 115
acaggaagaa cttgccaaga ttggt                                            25

SEQ ID NO: 116          moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 116
caggaagaac ttgccaagca tggtc                                            25

SEQ ID NO: 117          moltype = RNA   length = 25
FEATURE                 Location/Qualifiers
source                  1..25
                        mol_type = other RNA
                        organism = synthetic construct
                        note = Synthetic
SEQUENCE: 117
aggaagaact tgccaagcta ggtca                                            25

SEQ ID NO: 118          moltype = DNA   length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 118
ggaagaactt gccaagctta gtcat                                            25

SEQ ID NO: 119          moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 119
gaagaacttg ccaagcttga tcatc                                            25

SEQ ID NO: 120          moltype = DNA   length = 25
FEATURE                 Location/Qualifiers
source                  1..25
                        mol_type = other DNA
                        organism = synthetic construct
                        note = Synthetic
modified_base           25
```

```
                        mod_base = OTHER
                        note = thymine
SEQUENCE: 120
aagaacttgc caagcttgga catct                                           25

SEQ ID NO: 121          moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 121
agaacttgcc aagcttggta atcta                                           25

SEQ ID NO: 122          moltype = DNA   length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 122
gaacttgcca agcttggtca tctat                                           25

SEQ ID NO: 123          moltype = DNA   length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 123
aacttgccaa gcttggtcaa ctatg                                           25

SEQ ID NO: 124          moltype = RNA   length = 25
FEATURE                 Location/Qualifiers
source                  1..25
                        mol_type = other RNA
                        organism = synthetic construct
                        note = Synthetic
SEQUENCE: 124
acttgccaag cttggtcata tatga                                           25

SEQ ID NO: 125          moltype = RNA   length = 25
FEATURE                 Location/Qualifiers
source                  1..25
                        mol_type = other RNA
                        organism = synthetic construct
                        note = Synthetic
SEQUENCE: 125
cttgccaagc ttggtcatca atgac                                           25

SEQ ID NO: 126          moltype = RNA   length = 25
FEATURE                 Location/Qualifiers
source                  1..25
                        mol_type = other RNA
                        organism = synthetic construct
                        note = Synthetic
SEQUENCE: 126
ttgccaagct tggtcatcta tgaca                                           25

SEQ ID NO: 127          moltype = RNA   length = 25
FEATURE                 Location/Qualifiers
source                  1..25
                        mol_type = other RNA
                        organism = synthetic construct
                        note = Synthetic
SEQUENCE: 127
tgccaagctt ggtcatctaa gacac                                           25

SEQ ID NO: 128          moltype = RNA   length = 25
FEATURE                 Location/Qualifiers
```

```
source                  1..25
                        mol_type = other RNA
                        organism = synthetic construct
                        note = Synthetic
SEQUENCE: 128
gcttggtcat ctatgacaca acacc                                               25

SEQ ID NO: 129          moltype = RNA  length = 25
FEATURE                 Location/Qualifiers
source                  1..25
                        mol_type = other RNA
                        organism = synthetic construct
                        note = Synthetic
SEQUENCE: 129
ttggtcatct atgacaccaa accag                                               25

SEQ ID NO: 130          moltype = RNA  length = 25
FEATURE                 Location/Qualifiers
source                  1..25
                        mol_type = other RNA
                        organism = synthetic construct
                        note = Synthetic
SEQUENCE: 130
tggtcatcta tgacaccaca ccagc                                               25

SEQ ID NO: 131          moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 131
gtcatctatg acaccacaca agcat                                               25

SEQ ID NO: 132          moltype = RNA  length = 25
FEATURE                 Location/Qualifiers
source                  1..25
                        mol_type = other RNA
                        organism = synthetic construct
                        note = Synthetic
SEQUENCE: 132
catctatgac accacaccaa catag                                               25

SEQ ID NO: 133          moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 133
atctatgaca ccacaccaga atagt                                               25

SEQ ID NO: 134          moltype = DNA  length = 25
FEATURE                 Location/Qualifiers
source                  1..25
                        mol_type = other DNA
                        organism = synthetic construct
                        note = Synthetic
SEQUENCE: 134
ctatgacacc acaccagcaa agtcg                                               25

SEQ ID NO: 135          moltype = RNA  length = 25
FEATURE                 Location/Qualifiers
source                  1..25
                        mol_type = other RNA
                        organism = synthetic construct
                        note = Synthetic
SEQUENCE: 135
gtcggacccc agaaaactaa ccaaa                                               25

SEQ ID NO: 136          moltype = DNA  length = 25
FEATURE                 Location/Qualifiers
source                  1..25
```

```
                        mol_type = other DNA
                        organism = synthetic construct
                        note = Synthetic
modified_base           25
                        mod_base = OTHER
                        note = thymine
SEQUENCE: 136
tcggacccca gaaaactaca caaat                                               25

SEQ ID NO: 137          moltype = RNA   length = 25
FEATURE                 Location/Qualifiers
source                  1..25
                        mol_type = other RNA
                        organism = synthetic construct
                        note = Synthetic
SEQUENCE: 137
gaaaactacc caaatgctga cctga                                               25

SEQ ID NO: 138          moltype = RNA   length = 25
FEATURE                 Location/Qualifiers
source                  1..25
                        mol_type = other RNA
                        organism = synthetic construct
                        note = Synthetic
SEQUENCE: 138
gctgagattc gcccttggta ttaca                                               25

SEQ ID NO: 139          moltype = RNA   length = 25
FEATURE                 Location/Qualifiers
source                  1..25
                        mol_type = other RNA
                        organism = synthetic construct
                        note = Synthetic
SEQUENCE: 139
ctgagattcg cccttggtga tacac                                               25

SEQ ID NO: 140          moltype = RNA   length = 25
FEATURE                 Location/Qualifiers
source                  1..25
                        mol_type = other RNA
                        organism = synthetic construct
                        note = Synthetic
SEQUENCE: 140
gagattcgcc cttggtgtta cacca                                               25

SEQ ID NO: 141          moltype = DNA   length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 141
agattcgccc ttggtgttaa accat                                               25

SEQ ID NO: 142          moltype = RNA   length = 25
FEATURE                 Location/Qualifiers
source                  1..25
                        mol_type = other RNA
                        organism = synthetic construct
                        note = Synthetic
SEQUENCE: 142
ttcgcccttg gtgttacaca atgga                                               25

SEQ ID NO: 143          moltype = RNA   length = 25
FEATURE                 Location/Qualifiers
source                  1..25
                        mol_type = other RNA
                        organism = synthetic construct
                        note = Synthetic
SEQUENCE: 143
cttggtgtta caccatggaa cccag                                               25

SEQ ID NO: 144          moltype = DNA   length = 25
FEATURE                 Location/Qualifiers
source                  1..25
                        mol_type = other DNA
```

```
                        organism = synthetic construct
                        note = Synthetic
modified_base           25
                        mod_base = OTHER
                        note = thymine
SEQUENCE: 144
ttggtgttac accatggata ccagt                                                 25

SEQ ID NO: 145          moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
SEQUENCE: 145
tggtgttaca ccatggatca cagtg                                                 25

SEQ ID NO: 146          moltype = DNA  length = 25
FEATURE                 Location/Qualifiers
source                  1..25
                        mol_type = other DNA
                        organism = synthetic construct
                        note = Synthetic
modified_base           25
                        mod_base = OTHER
                        note = thymine
SEQUENCE: 146
ggtgttacac catggatcca agtgt                                                 25

SEQ ID NO: 147          moltype = RNA  length = 25
FEATURE                 Location/Qualifiers
source                  1..25
                        mol_type = other RNA
                        organism = synthetic construct
                        note = Synthetic
SEQUENCE: 147
tgttacacca tggatcccaa tgtca                                                 25

SEQ ID NO: 148          moltype = RNA  length = 25
FEATURE                 Location/Qualifiers
source                  1..25
                        mol_type = other RNA
                        organism = synthetic construct
                        note = Synthetic
SEQUENCE: 148
gaatcaagtg tccttgcaaa tctca                                                 25

SEQ ID NO: 149          moltype = RNA  length = 25
FEATURE                 Location/Qualifiers
source                  1..25
                        mol_type = other RNA
                        organism = synthetic construct
                        note = Synthetic
SEQUENCE: 149
aatcaagtgt ccttgcaaca ctcac                                                 25

SEQ ID NO: 150          moltype = RNA  length = 25
FEATURE                 Location/Qualifiers
source                  1..25
                        mol_type = other RNA
                        organism = synthetic construct
                        note = Synthetic
SEQUENCE: 150
atcaagtgtc cttgcaacta tcacg                                                 25

SEQ ID NO: 151          moltype = DNA  length = 25
FEATURE                 Location/Qualifiers
source                  1..25
                        mol_type = other DNA
                        organism = synthetic construct
                        note = Synthetic
modified_base           24
                        mod_base = OTHER
                        note = thymine
modified_base           25
                        mod_base = OTHER
```

```
                            note = thymine
SEQUENCE: 151
atggacagag ttatcgagga tcatt                                          25

SEQ ID NO: 152         moltype = DNA  length = 25
FEATURE                Location/Qualifiers
source                 1..25
                       mol_type = other DNA
                       organism = synthetic construct
                       note = Synthetic
modified_base          24
                       mod_base = OTHER
                       note = thymine
SEQUENCE: 152
tggacagagt tatcgaggca cattc                                          25

SEQ ID NO: 153         moltype = DNA  length = 25
FEATURE                Location/Qualifiers
source                 1..25
                       mol_type = other DNA
                       organism = synthetic construct
                       note = Synthetic
SEQUENCE: 153
acaccacact ggcatcagaa gacaa                                          25

SEQ ID NO: 154         moltype = DNA  length = 25
FEATURE                Location/Qualifiers
source                 1..25
                       mol_type = other DNA
                       organism = synthetic construct
                       note = Synthetic
modified_base          25
                       mod_base = OTHER
                       note = thymine
SEQUENCE: 154
ttggtgttat accatggata ccaat                                          25

SEQ ID NO: 155         moltype = DNA  length = 25
FEATURE                Location/Qualifiers
source                 1..25
                       mol_type = other DNA
                       organism = synthetic construct
                       note = Synthetic
modified_base          24
                       mod_base = OTHER
                       note = thymine
SEQUENCE: 155
tggtgttata ccatggatca caatg                                          25

SEQ ID NO: 156         moltype = DNA  length = 25
FEATURE                Location/Qualifiers
source                 1..25
                       mol_type = other DNA
                       organism = synthetic construct
                       note = Synthetic
modified_base          25
                       mod_base = OTHER
                       note = thymine
SEQUENCE: 156
ggtgttatac catggatcca aatgt                                          25

SEQ ID NO: 157         moltype = DNA  length = 25
FEATURE                Location/Qualifiers
source                 1..25
                       mol_type = other DNA
                       organism = synthetic construct
                       note = Synthetic
modified_base          24
                       mod_base = OTHER
                       note = thymine
SEQUENCE: 157
gtgttatacc atggatccca atgtc                                          25

SEQ ID NO: 158         moltype = RNA  length = 25
FEATURE                Location/Qualifiers
source                 1..25
                       mol_type = other RNA
                       organism = synthetic construct
                       note = Synthetic
```

```
SEQUENCE: 158
tcagatggga gtactgcaaa ctgac                                           25

SEQ ID NO: 159           moltype = RNA  length = 25
FEATURE                  Location/Qualifiers
source                   1..25
                         mol_type = other RNA
                         organism = synthetic construct
                         note = Synthetic
SEQUENCE: 159
gatgggagta ctgcaaccta acaca                                           25

SEQ ID NO: 160           moltype = RNA  length = 25
FEATURE                  Location/Qualifiers
source                   1..25
                         mol_type = other RNA
                         organism = synthetic construct
                         note = Synthetic
SEQUENCE: 160
atgggagtac tgcaacctga cacaa                                           25

SEQ ID NO: 161           moltype = DNA  length = 25
FEATURE                  Location/Qualifiers
source                   1..25
                         mol_type = other DNA
                         organism = synthetic construct
                         note = Synthetic
modified_base            25
                         mod_base = OTHER
                         note = thymine
SEQUENCE: 161
tgggagtact gcaacctgaa acaat                                           25

SEQ ID NO: 162           moltype = DNA  length = 25
FEATURE                  Location/Qualifiers
source                   1..25
                         mol_type = other DNA
                         organism = synthetic construct
                         note = Synthetic
modified_base            24
                         mod_base = OTHER
                         note = thymine
SEQUENCE: 162
gggagtactg caacctgaca caatg                                           25

SEQ ID NO: 163           moltype = RNA  length = 25
FEATURE                  Location/Qualifiers
source                   1..25
                         mol_type = other RNA
                         organism = synthetic construct
                         note = Synthetic
SEQUENCE: 163
ggctgtttct gaacaagcaa caacg                                           25

SEQ ID NO: 164           moltype = RNA  length = 25
FEATURE                  Location/Qualifiers
source                   1..25
                         mol_type = other RNA
                         organism = synthetic construct
                         note = Synthetic
SEQUENCE: 164
gtttctgaac aagcaccaaa ggagc                                           25

SEQ ID NO: 165           moltype = RNA  length = 25
FEATURE                  Location/Qualifiers
source                   1..25
                         mol_type = other RNA
                         organism = synthetic construct
                         note = Synthetic
SEQUENCE: 165
ctccaccact gttacaggaa ggaca                                           25

SEQ ID NO: 166           moltype = RNA  length = 24
FEATURE                  Location/Qualifiers
source                   1..24
                         mol_type = other RNA
                         organism = synthetic construct
                         note = Synthetic
SEQUENCE: 166
```

```
tccaccactg ttacaggaaa gaca                                             24

SEQ ID NO: 167          moltype = RNA   length = 24
FEATURE                 Location/Qualifiers
source                  1..24
                        mol_type = other RNA
                        organism = synthetic construct
                        note = Synthetic
SEQUENCE: 167
ccaccactgt tacaggaaga acag                                             24

SEQ ID NO: 168          moltype = RNA   length = 25
FEATURE                 Location/Qualifiers
source                  1..25
                        mol_type = other RNA
                        organism = synthetic construct
                        note = Synthetic
SEQUENCE: 168
gacaccacac tggcatcaga gaacc                                            25

SEQ ID NO: 169          moltype = RNA   length = 25
FEATURE                 Location/Qualifiers
source                  1..25
                        mol_type = other RNA
                        organism = synthetic construct
                        note = Synthetic
SEQUENCE: 169
acaccacact ggcatcagaa aacca                                            25

SEQ ID NO: 170          moltype = RNA   length = 24
FEATURE                 Location/Qualifiers
source                  1..24
                        mol_type = other RNA
                        organism = synthetic construct
                        note = Synthetic
SEQUENCE: 170
agaatactac ccaaatggta gccg                                             24

SEQ ID NO: 171          moltype = RNA   length = 25
FEATURE                 Location/Qualifiers
source                  1..25
                        mol_type = other RNA
                        organism = synthetic construct
                        note = Synthetic
SEQUENCE: 171
gaatactacc caaatggtga cctga                                            25

SEQ ID NO: 172          moltype = RNA   length = 25
FEATURE                 Location/Qualifiers
source                  1..25
                        mol_type = other RNA
                        organism = synthetic construct
                        note = Synthetic
SEQUENCE: 172
aatactaccc aaatggtgga ctgac                                            25

SEQ ID NO: 173          moltype = RNA   length = 25
FEATURE                 Location/Qualifiers
source                  1..25
                        mol_type = other RNA
                        organism = synthetic construct
                        note = Synthetic
SEQUENCE: 173
tccttctgaa gaagcaccaa ctgaa                                            25

SEQ ID NO: 174          moltype = RNA   length = 25
FEATURE                 Location/Qualifiers
source                  1..25
                        mol_type = other RNA
                        organism = synthetic construct
                        note = Synthetic
SEQUENCE: 174
ccttctgaag aagcaccaaa tgaaa                                            25

SEQ ID NO: 175          moltype = RNA   length = 25
FEATURE                 Location/Qualifiers
source                  1..25
                        mol_type = other RNA
                        organism = synthetic construct
```

```
SEQUENCE: 175
cttctgaaga agcaccaaca gaaaa                                            25

SEQ ID NO: 176          moltype = RNA  length = 25
FEATURE                 Location/Qualifiers
source                  1..25
                        mol_type = other RNA
                        organism = synthetic construct
                        note = Synthetic
SEQUENCE: 176
ttctgaagaa gcaccaacta aaaac                                            25

SEQ ID NO: 177          moltype = RNA  length = 25
FEATURE                 Location/Qualifiers
source                  1..25
                        mol_type = other RNA
                        organism = synthetic construct
                        note = Synthetic
SEQUENCE: 177
tctgaagaag caccaactga aaaca                                            25

SEQ ID NO: 178          moltype = RNA  length = 25
FEATURE                 Location/Qualifiers
source                  1..25
                        mol_type = other RNA
                        organism = synthetic construct
                        note = Synthetic
SEQUENCE: 178
ctgaagaagc accaactgaa aacag                                            25

SEQ ID NO: 179          moltype = RNA  length = 25
FEATURE                 Location/Qualifiers
source                  1..25
                        mol_type = other RNA
                        organism = synthetic construct
                        note = Synthetic
SEQUENCE: 179
tgaagaagca ccaactgaaa acagc                                            25

SEQ ID NO: 180          moltype = RNA  length = 25
FEATURE                 Location/Qualifiers
source                  1..25
                        mol_type = other RNA
                        organism = synthetic construct
                        note = Synthetic
SEQUENCE: 180
gaagaagcac caactgaaaa cagca                                            25

SEQ ID NO: 181          moltype = RNA  length = 25
FEATURE                 Location/Qualifiers
source                  1..25
                        mol_type = other RNA
                        organism = synthetic construct
                        note = Synthetic
SEQUENCE: 181
aagaagcacc aactgaaaaa agcac                                            25

SEQ ID NO: 182          moltype = RNA  length = 24
FEATURE                 Location/Qualifiers
source                  1..24
                        mol_type = other RNA
                        organism = synthetic construct
                        note = Synthetic
SEQUENCE: 182
agaagcacca actgaaaaca gcac                                             24

SEQ ID NO: 183          moltype = RNA  length = 24
FEATURE                 Location/Qualifiers
source                  1..24
                        mol_type = other RNA
                        organism = synthetic construct
                        note = Synthetic
SEQUENCE: 183
gaagcaccaa ctgaaaacaa cacg                                             24

SEQ ID NO: 184          moltype = RNA  length = 25
FEATURE                 Location/Qualifiers
source                  1..25
```

```
                              mol_type = other RNA
                              organism = synthetic construct
                              note = Synthetic
SEQUENCE: 184
aagcaccaac tgaaaacaga actgg                                          25

SEQ ID NO: 185                moltype = RNA   length = 25
FEATURE                       Location/Qualifiers
source                        1..25
                              mol_type = other RNA
                              organism = synthetic construct
                              note = Synthetic
SEQUENCE: 185
aggtgatgga cagagttata gaggc                                          25

SEQ ID NO: 186                moltype = RNA   length = 25
FEATURE                       Location/Qualifiers
source                        1..25
                              mol_type = other RNA
                              organism = synthetic construct
                              note = Synthetic
SEQUENCE: 186
ctccaccact atcacaggaa gaaca                                          25

SEQ ID NO: 187                moltype = RNA   length = 24
FEATURE                       Location/Qualifiers
source                        1..24
                              mol_type = other RNA
                              organism = synthetic construct
                              note = Synthetic
SEQUENCE: 187
tccaccacta tcacaggaaa aaca                                           24

SEQ ID NO: 188                moltype = RNA   length = 24
FEATURE                       Location/Qualifiers
source                        1..24
                              mol_type = other RNA
                              organism = synthetic construct
                              note = Synthetic
SEQUENCE: 188
ccaccactat cacaggaaga acag                                           24

SEQ ID NO: 189                moltype = RNA   length = 24
FEATURE                       Location/Qualifiers
source                        1..24
                              mol_type = other RNA
                              organism = synthetic construct
                              note = Synthetic
SEQUENCE: 189
caccactatc acaggaagaa catg                                           24

SEQ ID NO: 190                moltype = RNA   length = 24
FEATURE                       Location/Qualifiers
source                        1..24
                              mol_type = other RNA
                              organism = synthetic construct
                              note = Synthetic
SEQUENCE: 190
accactatca caggaagaaa atgc                                           24

SEQ ID NO: 191                moltype = RNA   length = 25
FEATURE                       Location/Qualifiers
source                        1..25
                              mol_type = other RNA
                              organism = synthetic construct
                              note = Synthetic
SEQUENCE: 191
ccactatcac aggaagaaca tgtca                                          25

SEQ ID NO: 192                moltype = RNA   length = 25
FEATURE                       Location/Qualifiers
source                        1..25
                              mol_type = other RNA
                              organism = synthetic construct
                              note = Synthetic
SEQUENCE: 192
cactatcaca ggaagaacaa gtcag                                          25

SEQ ID NO: 193                moltype = RNA   length = 24
```

```
FEATURE              Location/Qualifiers
source               1..24
                     mol_type = other RNA
                     organism = synthetic construct
                     note = Synthetic
SEQUENCE: 193
actatcacag gaagaacata tcag                                              24

SEQ ID NO: 194       moltype = RNA   length = 24
FEATURE              Location/Qualifiers
source               1..24
                     mol_type = other RNA
                     organism = synthetic construct
                     note = Synthetic
SEQUENCE: 194
ctatcacagg aagaacatga cagc                                              24

SEQ ID NO: 195       moltype = RNA   length = 24
FEATURE              Location/Qualifiers
source               1..24
                     mol_type = other RNA
                     organism = synthetic construct
                     note = Synthetic
SEQUENCE: 195
tatcacagga agaacatgta agtc                                              24

SEQ ID NO: 196       moltype = RNA   length = 23
FEATURE              Location/Qualifiers
source               1..23
                     mol_type = other RNA
                     organism = synthetic construct
                     note = Synthetic
SEQUENCE: 196
atcacaggaa gaacatgtca gtc                                               23

SEQ ID NO: 197       moltype = RNA   length = 24
FEATURE              Location/Qualifiers
source               1..24
                     mol_type = other RNA
                     organism = synthetic construct
                     note = Synthetic
SEQUENCE: 197
tcacaggaag aacatgtcaa tctg                                              24

SEQ ID NO: 198       moltype = RNA   length = 25
FEATURE              Location/Qualifiers
source               1..25
                     mol_type = other RNA
                     organism = synthetic construct
                     note = Synthetic
SEQUENCE: 198
cacaggaaga acatgtcaga cttgg                                             25

SEQ ID NO: 199       moltype = RNA   length = 24
FEATURE              Location/Qualifiers
source               1..24
                     mol_type = other RNA
                     organism = synthetic construct
                     note = Synthetic
SEQUENCE: 199
acaggaagaa catgtcagta ttgg                                              24

SEQ ID NO: 200       moltype = RNA   length = 24
FEATURE              Location/Qualifiers
source               1..24
                     mol_type = other RNA
                     organism = synthetic construct
                     note = Synthetic
SEQUENCE: 200
ggaagaacat gtcagtctta gtcg                                              24

SEQ ID NO: 201       moltype = RNA   length = 24
FEATURE              Location/Qualifiers
source               1..24
                     mol_type = other RNA
                     organism = synthetic construct
                     note = Synthetic
SEQUENCE: 201
gaagaacatg tcagtcttga tcgc                                              24
```

-continued

```
SEQ ID NO: 202           moltype = RNA   length = 24
FEATURE                  Location/Qualifiers
source                   1..24
                         mol_type = other RNA
                         organism = synthetic construct
                         note = Synthetic
SEQUENCE: 202
aagaacatgt cagtcttgga cgtc                                               24

SEQ ID NO: 203           moltype = RNA   length = 24
FEATURE                  Location/Qualifiers
source                   1..24
                         mol_type = other RNA
                         organism = synthetic construct
                         note = Synthetic
SEQUENCE: 203
agaacatgtc agtcttggta gtca                                               24

SEQ ID NO: 204           moltype = RNA   length = 24
FEATURE                  Location/Qualifiers
source                   1..24
                         mol_type = other RNA
                         organism = synthetic construct
                         note = Synthetic
SEQUENCE: 204
ggcatcggag gatcccatta taca                                               24

SEQ ID NO: 205           moltype = RNA   length = 25
FEATURE                  Location/Qualifiers
source                   1..25
                         mol_type = other RNA
                         organism = synthetic construct
                         note = Synthetic
SEQUENCE: 205
actatccaaa tgctggccta accag                                              25

SEQ ID NO: 206           moltype = RNA   length = 25
FEATURE                  Location/Qualifiers
source                   1..25
                         mol_type = other RNA
                         organism = synthetic construct
                         note = Synthetic
SEQUENCE: 206
gcacagaggc tccttctgaa caagc                                              25

SEQ ID NO: 207           moltype = RNA   length = 25
FEATURE                  Location/Qualifiers
source                   1..25
                         mol_type = other RNA
                         organism = synthetic construct
                         note = Synthetic
SEQUENCE: 207
tccttctgaa caagcaccaa ctgag                                              25

SEQ ID NO: 208           moltype = RNA   length = 25
FEATURE                  Location/Qualifiers
source                   1..25
                         mol_type = other RNA
                         organism = synthetic construct
                         note = Synthetic
SEQUENCE: 208
ccttctgaac aagcaccaca tgaga                                              25

SEQ ID NO: 209           moltype = RNA   length = 25
FEATURE                  Location/Qualifiers
source                   1..25
                         mol_type = other RNA
                         organism = synthetic construct
                         note = Synthetic
SEQUENCE: 209
cttctgaaca agcaccacca gagaa                                              25

SEQ ID NO: 210           moltype = RNA   length = 25
FEATURE                  Location/Qualifiers
source                   1..25
                         mol_type = other RNA
                         organism = synthetic construct
                         note = Synthetic
```

-continued

```
SEQUENCE: 210
ttctgaacaa gcaccaccta agaaa                                          25

SEQ ID NO: 211          moltype = RNA  length = 25
FEATURE                 Location/Qualifiers
source                  1..25
                        mol_type = other RNA
                        organism = synthetic construct
                        note = Synthetic
SEQUENCE: 211
tctgaacaag caccacctga gaaaa                                          25

SEQ ID NO: 212          moltype = RNA  length = 25
FEATURE                 Location/Qualifiers
source                  1..25
                        mol_type = other RNA
                        organism = synthetic construct
                        note = Synthetic
SEQUENCE: 212
ctgaacaagc accacctgaa aaaag                                          25

SEQ ID NO: 213          moltype = RNA  length = 25
FEATURE                 Location/Qualifiers
source                  1..25
                        mol_type = other RNA
                        organism = synthetic construct
                        note = Synthetic
SEQUENCE: 213
tgaacaagca ccacctgaga aaagc                                          25

SEQ ID NO: 214          moltype = RNA  length = 25
FEATURE                 Location/Qualifiers
source                  1..25
                        mol_type = other RNA
                        organism = synthetic construct
                        note = Synthetic
SEQUENCE: 214
gaacaagcac cacctgagaa aagcc                                          25

SEQ ID NO: 215          moltype = RNA  length = 25
FEATURE                 Location/Qualifiers
source                  1..25
                        mol_type = other RNA
                        organism = synthetic construct
                        note = Synthetic
SEQUENCE: 215
aacaagcacc acctgagaaa agccc                                          25

SEQ ID NO: 216          moltype = RNA  length = 24
FEATURE                 Location/Qualifiers
source                  1..24
                        mol_type = other RNA
                        organism = synthetic construct
                        note = Synthetic
SEQUENCE: 216
caagcaccac ctgagaaaaa cccg                                           24

SEQ ID NO: 217          moltype = RNA  length = 24
FEATURE                 Location/Qualifiers
source                  1..24
                        mol_type = other RNA
                        organism = synthetic construct
                        note = Synthetic
SEQUENCE: 217
aagcaccacc tgagaaaaga cctg                                           24

SEQ ID NO: 218          moltype = RNA  length = 24
FEATURE                 Location/Qualifiers
source                  1..24
                        mol_type = other RNA
                        organism = synthetic construct
                        note = Synthetic
SEQUENCE: 218
agcaccacct gagaaaagca ctgg                                           24

SEQ ID NO: 219          moltype = RNA  length = 25
FEATURE                 Location/Qualifiers
source                  1..25
                        mol_type = other RNA
```

```
                                organism = synthetic construct
                                note = Synthetic
SEQUENCE: 219
ctgagaaaag ccctgtggta cagga                                            25

SEQ ID NO: 220          moltype = RNA   length = 25
FEATURE                 Location/Qualifiers
source                  1..25
                        mol_type = other RNA
                        organism = synthetic construct
                        note = Synthetic
SEQUENCE: 220
gccctgtggt ccaggattga tacca                                            25

SEQ ID NO: 221          moltype = RNA   length = 25
FEATURE                 Location/Qualifiers
source                  1..25
                        mol_type = other RNA
                        organism = synthetic construct
                        note = Synthetic
SEQUENCE: 221
ctgtggtcca ggattgctaa catgg                                            25

SEQ ID NO: 222          moltype = RNA   length = 25
FEATURE                 Location/Qualifiers
source                  1..25
                        mol_type = other RNA
                        organism = synthetic construct
                        note = Synthetic
SEQUENCE: 222
ctccaccact gtcacaggaa ggacc                                            25

SEQ ID NO: 223          moltype = RNA   length = 24
FEATURE                 Location/Qualifiers
source                  1..24
                        mol_type = other RNA
                        organism = synthetic construct
                        note = Synthetic
SEQUENCE: 223
tccaccactg tcacaggaaa gacc                                             24

SEQ ID NO: 224          moltype = RNA   length = 24
FEATURE                 Location/Qualifiers
source                  1..24
                        mol_type = other RNA
                        organism = synthetic construct
                        note = Synthetic
SEQUENCE: 224
tcttggtcat ctatgataca acac                                             24

SEQ ID NO: 225          moltype = RNA   length = 24
FEATURE                 Location/Qualifiers
source                  1..24
                        mol_type = other RNA
                        organism = synthetic construct
                        note = Synthetic
SEQUENCE: 225
cttggtcatc tatgatacca cacg                                             24

SEQ ID NO: 226          moltype = RNA   length = 25
FEATURE                 Location/Qualifiers
source                  1..25
                        mol_type = other RNA
                        organism = synthetic construct
                        note = Synthetic
SEQUENCE: 226
ttggtcatct atgataccaa actgg                                            25

SEQ ID NO: 227          moltype = RNA   length = 25
FEATURE                 Location/Qualifiers
source                  1..25
                        mol_type = other RNA
                        organism = synthetic construct
                        note = Synthetic
SEQUENCE: 227
tggtcatcta tgataccaca ctggc                                            25

SEQ ID NO: 228          moltype = RNA   length = 25
FEATURE                 Location/Qualifiers
```

```
source                  1..25
                        mol_type = other RNA
                        organism = synthetic construct
                        note = Synthetic
SEQUENCE: 228
ggtcatctat gataccacaa tggca                                           25

SEQ ID NO: 229          moltype = RNA  length = 24
FEATURE                 Location/Qualifiers
source                  1..24
                        mol_type = other RNA
                        organism = synthetic construct
                        note = Synthetic
SEQUENCE: 229
gtcatctatg ataccacaca ggca                                            24

SEQ ID NO: 230          moltype = RNA  length = 24
FEATURE                 Location/Qualifiers
source                  1..24
                        mol_type = other RNA
                        organism = synthetic construct
                        note = Synthetic
SEQUENCE: 230
tcatctatga taccacacta gcac                                            24

SEQ ID NO: 231          moltype = RNA  length = 25
FEATURE                 Location/Qualifiers
source                  1..25
                        mol_type = other RNA
                        organism = synthetic construct
                        note = Synthetic
SEQUENCE: 231
catctatgat accacactga catca                                           25

SEQ ID NO: 232          moltype = RNA  length = 25
FEATURE                 Location/Qualifiers
source                  1..25
                        mol_type = other RNA
                        organism = synthetic construct
                        note = Synthetic
SEQUENCE: 232
atctatgata ccacactgga atcag                                           25

SEQ ID NO: 233          moltype = RNA  length = 25
FEATURE                 Location/Qualifiers
source                  1..25
                        mol_type = other RNA
                        organism = synthetic construct
                        note = Synthetic
SEQUENCE: 233
tctatgatac cacactggca tcaga                                           25

SEQ ID NO: 234          moltype = RNA  length = 25
FEATURE                 Location/Qualifiers
source                  1..25
                        mol_type = other RNA
                        organism = synthetic construct
                        note = Synthetic
SEQUENCE: 234
ctatgatacc acactggcaa cagag                                           25

SEQ ID NO: 235          moltype = RNA  length = 25
FEATURE                 Location/Qualifiers
source                  1..25
                        mol_type = other RNA
                        organism = synthetic construct
                        note = Synthetic
SEQUENCE: 235
tgataccaca ctggcatcaa aggac                                           25

SEQ ID NO: 236          moltype = RNA  length = 25
FEATURE                 Location/Qualifiers
source                  1..25
                        mol_type = other RNA
                        organism = synthetic construct
                        note = Synthetic
SEQUENCE: 236
ataccacact ggcatcagaa gaccc                                           25
```

-continued

```
SEQ ID NO: 237            moltype = RNA   length = 25
FEATURE                   Location/Qualifiers
source                    1..25
                          mol_type = other RNA
                          organism = synthetic construct
                          note = Synthetic
SEQUENCE: 237
agaggacccc agaaaactaa ccaaa                                               25

SEQ ID NO: 238            moltype = RNA   length = 24
FEATURE                   Location/Qualifiers
source                    1..24
                          mol_type = other RNA
                          organism = synthetic construct
                          note = Synthetic
SEQUENCE: 238
gaggacccca gaaaactaca caaa                                                24

SEQ ID NO: 239            moltype = RNA   length = 24
FEATURE                   Location/Qualifiers
source                    1..24
                          mol_type = other RNA
                          organism = synthetic construct
                          note = Synthetic
SEQUENCE: 239
agaactactg caggaatcca gatc                                                24

SEQ ID NO: 240            moltype = RNA   length = 25
FEATURE                   Location/Qualifiers
source                    1..25
                          mol_type = other RNA
                          organism = synthetic construct
                          note = Synthetic
SEQUENCE: 240
actactgcag gaatccagaa tctgg                                               25

SEQ ID NO: 241            moltype = RNA   length = 25
FEATURE                   Location/Qualifiers
source                    1..25
                          mol_type = other RNA
                          organism = synthetic construct
                          note = Synthetic
SEQUENCE: 241
tactgcagga atccagatta tggga                                               25

SEQ ID NO: 242            moltype = RNA   length = 25
FEATURE                   Location/Qualifiers
source                    1..25
                          mol_type = other RNA
                          organism = synthetic construct
                          note = Synthetic
SEQUENCE: 242
actgcaggaa tccagattca gggaa                                               25

SEQ ID NO: 243            moltype = RNA   length = 25
FEATURE                   Location/Qualifiers
source                    1..25
                          mol_type = other RNA
                          organism = synthetic construct
                          note = Synthetic
SEQUENCE: 243
ctgcaggaat ccagattcta ggaaa                                               25

SEQ ID NO: 244            moltype = RNA   length = 25
FEATURE                   Location/Qualifiers
source                    1..25
                          mol_type = other RNA
                          organism = synthetic construct
                          note = Synthetic
SEQUENCE: 244
tgcaggaatc cagattctga gaaac                                               25

SEQ ID NO: 245            moltype = RNA   length = 25
FEATURE                   Location/Qualifiers
source                    1..25
                          mol_type = other RNA
                          organism = synthetic construct
                          note = Synthetic
SEQUENCE: 245
```

```
gcaggaatcc agattctgga aaaca                                            25

SEQ ID NO: 246           moltype = RNA   length = 25
FEATURE                  Location/Qualifiers
source                   1..25
                         mol_type = other RNA
                         organism = synthetic construct
                         note = Synthetic
SEQUENCE: 246
ggaatccaga ttctgggaaa caacc                                            25

SEQ ID NO: 247           moltype = RNA   length = 25
FEATURE                  Location/Qualifiers
source                   1..25
                         mol_type = other RNA
                         organism = synthetic construct
                         note = Synthetic
SEQUENCE: 247
gggaaacaac cctggtgtta cacaa                                            25

SEQ ID NO: 248           moltype = RNA   length = 25
FEATURE                  Location/Qualifiers
source                   1..25
                         mol_type = other RNA
                         organism = synthetic construct
                         note = Synthetic
SEQUENCE: 248
ggaaacaacc ctggtgttaa acaac                                            25

SEQ ID NO: 249           moltype = RNA   length = 24
FEATURE                  Location/Qualifiers
source                   1..24
                         mol_type = other RNA
                         organism = synthetic construct
                         note = Synthetic
SEQUENCE: 249
tgtgtgaggt gggagtacta caac                                             24

SEQ ID NO: 250           moltype = RNA   length = 24
FEATURE                  Location/Qualifiers
source                   1..24
                         mol_type = other RNA
                         organism = synthetic construct
                         note = Synthetic
SEQUENCE: 250
gtgtgaggtg ggagtactga aatc                                             24

SEQ ID NO: 251           moltype = RNA   length = 25
FEATURE                  Location/Qualifiers
source                   1..25
                         mol_type = other RNA
                         organism = synthetic construct
                         note = Synthetic
SEQUENCE: 251
gtgaggtggg agtactgcaa tctga                                            25

SEQ ID NO: 252           moltype = RNA   length = 25
FEATURE                  Location/Qualifiers
source                   1..25
                         mol_type = other RNA
                         organism = synthetic construct
                         note = Synthetic
SEQUENCE: 252
tgaggtggga gtactgcaaa ctgac                                            25

SEQ ID NO: 253           moltype = RNA   length = 24
FEATURE                  Location/Qualifiers
source                   1..24
                         mol_type = other RNA
                         organism = synthetic construct
                         note = Synthetic
SEQUENCE: 253
ctgacacaat gctcagaaaa agaa                                             24

SEQ ID NO: 254           moltype = RNA   length = 24
FEATURE                  Location/Qualifiers
source                   1..24
                         mol_type = other RNA
                         organism = synthetic construct
```

```
                              note = Synthetic
SEQUENCE: 254
tgacacaatg ctcagaaaca gaac                                          24

SEQ ID NO: 255          moltype = RNA   length = 25
FEATURE                 Location/Qualifiers
source                  1..25
                        mol_type = other RNA
                        organism = synthetic construct
                        note = Synthetic
SEQUENCE: 255
gacacaatgc tcagaaacaa aatca                                         25

SEQ ID NO: 256          moltype = RNA   length = 25
FEATURE                 Location/Qualifiers
source                  1..25
                        mol_type = other RNA
                        organism = synthetic construct
                        note = Synthetic
SEQUENCE: 256
acacaatgct cagaaacaga atcag                                         25

SEQ ID NO: 257          moltype = RNA   length = 25
FEATURE                 Location/Qualifiers
source                  1..25
                        mol_type = other RNA
                        organism = synthetic construct
                        note = Synthetic
SEQUENCE: 257
cacaatgctc agaaacagaa tcagg                                         25

SEQ ID NO: 258          moltype = RNA   length = 24
FEATURE                 Location/Qualifiers
source                  1..24
                        mol_type = other RNA
                        organism = synthetic construct
                        note = Synthetic
SEQUENCE: 258
acaatgctca gaaacagaaa cagg                                          24

SEQ ID NO: 259          moltype = RNA   length = 24
FEATURE                 Location/Qualifiers
source                  1..24
                        mol_type = other RNA
                        organism = synthetic construct
                        note = Synthetic
SEQUENCE: 259
caatgctcag aaacagaata aggg                                          24

SEQ ID NO: 260          moltype = RNA   length = 24
FEATURE                 Location/Qualifiers
source                  1..24
                        mol_type = other RNA
                        organism = synthetic construct
                        note = Synthetic
SEQUENCE: 260
aatgctcaga aacagaatca ggtg                                          24

SEQ ID NO: 261          moltype = RNA   length = 24
FEATURE                 Location/Qualifiers
source                  1..24
                        mol_type = other RNA
                        organism = synthetic construct
                        note = Synthetic
SEQUENCE: 261
atgctcagaa acagaatcaa gtgc                                          24

SEQ ID NO: 262          moltype = RNA   length = 25
FEATURE                 Location/Qualifiers
source                  1..25
                        mol_type = other RNA
                        organism = synthetic construct
                        note = Synthetic
SEQUENCE: 262
tgctcagaaa cagaatcaga tgtcc                                         25

SEQ ID NO: 263          moltype = RNA   length = 24
FEATURE                 Location/Qualifiers
source                  1..24
```

```
                              mol_type = other RNA
                              organism = synthetic construct
                              note = Synthetic
SEQUENCE: 263
ctcagaaaca gaatcaggta tcca                                              24

SEQ ID NO: 264                moltype = RNA   length = 25
FEATURE                       Location/Qualifiers
source                        1..25
                              mol_type = other RNA
                              organism = synthetic construct
                              note = Synthetic
SEQUENCE: 264
cagaaacaga atcaggtgta ctaga                                             25

SEQ ID NO: 265                moltype = RNA   length = 25
FEATURE                       Location/Qualifiers
source                        1..25
                              mol_type = other RNA
                              organism = synthetic construct
                              note = Synthetic
SEQUENCE: 265
agaaacagaa tcaggtgtca tagag                                             25

SEQ ID NO: 266                moltype = RNA   length = 25
FEATURE                       Location/Qualifiers
source                        1..25
                              mol_type = other RNA
                              organism = synthetic construct
                              note = Synthetic
SEQUENCE: 266
gaaacagaat caggtgtcca agaga                                             25

SEQ ID NO: 267                moltype = RNA   length = 25
FEATURE                       Location/Qualifiers
source                        1..25
                              mol_type = other RNA
                              organism = synthetic construct
                              note = Synthetic
SEQUENCE: 267
aaacagaatc aggtgtccta gagac                                             25

SEQ ID NO: 268                moltype = RNA   length = 24
FEATURE                       Location/Qualifiers
source                        1..24
                              mol_type = other RNA
                              organism = synthetic construct
                              note = Synthetic
SEQUENCE: 268
aacagaatca ggtgtcctaa agac                                              24

SEQ ID NO: 269                moltype = RNA   length = 25
FEATURE                       Location/Qualifiers
source                        1..25
                              mol_type = other RNA
                              organism = synthetic construct
                              note = Synthetic
SEQUENCE: 269
cagaatcagg tgtcctagaa actcc                                             25

SEQ ID NO: 270                moltype = RNA   length = 25
FEATURE                       Location/Qualifiers
source                        1..25
                              mol_type = other RNA
                              organism = synthetic construct
                              note = Synthetic
SEQUENCE: 270
gaatcaggtg tcctagagaa tccca                                             25

SEQ ID NO: 271                moltype = RNA   length = 24
FEATURE                       Location/Qualifiers
source                        1..24
                              mol_type = other RNA
                              organism = synthetic construct
                              note = Synthetic
SEQUENCE: 271
atcaggtgtc ctagagacta ccac                                              24

SEQ ID NO: 272                moltype = RNA   length = 24
```

```
FEATURE                 Location/Qualifiers
source                  1..24
                        mol_type = other RNA
                        organism = synthetic construct
                        note = Synthetic
SEQUENCE: 272
ggtgtcctag agactcccaa tgtg                                              24

SEQ ID NO: 273          moltype = RNA   length = 25
FEATURE                 Location/Qualifiers
source                  1..25
                        mol_type = other RNA
                        organism = synthetic construct
                        note = Synthetic
SEQUENCE: 273
cctagagact cccactgtta ttcca                                             25

SEQ ID NO: 274          moltype = RNA   length = 25
FEATURE                 Location/Qualifiers
source                  1..25
                        mol_type = other RNA
                        organism = synthetic construct
                        note = Synthetic
SEQUENCE: 274
ctagagactc ccactgttga tccag                                             25

SEQ ID NO: 275          moltype = RNA   length = 24
FEATURE                 Location/Qualifiers
source                  1..24
                        mol_type = other RNA
                        organism = synthetic construct
                        note = Synthetic
SEQUENCE: 275
tagagactcc cactgttgta ccag                                              24

SEQ ID NO: 276          moltype = RNA   length = 23
FEATURE                 Location/Qualifiers
source                  1..23
                        mol_type = other RNA
                        organism = synthetic construct
                        note = Synthetic
SEQUENCE: 276
agagactccc actgttgtta cag                                               23

SEQ ID NO: 277          moltype = RNA   length = 24
FEATURE                 Location/Qualifiers
source                  1..24
                        mol_type = other RNA
                        organism = synthetic construct
                        note = Synthetic
SEQUENCE: 277
gagactccca ctgttgttca agtc                                              24

SEQ ID NO: 278          moltype = RNA   length = 25
FEATURE                 Location/Qualifiers
source                  1..25
                        mol_type = other RNA
                        organism = synthetic construct
                        note = Synthetic
SEQUENCE: 278
agactcccac tgttgttcca gttcc                                             25

SEQ ID NO: 279          moltype = RNA   length = 24
FEATURE                 Location/Qualifiers
source                  1..24
                        mol_type = other RNA
                        organism = synthetic construct
                        note = Synthetic
SEQUENCE: 279
gctcattctg aagcagcaca aacg                                              24

SEQ ID NO: 280          moltype = RNA   length = 25
FEATURE                 Location/Qualifiers
source                  1..25
                        mol_type = other RNA
                        organism = synthetic construct
                        note = Synthetic
SEQUENCE: 280
ctcattctga agcagcacca actga                                             25
```

SEQ ID NO: 281        moltype = RNA   length = 25
FEATURE               Location/Qualifiers
source                1..25
                      mol_type = other RNA
                      organism = synthetic construct
                      note = Synthetic
SEQUENCE: 281
tcattctgaa gcagcaccaa ctgag                                              25

SEQ ID NO: 282        moltype = RNA   length = 25
FEATURE               Location/Qualifiers
source                1..25
                      mol_type = other RNA
                      organism = synthetic construct
                      note = Synthetic
SEQUENCE: 282
cattctgaag cagcaccaaa tgagc                                              25

SEQ ID NO: 283        moltype = RNA   length = 25
FEATURE               Location/Qualifiers
source                1..25
                      mol_type = other RNA
                      organism = synthetic construct
                      note = Synthetic
SEQUENCE: 283
attctgaagc agcaccaaca gagca                                              25

SEQ ID NO: 284        moltype = RNA   length = 25
FEATURE               Location/Qualifiers
source                1..25
                      mol_type = other RNA
                      organism = synthetic construct
                      note = Synthetic
SEQUENCE: 284
ttctgaagca gcaccaacta agcaa                                              25

SEQ ID NO: 285        moltype = RNA   length = 25
FEATURE               Location/Qualifiers
source                1..25
                      mol_type = other RNA
                      organism = synthetic construct
                      note = Synthetic
SEQUENCE: 285
tctgaagcag caccaactga gcaaa                                              25

SEQ ID NO: 286        moltype = RNA   length = 25
FEATURE               Location/Qualifiers
source                1..25
                      mol_type = other RNA
                      organism = synthetic construct
                      note = Synthetic
SEQUENCE: 286
ctgaagcagc accaactgaa caaac                                              25

SEQ ID NO: 287        moltype = RNA   length = 25
FEATURE               Location/Qualifiers
source                1..25
                      mol_type = other RNA
                      organism = synthetic construct
                      note = Synthetic
SEQUENCE: 287
tgaagcagca ccaactgaga aaacc                                              25

SEQ ID NO: 288        moltype = RNA   length = 25
FEATURE               Location/Qualifiers
source                1..25
                      mol_type = other RNA
                      organism = synthetic construct
                      note = Synthetic
SEQUENCE: 288
gaagcagcac caactgagca aaccc                                              25

SEQ ID NO: 289        moltype = RNA   length = 25
FEATURE               Location/Qualifiers
source                1..25
                      mol_type = other RNA
                      organism = synthetic construct
                      note = Synthetic

```
SEQUENCE: 289
aagcagcacc aactgagcaa acccc                                              25

SEQ ID NO: 291          moltype = RNA   length = 25
FEATURE                 Location/Qualifiers
source                  1..25
                        mol_type = other RNA
                        organism = synthetic construct
                        note = Synthetic
SEQUENCE: 290
cagtgctacc atggtaatga ccaga                                              25

SEQ ID NO: 291          moltype = RNA   length = 25
FEATURE                 Location/Qualifiers
source                  1..25
                        mol_type = other RNA
                        organism = synthetic construct
                        note = Synthetic
SEQUENCE: 291
agtgctacca tggtaatgga cagag                                              25

SEQ ID NO: 292          moltype = RNA   length = 25
FEATURE                 Location/Qualifiers
source                  1..25
                        mol_type = other RNA
                        organism = synthetic construct
                        note = Synthetic
SEQUENCE: 292
acattctcca ccactgtcaa aggaa                                              25

SEQ ID NO: 293          moltype = RNA   length = 25
FEATURE                 Location/Qualifiers
source                  1..25
                        mol_type = other RNA
                        organism = synthetic construct
                        note = Synthetic
SEQUENCE: 293
cactgtcaca ggaaggacaa gtcaa                                              25

SEQ ID NO: 294          moltype = RNA   length = 24
FEATURE                 Location/Qualifiers
source                  1..24
                        mol_type = other RNA
                        organism = synthetic construct
                        note = Synthetic
SEQUENCE: 294
actgtcacag gaaggacata tcaa                                               24

SEQ ID NO: 295          moltype = RNA   length = 24
FEATURE                 Location/Qualifiers
source                  1..24
                        mol_type = other RNA
                        organism = synthetic construct
                        note = Synthetic
SEQUENCE: 295
ctgtcacagg aaggacatga caac                                               24

SEQ ID NO: 296          moltype = RNA   length = 24
FEATURE                 Location/Qualifiers
source                  1..24
                        mol_type = other RNA
                        organism = synthetic construct
                        note = Synthetic
SEQUENCE: 296
tgtcacagga aggacatgta aatc                                               24

SEQ ID NO: 297          moltype = RNA   length = 23
FEATURE                 Location/Qualifiers
source                  1..23
                        mol_type = other RNA
                        organism = synthetic construct
                        note = Synthetic
SEQUENCE: 297
gtcacaggaa ggacatgtca atc                                                23

SEQ ID NO: 298          moltype = RNA   length = 24
FEATURE                 Location/Qualifiers
source                  1..24
                        mol_type = other RNA
```

```
                            organism = synthetic construct
                            note = Synthetic
SEQUENCE: 298
tcacaggaag gacatgtcaa tctg                                                 24

SEQ ID NO: 299              moltype = RNA   length = 24
FEATURE                     Location/Qualifiers
source                      1..24
                            mol_type = other RNA
                            organism = synthetic construct
                            note = Synthetic
SEQUENCE: 299
acaggaagga catgtcaata ttgg                                                 24

SEQ ID NO: 300              moltype = RNA   length = 24
FEATURE                     Location/Qualifiers
source                      1..24
                            mol_type = other RNA
                            organism = synthetic construct
                            note = Synthetic
SEQUENCE: 300
caggaaggac atgtcaatca tggc                                                 24

SEQ ID NO: 301              moltype = RNA   length = 25
FEATURE                     Location/Qualifiers
source                      1..25
                            mol_type = other RNA
                            organism = synthetic construct
                            note = Synthetic
SEQUENCE: 301
aggaaggaca tgtcaatcta ggtca                                                25

SEQ ID NO: 302              moltype = RNA   length = 24
FEATURE                     Location/Qualifiers
source                      1..24
                            mol_type = other RNA
                            organism = synthetic construct
                            note = Synthetic
SEQUENCE: 302
ggaaggacat gtcaatctta gtca                                                 24

SEQ ID NO: 303              moltype = RNA   length = 24
FEATURE                     Location/Qualifiers
source                      1..24
                            mol_type = other RNA
                            organism = synthetic construct
                            note = Synthetic
SEQUENCE: 303
gaaggacatg tcaatcttga tcac                                                 24

SEQ ID NO: 304              moltype = RNA   length = 25
FEATURE                     Location/Qualifiers
source                      1..25
                            mol_type = other RNA
                            organism = synthetic construct
                            note = Synthetic
SEQUENCE: 304
aaggacatgt caatcttgga catcc                                                25

SEQ ID NO: 305              moltype = RNA   length = 25
FEATURE                     Location/Qualifiers
source                      1..25
                            mol_type = other RNA
                            organism = synthetic construct
                            note = Synthetic
SEQUENCE: 305
aggacatgtc aatcttggta atcca                                                25

SEQ ID NO: 306              moltype = RNA   length = 24
FEATURE                     Location/Qualifiers
source                      1..24
                            mol_type = other RNA
                            organism = synthetic construct
                            note = Synthetic
SEQUENCE: 306
ggacatgtca atcttggtca tcca                                                 24

SEQ ID NO: 307              moltype = RNA   length = 24
FEATURE                     Location/Qualifiers
```

```
source                  1..24
                        mol_type = other RNA
                        organism = synthetic construct
                        note = Synthetic
SEQUENCE: 307
gacatgtcaa tcttggtcaa ccag                                              24

SEQ ID NO: 308          moltype = RNA   length = 25
FEATURE                 Location/Qualifiers
source                  1..25
                        mol_type = other RNA
                        organism = synthetic construct
                        note = Synthetic
SEQUENCE: 308
acatgtcaat cttggtcata catga                                             25

SEQ ID NO: 309          moltype = RNA   length = 25
FEATURE                 Location/Qualifiers
source                  1..25
                        mol_type = other RNA
                        organism = synthetic construct
                        note = Synthetic
SEQUENCE: 309
catgtcaatc ttggtcatca atgac                                             25

SEQ ID NO: 310          moltype = RNA   length = 25
FEATURE                 Location/Qualifiers
source                  1..25
                        mol_type = other RNA
                        organism = synthetic construct
                        note = Synthetic
SEQUENCE: 310
atgtcaatct tggtcatcca tgaca                                             25

SEQ ID NO: 311          moltype = RNA   length = 25
FEATURE                 Location/Qualifiers
source                  1..25
                        mol_type = other RNA
                        organism = synthetic construct
                        note = Synthetic
SEQUENCE: 311
tgtcaatctt ggtcatccaa gacac                                             25

SEQ ID NO: 312          moltype = RNA   length = 25
FEATURE                 Location/Qualifiers
source                  1..25
                        mol_type = other RNA
                        organism = synthetic construct
                        note = Synthetic
SEQUENCE: 312
gtcaatcttg gtcatccata acacc                                             25

SEQ ID NO: 313          moltype = RNA   length = 25
FEATURE                 Location/Qualifiers
source                  1..25
                        mol_type = other RNA
                        organism = synthetic construct
                        note = Synthetic
SEQUENCE: 313
tcaatcttgg tcatccatga cacca                                             25

SEQ ID NO: 314          moltype = RNA   length = 25
FEATURE                 Location/Qualifiers
source                  1..25
                        mol_type = other RNA
                        organism = synthetic construct
                        note = Synthetic
SEQUENCE: 314
caatcttggt catccatgaa accac                                             25

SEQ ID NO: 315          moltype = RNA   length = 25
FEATURE                 Location/Qualifiers
source                  1..25
                        mol_type = other RNA
                        organism = synthetic construct
                        note = Synthetic
SEQUENCE: 315
aatcttggtc atccatgaca ccaca                                             25
```

```
SEQ ID NO: 316            moltype = RNA   length = 25
FEATURE                   Location/Qualifiers
source                    1..25
                          mol_type = other RNA
                          organism = synthetic construct
                          note = Synthetic
SEQUENCE: 316
atcttggtca tccatgacaa cacac                                              25

SEQ ID NO: 317            moltype = RNA   length = 25
FEATURE                   Location/Qualifiers
source                    1..25
                          mol_type = other RNA
                          organism = synthetic construct
                          note = Synthetic
SEQUENCE: 317
tgacaatgaa ctactgcaga aatcc                                              25

SEQ ID NO: 318            moltype = RNA   length = 25
FEATURE                   Location/Qualifiers
source                    1..25
                          mol_type = other RNA
                          organism = synthetic construct
                          note = Synthetic
SEQUENCE: 318
gacaatgaac tactgcagga atcca                                              25

SEQ ID NO: 319            moltype = RNA   length = 25
FEATURE                   Location/Qualifiers
source                    1..25
                          mol_type = other RNA
                          organism = synthetic construct
                          note = Synthetic
SEQUENCE: 319
acaatgaact actgcaggaa tccag                                              25

SEQ ID NO: 320            moltype = RNA   length = 25
FEATURE                   Location/Qualifiers
source                    1..25
                          mol_type = other RNA
                          organism = synthetic construct
                          note = Synthetic
SEQUENCE: 320
caatgaacta ctgcaggaaa ccaga                                              25

SEQ ID NO: 321            moltype = RNA   length = 24
FEATURE                   Location/Qualifiers
source                    1..24
                          mol_type = other RNA
                          organism = synthetic construct
                          note = Synthetic
SEQUENCE: 321
aatgaactac tgcaggaata caga                                               24

SEQ ID NO: 322            moltype = RNA   length = 24
FEATURE                   Location/Qualifiers
source                    1..24
                          mol_type = other RNA
                          organism = synthetic construct
                          note = Synthetic
SEQUENCE: 322
atgaactact gcaggaatca agag                                               24

SEQ ID NO: 323            moltype = RNA   length = 25
FEATURE                   Location/Qualifiers
source                    1..25
                          mol_type = other RNA
                          organism = synthetic construct
                          note = Synthetic
SEQUENCE: 323
tgaactactg caggaatcca gatgc                                              25

SEQ ID NO: 324            moltype = RNA   length = 24
FEATURE                   Location/Qualifiers
source                    1..24
                          mol_type = other RNA
                          organism = synthetic construct
                          note = Synthetic
SEQUENCE: 324
```

-continued

```
ctactgcagg aatccagata ccga                                              24

SEQ ID NO: 325          moltype = RNA  length = 25
FEATURE                 Location/Qualifiers
source                  1..25
                        mol_type = other RNA
                        organism = synthetic construct
                        note = Synthetic
SEQUENCE: 325
caggcccttg gtgttttaca atgga                                             25

SEQ ID NO: 326          moltype = RNA  length = 25
FEATURE                 Location/Qualifiers
source                  1..25
                        mol_type = other RNA
                        organism = synthetic construct
                        note = Synthetic
SEQUENCE: 326
cttggtgttt taccatggaa cccag                                             25

SEQ ID NO: 327          moltype = RNA  length = 25
FEATURE                 Location/Qualifiers
source                  1..25
                        mol_type = other RNA
                        organism = synthetic construct
                        note = Synthetic
SEQUENCE: 327
ttggtgtttt accatggaca ccagc                                             25

SEQ ID NO: 328          moltype = RNA  length = 25
FEATURE                 Location/Qualifiers
source                  1..25
                        mol_type = other RNA
                        organism = synthetic construct
                        note = Synthetic
SEQUENCE: 328
tggtgtttta ccatggacca cagca                                             25

SEQ ID NO: 329          moltype = RNA  length = 24
FEATURE                 Location/Qualifiers
source                  1..24
                        mol_type = other RNA
                        organism = synthetic construct
                        note = Synthetic
SEQUENCE: 329
ggtgttttac catggaccca agca                                              24

SEQ ID NO: 330          moltype = RNA  length = 24
FEATURE                 Location/Qualifiers
source                  1..24
                        mol_type = other RNA
                        organism = synthetic construct
                        note = Synthetic
SEQUENCE: 330
gtgttttacc atggacccca gcac                                              24

SEQ ID NO: 331          moltype = RNA  length = 25
FEATURE                 Location/Qualifiers
source                  1..25
                        mol_type = other RNA
                        organism = synthetic construct
                        note = Synthetic
SEQUENCE: 331
gttttaccat ggaccccaga atcag                                             25

SEQ ID NO: 332          moltype = RNA  length = 25
FEATURE                 Location/Qualifiers
source                  1..25
                        mol_type = other RNA
                        organism = synthetic construct
                        note = Synthetic
SEQUENCE: 332
ggagtactgc aacctgacga gatgc                                             25

SEQ ID NO: 333          moltype = RNA  length = 24
FEATURE                 Location/Qualifiers
source                  1..24
                        mol_type = other RNA
                        organism = synthetic construct
```

-continued

```
                        note = Synthetic
SEQUENCE: 333
gagtactgca acctgacgca atgc                                          24

SEQ ID NO: 334          moltype = RNA   length = 25
FEATURE                 Location/Qualifiers
source                  1..25
                        mol_type = other RNA
                        organism = synthetic construct
                        note = Synthetic
SEQUENCE: 334
gtactgcaac ctgacgcgaa gctca                                         25

SEQ ID NO: 335          moltype = RNA   length = 25
FEATURE                 Location/Qualifiers
source                  1..25
                        mol_type = other RNA
                        organism = synthetic construct
                        note = Synthetic
SEQUENCE: 335
tactgcaacc tgacgcgata ctcag                                         25

SEQ ID NO: 336          moltype = RNA   length = 25
FEATURE                 Location/Qualifiers
source                  1..25
                        mol_type = other RNA
                        organism = synthetic construct
                        note = Synthetic
SEQUENCE: 336
tgcaacctga cgcgatgcta agaca                                         25

SEQ ID NO: 337          moltype = RNA   length = 25
FEATURE                 Location/Qualifiers
source                  1..25
                        mol_type = other RNA
                        organism = synthetic construct
                        note = Synthetic
SEQUENCE: 337
cctgacgcga tgctcagaca cagaa                                         25

SEQ ID NO: 338          moltype = RNA   length = 25
FEATURE                 Location/Qualifiers
source                  1..25
                        mol_type = other RNA
                        organism = synthetic construct
                        note = Synthetic
SEQUENCE: 338
ctgacgcgat gctcagacaa agaag                                         25

SEQ ID NO: 339          moltype = RNA   length = 24
FEATURE                 Location/Qualifiers
source                  1..24
                        mol_type = other RNA
                        organism = synthetic construct
                        note = Synthetic
SEQUENCE: 339
gatgctcaga cacagaagga actg                                          24

SEQ ID NO: 340          moltype = RNA   length = 24
FEATURE                 Location/Qualifiers
source                  1..24
                        mol_type = other RNA
                        organism = synthetic construct
                        note = Synthetic
SEQUENCE: 340
atgctcagac acagaaggga ctgg                                          24

SEQ ID NO: 341          moltype = RNA   length = 24
FEATURE                 Location/Qualifiers
source                  1..24
                        mol_type = other RNA
                        organism = synthetic construct
                        note = Synthetic
SEQUENCE: 341
agacacagaa gggactgtga tcgc                                          24

SEQ ID NO: 342          moltype = RNA   length = 25
FEATURE                 Location/Qualifiers
source                  1..25
```

```
                              mol_type = other RNA
                              organism = synthetic construct
                              note = Synthetic
SEQUENCE: 342
gcatcctctt catttgatta tggga                                          25

SEQ ID NO: 343           moltype = RNA   length = 25
FEATURE                  Location/Qualifiers
source                   1..25
                         mol_type = other RNA
                         organism = synthetic construct
                         note = Synthetic
SEQUENCE: 343
catcctcttc atttgattga gggaa                                          25

SEQ ID NO: 344           moltype = RNA   length = 25
FEATURE                  Location/Qualifiers
source                   1..25
                         mol_type = other RNA
                         organism = synthetic construct
                         note = Synthetic
SEQUENCE: 344
atcctcttca tttgattgta ggaag                                          25

SEQ ID NO: 345           moltype = RNA   length = 25
FEATURE                  Location/Qualifiers
source                   1..25
                         mol_type = other RNA
                         organism = synthetic construct
                         note = Synthetic
SEQUENCE: 345
tcctcttcat tgattgtga gaagc                                           25

SEQ ID NO: 346           moltype = RNA   length = 25
FEATURE                  Location/Qualifiers
source                   1..25
                         mol_type = other RNA
                         organism = synthetic construct
                         note = Synthetic
SEQUENCE: 346
cctcttcatt tgattgtgga aagcc                                          25

SEQ ID NO: 347           moltype = RNA   length = 25
FEATURE                  Location/Qualifiers
source                   1..25
                         mol_type = other RNA
                         organism = synthetic construct
                         note = Synthetic
SEQUENCE: 347
cttcatttga ttgtgggaaa cctca                                          25

SEQ ID NO: 348           moltype = RNA   length = 25
FEATURE                  Location/Qualifiers
source                   1..25
                         mol_type = other RNA
                         organism = synthetic construct
                         note = Synthetic
SEQUENCE: 348
ttcatttgat tgtgggaaga ctcaa                                          25

SEQ ID NO: 349           moltype = RNA   length = 25
FEATURE                  Location/Qualifiers
source                   1..25
                         mol_type = other RNA
                         organism = synthetic construct
                         note = Synthetic
SEQUENCE: 349
tcatttgatt gtgggaagca tcaag                                          25

SEQ ID NO: 350           moltype = RNA   length = 24
FEATURE                  Location/Qualifiers
source                   1..24
                         mol_type = other RNA
                         organism = synthetic construct
                         note = Synthetic
SEQUENCE: 350
catttgattg tgggaagcca caag                                           24

SEQ ID NO: 351           moltype = RNA   length = 24
```

```
FEATURE                 Location/Qualifiers
source                  1..24
                        mol_type = other RNA
                        organism = synthetic construct
                        note = Synthetic
SEQUENCE: 351
atttgattgt gggaagccta aagg                                              24

SEQ ID NO: 352          moltype = RNA   length = 25
FEATURE                 Location/Qualifiers
source                  1..25
                        mol_type = other RNA
                        organism = synthetic construct
                        note = Synthetic
SEQUENCE: 352
gtgggaagcc tcaagtggaa ccgaa                                             25

SEQ ID NO: 353          moltype = RNA   length = 25
FEATURE                 Location/Qualifiers
source                  1..25
                        mol_type = other RNA
                        organism = synthetic construct
                        note = Synthetic
SEQUENCE: 353
aagaaatgtc ctggaagcaa tgtag                                             25

SEQ ID NO: 354          moltype = RNA   length = 25
FEATURE                 Location/Qualifiers
source                  1..25
                        mol_type = other RNA
                        organism = synthetic construct
                        note = Synthetic
SEQUENCE: 354
agaaatgtcc tggaagcata gtagg                                             25

SEQ ID NO: 355          moltype = RNA   length = 25
FEATURE                 Location/Qualifiers
source                  1..25
                        mol_type = other RNA
                        organism = synthetic construct
                        note = Synthetic
SEQUENCE: 355
gaaatgtcct ggaagcatta taggg                                             25

SEQ ID NO: 356          moltype = RNA   length = 25
FEATURE                 Location/Qualifiers
source                  1..25
                        mol_type = other RNA
                        organism = synthetic construct
                        note = Synthetic
SEQUENCE: 356
aatgtcctgg aagcattgta ggggg                                             25

SEQ ID NO: 357          moltype = RNA   length = 25
FEATURE                 Location/Qualifiers
source                  1..25
                        mol_type = other RNA
                        organism = synthetic construct
                        note = Synthetic
SEQUENCE: 357
atgtcctgga agcattgtaa ggggg                                             25

SEQ ID NO: 358          moltype = RNA   length = 24
FEATURE                 Location/Qualifiers
source                  1..24
                        mol_type = other RNA
                        organism = synthetic construct
                        note = Synthetic
SEQUENCE: 358
agaacaaggt ttggaaagca cttc                                              24

SEQ ID NO: 359          moltype = RNA   length = 24
FEATURE                 Location/Qualifiers
source                  1..24
                        mol_type = other RNA
                        organism = synthetic construct
                        note = Synthetic
SEQUENCE: 359
gaacaaggtt tggaaagcaa ttcg                                              24
```

```
SEQ ID NO: 360           moltype = RNA   length = 24
FEATURE                  Location/Qualifiers
source                   1..24
                         mol_type = other RNA
                         organism = synthetic construct
                         note = Synthetic
SEQUENCE: 360
aacaaggttt ggaaagcaca tctg                                           24

SEQ ID NO: 361           moltype = RNA   length = 24
FEATURE                  Location/Qualifiers
source                   1..24
                         mol_type = other RNA
                         organism = synthetic construct
                         note = Synthetic
SEQUENCE: 361
acaaggtttg gaaagcacta ctgg                                           24

SEQ ID NO: 362           moltype = RNA   length = 25
FEATURE                  Location/Qualifiers
source                   1..25
                         mol_type = other RNA
                         organism = synthetic construct
                         note = Synthetic
SEQUENCE: 362
caaggtttgg aaagcactta tgtgg                                          25

SEQ ID NO: 363           moltype = RNA   length = 25
FEATURE                  Location/Qualifiers
source                   1..25
                         mol_type = other RNA
                         organism = synthetic construct
                         note = Synthetic
SEQUENCE: 363
aaggtttgga agcacttca gtgga                                           25

SEQ ID NO: 364           moltype = RNA   length = 25
FEATURE                  Location/Qualifiers
source                   1..25
                         mol_type = other RNA
                         organism = synthetic construct
                         note = Synthetic
SEQUENCE: 364
aggtttggaa agcacttcta tggag                                          25

SEQ ID NO: 365           moltype = RNA   length = 25
FEATURE                  Location/Qualifiers
source                   1..25
                         mol_type = other RNA
                         organism = synthetic construct
                         note = Synthetic
SEQUENCE: 365
tggaaagcac ttctgtggaa gcacc                                          25

SEQ ID NO: 366           moltype = RNA   length = 25
FEATURE                  Location/Qualifiers
source                   1..25
                         mol_type = other RNA
                         organism = synthetic construct
                         note = Synthetic
SEQUENCE: 366
gtggaggcac cttaatatca ccaga                                          25

SEQ ID NO: 367           moltype = RNA   length = 24
FEATURE                  Location/Qualifiers
source                   1..24
                         mol_type = other RNA
                         organism = synthetic construct
                         note = Synthetic
SEQUENCE: 367
cttaatatcc ccagagtgga tgcg                                           24

SEQ ID NO: 368           moltype = RNA   length = 25
FEATURE                  Location/Qualifiers
source                   1..25
                         mol_type = other RNA
                         organism = synthetic construct
                         note = Synthetic
```

```
SEQUENCE: 368
taatatcccc agagtgggta ctgac                                              25

SEQ ID NO: 369          moltype = RNA   length = 25
FEATURE                 Location/Qualifiers
source                  1..25
                        mol_type = other RNA
                        organism = synthetic construct
                        note = Synthetic
SEQUENCE: 369
agagtgggtg ctgactgcta ctcac                                              25

SEQ ID NO: 370          moltype = RNA   length = 25
FEATURE                 Location/Qualifiers
source                  1..25
                        mol_type = other RNA
                        organism = synthetic construct
                        note = Synthetic
SEQUENCE: 370
caaggtcatc ctgggtgcaa accaa                                              25

SEQ ID NO: 371          moltype = RNA   length = 25
FEATURE                 Location/Qualifiers
source                  1..25
                        mol_type = other RNA
                        organism = synthetic construct
                        note = Synthetic
SEQUENCE: 371
cctgggtgca caccaagaaa tgaac                                              25

SEQ ID NO: 372          moltype = RNA   length = 25
FEATURE                 Location/Qualifiers
source                  1..25
                        mol_type = other RNA
                        organism = synthetic construct
                        note = Synthetic
SEQUENCE: 372
gtgcacacca agaagtgaaa ctcga                                              25

SEQ ID NO: 373          moltype = RNA   length = 24
FEATURE                 Location/Qualifiers
source                  1..24
                        mol_type = other RNA
                        organism = synthetic construct
                        note = Synthetic
SEQUENCE: 373
agcagatatt gccttgctaa agca                                               24

SEQ ID NO: 374          moltype = RNA   length = 25
FEATURE                 Location/Qualifiers
source                  1..25
                        mol_type = other RNA
                        organism = synthetic construct
                        note = Synthetic
SEQUENCE: 374
gcagatattg ccttgctaaa gctaa                                              25

SEQ ID NO: 375          moltype = RNA   length = 25
FEATURE                 Location/Qualifiers
source                  1..25
                        mol_type = other RNA
                        organism = synthetic construct
                        note = Synthetic
SEQUENCE: 375
cagatattgc cttgctaaaa ctaag                                              25

SEQ ID NO: 376          moltype = RNA   length = 25
FEATURE                 Location/Qualifiers
source                  1..25
                        mol_type = other RNA
                        organism = synthetic construct
                        note = Synthetic
SEQUENCE: 376
agatattgcc ttgctaaaga taagc                                              25

SEQ ID NO: 377          moltype = RNA   length = 25
FEATURE                 Location/Qualifiers
source                  1..25
                        mol_type = other RNA
```

```
                        organism = synthetic construct
                        note = Synthetic
SEQUENCE: 377
gatattgcct tgctaaagca aagca                                          25

SEQ ID NO: 378          moltype = RNA   length = 25
FEATURE                 Location/Qualifiers
source                  1..25
                        mol_type = other RNA
                        organism = synthetic construct
                        note = Synthetic
SEQUENCE: 378
atattgcctt gctaaagcta agcag                                          25

SEQ ID NO: 379          moltype = RNA   length = 25
FEATURE                 Location/Qualifiers
source                  1..25
                        mol_type = other RNA
                        organism = synthetic construct
                        note = Synthetic
SEQUENCE: 379
tattgccttg ctaaagctaa gcagg                                          25

SEQ ID NO: 380          moltype = RNA   length = 25
FEATURE                 Location/Qualifiers
source                  1..25
                        mol_type = other RNA
                        organism = synthetic construct
                        note = Synthetic
SEQUENCE: 380
tcatcactga caaagtaata ccagc                                          25

SEQ ID NO: 381          moltype = RNA   length = 24
FEATURE                 Location/Qualifiers
source                  1..24
                        mol_type = other RNA
                        organism = synthetic construct
                        note = Synthetic
SEQUENCE: 381
ggactgaatg ttacatcaca ggcg                                           24

SEQ ID NO: 382          moltype = RNA   length = 25
FEATURE                 Location/Qualifiers
source                  1..25
                        mol_type = other RNA
                        organism = synthetic construct
                        note = Synthetic
SEQUENCE: 382
gactgaatgt tacatcacta gctgg                                          25

SEQ ID NO: 383          moltype = RNA   length = 25
FEATURE                 Location/Qualifiers
source                  1..25
                        mol_type = other RNA
                        organism = synthetic construct
                        note = Synthetic
SEQUENCE: 383
actgaatgtt acatcactga ctggg                                          25

SEQ ID NO: 384          moltype = RNA   length = 25
FEATURE                 Location/Qualifiers
source                  1..25
                        mol_type = other RNA
                        organism = synthetic construct
                        note = Synthetic
SEQUENCE: 384
ctgaatgtta catcactgga tgggg                                          25

SEQ ID NO: 385          moltype = RNA   length = 25
FEATURE                 Location/Qualifiers
source                  1..25
                        mol_type = other RNA
                        organism = synthetic construct
                        note = Synthetic
SEQUENCE: 385
tgaatgttac atcactggca gggga                                          25

SEQ ID NO: 386          moltype = RNA   length = 25
FEATURE                 Location/Qualifiers
```

```
source                  1..25
                        mol_type = other RNA
                        organism = synthetic construct
                        note = Synthetic
SEQUENCE: 386
aatgttacat cactggctga ggaga                                          25

SEQ ID NO: 387          moltype = RNA  length = 24
FEATURE                 Location/Qualifiers
source                  1..24
                        mol_type = other RNA
                        organism = synthetic construct
                        note = Synthetic
SEQUENCE: 387
gaaacccaag gtacctttga gacg                                           24

SEQ ID NO: 388          moltype = RNA  length = 36
FEATURE                 Location/Qualifiers
source                  1..36
                        mol_type = other RNA
                        organism = synthetic construct
                        note = Synthetic
SEQUENCE: 388
tccaccactg tcacaggaaa gcagccgaaa ggctgc                              36

SEQ ID NO: 389          moltype = RNA  length = 36
FEATURE                 Location/Qualifiers
source                  1..36
                        mol_type = other RNA
                        organism = synthetic construct
                        note = Synthetic
SEQUENCE: 389
tggtaatgga cagagttata gcagccgaaa ggctgc                              36

SEQ ID NO: 390          moltype = RNA  length = 36
FEATURE                 Location/Qualifiers
source                  1..36
                        mol_type = other RNA
                        organism = synthetic construct
                        note = Synthetic
SEQUENCE: 390
tactgcaacc tgacacgata gcagccgaaa ggctgc                              36

SEQ ID NO: 391          moltype = RNA  length = 36
FEATURE                 Location/Qualifiers
source                  1..36
                        mol_type = other RNA
                        organism = synthetic construct
                        note = Synthetic
SEQUENCE: 391
agaacttgcc aagcttggta gcagccgaaa ggctgc                              36

SEQ ID NO: 392          moltype = RNA  length = 36
FEATURE                 Location/Qualifiers
source                  1..36
                        mol_type = other RNA
                        organism = synthetic construct
                        note = Synthetic
SEQUENCE: 392
aacttgccaa gcttggtcaa gcagccgaaa ggctgc                              36

SEQ ID NO: 393          moltype = RNA  length = 36
FEATURE                 Location/Qualifiers
source                  1..36
                        mol_type = other RNA
                        organism = synthetic construct
                        note = Synthetic
SEQUENCE: 393
ttgccaagct tggtcatcta gcagccgaaa ggctgc                              36

SEQ ID NO: 394          moltype = RNA  length = 36
FEATURE                 Location/Qualifiers
source                  1..36
                        mol_type = other RNA
                        organism = synthetic construct
                        note = Synthetic
SEQUENCE: 394
atggacagag ttatcgagga gcagccgaaa ggctgc                              36
```

| | | |
|---|---|---|
| SEQ ID NO: 395 | moltype = RNA length = 36 | |
| FEATURE | Location/Qualifiers | |
| source | 1..36 mol_type = other RNA organism = synthetic construct note = Synthetic | |
| SEQUENCE: 395 | | |
| tggacagagt tatcgaggca gcagccgaaa ggctgc | | 36 |
| SEQ ID NO: 396 | moltype = RNA length = 36 | |
| FEATURE | Location/Qualifiers | |
| source | 1..36 mol_type = other RNA organism = synthetic construct note = Synthetic | |
| SEQUENCE: 396 | | |
| tggtcatcta tgataccaca gcagccgaaa ggctgc | | 36 |
| SEQ ID NO: 397 | moltype = RNA length = 36 | |
| FEATURE | Location/Qualifiers | |
| source | 1..36 mol_type = other RNA organism = synthetic construct note = Synthetic | |
| SEQUENCE: 397 | | |
| tactgcagga atccagatta gcagccgaaa ggctgc | | 36 |
| SEQ ID NO: 398 | moltype = RNA length = 36 | |
| FEATURE | Location/Qualifiers | |
| source | 1..36 mol_type = other RNA organism = synthetic construct note = Synthetic | |
| SEQUENCE: 398 | | |
| agaaatgtcc tggaagcata gcagccgaaa ggctgc | | 36 |
| SEQ ID NO: 399 | moltype = RNA length = 36 | |
| FEATURE | Location/Qualifiers | |
| source | 1..36 mol_type = other RNA organism = synthetic construct note = Synthetic | |
| SEQUENCE: 399 | | |
| gacaacagaa tattatccaa gcagccgaaa ggctgc | | 36 |
| SEQ ID NO: 400 | moltype = RNA length = 36 | |
| FEATURE | Location/Qualifiers | |
| source | 1..36 mol_type = other RNA organism = synthetic construct note = Synthetic | |
| SEQUENCE: 400 | | |
| atggacagag ttatcaagga gcagccgaaa ggctgc | | 36 |
| SEQ ID NO: 401 | moltype = RNA length = 36 | |
| FEATURE | Location/Qualifiers | |
| source | 1..36 mol_type = other RNA organism = synthetic construct note = Synthetic | |
| SEQUENCE: 401 | | |
| gacaacagaa tattatccaa gcagccgaaa ggctgc | | 36 |
| SEQ ID NO: 402 | moltype = RNA length = 36 | |
| FEATURE | Location/Qualifiers | |
| source | 1..36 mol_type = other RNA organism = synthetic construct note = Synthetic | |
| SEQUENCE: 402 | | |
| atggacagag ttatcaagga gcagccgaaa ggctgc | | 36 |
| SEQ ID NO: 403 | moltype = RNA length = 36 | |
| FEATURE | Location/Qualifiers | |
| source | 1..36 mol_type = other RNA organism = synthetic construct note = Synthetic | |
| SEQUENCE: 403 | | |

```
gacaacagaa tattatccaa gcagccgaaa ggctgc                                    36

SEQ ID NO: 404          moltype = RNA   length = 27
FEATURE                 Location/Qualifiers
source                  1..27
                        mol_type = other RNA
                        organism = synthetic construct
                        note = Synthetic
SEQUENCE: 404
tcctgtacca catggctttg ctcaggt                                              27

SEQ ID NO: 405          moltype = RNA   length = 27
FEATURE                 Location/Qualifiers
source                  1..27
                        mol_type = other RNA
                        organism = synthetic construct
                        note = Synthetic
SEQUENCE: 405
caatcttgga ccacatggct ttgctca                                              27

SEQ ID NO: 406          moltype = RNA   length = 27
FEATURE                 Location/Qualifiers
source                  1..27
                        mol_type = other RNA
                        organism = synthetic construct
                        note = Synthetic
SEQUENCE: 406
gtagctatcc tggaccacat ggctttg                                              27

SEQ ID NO: 407          moltype = RNA   length = 27
FEATURE                 Location/Qualifiers
source                  1..27
                        mol_type = other RNA
                        organism = synthetic construct
                        note = Synthetic
SEQUENCE: 407
ggtagtaatc ctggaccaca tggcttt                                              27

SEQ ID NO: 408          moltype = RNA   length = 27
FEATURE                 Location/Qualifiers
source                  1..27
                        mol_type = other RNA
                        organism = synthetic construct
                        note = Synthetic
SEQUENCE: 408
tggtatcaat cctggaccac atggctt                                              27

SEQ ID NO: 409          moltype = RNA   length = 27
FEATURE                 Location/Qualifiers
source                  1..27
                        mol_type = other RNA
                        organism = synthetic construct
                        note = Synthetic
SEQUENCE: 409
atggttgcaa tcctggacca catggct                                              27

SEQ ID NO: 410          moltype = RNA   length = 27
FEATURE                 Location/Qualifiers
source                  1..27
                        mol_type = other RNA
                        organism = synthetic construct
                        note = Synthetic
SEQUENCE: 410
catggtagca atcctggacc acatggc                                              27

SEQ ID NO: 411          moltype = RNA   length = 27
FEATURE                 Location/Qualifiers
source                  1..27
                        mol_type = other RNA
                        organism = synthetic construct
                        note = Synthetic
SEQUENCE: 411
ccatgttagc aatcctggac cacatgg                                              27

SEQ ID NO: 412          moltype = RNA   length = 27
FEATURE                 Location/Qualifiers
source                  1..27
                        mol_type = other RNA
                        organism = synthetic construct
```

```
                              note = Synthetic
SEQUENCE: 412
accattgtag caatcctgga ccacatg                                              27

SEQ ID NO: 413            moltype = RNA   length = 27
FEATURE                   Location/Qualifiers
source                    1..27
                          mol_type = other RNA
                          organism = synthetic construct
                          note = Synthetic
SEQUENCE: 413
tgccttgata actctgtcca tcaccat                                              27

SEQ ID NO: 414            moltype = RNA   length = 27
FEATURE                   Location/Qualifiers
source                    1..27
                          mol_type = other RNA
                          organism = synthetic construct
                          note = Synthetic
SEQUENCE: 414
aggtctttcc tgtgacagtg gtggagt                                              27

SEQ ID NO: 415            moltype = RNA   length = 27
FEATURE                   Location/Qualifiers
source                    1..27
                          mol_type = other RNA
                          organism = synthetic construct
                          note = Synthetic
SEQUENCE: 415
caggttcttc ctgtgacagt ggtggag                                              27

SEQ ID NO: 416            moltype = RNA   length = 27
FEATURE                   Location/Qualifiers
source                    1..27
                          mol_type = other RNA
                          organism = synthetic construct
                          note = Synthetic
SEQUENCE: 416
gcttgtcagg tccttcctgt gacagtg                                              27

SEQ ID NO: 417            moltype = RNA   length = 27
FEATURE                   Location/Qualifiers
source                    1..27
                          mol_type = other RNA
                          organism = synthetic construct
                          note = Synthetic
SEQUENCE: 417
atgactaagc ttggcaggtc cttcctg                                              27

SEQ ID NO: 418            moltype = RNA   length = 27
FEATURE                   Location/Qualifiers
source                    1..27
                          mol_type = other RNA
                          organism = synthetic construct
                          note = Synthetic
SEQUENCE: 418
gatgatcaag cttggcaggt ccttcct                                              27

SEQ ID NO: 419            moltype = RNA   length = 27
FEATURE                   Location/Qualifiers
source                    1..27
                          mol_type = other RNA
                          organism = synthetic construct
                          note = Synthetic
SEQUENCE: 419
tagattacca agcttggcag gtccttc                                              27

SEQ ID NO: 420            moltype = RNA   length = 27
FEATURE                   Location/Qualifiers
source                    1..27
                          mol_type = other RNA
                          organism = synthetic construct
                          note = Synthetic
SEQUENCE: 420
atagatgacc aagcttggca ggtcctt                                              27

SEQ ID NO: 421            moltype = RNA   length = 27
FEATURE                   Location/Qualifiers
source                    1..27
```

```
                    mol_type = other RNA
                    organism = synthetic construct
                    note = Synthetic
SEQUENCE: 421
catagttgac caagcttggc aggtcct                                      27

SEQ ID NO: 422      moltype = RNA  length = 27
FEATURE             Location/Qualifiers
source              1..27
                    mol_type = other RNA
                    organism = synthetic construct
                    note = Synthetic
SEQUENCE: 422
tcatatatga ccaagcttgg caggtcc                                      27

SEQ ID NO: 423      moltype = RNA  length = 27
FEATURE             Location/Qualifiers
source              1..27
                    mol_type = other RNA
                    organism = synthetic construct
                    note = Synthetic
SEQUENCE: 423
gtcattgatg accaagcttg gcaggtc                                      27

SEQ ID NO: 424      moltype = RNA  length = 27
FEATURE             Location/Qualifiers
source              1..27
                    mol_type = other RNA
                    organism = synthetic construct
                    note = Synthetic
SEQUENCE: 424
atgtgttgtc atagatgacc aagcttg                                      27

SEQ ID NO: 425      moltype = RNA  length = 27
FEATURE             Location/Qualifiers
source              1..27
                    mol_type = other RNA
                    organism = synthetic construct
                    note = Synthetic
SEQUENCE: 425
atgtttatgt ggtgtcatag atgacca                                      27

SEQ ID NO: 426      moltype = RNA  length = 27
FEATURE             Location/Qualifiers
source              1..27
                    mol_type = other RNA
                    organism = synthetic construct
                    note = Synthetic
SEQUENCE: 426
gccagtattt gggtagtttt ctgtggt                                      27

SEQ ID NO: 427      moltype = RNA  length = 27
FEATURE             Location/Qualifiers
source              1..27
                    mol_type = other RNA
                    organism = synthetic construct
                    note = Synthetic
SEQUENCE: 427
caagctagca tttgggtagt tttctgt                                      27

SEQ ID NO: 428      moltype = RNA  length = 27
FEATURE             Location/Qualifiers
source              1..27
                    mol_type = other RNA
                    organism = synthetic construct
                    note = Synthetic
SEQUENCE: 428
atcaatccag catttgggta gttttct                                      27

SEQ ID NO: 429      moltype = RNA  length = 27
FEATURE             Location/Qualifiers
source              1..27
                    mol_type = other RNA
                    organism = synthetic construct
                    note = Synthetic
SEQUENCE: 429
ttcattatca agccagcatt tgggtag                                      27

SEQ ID NO: 430      moltype = RNA  length = 27
```

```
FEATURE                 Location/Qualifiers
source                  1..27
                        mol_type = other RNA
                        organism = synthetic construct
                        note = Synthetic
SEQUENCE: 430
gttcatgatc aagccagcat ttgggta                                               27

SEQ ID NO: 431          moltype = RNA   length = 27
FEATURE                 Location/Qualifiers
source                  1..27
                        mol_type = other RNA
                        organism = synthetic construct
                        note = Synthetic
SEQUENCE: 431
agcatttgga ttcctgcagt agttcat                                               27

SEQ ID NO: 432          moltype = RNA   length = 27
FEATURE                 Location/Qualifiers
source                  1..27
                        mol_type = other RNA
                        organism = synthetic construct
                        note = Synthetic
SEQUENCE: 432
ccacatcatc tggattcctg cagtagt                                               27

SEQ ID NO: 433          moltype = RNA   length = 27
FEATURE                 Location/Qualifiers
source                  1..27
                        mol_type = other RNA
                        organism = synthetic construct
                        note = Synthetic
SEQUENCE: 433
gccactgcat ctggattcct gcagtag                                               27

SEQ ID NO: 434          moltype = RNA   length = 27
FEATURE                 Location/Qualifiers
source                  1..27
                        mol_type = other RNA
                        organism = synthetic construct
                        note = Synthetic
SEQUENCE: 434
ctgcctcagc atctggattc ctgcagt                                               27

SEQ ID NO: 435          moltype = RNA   length = 27
FEATURE                 Location/Qualifiers
source                  1..27
                        mol_type = other RNA
                        organism = synthetic construct
                        note = Synthetic
SEQUENCE: 435
gcgtctggtt gcagtactcc cacctga                                               27

SEQ ID NO: 436          moltype = RNA   length = 27
FEATURE                 Location/Qualifiers
source                  1..27
                        mol_type = other RNA
                        organism = synthetic construct
                        note = Synthetic
SEQUENCE: 436
gcagttcctt ctgcgtctga gcattgc                                               27

SEQ ID NO: 437          moltype = RNA   length = 27
FEATURE                 Location/Qualifiers
source                  1..27
                        mol_type = other RNA
                        organism = synthetic construct
                        note = Synthetic
SEQUENCE: 437
taggcttgga accggggtaa cagtcgg                                               27

SEQ ID NO: 438          moltype = RNA   length = 27
FEATURE                 Location/Qualifiers
source                  1..27
                        mol_type = other RNA
                        organism = synthetic construct
                        note = Synthetic
SEQUENCE: 438
ctaggtttgg aaccggggta acagtcg                                               27
```

```
SEQ ID NO: 439           moltype = RNA  length = 27
FEATURE                  Location/Qualifiers
source                   1..27
                         mol_type = other RNA
                         organism = synthetic construct
                         note = Synthetic
SEQUENCE: 439
tctagtcttg gaaccggggt aacagtc                                        27

SEQ ID NO: 440           moltype = RNA  length = 27
FEATURE                  Location/Qualifiers
source                   1..27
                         mol_type = other RNA
                         organism = synthetic construct
                         note = Synthetic
SEQUENCE: 440
ctctatgctt ggaaccgggg taacagt                                        27

SEQ ID NO: 441           moltype = RNA  length = 27
FEATURE                  Location/Qualifiers
source                   1..27
                         mol_type = other RNA
                         organism = synthetic construct
                         note = Synthetic
SEQUENCE: 441
cctcttggct tggaaccggg gtaacag                                        27

SEQ ID NO: 442           moltype = RNA  length = 27
FEATURE                  Location/Qualifiers
source                   1..27
                         mol_type = other RNA
                         organism = synthetic construct
                         note = Synthetic
SEQUENCE: 442
gcctctaggc ttggaaccgg ggtaaca                                        27

SEQ ID NO: 443           moltype = RNA  length = 27
FEATURE                  Location/Qualifiers
source                   1..27
                         mol_type = other RNA
                         organism = synthetic construct
                         note = Synthetic
SEQUENCE: 443
agcctttagg cttggaaccg gggtaac                                        27

SEQ ID NO: 444           moltype = RNA  length = 27
FEATURE                  Location/Qualifiers
source                   1..27
                         mol_type = other RNA
                         organism = synthetic construct
                         note = Synthetic
SEQUENCE: 444
actctttcca ttaccatggt agcactc                                        27

SEQ ID NO: 445           moltype = RNA  length = 27
FEATURE                  Location/Qualifiers
source                   1..27
                         mol_type = other RNA
                         organism = synthetic construct
                         note = Synthetic
SEQUENCE: 445
aactctgtcc attaccatgg tagcact                                        27

SEQ ID NO: 446           moltype = RNA  length = 27
FEATURE                  Location/Qualifiers
source                   1..27
                         mol_type = other RNA
                         organism = synthetic construct
                         note = Synthetic
SEQUENCE: 446
taactttgtc cattaccatg gtagcac                                        27

SEQ ID NO: 447           moltype = RNA  length = 27
FEATURE                  Location/Qualifiers
source                   1..27
                         mol_type = other RNA
                         organism = synthetic construct
                         note = Synthetic
```

```
SEQUENCE: 447
ataactctgt ccattaccat ggtagca                                              27

SEQ ID NO: 448          moltype = RNA  length = 27
FEATURE                 Location/Qualifiers
source                  1..27
                        mol_type = other RNA
                        organism = synthetic construct
                        note = Synthetic
SEQUENCE: 448
gataattctg tccattacca tggtagc                                              27

SEQ ID NO: 449          moltype = RNA  length = 27
FEATURE                 Location/Qualifiers
source                  1..27
                        mol_type = other RNA
                        organism = synthetic construct
                        note = Synthetic
SEQUENCE: 449
cgatatctct gtccattacc atggtag                                              27

SEQ ID NO: 450          moltype = RNA  length = 27
FEATURE                 Location/Qualifiers
source                  1..27
                        mol_type = other RNA
                        organism = synthetic construct
                        note = Synthetic
SEQUENCE: 450
tcgattactc tgtccattac catggta                                              27

SEQ ID NO: 451          moltype = RNA  length = 27
FEATURE                 Location/Qualifiers
source                  1..27
                        mol_type = other RNA
                        organism = synthetic construct
                        note = Synthetic
SEQUENCE: 451
ctcgataact ctgtccatta ccatggt                                              27

SEQ ID NO: 452          moltype = RNA  length = 27
FEATURE                 Location/Qualifiers
source                  1..27
                        mol_type = other RNA
                        organism = synthetic construct
                        note = Synthetic
SEQUENCE: 452
cctcgttaac tctgtccatt accatgg                                              27

SEQ ID NO: 453          moltype = RNA  length = 27
FEATURE                 Location/Qualifiers
source                  1..27
                        mol_type = other RNA
                        organism = synthetic construct
                        note = Synthetic
SEQUENCE: 453
gcctctataa ctctgtccat taccatg                                              27

SEQ ID NO: 454          moltype = RNA  length = 27
FEATURE                 Location/Qualifiers
source                  1..27
                        mol_type = other RNA
                        organism = synthetic construct
                        note = Synthetic
SEQUENCE: 454
tgccttgata actctgtcca ttaccat                                              27

SEQ ID NO: 455          moltype = RNA  length = 27
FEATURE                 Location/Qualifiers
source                  1..27
                        mol_type = other RNA
                        organism = synthetic construct
                        note = Synthetic
SEQUENCE: 455
gtgcctcgat aactctgtcc attacca                                              27

SEQ ID NO: 456          moltype = RNA  length = 27
FEATURE                 Location/Qualifiers
source                  1..27
                        mol_type = other RNA
```

```
                        organism = synthetic construct
                        note = Synthetic
SEQUENCE: 456
ctgtgtcagt ggtggagtat gtgcctc                                               27

SEQ ID NO: 457          moltype = RNA   length = 27
FEATURE                 Location/Qualifiers
source                  1..27
                        mol_type = other RNA
                        organism = synthetic construct
                        note = Synthetic
SEQUENCE: 457
gagtgtggtg tcatagatga ccaagct                                               27

SEQ ID NO: 458          moltype = RNA   length = 27
FEATURE                 Location/Qualifiers
source                  1..27
                        mol_type = other RNA
                        organism = synthetic construct
                        note = Synthetic
SEQUENCE: 458
atgcgtgtgt ggtgtcatag atgacca                                               27

SEQ ID NO: 459          moltype = RNA   length = 27
FEATURE                 Location/Qualifiers
source                  1..27
                        mol_type = other RNA
                        organism = synthetic construct
                        note = Synthetic
SEQUENCE: 459
tatgctagtg tggtgtcata gatgacc                                               27

SEQ ID NO: 460          moltype = RNA   length = 27
FEATURE                 Location/Qualifiers
source                  1..27
                        mol_type = other RNA
                        organism = synthetic construct
                        note = Synthetic
SEQUENCE: 460
ctatgtgagt gtggtgtcat agatgac                                               27

SEQ ID NO: 461          moltype = RNA   length = 27
FEATURE                 Location/Qualifiers
source                  1..27
                        mol_type = other RNA
                        organism = synthetic construct
                        note = Synthetic
SEQUENCE: 461
ccagttacag tggtggagta tgtgcct                                               27

SEQ ID NO: 462          moltype = RNA   length = 27
FEATURE                 Location/Qualifiers
source                  1..27
                        mol_type = other RNA
                        organism = synthetic construct
                        note = Synthetic
SEQUENCE: 462
atccctcgta taacaataag gggctgc                                               27

SEQ ID NO: 463          moltype = RNA   length = 27
FEATURE                 Location/Qualifiers
source                  1..27
                        mol_type = other RNA
                        organism = synthetic construct
                        note = Synthetic
SEQUENCE: 463
gatccttcgt ataacaataa ggggctg                                               27

SEQ ID NO: 464          moltype = RNA   length = 27
FEATURE                 Location/Qualifiers
source                  1..27
                        mol_type = other RNA
                        organism = synthetic construct
                        note = Synthetic
SEQUENCE: 464
gttcataagg agcctctagg cttggaa                                               27

SEQ ID NO: 465          moltype = RNA   length = 27
FEATURE                 Location/Qualifiers
```

```
source                  1..27
                        mol_type = other RNA
                        organism = synthetic construct
                        note = Synthetic
SEQUENCE: 465
gttggtgctt gttcagaagg agcctct                                              27

SEQ ID NO: 466          moltype = RNA  length = 27
FEATURE                 Location/Qualifiers
source                  1..27
                        mol_type = other RNA
                        organism = synthetic construct
                        note = Synthetic
SEQUENCE: 466
tatgttcctt gataactctg tccattt                                              27

SEQ ID NO: 467          moltype = RNA  length = 27
FEATURE                 Location/Qualifiers
source                  1..27
                        mol_type = other RNA
                        organism = synthetic construct
                        note = Synthetic
SEQUENCE: 467
gtatgtgcct tgataactct gtccatt                                              27

SEQ ID NO: 468          moltype = RNA  length = 27
FEATURE                 Location/Qualifiers
source                  1..27
                        mol_type = other RNA
                        organism = synthetic construct
                        note = Synthetic
SEQUENCE: 468
agtatttgcc ttgataactc tgtccat                                              27

SEQ ID NO: 469          moltype = RNA  length = 27
FEATURE                 Location/Qualifiers
source                  1..27
                        mol_type = other RNA
                        organism = synthetic construct
                        note = Synthetic
SEQUENCE: 469
aagtatgtgc cttgataact ctgtcca                                              27

SEQ ID NO: 470          moltype = RNA  length = 27
FEATURE                 Location/Qualifiers
source                  1..27
                        mol_type = other RNA
                        organism = synthetic construct
                        note = Synthetic
SEQUENCE: 470
gaagtttgtg ccttgataac tctgtcc                                              27

SEQ ID NO: 471          moltype = RNA  length = 27
FEATURE                 Location/Qualifiers
source                  1..27
                        mol_type = other RNA
                        organism = synthetic construct
                        note = Synthetic
SEQUENCE: 471
tgaagtatgt gccttgataa ctctgtc                                              27

SEQ ID NO: 472          moltype = RNA  length = 27
FEATURE                 Location/Qualifiers
source                  1..27
                        mol_type = other RNA
                        organism = synthetic construct
                        note = Synthetic
SEQUENCE: 472
tcttgttcaa gccagcattt gggtagt                                              27

SEQ ID NO: 473          moltype = RNA  length = 27
FEATURE                 Location/Qualifiers
source                  1..27
                        mol_type = other RNA
                        organism = synthetic construct
                        note = Synthetic
SEQUENCE: 473
agttcttgat caagccagca tttgggt                                              27
```

```
SEQ ID NO: 474          moltype = RNA  length = 27
FEATURE                 Location/Qualifiers
source                  1..27
                        mol_type = other RNA
                        organism = synthetic construct
                        note = Synthetic
SEQUENCE: 474
tctggttttc ggcagtagtt cttgatc                                            27

SEQ ID NO: 475          moltype = RNA  length = 27
FEATURE                 Location/Qualifiers
source                  1..27
                        mol_type = other RNA
                        organism = synthetic construct
                        note = Synthetic
SEQUENCE: 475
atctgtattt cggcagtagt tcttgat                                            27

SEQ ID NO: 476          moltype = RNA  length = 27
FEATURE                 Location/Qualifiers
source                  1..27
                        mol_type = other RNA
                        organism = synthetic construct
                        note = Synthetic
SEQUENCE: 476
gatcttgatt tcggcagtag ttcttga                                            27

SEQ ID NO: 477          moltype = RNA  length = 27
FEATURE                 Location/Qualifiers
source                  1..27
                        mol_type = other RNA
                        organism = synthetic construct
                        note = Synthetic
SEQUENCE: 477
aggatttgga tttcggcagt agttctt                                            27

SEQ ID NO: 478          moltype = RNA  length = 27
FEATURE                 Location/Qualifiers
source                  1..27
                        mol_type = other RNA
                        organism = synthetic construct
                        note = Synthetic
SEQUENCE: 478
cacagtatct ggatttcggc agtagtt                                            27

SEQ ID NO: 479          moltype = RNA  length = 27
FEATURE                 Location/Qualifiers
source                  1..27
                        mol_type = other RNA
                        organism = synthetic construct
                        note = Synthetic
SEQUENCE: 479
tgtattacac caaggggctg ccacagg                                            27

SEQ ID NO: 480          moltype = RNA  length = 27
FEATURE                 Location/Qualifiers
source                  1..27
                        mol_type = other RNA
                        organism = synthetic construct
                        note = Synthetic
SEQUENCE: 480
ttgtataaca ccaaggggct gccacag                                            27

SEQ ID NO: 481          moltype = RNA  length = 27
FEATURE                 Location/Qualifiers
source                  1..27
                        mol_type = other RNA
                        organism = synthetic construct
                        note = Synthetic
SEQUENCE: 481
gttgtttaac accaagggc tgccaca                                             27

SEQ ID NO: 482          moltype = RNA  length = 27
FEATURE                 Location/Qualifiers
source                  1..27
                        mol_type = other RNA
                        organism = synthetic construct
                        note = Synthetic
SEQUENCE: 482
```
tgttgtataa caccaagggg ctgccac                                        27

SEQ ID NO: 483          moltype = RNA   length = 27
FEATURE                 Location/Qualifiers
source                  1..27
                        mol_type = other RNA
                        organism = synthetic construct
                        note = Synthetic
SEQUENCE: 483
ctgttttata acaccaaggg gctgcca                                        27

SEQ ID NO: 484          moltype = RNA   length = 27
FEATURE                 Location/Qualifiers
source                  1..27
                        mol_type = other RNA
                        organism = synthetic construct
                        note = Synthetic
SEQUENCE: 484
tctgttgtat aacaccaagg ggctgcc                                        27

SEQ ID NO: 485          moltype = RNA   length = 27
FEATURE                 Location/Qualifiers
source                  1..27
                        mol_type = other RNA
                        organism = synthetic construct
                        note = Synthetic
SEQUENCE: 485
atctgttgta taacaccaag gggctgc                                        27

SEQ ID NO: 486          moltype = RNA   length = 27
FEATURE                 Location/Qualifiers
source                  1..27
                        mol_type = other RNA
                        organism = synthetic construct
                        note = Synthetic
SEQUENCE: 486
gatcttttgt ataacaccaa ggggctg                                        27

SEQ ID NO: 487          moltype = RNA   length = 27
FEATURE                 Location/Qualifiers
source                  1..27
                        mol_type = other RNA
                        organism = synthetic construct
                        note = Synthetic
SEQUENCE: 487
ggatctgttg tataacacca aggggct                                        27

SEQ ID NO: 488          moltype = RNA   length = 27
FEATURE                 Location/Qualifiers
source                  1..27
                        mol_type = other RNA
                        organism = synthetic construct
                        note = Synthetic
SEQUENCE: 488
cgtgttaggt tgcagtactc ccacctg                                        27

SEQ ID NO: 489          moltype = RNA   length = 27
FEATURE                 Location/Qualifiers
source                  1..27
                        mol_type = other RNA
                        organism = synthetic construct
                        note = Synthetic
SEQUENCE: 489
tcgtgtcagg ttgcagtact cccacct                                        27

SEQ ID NO: 490          moltype = RNA   length = 27
FEATURE                 Location/Qualifiers
source                  1..27
                        mol_type = other RNA
                        organism = synthetic construct
                        note = Synthetic
SEQUENCE: 490
gcatcttgtc aggttgcagt actccca                                        27

SEQ ID NO: 491          moltype = RNA   length = 27
FEATURE                 Location/Qualifiers
source                  1..27
                        mol_type = other RNA
                        organism = synthetic construct

```
                                  note = Synthetic
SEQUENCE: 491
agcattgtgt caggttgcag tactccc                                            27

SEQ ID NO: 492          moltype = RNA  length = 27
FEATURE                 Location/Qualifiers
source                  1..27
                        mol_type = other RNA
                        organism = synthetic construct
                        note = Synthetic
SEQUENCE: 492
tgagcttcgt gtcaggttgc agtactc                                            27

SEQ ID NO: 493          moltype = RNA  length = 27
FEATURE                 Location/Qualifiers
source                  1..27
                        mol_type = other RNA
                        organism = synthetic construct
                        note = Synthetic
SEQUENCE: 493
ctgagtatcg tgtcaggttg cagtact                                            27

SEQ ID NO: 494          moltype = RNA  length = 27
FEATURE                 Location/Qualifiers
source                  1..27
                        mol_type = other RNA
                        organism = synthetic construct
                        note = Synthetic
SEQUENCE: 494
tctgatcatc gtgtcaggtt gcagtac                                            27

SEQ ID NO: 495          moltype = RNA  length = 27
FEATURE                 Location/Qualifiers
source                  1..27
                        mol_type = other RNA
                        organism = synthetic construct
                        note = Synthetic
SEQUENCE: 495
atctgtgcat cgtgtcaggt tgcagta                                            27

SEQ ID NO: 496          moltype = RNA  length = 27
FEATURE                 Location/Qualifiers
source                  1..27
                        mol_type = other RNA
                        organism = synthetic construct
                        note = Synthetic
SEQUENCE: 496
catcttagca tcgtgtcagg ttgcagt                                            27

SEQ ID NO: 497          moltype = RNA  length = 27
FEATURE                 Location/Qualifiers
source                  1..27
                        mol_type = other RNA
                        organism = synthetic construct
                        note = Synthetic
SEQUENCE: 497
tgcatttgag catcgtgtca ggttgca                                            27

SEQ ID NO: 498          moltype = RNA  length = 27
FEATURE                 Location/Qualifiers
source                  1..27
                        mol_type = other RNA
                        organism = synthetic construct
                        note = Synthetic
SEQUENCE: 498
tctgcttctg agcatcgtgt caggttg                                            27

SEQ ID NO: 499          moltype = RNA  length = 27
FEATURE                 Location/Qualifiers
source                  1..27
                        mol_type = other RNA
                        organism = synthetic construct
                        note = Synthetic
SEQUENCE: 499
ttctgtatct gagcatcgtg tcaggtt                                            27

SEQ ID NO: 500          moltype = RNA  length = 27
FEATURE                 Location/Qualifiers
source                  1..27
```

```
                        mol_type = other RNA
                        organism = synthetic construct
                        note = Synthetic
SEQUENCE: 500
attcttcatc tgagcatcgt gtcaggt                                           27

SEQ ID NO: 501          moltype = RNA   length = 27
FEATURE                 Location/Qualifiers
source                  1..27
                        mol_type = other RNA
                        organism = synthetic construct
                        note = Synthetic
SEQUENCE: 501
cattctgcat ctgagcatcg tgtcagg                                           27

SEQ ID NO: 502          moltype = RNA   length = 27
FEATURE                 Location/Qualifiers
source                  1..27
                        mol_type = other RNA
                        organism = synthetic construct
                        note = Synthetic
SEQUENCE: 502
ccattttgca tctgagcatc gtgtcag                                           27

SEQ ID NO: 503          moltype = RNA   length = 27
FEATURE                 Location/Qualifiers
source                  1..27
                        mol_type = other RNA
                        organism = synthetic construct
                        note = Synthetic
SEQUENCE: 503
tccattctgc atctgagcat cgtgtca                                           27

SEQ ID NO: 504          moltype = RNA   length = 27
FEATURE                 Location/Qualifiers
source                  1..27
                        mol_type = other RNA
                        organism = synthetic construct
                        note = Synthetic
SEQUENCE: 504
gtccattctg catctgagca tcgtgtc                                           27

SEQ ID NO: 505          moltype = RNA   length = 27
FEATURE                 Location/Qualifiers
source                  1..27
                        mol_type = other RNA
                        organism = synthetic construct
                        note = Synthetic
SEQUENCE: 505
aactctgtcc ataatggtag tagcagt                                           27

SEQ ID NO: 506          moltype = RNA   length = 27
FEATURE                 Location/Qualifiers
source                  1..27
                        mol_type = other RNA
                        organism = synthetic construct
                        note = Synthetic
SEQUENCE: 506
taactttgtc cataatggta gtagcag                                           27

SEQ ID NO: 507          moltype = RNA   length = 27
FEATURE                 Location/Qualifiers
source                  1..27
                        mol_type = other RNA
                        organism = synthetic construct
                        note = Synthetic
SEQUENCE: 507
gtaactctgt ccataatggt agtagca                                           27

SEQ ID NO: 508          moltype = RNA   length = 27
FEATURE                 Location/Qualifiers
source                  1..27
                        mol_type = other RNA
                        organism = synthetic construct
                        note = Synthetic
SEQUENCE: 508
ggtaattctg tccataatgg tagtagc                                           27

SEQ ID NO: 509          moltype = RNA   length = 27
```

```
FEATURE                 Location/Qualifiers
source                  1..27
                        mol_type = other RNA
                        organism = synthetic construct
                        note = Synthetic
SEQUENCE: 509
cggtatctct gtccataatg gtagtag                                              27

SEQ ID NO: 510          moltype = RNA   length = 27
FEATURE                 Location/Qualifiers
source                  1..27
                        mol_type = other RNA
                        organism = synthetic construct
                        note = Synthetic
SEQUENCE: 510
tcggttactc tgtccataat ggtagta                                              27

SEQ ID NO: 511          moltype = RNA   length = 27
FEATURE                 Location/Qualifiers
source                  1..27
                        mol_type = other RNA
                        organism = synthetic construct
                        note = Synthetic
SEQUENCE: 511
ctcggtaact ctgtccataa tggtagt                                              27

SEQ ID NO: 512          moltype = RNA   length = 27
FEATURE                 Location/Qualifiers
source                  1..27
                        mol_type = other RNA
                        organism = synthetic construct
                        note = Synthetic
SEQUENCE: 512
cctcgttaac tctgtccata atggtag                                              27

SEQ ID NO: 513          moltype = RNA   length = 27
FEATURE                 Location/Qualifiers
source                  1..27
                        mol_type = other RNA
                        organism = synthetic construct
                        note = Synthetic
SEQUENCE: 513
gtgactgtgg tggagtatgt gcctcgg                                              27

SEQ ID NO: 514          moltype = RNA   length = 27
FEATURE                 Location/Qualifiers
source                  1..27
                        mol_type = other RNA
                        organism = synthetic construct
                        note = Synthetic
SEQUENCE: 514
agttcttcct gtgacagtgg tggagta                                              27

SEQ ID NO: 515          moltype = RNA   length = 27
FEATURE                 Location/Qualifiers
source                  1..27
                        mol_type = other RNA
                        organism = synthetic construct
                        note = Synthetic
SEQUENCE: 515
accaatcttg gcaagttctt cctgtga                                              27

SEQ ID NO: 516          moltype = RNA   length = 27
FEATURE                 Location/Qualifiers
source                  1..27
                        mol_type = other RNA
                        organism = synthetic construct
                        note = Synthetic
SEQUENCE: 516
gaccatgctt ggcaagttct tcctgtg                                              27

SEQ ID NO: 517          moltype = RNA   length = 27
FEATURE                 Location/Qualifiers
source                  1..27
                        mol_type = other RNA
                        organism = synthetic construct
                        note = Synthetic
SEQUENCE: 517
tgacctagct tggcaagttc ttcctgt                                              27
```

-continued

```
SEQ ID NO: 518          moltype = RNA  length = 27
FEATURE                 Location/Qualifiers
source                  1..27
                        mol_type = other RNA
                        organism = synthetic construct
                        note = Synthetic
SEQUENCE: 518
atgactaagc ttggcaagtt cttcctg                                             27

SEQ ID NO: 519          moltype = RNA  length = 27
FEATURE                 Location/Qualifiers
source                  1..27
                        mol_type = other RNA
                        organism = synthetic construct
                        note = Synthetic
SEQUENCE: 519
gatgatcaag cttggcaagt tcttcct                                             27

SEQ ID NO: 520          moltype = RNA  length = 27
FEATURE                 Location/Qualifiers
source                  1..27
                        mol_type = other RNA
                        organism = synthetic construct
                        note = Synthetic
SEQUENCE: 520
agatgtccaa gcttggcaag ttcttcc                                             27

SEQ ID NO: 521          moltype = RNA  length = 27
FEATURE                 Location/Qualifiers
source                  1..27
                        mol_type = other RNA
                        organism = synthetic construct
                        note = Synthetic
SEQUENCE: 521
tagattacca agcttggcaa gttcttc                                             27

SEQ ID NO: 522          moltype = RNA  length = 27
FEATURE                 Location/Qualifiers
source                  1..27
                        mol_type = other RNA
                        organism = synthetic construct
                        note = Synthetic
SEQUENCE: 522
atagatgacc aagcttggca agttctt                                             27

SEQ ID NO: 523          moltype = RNA  length = 27
FEATURE                 Location/Qualifiers
source                  1..27
                        mol_type = other RNA
                        organism = synthetic construct
                        note = Synthetic
SEQUENCE: 523
catagttgac caagcttggc aagttct                                             27

SEQ ID NO: 524          moltype = RNA  length = 27
FEATURE                 Location/Qualifiers
source                  1..27
                        mol_type = other RNA
                        organism = synthetic construct
                        note = Synthetic
SEQUENCE: 524
tcatatatga ccaagcttgg caagttc                                             27

SEQ ID NO: 525          moltype = RNA  length = 27
FEATURE                 Location/Qualifiers
source                  1..27
                        mol_type = other RNA
                        organism = synthetic construct
                        note = Synthetic
SEQUENCE: 525
gtcattgatg accaagcttg gcaagtt                                             27

SEQ ID NO: 526          moltype = RNA  length = 27
FEATURE                 Location/Qualifiers
source                  1..27
                        mol_type = other RNA
                        organism = synthetic construct
                        note = Synthetic
```

-continued

| | | |
|---|---|---|
| SEQUENCE: 526 tgtcatagat gaccaagctt ggcaagt | | 27 |
| SEQ ID NO: 527 FEATURE source | moltype = RNA length = 27 Location/Qualifiers 1..27 mol_type = other RNA organism = synthetic construct note = Synthetic | |
| SEQUENCE: 527 gtgtcttaga tgaccaagct tggcaag | | 27 |
| SEQ ID NO: 528 FEATURE source | moltype = RNA length = 27 Location/Qualifiers 1..27 mol_type = other RNA organism = synthetic construct note = Synthetic | |
| SEQUENCE: 528 ggtgttgtgt catagatgac caagctt | | 27 |
| SEQ ID NO: 529 FEATURE source | moltype = RNA length = 27 Location/Qualifiers 1..27 mol_type = other RNA organism = synthetic construct note = Synthetic | |
| SEQUENCE: 529 ctggtttggt gtcatagatg accaagc | | 27 |
| SEQ ID NO: 530 FEATURE source | moltype = RNA length = 27 Location/Qualifiers 1..27 mol_type = other RNA organism = synthetic construct note = Synthetic | |
| SEQUENCE: 530 gctggtgtgg tgtcatagat gaccaag | | 27 |
| SEQ ID NO: 531 FEATURE source | moltype = RNA length = 27 Location/Qualifiers 1..27 mol_type = other RNA organism = synthetic construct note = Synthetic | |
| SEQUENCE: 531 atgcttgtgt ggtgtcatag atgacca | | 27 |
| SEQ ID NO: 532 FEATURE source | moltype = RNA length = 27 Location/Qualifiers 1..27 mol_type = other RNA organism = synthetic construct note = Synthetic | |
| SEQUENCE: 532 ctatgttggt gtggtgtcat agatgac | | 27 |
| SEQ ID NO: 533 FEATURE source | moltype = RNA length = 27 Location/Qualifiers 1..27 mol_type = other RNA organism = synthetic construct note = Synthetic | |
| SEQUENCE: 533 actattctgg tgtggtgtca tagatga | | 27 |
| SEQ ID NO: 534 FEATURE source | moltype = RNA length = 27 Location/Qualifiers 1..27 mol_type = other RNA organism = synthetic construct note = Synthetic | |
| SEQUENCE: 534 cgactttgct ggtgtggtgt catagat | | 27 |
| SEQ ID NO: 535 FEATURE source | moltype = RNA length = 27 Location/Qualifiers 1..27 mol_type = other RNA | |

-continued

```
                        organism = synthetic construct
                        note = Synthetic
SEQUENCE: 535
tttggttagt tttctggggt ccgacta                                   27

SEQ ID NO: 536          moltype = RNA  length = 27
FEATURE                 Location/Qualifiers
source                  1..27
                        mol_type = other RNA
                        organism = synthetic construct
                        note = Synthetic
SEQUENCE: 536
atttgtgtag ttttctgggg tccgact                                   27

SEQ ID NO: 537          moltype = RNA  length = 27
FEATURE                 Location/Qualifiers
source                  1..27
                        mol_type = other RNA
                        organism = synthetic construct
                        note = Synthetic
SEQUENCE: 537
tcaggtcagc atttgggtag ttttctg                                   27

SEQ ID NO: 538          moltype = RNA  length = 27
FEATURE                 Location/Qualifiers
source                  1..27
                        mol_type = other RNA
                        organism = synthetic construct
                        note = Synthetic
SEQUENCE: 538
tgtaatacca agggcgaatc tcagcat                                   27

SEQ ID NO: 539          moltype = RNA  length = 27
FEATURE                 Location/Qualifiers
source                  1..27
                        mol_type = other RNA
                        organism = synthetic construct
                        note = Synthetic
SEQUENCE: 539
gtgtatcacc aagggcgaat ctcagca                                   27

SEQ ID NO: 540          moltype = RNA  length = 27
FEATURE                 Location/Qualifiers
source                  1..27
                        mol_type = other RNA
                        organism = synthetic construct
                        note = Synthetic
SEQUENCE: 540
tggtgtaaca ccaagggcga atctcag                                   27

SEQ ID NO: 541          moltype = RNA  length = 27
FEATURE                 Location/Qualifiers
source                  1..27
                        mol_type = other RNA
                        organism = synthetic construct
                        note = Synthetic
SEQUENCE: 541
atggtttaac accaagggcg aatctca                                   27

SEQ ID NO: 542          moltype = RNA  length = 27
FEATURE                 Location/Qualifiers
source                  1..27
                        mol_type = other RNA
                        organism = synthetic construct
                        note = Synthetic
SEQUENCE: 542
tccattgtgt aacaccaagg gcgaatc                                   27

SEQ ID NO: 543          moltype = RNA  length = 27
FEATURE                 Location/Qualifiers
source                  1..27
                        mol_type = other RNA
                        organism = synthetic construct
                        note = Synthetic
SEQUENCE: 543
ctgggttcca tggtgtaaca ccaaggg                                   27

SEQ ID NO: 544          moltype = RNA  length = 27
FEATURE                 Location/Qualifiers
```

|                      |                                                                                                                                              |    |
|----------------------|----------------------------------------------------------------------------------------------------------------------------------------------|----|
| source               | 1..27<br>mol_type = other RNA<br>organism = synthetic construct<br>note = Synthetic                                                          |    |
| SEQUENCE: 544<br>actggtatcc atggtgtaac accaagg                                                                                                                     |                                                                                                                                              | 27 |
| SEQ ID NO: 545<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 545<br>cactgtgatc catggtgtaa caccaag                                                                                                                     |                                                                                                                                              | 27 |
| SEQ ID NO: 546<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 546<br>acacttggat ccatggtgta acaccaa                                                                                                                     |                                                                                                                                              | 27 |
| SEQ ID NO: 547<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 547<br>tgacattggg atccatggtg taacacc                                                                                                                     |                                                                                                                                              | 27 |
| SEQ ID NO: 548<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 548<br>tgagatttgc aaggacactt gattctg                                                                                                                     |                                                                                                                                              | 27 |
| SEQ ID NO: 549<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 549<br>gtgagtgttg caaggacact tgattct                                                                                                                     |                                                                                                                                              | 27 |
| SEQ ID NO: 550<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 550<br>cgtgatagtt gcaaggacac ttgattc                                                                                                                     |                                                                                                                                              | 27 |
| SEQ ID NO: 551<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 551<br>aatgatcctc gataactctg tccatca                                                                                                                     |                                                                                                                                              | 27 |
| SEQ ID NO: 552<br>FEATURE<br>source | moltype = RNA   length = 27<br>Location/Qualifiers<br>1..27<br>mol_type = other RNA<br>organism = synthetic construct<br>note = Synthetic |    |
| SEQUENCE: 552<br>gaatgtgcct cgataactct gtccatc                                                                                                                     |                                                                                                                                              | 27 |

| | | |
|---|---|---|
| SEQ ID NO: 553 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 553 | | |
| ttgtcttctg atgccagtgt ggtgtca | | 27 |
| | | |
| SEQ ID NO: 554 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 554 | | |
| attggtatcc atggtataac accaagg | | 27 |
| | | |
| SEQ ID NO: 555 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 555 | | |
| cattgtgatc catggtataa caccaag | | 27 |
| | | |
| SEQ ID NO: 556 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 556 | | |
| acatttggat ccatggtata acaccaa | | 27 |
| | | |
| SEQ ID NO: 557 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 557 | | |
| gacattggga tccatggtat aacacca | | 27 |
| | | |
| SEQ ID NO: 558 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 558 | | |
| gtcagtttgc agtactccca tctgaca | | 27 |
| | | |
| SEQ ID NO: 559 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 559 | | |
| tgtgttaggt tgcagtactc ccatctg | | 27 |
| | | |
| SEQ ID NO: 560 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 560 | | |
| ttgtgtcagg ttgcagtact cccatct | | 27 |
| | | |
| SEQ ID NO: 561 | moltype = RNA   length = 27 | |
| FEATURE | Location/Qualifiers | |
| source | 1..27 | |
| | mol_type = other RNA | |
| | organism = synthetic construct | |
| | note = Synthetic | |
| SEQUENCE: 561 | | |

```
attgtttcag gttgcagtac tcccatc                                               27

SEQ ID NO: 562         moltype = RNA   length = 27
FEATURE                Location/Qualifiers
source                 1..27
                       mol_type = other RNA
                       organism = synthetic construct
                       note = Synthetic
SEQUENCE: 562
cattgtgtca ggttgcagta ctcccat                                               27

SEQ ID NO: 563         moltype = RNA   length = 27
FEATURE                Location/Qualifiers
source                 1..27
                       mol_type = other RNA
                       organism = synthetic construct
                       note = Synthetic
SEQUENCE: 563
cgttgttgct tgttcagaaa cagccgt                                               27

SEQ ID NO: 564         moltype = RNA   length = 27
FEATURE                Location/Qualifiers
source                 1..27
                       mol_type = other RNA
                       organism = synthetic construct
                       note = Synthetic
SEQUENCE: 564
gctcctttgg tgcttgttca gaaacag                                               27

SEQ ID NO: 565         moltype = RNA   length = 27
FEATURE                Location/Qualifiers
source                 1..27
                       mol_type = other RNA
                       organism = synthetic construct
                       note = Synthetic
SEQUENCE: 565
tgtccttcct gtaacagtgg tggagaa                                               27

SEQ ID NO: 566         moltype = RNA   length = 27
FEATURE                Location/Qualifiers
source                 1..27
                       mol_type = other RNA
                       organism = synthetic construct
                       note = Synthetic
SEQUENCE: 566
atgtctttcc tgtaacagtg gtggaga                                               27

SEQ ID NO: 567         moltype = RNA   length = 27
FEATURE                Location/Qualifiers
source                 1..27
                       mol_type = other RNA
                       organism = synthetic construct
                       note = Synthetic
SEQUENCE: 567
catgttcttc ctgtaacagt ggtggag                                               27

SEQ ID NO: 568         moltype = RNA   length = 27
FEATURE                Location/Qualifiers
source                 1..27
                       mol_type = other RNA
                       organism = synthetic construct
                       note = Synthetic
SEQUENCE: 568
ggttctctga tgccagtgtg gtgtcat                                               27

SEQ ID NO: 569         moltype = RNA   length = 27
FEATURE                Location/Qualifiers
source                 1..27
                       mol_type = other RNA
                       organism = synthetic construct
                       note = Synthetic
SEQUENCE: 569
tggttttctg atgccagtgt ggtgtca                                               27

SEQ ID NO: 570         moltype = RNA   length = 27
FEATURE                Location/Qualifiers
source                 1..27
                       mol_type = other RNA
                       organism = synthetic construct
```

```
                              note = Synthetic
SEQUENCE: 570
caggctacca tttgggtagt attctgt                                              27

SEQ ID NO: 571           moltype = RNA   length = 27
FEATURE                  Location/Qualifiers
source                   1..27
                         mol_type = other RNA
                         organism = synthetic construct
                         note = Synthetic
SEQUENCE: 571
tcaggtcacc atttgggtag tattctg                                              27

SEQ ID NO: 572           moltype = RNA   length = 27
FEATURE                  Location/Qualifiers
source                   1..27
                         mol_type = other RNA
                         organism = synthetic construct
                         note = Synthetic
SEQUENCE: 572
gtcagtccac catttgggta gtattct                                              27

SEQ ID NO: 573           moltype = RNA   length = 27
FEATURE                  Location/Qualifiers
source                   1..27
                         mol_type = other RNA
                         organism = synthetic construct
                         note = Synthetic
SEQUENCE: 573
ttcagttggt gcttcttcag aaggaag                                              27

SEQ ID NO: 574           moltype = RNA   length = 27
FEATURE                  Location/Qualifiers
source                   1..27
                         mol_type = other RNA
                         organism = synthetic construct
                         note = Synthetic
SEQUENCE: 574
tttcatttgg tgcttcttca gaaggaa                                              27

SEQ ID NO: 575           moltype = RNA   length = 27
FEATURE                  Location/Qualifiers
source                   1..27
                         mol_type = other RNA
                         organism = synthetic construct
                         note = Synthetic
SEQUENCE: 575
ttttctgttg gtgcttcttc agaagga                                              27

SEQ ID NO: 576           moltype = RNA   length = 27
FEATURE                  Location/Qualifiers
source                   1..27
                         mol_type = other RNA
                         organism = synthetic construct
                         note = Synthetic
SEQUENCE: 576
gtttttagtt ggtgcttctt cagaagg                                              27

SEQ ID NO: 577           moltype = RNA   length = 27
FEATURE                  Location/Qualifiers
source                   1..27
                         mol_type = other RNA
                         organism = synthetic construct
                         note = Synthetic
SEQUENCE: 577
tgttttcagt tggtgcttct tcagaag                                              27

SEQ ID NO: 578           moltype = RNA   length = 27
FEATURE                  Location/Qualifiers
source                   1..27
                         mol_type = other RNA
                         organism = synthetic construct
                         note = Synthetic
SEQUENCE: 578
ctgttttcag ttggtgcttc ttcagaa                                              27

SEQ ID NO: 579           moltype = RNA   length = 27
FEATURE                  Location/Qualifiers
source                   1..27
```

-continued

```
                        mol_type = other RNA
                        organism = synthetic construct
                        note = Synthetic
SEQUENCE: 579
gctgttttca gttggtgctt cttcaga                                   27

SEQ ID NO: 580          moltype = RNA   length = 27
FEATURE                 Location/Qualifiers
source                  1..27
                        mol_type = other RNA
                        organism = synthetic construct
                        note = Synthetic
SEQUENCE: 580
tgctgttttc agttggtgct tcttcag                                   27

SEQ ID NO: 581          moltype = RNA   length = 27
FEATURE                 Location/Qualifiers
source                  1..27
                        mol_type = other RNA
                        organism = synthetic construct
                        note = Synthetic
SEQUENCE: 581
gtgctttttt cagttggtgc ttcttca                                   27

SEQ ID NO: 582          moltype = RNA   length = 27
FEATURE                 Location/Qualifiers
source                  1..27
                        mol_type = other RNA
                        organism = synthetic construct
                        note = Synthetic
SEQUENCE: 582
agtgctgttt tcagttggtg cttcttc                                   27

SEQ ID NO: 583          moltype = RNA   length = 27
FEATURE                 Location/Qualifiers
source                  1..27
                        mol_type = other RNA
                        organism = synthetic construct
                        note = Synthetic
SEQUENCE: 583
cagtgttgtt ttcagttggt gcttctt                                   27

SEQ ID NO: 584          moltype = RNA   length = 27
FEATURE                 Location/Qualifiers
source                  1..27
                        mol_type = other RNA
                        organism = synthetic construct
                        note = Synthetic
SEQUENCE: 584
ccagttctgt tttcagttgg tgcttct                                   27

SEQ ID NO: 585          moltype = RNA   length = 27
FEATURE                 Location/Qualifiers
source                  1..27
                        mol_type = other RNA
                        organism = synthetic construct
                        note = Synthetic
SEQUENCE: 585
gcctctataa ctctgtccat cacctcg                                   27

SEQ ID NO: 586          moltype = RNA   length = 27
FEATURE                 Location/Qualifiers
source                  1..27
                        mol_type = other RNA
                        organism = synthetic construct
                        note = Synthetic
SEQUENCE: 586
tgttcttcct gtgatagtgg tggagag                                   27

SEQ ID NO: 587          moltype = RNA   length = 27
FEATURE                 Location/Qualifiers
source                  1..27
                        mol_type = other RNA
                        organism = synthetic construct
                        note = Synthetic
SEQUENCE: 587
atgttttttcc tgtgatagtg gtggaga                                  27

SEQ ID NO: 588          moltype = RNA   length = 27
```

| | | |
|---|---|---|
| FEATURE | Location/Qualifiers | |
| source | 1..27<br>mol_type = other RNA<br>organism = synthetic construct<br>note = Synthetic | |
| SEQUENCE: 588 | | |
| catgttcttc ctgtgatagt ggtggag | | 27 |
| SEQ ID NO: 589 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 589 | | |
| acatgttctt cctgtgatag tggtgga | | 27 |
| SEQ ID NO: 590 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 590 | | |
| gacattttct tcctgtgata gtggtgg | | 27 |
| SEQ ID NO: 591 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 591 | | |
| tgacatgttc ttcctgtgat agtggtg | | 27 |
| SEQ ID NO: 592 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 592 | | |
| ctgacttgtt cttcctgtga tagtggt | | 27 |
| SEQ ID NO: 593 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 593 | | |
| actgatatgt tcttcctgtg atagtgg | | 27 |
| SEQ ID NO: 594 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 594 | | |
| gactgtcatg ttcttcctgt gatagtg | | 27 |
| SEQ ID NO: 595 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 595 | | |
| agacttacat gttcttcctg tgatagt | | 27 |
| SEQ ID NO: 596 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 596 | | |
| aagactgaca tgttcttcct gtgatag | | 27 |

```
SEQ ID NO: 597           moltype = RNA   length = 27
FEATURE                  Location/Qualifiers
source                   1..27
                         mol_type = other RNA
                         organism = synthetic construct
                         note = Synthetic
SEQUENCE: 597
caagattgac atgttcttcc tgtgata                                              27

SEQ ID NO: 598           moltype = RNA   length = 27
FEATURE                  Location/Qualifiers
source                   1..27
                         mol_type = other RNA
                         organism = synthetic construct
                         note = Synthetic
SEQUENCE: 598
ccaagtctga catgttcttc ctgtgat                                              27

SEQ ID NO: 599           moltype = RNA   length = 27
FEATURE                  Location/Qualifiers
source                   1..27
                         mol_type = other RNA
                         organism = synthetic construct
                         note = Synthetic
SEQUENCE: 599
accaatactg acatgttctt cctgtga                                              27

SEQ ID NO: 600           moltype = RNA   length = 27
FEATURE                  Location/Qualifiers
source                   1..27
                         mol_type = other RNA
                         organism = synthetic construct
                         note = Synthetic
SEQUENCE: 600
acgactaaga ctgacatgtt cttcctg                                              27

SEQ ID NO: 601           moltype = RNA   length = 27
FEATURE                  Location/Qualifiers
source                   1..27
                         mol_type = other RNA
                         organism = synthetic construct
                         note = Synthetic
SEQUENCE: 601
gacgatcaag actgacatgt tcttcct                                              27

SEQ ID NO: 602           moltype = RNA   length = 27
FEATURE                  Location/Qualifiers
source                   1..27
                         mol_type = other RNA
                         organism = synthetic construct
                         note = Synthetic
SEQUENCE: 602
agacgtccaa gactgacatg ttcttcc                                              27

SEQ ID NO: 603           moltype = RNA   length = 27
FEATURE                  Location/Qualifiers
source                   1..27
                         mol_type = other RNA
                         organism = synthetic construct
                         note = Synthetic
SEQUENCE: 603
tagactacca agactgacat gttcttc                                              27

SEQ ID NO: 604           moltype = RNA   length = 27
FEATURE                  Location/Qualifiers
source                   1..27
                         mol_type = other RNA
                         organism = synthetic construct
                         note = Synthetic
SEQUENCE: 604
tagtataatg ggatcctccg atgccaa                                              27

SEQ ID NO: 605           moltype = RNA   length = 27
FEATURE                  Location/Qualifiers
source                   1..27
                         mol_type = other RNA
                         organism = synthetic construct
                         note = Synthetic
```

```
SEQUENCE: 605
ctggttaggc cagcatttgg atagtat                                              27

SEQ ID NO: 606           moltype = RNA  length = 27
FEATURE                  Location/Qualifiers
source                   1..27
                         mol_type = other RNA
                         organism = synthetic construct
                         note = Synthetic
SEQUENCE: 606
gcttgttcag aaggagcctc tgtgctt                                              27

SEQ ID NO: 607           moltype = RNA  length = 27
FEATURE                  Location/Qualifiers
source                   1..27
                         mol_type = other RNA
                         organism = synthetic construct
                         note = Synthetic
SEQUENCE: 607
ctcagttggt gcttgttcag aaggagc                                              27

SEQ ID NO: 608           moltype = RNA  length = 27
FEATURE                  Location/Qualifiers
source                   1..27
                         mol_type = other RNA
                         organism = synthetic construct
                         note = Synthetic
SEQUENCE: 608
tctcatgtgg tgcttgttca gaaggag                                              27

SEQ ID NO: 609           moltype = RNA  length = 27
FEATURE                  Location/Qualifiers
source                   1..27
                         mol_type = other RNA
                         organism = synthetic construct
                         note = Synthetic
SEQUENCE: 609
ttctctggtg gtgcttgttc agaagga                                              27

SEQ ID NO: 610           moltype = RNA  length = 27
FEATURE                  Location/Qualifiers
source                   1..27
                         mol_type = other RNA
                         organism = synthetic construct
                         note = Synthetic
SEQUENCE: 610
tttcttaggt ggtgcttgtt cagaagg                                              27

SEQ ID NO: 611           moltype = RNA  length = 27
FEATURE                  Location/Qualifiers
source                   1..27
                         mol_type = other RNA
                         organism = synthetic construct
                         note = Synthetic
SEQUENCE: 611
ttttctcagg tggtgcttgt tcagaag                                              27

SEQ ID NO: 612           moltype = RNA  length = 27
FEATURE                  Location/Qualifiers
source                   1..27
                         mol_type = other RNA
                         organism = synthetic construct
                         note = Synthetic
SEQUENCE: 612
cttttttcag gtggtgcttg ttcagaa                                              27

SEQ ID NO: 613           moltype = RNA  length = 27
FEATURE                  Location/Qualifiers
source                   1..27
                         mol_type = other RNA
                         organism = synthetic construct
                         note = Synthetic
SEQUENCE: 613
gcttttctca ggtggtgctt gttcaga                                              27

SEQ ID NO: 614           moltype = RNA  length = 27
FEATURE                  Location/Qualifiers
source                   1..27
                         mol_type = other RNA
```

```
                            organism = synthetic construct
                            note = Synthetic
SEQUENCE: 614
ggcttttctc aggtggtgct tgttcag                                              27

SEQ ID NO: 615              moltype = RNA   length = 27
FEATURE                     Location/Qualifiers
source                      1..27
                            mol_type = other RNA
                            organism = synthetic construct
                            note = Synthetic
SEQUENCE: 615
gggcttttct caggtggtgc ttgttca                                              27

SEQ ID NO: 616              moltype = RNA   length = 27
FEATURE                     Location/Qualifiers
source                      1..27
                            mol_type = other RNA
                            organism = synthetic construct
                            note = Synthetic
SEQUENCE: 616
cagggttttt ctcaggtggt gcttgtt                                              27

SEQ ID NO: 617              moltype = RNA   length = 27
FEATURE                     Location/Qualifiers
source                      1..27
                            mol_type = other RNA
                            organism = synthetic construct
                            note = Synthetic
SEQUENCE: 617
acaggtcttt tctcaggtgg tgcttgt                                              27

SEQ ID NO: 618              moltype = RNA   length = 27
FEATURE                     Location/Qualifiers
source                      1..27
                            mol_type = other RNA
                            organism = synthetic construct
                            note = Synthetic
SEQUENCE: 618
cacagtgctt ttctcaggtg gtgcttg                                              27

SEQ ID NO: 619              moltype = RNA   length = 27
FEATURE                     Location/Qualifiers
source                      1..27
                            mol_type = other RNA
                            organism = synthetic construct
                            note = Synthetic
SEQUENCE: 619
tcctgtacca cagggctttt ctcaggt                                              27

SEQ ID NO: 620              moltype = RNA   length = 27
FEATURE                     Location/Qualifiers
source                      1..27
                            mol_type = other RNA
                            organism = synthetic construct
                            note = Synthetic
SEQUENCE: 620
tggtatcaat cctggaccac agggctt                                              27

SEQ ID NO: 621              moltype = RNA   length = 27
FEATURE                     Location/Qualifiers
source                      1..27
                            mol_type = other RNA
                            organism = synthetic construct
                            note = Synthetic
SEQUENCE: 621
ccatgttagc aatcctggac cacaggg                                              27

SEQ ID NO: 622              moltype = RNA   length = 27
FEATURE                     Location/Qualifiers
source                      1..27
                            mol_type = other RNA
                            organism = synthetic construct
                            note = Synthetic
SEQUENCE: 622
ggtccttcct gtgacagtgg tggagga                                              27

SEQ ID NO: 623              moltype = RNA   length = 27
FEATURE                     Location/Qualifiers
```

```
source                  1..27
                        mol_type = other RNA
                        organism = synthetic construct
                        note = Synthetic
SEQUENCE: 623
aggtctttcc tgtgacagtg gtggagg                                              27

SEQ ID NO: 624          moltype = RNA   length = 27
FEATURE                 Location/Qualifiers
source                  1..27
                        mol_type = other RNA
                        organism = synthetic construct
                        note = Synthetic
SEQUENCE: 624
agtgttgtat catagatgac caagatt                                              27

SEQ ID NO: 625          moltype = RNA   length = 27
FEATURE                 Location/Qualifiers
source                  1..27
                        mol_type = other RNA
                        organism = synthetic construct
                        note = Synthetic
SEQUENCE: 625
cagtgtggta tcatagatga ccaagat                                              27

SEQ ID NO: 626          moltype = RNA   length = 27
FEATURE                 Location/Qualifiers
source                  1..27
                        mol_type = other RNA
                        organism = synthetic construct
                        note = Synthetic
SEQUENCE: 626
ccagtttggt atcatagatg accaaga                                              27

SEQ ID NO: 627          moltype = RNA   length = 27
FEATURE                 Location/Qualifiers
source                  1..27
                        mol_type = other RNA
                        organism = synthetic construct
                        note = Synthetic
SEQUENCE: 627
gccagtgtgg tatcatagat gaccaag                                              27

SEQ ID NO: 628          moltype = RNA   length = 27
FEATURE                 Location/Qualifiers
source                  1..27
                        mol_type = other RNA
                        organism = synthetic construct
                        note = Synthetic
SEQUENCE: 628
tgccattgtg gtatcataga tgaccaa                                              27

SEQ ID NO: 629          moltype = RNA   length = 27
FEATURE                 Location/Qualifiers
source                  1..27
                        mol_type = other RNA
                        organism = synthetic construct
                        note = Synthetic
SEQUENCE: 629
atgcctgtgt ggtatcatag atgacca                                              27

SEQ ID NO: 630          moltype = RNA   length = 27
FEATURE                 Location/Qualifiers
source                  1..27
                        mol_type = other RNA
                        organism = synthetic construct
                        note = Synthetic
SEQUENCE: 630
gatgctagtg tggtatcata gatgacc                                              27

SEQ ID NO: 631          moltype = RNA   length = 27
FEATURE                 Location/Qualifiers
source                  1..27
                        mol_type = other RNA
                        organism = synthetic construct
                        note = Synthetic
SEQUENCE: 631
tgatgtcagt gtggtatcat agatgac                                              27
```

| | | |
|---|---|---|
| SEQ ID NO: 632 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 632 | | |
| ctgattccag tgtggtatca tagatga | | 27 |
| SEQ ID NO: 633 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 633 | | |
| tctgatgcca gtgtggtatc atagatg | | 27 |
| SEQ ID NO: 634 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 634 | | |
| ctctgttgcc agtgtggtat catagat | | 27 |
| SEQ ID NO: 635 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 635 | | |
| gtcctttgat gccagtgtgg tatcata | | 27 |
| SEQ ID NO: 636 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 636 | | |
| gggtcttctg atgccagtgt ggtatca | | 27 |
| SEQ ID NO: 637 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 637 | | |
| tttggttagt tttctggggt cctctga | | 27 |
| SEQ ID NO: 638 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 638 | | |
| atttgtgtag ttttctgggg tcctctg | | 27 |
| SEQ ID NO: 639 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 639 | | |
| gaatctggat tcctgcagta gttctcg | | 27 |
| SEQ ID NO: 640 | moltype = RNA length = 27 | |
| FEATURE | Location/Qualifiers | |
| source | 1..27 | |
| | mol_type = other RNA | |
| | organism = synthetic construct | |
| | note = Synthetic | |
| SEQUENCE: 640 | | | ccagattctg gattcctgca gtagttc                                              27

SEQ ID NO: 641          moltype = RNA   length = 27
FEATURE                 Location/Qualifiers
source                  1..27
                        mol_type = other RNA
                        organism = synthetic construct
                        note = Synthetic
SEQUENCE: 641
tcccataatc tggattcctg cagtagt                                              27

SEQ ID NO: 642          moltype = RNA   length = 27
FEATURE                 Location/Qualifiers
source                  1..27
                        mol_type = other RNA
                        organism = synthetic construct
                        note = Synthetic
SEQUENCE: 642
ttccctgaat ctggattcct gcagtag                                              27

SEQ ID NO: 643          moltype = RNA   length = 27
FEATURE                 Location/Qualifiers
source                  1..27
                        mol_type = other RNA
                        organism = synthetic construct
                        note = Synthetic
SEQUENCE: 643
tttcctagaa tctggattcc tgcagta                                              27

SEQ ID NO: 644          moltype = RNA   length = 27
FEATURE                 Location/Qualifiers
source                  1..27
                        mol_type = other RNA
                        organism = synthetic construct
                        note = Synthetic
SEQUENCE: 644
gtttctcaga atctggattc ctgcagt                                              27

SEQ ID NO: 645          moltype = RNA   length = 27
FEATURE                 Location/Qualifiers
source                  1..27
                        mol_type = other RNA
                        organism = synthetic construct
                        note = Synthetic
SEQUENCE: 645
tgttttccag aatctggatt cctgcag                                              27

SEQ ID NO: 646          moltype = RNA   length = 27
FEATURE                 Location/Qualifiers
source                  1..27
                        mol_type = other RNA
                        organism = synthetic construct
                        note = Synthetic
SEQUENCE: 646
ggttgtttcc cagaatctgg attcctg                                              27

SEQ ID NO: 647          moltype = RNA   length = 27
FEATURE                 Location/Qualifiers
source                  1..27
                        mol_type = other RNA
                        organism = synthetic construct
                        note = Synthetic
SEQUENCE: 647
ttgtgtaaca ccagggttgt ttcccag                                              27

SEQ ID NO: 648          moltype = RNA   length = 27
FEATURE                 Location/Qualifiers
source                  1..27
                        mol_type = other RNA
                        organism = synthetic construct
                        note = Synthetic
SEQUENCE: 648
gttgtttaac accagggttg tttccca                                              27

SEQ ID NO: 649          moltype = RNA   length = 27
FEATURE                 Location/Qualifiers
source                  1..27
                        mol_type = other RNA
                        organism = synthetic construct -continued

```
                        note = Synthetic
SEQUENCE: 649
gattgtagta ctcccacctc acacacg                                              27

SEQ ID NO: 650          moltype = RNA   length = 27
FEATURE                 Location/Qualifiers
source                  1..27
                        mol_type = other RNA
                        organism = synthetic construct
                        note = Synthetic
SEQUENCE: 650
agatttcagt actcccacct cacacac                                              27

SEQ ID NO: 651          moltype = RNA   length = 27
FEATURE                 Location/Qualifiers
source                  1..27
                        mol_type = other RNA
                        organism = synthetic construct
                        note = Synthetic
SEQUENCE: 651
tcagattgca gtactcccac ctcacac                                              27

SEQ ID NO: 652          moltype = RNA   length = 27
FEATURE                 Location/Qualifiers
source                  1..27
                        mol_type = other RNA
                        organism = synthetic construct
                        note = Synthetic
SEQUENCE: 652
gtcagtttgc agtactccca cctcaca                                              27

SEQ ID NO: 653          moltype = RNA   length = 27
FEATURE                 Location/Qualifiers
source                  1..27
                        mol_type = other RNA
                        organism = synthetic construct
                        note = Synthetic
SEQUENCE: 653
attcttttc tgagcattgt gtcagat                                               27

SEQ ID NO: 654          moltype = RNA   length = 27
FEATURE                 Location/Qualifiers
source                  1..27
                        mol_type = other RNA
                        organism = synthetic construct
                        note = Synthetic
SEQUENCE: 654
gattctgttt ctgagcattg tgtcaga                                              27

SEQ ID NO: 655          moltype = RNA   length = 27
FEATURE                 Location/Qualifiers
source                  1..27
                        mol_type = other RNA
                        organism = synthetic construct
                        note = Synthetic
SEQUENCE: 655
tgattttgtt tctgagcatt gtgtcag                                              27

SEQ ID NO: 656          moltype = RNA   length = 27
FEATURE                 Location/Qualifiers
source                  1..27
                        mol_type = other RNA
                        organism = synthetic construct
                        note = Synthetic
SEQUENCE: 656
ctgattctgt ttctgagcat tgtgtca                                              27

SEQ ID NO: 657          moltype = RNA   length = 27
FEATURE                 Location/Qualifiers
source                  1..27
                        mol_type = other RNA
                        organism = synthetic construct
                        note = Synthetic
SEQUENCE: 657
cctgattctg tttctgagca ttgtgtc                                              27

SEQ ID NO: 658          moltype = RNA   length = 27
FEATURE                 Location/Qualifiers
source                  1..27
```

```
                              mol_type = other RNA
                              organism = synthetic construct
                              note = Synthetic
SEQUENCE: 658
acctgtttct gtttctgagc attgtgt                                              27

SEQ ID NO: 659            moltype = RNA   length = 27
FEATURE                   Location/Qualifiers
source                    1..27
                          mol_type = other RNA
                          organism = synthetic construct
                          note = Synthetic
SEQUENCE: 659
caccttattc tgtttctgag cattgtg                                              27

SEQ ID NO: 660            moltype = RNA   length = 27
FEATURE                   Location/Qualifiers
source                    1..27
                          mol_type = other RNA
                          organism = synthetic construct
                          note = Synthetic
SEQUENCE: 660
acacctgatt ctgtttctga gcattgt                                              27

SEQ ID NO: 661            moltype = RNA   length = 27
FEATURE                   Location/Qualifiers
source                    1..27
                          mol_type = other RNA
                          organism = synthetic construct
                          note = Synthetic
SEQUENCE: 661
gacacttgat tctgtttctg agcattg                                              27

SEQ ID NO: 662            moltype = RNA   length = 27
FEATURE                   Location/Qualifiers
source                    1..27
                          mol_type = other RNA
                          organism = synthetic construct
                          note = Synthetic
SEQUENCE: 662
ggacatctga ttctgtttct gagcatt                                              27

SEQ ID NO: 663            moltype = RNA   length = 27
FEATURE                   Location/Qualifiers
source                    1..27
                          mol_type = other RNA
                          organism = synthetic construct
                          note = Synthetic
SEQUENCE: 663
taggatacct gattctgttt ctgagca                                              27

SEQ ID NO: 664            moltype = RNA   length = 27
FEATURE                   Location/Qualifiers
source                    1..27
                          mol_type = other RNA
                          organism = synthetic construct
                          note = Synthetic
SEQUENCE: 664
tctagtacac ctgattctgt ttctgag                                              27

SEQ ID NO: 665            moltype = RNA   length = 27
FEATURE                   Location/Qualifiers
source                    1..27
                          mol_type = other RNA
                          organism = synthetic construct
                          note = Synthetic
SEQUENCE: 665
ctctatgaca cctgattctg tttctga                                              27

SEQ ID NO: 666            moltype = RNA   length = 27
FEATURE                   Location/Qualifiers
source                    1..27
                          mol_type = other RNA
                          organism = synthetic construct
                          note = Synthetic
SEQUENCE: 666
tctcttggac acctgattct gtttctg                                              27

SEQ ID NO: 667            moltype = RNA   length = 27
```

```
FEATURE                 Location/Qualifiers
source                  1..27
                        mol_type = other RNA
                        organism = synthetic construct
                        note = Synthetic
SEQUENCE: 667
gtctctagga cacctgattc tgtttct                                              27

SEQ ID NO: 668          moltype = RNA  length = 27
FEATURE                 Location/Qualifiers
source                  1..27
                        mol_type = other RNA
                        organism = synthetic construct
                        note = Synthetic
SEQUENCE: 668
agtctttagg acacctgatt ctgtttc                                              27

SEQ ID NO: 669          moltype = RNA  length = 27
FEATURE                 Location/Qualifiers
source                  1..27
                        mol_type = other RNA
                        organism = synthetic construct
                        note = Synthetic
SEQUENCE: 669
ggagtttcta ggacacctga ttctgtt                                              27

SEQ ID NO: 670          moltype = RNA  length = 27
FEATURE                 Location/Qualifiers
source                  1..27
                        mol_type = other RNA
                        organism = synthetic construct
                        note = Synthetic
SEQUENCE: 670
tgggattctc taggacacct gattctg                                              27

SEQ ID NO: 671          moltype = RNA  length = 27
FEATURE                 Location/Qualifiers
source                  1..27
                        mol_type = other RNA
                        organism = synthetic construct
                        note = Synthetic
SEQUENCE: 671
agtggtagtc tctaggacac ctgattc                                              27

SEQ ID NO: 672          moltype = RNA  length = 27
FEATURE                 Location/Qualifiers
source                  1..27
                        mol_type = other RNA
                        organism = synthetic construct
                        note = Synthetic
SEQUENCE: 672
caacattggg agtctctagg acacctg                                              27

SEQ ID NO: 673          moltype = RNA  length = 27
FEATURE                 Location/Qualifiers
source                  1..27
                        mol_type = other RNA
                        organism = synthetic construct
                        note = Synthetic
SEQUENCE: 673
tggaataaca gtgggagtct ctaggac                                              27

SEQ ID NO: 674          moltype = RNA  length = 27
FEATURE                 Location/Qualifiers
source                  1..27
                        mol_type = other RNA
                        organism = synthetic construct
                        note = Synthetic
SEQUENCE: 674
ctggatcaac agtgggagtc tctagga                                              27

SEQ ID NO: 675          moltype = RNA  length = 27
FEATURE                 Location/Qualifiers
source                  1..27
                        mol_type = other RNA
                        organism = synthetic construct
                        note = Synthetic
SEQUENCE: 675
actggtacaa cagtgggagt ctctagg                                              27
```

```
SEQ ID NO: 676          moltype = RNA   length = 27
FEATURE                 Location/Qualifiers
source                  1..27
                        mol_type = other RNA
                        organism = synthetic construct
                        note = Synthetic
SEQUENCE: 676
aactgtaaca acagtgggag tctctag                                              27

SEQ ID NO: 677          moltype = RNA   length = 27
FEATURE                 Location/Qualifiers
source                  1..27
                        mol_type = other RNA
                        organism = synthetic construct
                        note = Synthetic
SEQUENCE: 677
gaacttgaac aacagtggga gtctcta                                              27

SEQ ID NO: 678          moltype = RNA   length = 27
FEATURE                 Location/Qualifiers
source                  1..27
                        mol_type = other RNA
                        organism = synthetic construct
                        note = Synthetic
SEQUENCE: 678
ggaactggaa caacagtggg agtctct                                              27

SEQ ID NO: 679          moltype = RNA   length = 27
FEATURE                 Location/Qualifiers
source                  1..27
                        mol_type = other RNA
                        organism = synthetic construct
                        note = Synthetic
SEQUENCE: 679
cagtttgtgc tgcttcagaa tgagcct                                              27

SEQ ID NO: 680          moltype = RNA   length = 27
FEATURE                 Location/Qualifiers
source                  1..27
                        mol_type = other RNA
                        organism = synthetic construct
                        note = Synthetic
SEQUENCE: 680
tcagttggtg ctgcttcaga atgagcc                                              27

SEQ ID NO: 681          moltype = RNA   length = 27
FEATURE                 Location/Qualifiers
source                  1..27
                        mol_type = other RNA
                        organism = synthetic construct
                        note = Synthetic
SEQUENCE: 681
ctcagttggt gctgcttcag aatgagc                                              27

SEQ ID NO: 682          moltype = RNA   length = 27
FEATURE                 Location/Qualifiers
source                  1..27
                        mol_type = other RNA
                        organism = synthetic construct
                        note = Synthetic
SEQUENCE: 682
gctcatttgg tgctgcttca gaatgag                                              27

SEQ ID NO: 683          moltype = RNA   length = 27
FEATURE                 Location/Qualifiers
source                  1..27
                        mol_type = other RNA
                        organism = synthetic construct
                        note = Synthetic
SEQUENCE: 683
tgctctgttg gtgctgcttc agaatga                                              27

SEQ ID NO: 684          moltype = RNA   length = 27
FEATURE                 Location/Qualifiers
source                  1..27
                        mol_type = other RNA
                        organism = synthetic construct
                        note = Synthetic
```

```
SEQUENCE: 684
ttgcttagtt ggtgctgctt cagaatg                                              27

SEQ ID NO: 685          moltype = RNA  length = 27
FEATURE                 Location/Qualifiers
source                  1..27
                        mol_type = other RNA
                        organism = synthetic construct
                        note = Synthetic
SEQUENCE: 685
tttgctcagt tggtgctgct tcagaat                                              27

SEQ ID NO: 686          moltype = RNA  length = 27
FEATURE                 Location/Qualifiers
source                  1..27
                        mol_type = other RNA
                        organism = synthetic construct
                        note = Synthetic
SEQUENCE: 686
gtttgttcag ttggtgctgc ttcagaa                                              27

SEQ ID NO: 687          moltype = RNA  length = 27
FEATURE                 Location/Qualifiers
source                  1..27
                        mol_type = other RNA
                        organism = synthetic construct
                        note = Synthetic
SEQUENCE: 687
ggttttctca gttggtgctg cttcaga                                              27

SEQ ID NO: 688          moltype = RNA  length = 27
FEATURE                 Location/Qualifiers
source                  1..27
                        mol_type = other RNA
                        organism = synthetic construct
                        note = Synthetic
SEQUENCE: 688
gggtttgctc agttggtgct gcttcag                                              27

SEQ ID NO: 689          moltype = RNA  length = 27
FEATURE                 Location/Qualifiers
source                  1..27
                        mol_type = other RNA
                        organism = synthetic construct
                        note = Synthetic
SEQUENCE: 689
ggggtttgct cagttggtgc tgcttca                                              27

SEQ ID NO: 690          moltype = RNA  length = 27
FEATURE                 Location/Qualifiers
source                  1..27
                        mol_type = other RNA
                        organism = synthetic construct
                        note = Synthetic
SEQUENCE: 690
tctggtcatt accatggtag cactgcc                                              27

SEQ ID NO: 691          moltype = RNA  length = 27
FEATURE                 Location/Qualifiers
source                  1..27
                        mol_type = other RNA
                        organism = synthetic construct
                        note = Synthetic
SEQUENCE: 691
ctctgtccat taccatggta gcactgc                                              27

SEQ ID NO: 692          moltype = RNA  length = 27
FEATURE                 Location/Qualifiers
source                  1..27
                        mol_type = other RNA
                        organism = synthetic construct
                        note = Synthetic
SEQUENCE: 692
ttcctttgac agtggtggag aatgtgc                                              27

SEQ ID NO: 693          moltype = RNA  length = 27
FEATURE                 Location/Qualifiers
source                  1..27
                        mol_type = other RNA
```

```
                                    -continued
                      organism = synthetic construct
                      note = Synthetic
SEQUENCE: 693
ttgacttgtc cttcctgtga cagtggt                                          27

SEQ ID NO: 694        moltype = RNA   length = 27
FEATURE               Location/Qualifiers
source                1..27
                      mol_type = other RNA
                      organism = synthetic construct
                      note = Synthetic
SEQUENCE: 694
attgatatgt ccttcctgtg acagtgg                                          27

SEQ ID NO: 695        moltype = RNA   length = 27
FEATURE               Location/Qualifiers
source                1..27
                      mol_type = other RNA
                      organism = synthetic construct
                      note = Synthetic
SEQUENCE: 695
gattgtcatg tccttcctgt gacagtg                                          27

SEQ ID NO: 696        moltype = RNA   length = 27
FEATURE               Location/Qualifiers
source                1..27
                      mol_type = other RNA
                      organism = synthetic construct
                      note = Synthetic
SEQUENCE: 696
agatttacat gtccttcctg tgacagt                                          27

SEQ ID NO: 697        moltype = RNA   length = 27
FEATURE               Location/Qualifiers
source                1..27
                      mol_type = other RNA
                      organism = synthetic construct
                      note = Synthetic
SEQUENCE: 697
aagattgaca tgtccttcct gtgacag                                          27

SEQ ID NO: 698        moltype = RNA   length = 27
FEATURE               Location/Qualifiers
source                1..27
                      mol_type = other RNA
                      organism = synthetic construct
                      note = Synthetic
SEQUENCE: 698
caagattgac atgtccttcc tgtgaca                                          27

SEQ ID NO: 699        moltype = RNA   length = 27
FEATURE               Location/Qualifiers
source                1..27
                      mol_type = other RNA
                      organism = synthetic construct
                      note = Synthetic
SEQUENCE: 699
accaatattg acatgtcctt cctgtga                                          27

SEQ ID NO: 700        moltype = RNA   length = 27
FEATURE               Location/Qualifiers
source                1..27
                      mol_type = other RNA
                      organism = synthetic construct
                      note = Synthetic
SEQUENCE: 700
gaccatgatt gacatgtcct tcctgtg                                          27

SEQ ID NO: 701        moltype = RNA   length = 27
FEATURE               Location/Qualifiers
source                1..27
                      mol_type = other RNA
                      organism = synthetic construct
                      note = Synthetic
SEQUENCE: 701
tgacctagat tgacatgtcc ttcctgt                                          27

SEQ ID NO: 702        moltype = RNA   length = 27
FEATURE               Location/Qualifiers
```

```
source                  1..27
                        mol_type = other RNA
                        organism = synthetic construct
                        note = Synthetic
SEQUENCE: 702
atgactaaga ttgacatgtc cttcctg                                              27

SEQ ID NO: 703          moltype = RNA  length = 27
FEATURE                 Location/Qualifiers
source                  1..27
                        mol_type = other RNA
                        organism = synthetic construct
                        note = Synthetic
SEQUENCE: 703
gatgatcaag attgacatgt ccttcct                                              27

SEQ ID NO: 704          moltype = RNA  length = 27
FEATURE                 Location/Qualifiers
source                  1..27
                        mol_type = other RNA
                        organism = synthetic construct
                        note = Synthetic
SEQUENCE: 704
ggatgtccaa gattgacatg tccttcc                                              27

SEQ ID NO: 705          moltype = RNA  length = 27
FEATURE                 Location/Qualifiers
source                  1..27
                        mol_type = other RNA
                        organism = synthetic construct
                        note = Synthetic
SEQUENCE: 705
tggattacca agattgacat gtccttc                                              27

SEQ ID NO: 706          moltype = RNA  length = 27
FEATURE                 Location/Qualifiers
source                  1..27
                        mol_type = other RNA
                        organism = synthetic construct
                        note = Synthetic
SEQUENCE: 706
atggatgacc aagattgaca tgtcctt                                              27

SEQ ID NO: 707          moltype = RNA  length = 27
FEATURE                 Location/Qualifiers
source                  1..27
                        mol_type = other RNA
                        organism = synthetic construct
                        note = Synthetic
SEQUENCE: 707
catggttgac caagattgac atgtcct                                              27

SEQ ID NO: 708          moltype = RNA  length = 27
FEATURE                 Location/Qualifiers
source                  1..27
                        mol_type = other RNA
                        organism = synthetic construct
                        note = Synthetic
SEQUENCE: 708
tcatgtatga ccaagattga catgtcc                                              27

SEQ ID NO: 709          moltype = RNA  length = 27
FEATURE                 Location/Qualifiers
source                  1..27
                        mol_type = other RNA
                        organism = synthetic construct
                        note = Synthetic
SEQUENCE: 709
gtcattgatg accaagattg acatgtc                                              27

SEQ ID NO: 710          moltype = RNA  length = 27
FEATURE                 Location/Qualifiers
source                  1..27
                        mol_type = other RNA
                        organism = synthetic construct
                        note = Synthetic
SEQUENCE: 710
tgtcatggat gaccaagatt gacatgt                                              27
```

| | | |
|---|---|---|
| SEQ ID NO: 711 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 711 | | |
| gtgtcttgga tgaccaagat tgacatg | | 27 |
| SEQ ID NO: 712 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 712 | | |
| ggtgttatgg atgaccaaga ttgacat | | 27 |
| SEQ ID NO: 713 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 713 | | |
| tggtgtcatg gatgaccaag attgaca | | 27 |
| SEQ ID NO: 714 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 714 | | |
| gtggtttcat ggatgaccaa gattgac | | 27 |
| SEQ ID NO: 715 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 715 | | |
| tgtggtgtca tggatgacca agattga | | 27 |
| SEQ ID NO: 716 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 716 | | |
| gtgtgttgtc atggatgacc aagattg | | 27 |
| SEQ ID NO: 717 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 717 | | |
| ggatttctgc agtagttcat tgtcagg | | 27 |
| SEQ ID NO: 718 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 718 | | |
| tggattcctg cagtagttca ttgtcag | | 27 |
| SEQ ID NO: 719 | moltype = RNA length = 27 | |
| FEATURE | Location/Qualifiers | |
| source | 1..27<br>mol_type = other RNA<br>organism = synthetic construct<br>note = Synthetic | |
| SEQUENCE: 719 | | |

```
ctggattcct gcagtagttc attgtca                                              27

SEQ ID NO: 720          moltype = RNA   length = 27
FEATURE                 Location/Qualifiers
source                  1..27
                        mol_type = other RNA
                        organism = synthetic construct
                        note = Synthetic
SEQUENCE: 720
tctggtttcc tgcagtagtt cattgtc                                              27

SEQ ID NO: 721          moltype = RNA   length = 27
FEATURE                 Location/Qualifiers
source                  1..27
                        mol_type = other RNA
                        organism = synthetic construct
                        note = Synthetic
SEQUENCE: 721
atctgtattc ctgcagtagt tcattgt                                              27

SEQ ID NO: 722          moltype = RNA   length = 27
FEATURE                 Location/Qualifiers
source                  1..27
                        mol_type = other RNA
                        organism = synthetic construct
                        note = Synthetic
SEQUENCE: 722
catcttgatt cctgcagtag ttcattg                                              27

SEQ ID NO: 723          moltype = RNA   length = 27
FEATURE                 Location/Qualifiers
source                  1..27
                        mol_type = other RNA
                        organism = synthetic construct
                        note = Synthetic
SEQUENCE: 723
gcatctggat tcctgcagta gttcatt                                              27

SEQ ID NO: 724          moltype = RNA   length = 27
FEATURE                 Location/Qualifiers
source                  1..27
                        mol_type = other RNA
                        organism = synthetic construct
                        note = Synthetic
SEQUENCE: 724
atcggtatct ggattcctgc agtagtt                                              27

SEQ ID NO: 725          moltype = RNA   length = 27
FEATURE                 Location/Qualifiers
source                  1..27
                        mol_type = other RNA
                        organism = synthetic construct
                        note = Synthetic
SEQUENCE: 725
tccattgtaa aacaccaagg gcctgta                                              27

SEQ ID NO: 726          moltype = RNA   length = 27
FEATURE                 Location/Qualifiers
source                  1..27
                        mol_type = other RNA
                        organism = synthetic construct
                        note = Synthetic
SEQUENCE: 726
ctgggttcca tggtaaaaca ccaaggg                                              27

SEQ ID NO: 727          moltype = RNA   length = 27
FEATURE                 Location/Qualifiers
source                  1..27
                        mol_type = other RNA
                        organism = synthetic construct
                        note = Synthetic
SEQUENCE: 727
gctggtgtcc atggtaaaac accaagg                                              27

SEQ ID NO: 728          moltype = RNA   length = 27
FEATURE                 Location/Qualifiers
source                  1..27
                        mol_type = other RNA
                        organism = synthetic construct
```

-continued

```
                          note = Synthetic
SEQUENCE: 728
tgctgtggtc catggtaaaa caccaag                                          27

SEQ ID NO: 729          moltype = RNA  length = 27
FEATURE                 Location/Qualifiers
source                  1..27
                        mol_type = other RNA
                        organism = synthetic construct
                        note = Synthetic
SEQUENCE: 729
atgcttgggt ccatggtaaa acaccaa                                          27

SEQ ID NO: 730          moltype = RNA  length = 27
FEATURE                 Location/Qualifiers
source                  1..27
                        mol_type = other RNA
                        organism = synthetic construct
                        note = Synthetic
SEQUENCE: 730
gatgctgggg tccatggtaa aacacca                                          27

SEQ ID NO: 731          moltype = RNA  length = 27
FEATURE                 Location/Qualifiers
source                  1..27
                        mol_type = other RNA
                        organism = synthetic construct
                        note = Synthetic
SEQUENCE: 731
ctgattctgg ggtccatggt aaaacac                                          27

SEQ ID NO: 732          moltype = RNA  length = 27
FEATURE                 Location/Qualifiers
source                  1..27
                        mol_type = other RNA
                        organism = synthetic construct
                        note = Synthetic
SEQUENCE: 732
gcatctcgtc aggttgcagt actccca                                          27

SEQ ID NO: 733          moltype = RNA  length = 27
FEATURE                 Location/Qualifiers
source                  1..27
                        mol_type = other RNA
                        organism = synthetic construct
                        note = Synthetic
SEQUENCE: 733
agcattgcgt caggttgcag tactccc                                          27

SEQ ID NO: 734          moltype = RNA  length = 27
FEATURE                 Location/Qualifiers
source                  1..27
                        mol_type = other RNA
                        organism = synthetic construct
                        note = Synthetic
SEQUENCE: 734
tgagcttcgc gtcaggttgc agtactc                                          27

SEQ ID NO: 735          moltype = RNA  length = 27
FEATURE                 Location/Qualifiers
source                  1..27
                        mol_type = other RNA
                        organism = synthetic construct
                        note = Synthetic
SEQUENCE: 735
ctgagtatcg cgtcaggttg cagtact                                          27

SEQ ID NO: 736          moltype = RNA  length = 27
FEATURE                 Location/Qualifiers
source                  1..27
                        mol_type = other RNA
                        organism = synthetic construct
                        note = Synthetic
SEQUENCE: 736
tgtcttagca tcgcgtcagg ttgcagt                                          27

SEQ ID NO: 737          moltype = RNA  length = 27
FEATURE                 Location/Qualifiers
source                  1..27
```

```
                              mol_type = other RNA
                              organism = synthetic construct
                              note = Synthetic
SEQUENCE: 737
ttctgtgtct gagcatcgcg tcaggtt                                            27

SEQ ID NO: 738         moltype = RNA  length = 27
FEATURE                Location/Qualifiers
source                 1..27
                       mol_type = other RNA
                       organism = synthetic construct
                       note = Synthetic
SEQUENCE: 738
cttctttgtc tgagcatcgc gtcaggt                                            27

SEQ ID NO: 739         moltype = RNA  length = 27
FEATURE                Location/Qualifiers
source                 1..27
                       mol_type = other RNA
                       organism = synthetic construct
                       note = Synthetic
SEQUENCE: 739
acagttcctt ctgtgtctga gcatcgc                                            27

SEQ ID NO: 740         moltype = RNA  length = 27
FEATURE                Location/Qualifiers
source                 1..27
                       mol_type = other RNA
                       organism = synthetic construct
                       note = Synthetic
SEQUENCE: 740
cacagtccct tctgtgtctg agcatcg                                            27

SEQ ID NO: 741         moltype = RNA  length = 27
FEATURE                Location/Qualifiers
source                 1..27
                       mol_type = other RNA
                       organism = synthetic construct
                       note = Synthetic
SEQUENCE: 741
agcgatcaca gtcccttctg tgtctga                                            27

SEQ ID NO: 742         moltype = RNA  length = 27
FEATURE                Location/Qualifiers
source                 1..27
                       mol_type = other RNA
                       organism = synthetic construct
                       note = Synthetic
SEQUENCE: 742
tcccataatc aaatgaagag gatgcac                                            27

SEQ ID NO: 743         moltype = RNA  length = 27
FEATURE                Location/Qualifiers
source                 1..27
                       mol_type = other RNA
                       organism = synthetic construct
                       note = Synthetic
SEQUENCE: 743
ttccctcaat caaatgaaga ggatgca                                            27

SEQ ID NO: 744         moltype = RNA  length = 27
FEATURE                Location/Qualifiers
source                 1..27
                       mol_type = other RNA
                       organism = synthetic construct
                       note = Synthetic
SEQUENCE: 744
cttcctacaa tcaaatgaag aggatgc                                            27

SEQ ID NO: 745         moltype = RNA  length = 27
FEATURE                Location/Qualifiers
source                 1..27
                       mol_type = other RNA
                       organism = synthetic construct
                       note = Synthetic
SEQUENCE: 745
gcttctcaca atcaaatgaa gaggatg                                            27

SEQ ID NO: 746         moltype = RNA  length = 27
```

-continued

| FEATURE | Location/Qualifiers |
|---|---|
| source | 1..27<br>mol_type = other RNA<br>organism = synthetic construct<br>note = Synthetic |

SEQUENCE: 746
ggctttccac aatcaaatga agaggat 27

SEQ ID NO: 747      moltype = RNA   length = 27
FEATURE             Location/Qualifiers
source              1..27
                    mol_type = other RNA
                    organism = synthetic construct
                    note = Synthetic
SEQUENCE: 747
tgaggtttcc cacaatcaaa tgaagag 27

SEQ ID NO: 748      moltype = RNA   length = 27
FEATURE             Location/Qualifiers
source              1..27
                    mol_type = other RNA
                    organism = synthetic construct
                    note = Synthetic
SEQUENCE: 748
ttgagtcttc ccacaatcaa atgaaga 27

SEQ ID NO: 749      moltype = RNA   length = 27
FEATURE             Location/Qualifiers
source              1..27
                    mol_type = other RNA
                    organism = synthetic construct
                    note = Synthetic
SEQUENCE: 749
cttgatgctt cccacaatca aatgaag 27

SEQ ID NO: 750      moltype = RNA   length = 27
FEATURE             Location/Qualifiers
source              1..27
                    mol_type = other RNA
                    organism = synthetic construct
                    note = Synthetic
SEQUENCE: 750
acttgtggct tcccacaatc aaatgaa 27

SEQ ID NO: 751      moltype = RNA   length = 27
FEATURE             Location/Qualifiers
source              1..27
                    mol_type = other RNA
                    organism = synthetic construct
                    note = Synthetic
SEQUENCE: 751
cactttaggc ttcccacaat caaatga 27

SEQ ID NO: 752      moltype = RNA   length = 27
FEATURE             Location/Qualifiers
source              1..27
                    mol_type = other RNA
                    organism = synthetic construct
                    note = Synthetic
SEQUENCE: 752
ttcggttcca cttgaggctt cccacaa 27

SEQ ID NO: 753      moltype = RNA   length = 27
FEATURE             Location/Qualifiers
source              1..27
                    mol_type = other RNA
                    organism = synthetic construct
                    note = Synthetic
SEQUENCE: 753
ctacattgct tccaggacat ttcttcg 27

SEQ ID NO: 754      moltype = RNA   length = 27
FEATURE             Location/Qualifiers
source              1..27
                    mol_type = other RNA
                    organism = synthetic construct
                    note = Synthetic
SEQUENCE: 754
cctactatgc ttccaggaca tttcttc 27

```
SEQ ID NO: 755          moltype = RNA   length = 27
FEATURE                 Location/Qualifiers
source                  1..27
                        mol_type = other RNA
                        organism = synthetic construct
                        note = Synthetic
SEQUENCE: 755
ccctataatg cttccaggac atttctt                                              27

SEQ ID NO: 756          moltype = RNA   length = 27
FEATURE                 Location/Qualifiers
source                  1..27
                        mol_type = other RNA
                        organism = synthetic construct
                        note = Synthetic
SEQUENCE: 756
cccccctacaa tgcttccagg acatttc                                             27

SEQ ID NO: 757          moltype = RNA   length = 27
FEATURE                 Location/Qualifiers
source                  1..27
                        mol_type = other RNA
                        organism = synthetic construct
                        note = Synthetic
SEQUENCE: 757
cccccttaca atgcttccag gacattt                                              27

SEQ ID NO: 758          moltype = RNA   length = 27
FEATURE                 Location/Qualifiers
source                  1..27
                        mol_type = other RNA
                        organism = synthetic construct
                        note = Synthetic
SEQUENCE: 758
agaagtgctt tccaaacctt gttctga                                              27

SEQ ID NO: 759          moltype = RNA   length = 27
FEATURE                 Location/Qualifiers
source                  1..27
                        mol_type = other RNA
                        organism = synthetic construct
                        note = Synthetic
SEQUENCE: 759
cagaattgct ttccaaacct tgttctg                                              27

SEQ ID NO: 760          moltype = RNA   length = 27
FEATURE                 Location/Qualifiers
source                  1..27
                        mol_type = other RNA
                        organism = synthetic construct
                        note = Synthetic
SEQUENCE: 760
acagatgtgc tttccaaacc ttgttct                                              27

SEQ ID NO: 761          moltype = RNA   length = 27
FEATURE                 Location/Qualifiers
source                  1..27
                        mol_type = other RNA
                        organism = synthetic construct
                        note = Synthetic
SEQUENCE: 761
cacagtagtg ctttccaaac cttgttc                                              27

SEQ ID NO: 762          moltype = RNA   length = 27
FEATURE                 Location/Qualifiers
source                  1..27
                        mol_type = other RNA
                        organism = synthetic construct
                        note = Synthetic
SEQUENCE: 762
ccacataagt gctttccaaa ccttgtt                                              27

SEQ ID NO: 763          moltype = RNA   length = 27
FEATURE                 Location/Qualifiers
source                  1..27
                        mol_type = other RNA
                        organism = synthetic construct
                        note = Synthetic
```

| SEQUENCE: 763 | | |
|---|---|---|
| tccactgaag tgctttccaa accttgt | | 27 |

| SEQ ID NO: 764 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 764 | | |
| ctccatagaa gtgctttcca aaccttg | | 27 |

| SEQ ID NO: 765 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 765 | | |
| ggtgcttcca cagaagtgct ttccaaa | | 27 |

| SEQ ID NO: 766 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 766 | | |
| tctggtgata ttaaggtgcc tccacag | | 27 |

| SEQ ID NO: 767 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 767 | | |
| cagcatccac tctggggata ttaaggt | | 27 |

| SEQ ID NO: 768 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 768 | | |
| gtcagtaccc actctgggga tattaag | | 27 |

| SEQ ID NO: 769 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 769 | | |
| gtgagtagca gtcagcaccc actctgg | | 27 |

| SEQ ID NO: 770 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 770 | | |
| ttggtttgca cccaggatga ccttgta | | 27 |

| SEQ ID NO: 771 | moltype = RNA  length = 27 | |
|---|---|---|
| FEATURE | Location/Qualifiers | |
| source | 1..27<br>mol_type = other RNA<br>organism = synthetic construct<br>note = Synthetic | |
| SEQUENCE: 771 | | |
| gttcatttct tggtgtgcac ccaggat | | 27 |

| SEQ ID NO: 772 | moltype = RNA  length = 27 | |
|---|---|---|
| FEATURE | Location/Qualifiers | |
| source | 1..27<br>mol_type = other RNA | |

```
                           organism = synthetic construct
                           note = Synthetic
SEQUENCE: 772
tcgagtttca cttcttggtg tgcaccc                                          27

SEQ ID NO: 773             moltype = RNA  length = 27
FEATURE                    Location/Qualifiers
source                     1..27
                           mol_type = other RNA
                           organism = synthetic construct
                           note = Synthetic
SEQUENCE: 773
tagctttagc aaggcaatat ctgcttg                                          27

SEQ ID NO: 774             moltype = RNA  length = 27
FEATURE                    Location/Qualifiers
source                     1..27
                           mol_type = other RNA
                           organism = synthetic construct
                           note = Synthetic
SEQUENCE: 774
ttagctttag caaggcaata tctgctt                                          27

SEQ ID NO: 775             moltype = RNA  length = 27
FEATURE                    Location/Qualifiers
source                     1..27
                           mol_type = other RNA
                           organism = synthetic construct
                           note = Synthetic
SEQUENCE: 775
cttagtttta gcaaggcaat atctgct                                          27

SEQ ID NO: 776             moltype = RNA  length = 27
FEATURE                    Location/Qualifiers
source                     1..27
                           mol_type = other RNA
                           organism = synthetic construct
                           note = Synthetic
SEQUENCE: 776
gcttatcttt agcaaggcaa tatctgc                                          27

SEQ ID NO: 777             moltype = RNA  length = 27
FEATURE                    Location/Qualifiers
source                     1..27
                           mol_type = other RNA
                           organism = synthetic construct
                           note = Synthetic
SEQUENCE: 777
tgctttgctt tagcaaggca atatctg                                          27

SEQ ID NO: 778             moltype = RNA  length = 27
FEATURE                    Location/Qualifiers
source                     1..27
                           mol_type = other RNA
                           organism = synthetic construct
                           note = Synthetic
SEQUENCE: 778
ctgcttagct ttagcaaggc aatatct                                          27

SEQ ID NO: 779             moltype = RNA  length = 27
FEATURE                    Location/Qualifiers
source                     1..27
                           mol_type = other RNA
                           organism = synthetic construct
                           note = Synthetic
SEQUENCE: 779
cctgcttagc tttagcaagg caatatc                                          27

SEQ ID NO: 780             moltype = RNA  length = 27
FEATURE                    Location/Qualifiers
source                     1..27
                           mol_type = other RNA
                           organism = synthetic construct
                           note = Synthetic
SEQUENCE: 780
gctggtatta ctttgtcagt gatgacg                                          27

SEQ ID NO: 781             moltype = RNA  length = 27
FEATURE                    Location/Qualifiers
```

```
source                   1..27
                         mol_type = other RNA
                         organism = synthetic construct
                         note = Synthetic
SEQUENCE: 781
cagcctgtga tgtaacattc agtcctg                                            27

SEQ ID NO: 782           moltype = RNA  length = 27
FEATURE                  Location/Qualifiers
source                   1..27
                         mol_type = other RNA
                         organism = synthetic construct
                         note = Synthetic
SEQUENCE: 782
ccagctagtg atgtaacatt cagtcct                                            27

SEQ ID NO: 783           moltype = RNA  length = 27
FEATURE                  Location/Qualifiers
source                   1..27
                         mol_type = other RNA
                         organism = synthetic construct
                         note = Synthetic
SEQUENCE: 783
cccagtcagt gatgtaacat tcagtcc                                            27

SEQ ID NO: 784           moltype = RNA  length = 27
FEATURE                  Location/Qualifiers
source                   1..27
                         mol_type = other RNA
                         organism = synthetic construct
                         note = Synthetic
SEQUENCE: 784
ccccatccag tgatgtaaca ttcagtc                                            27

SEQ ID NO: 785           moltype = RNA  length = 27
FEATURE                  Location/Qualifiers
source                   1..27
                         mol_type = other RNA
                         organism = synthetic construct
                         note = Synthetic
SEQUENCE: 785
tcccctgcca gtgatgtaac attcagt                                            27

SEQ ID NO: 786           moltype = RNA  length = 27
FEATURE                  Location/Qualifiers
source                   1..27
                         mol_type = other RNA
                         organism = synthetic construct
                         note = Synthetic
SEQUENCE: 786
tctcctcagc cagtgatgta acattca                                            27

SEQ ID NO: 787           moltype = RNA  length = 27
FEATURE                  Location/Qualifiers
source                   1..27
                         mol_type = other RNA
                         organism = synthetic construct
                         note = Synthetic
SEQUENCE: 787
cagtctcaaa ggtaccttgg gtttctc                                            27

SEQ ID NO: 788           moltype = RNA  length = 22
FEATURE                  Location/Qualifiers
source                   1..22
                         mol_type = other RNA
                         organism = synthetic construct
                         note = Synthetic
SEQUENCE: 788
tttcctgtga cagtggtgga gg                                                 22

SEQ ID NO: 789           moltype = RNA  length = 22
FEATURE                  Location/Qualifiers
source                   1..22
                         mol_type = other RNA
                         organism = synthetic construct
                         note = Synthetic
SEQUENCE: 789
tataactctg tccattacca gg                                                 22
```

-continued

| | | |
|---|---|---|
| SEQ ID NO: 790<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 790<br>tatcgtgtca ggttgcagta gg | | 22 |
| SEQ ID NO: 791<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 791<br>taccaagctt ggcaagttct gg | | 22 |
| SEQ ID NO: 792<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 792<br>ttgaccaagc ttggcaagtt gg | | 22 |
| SEQ ID NO: 793<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 793<br>tagatgacca agcttggcaa gg | | 22 |
| SEQ ID NO: 794<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 794<br>tcctcgataa ctctgtccat gg | | 22 |
| SEQ ID NO: 795<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 795<br>tgcctcgata actctgtcca gg | | 22 |
| SEQ ID NO: 796<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 796<br>tgtggtatca tagatgacca gg | | 22 |
| SEQ ID NO: 797<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 797<br>taatctggat tcctgcagta gg | | 22 |
| SEQ ID NO: 798<br>FEATURE<br>source | moltype = RNA  length = 22<br>Location/Qualifiers<br>1..22<br>mol_type = other RNA<br>organism = synthetic construct<br>note = Synthetic | |
| SEQUENCE: 798 | | |

```
tatgcttcca ggacatttct gg                                                    22

SEQ ID NO: 799          moltype = RNA   length = 22
FEATURE                 Location/Qualifiers
source                  1..22
                        mol_type = other RNA
                        organism = synthetic construct
                        note = Synthetic
SEQUENCE: 799
ttggataata ttctgttgtc gg                                                    22

SEQ ID NO: 800          moltype = RNA   length = 22
FEATURE                 Location/Qualifiers
source                  1..22
                        mol_type = other RNA
                        organism = synthetic construct
                        note = Synthetic
SEQUENCE: 800
tccttgataa ctctgtccat gg                                                    22

SEQ ID NO: 801          moltype = RNA   length = 22
FEATURE                 Location/Qualifiers
source                  1..22
                        mol_type = other RNA
                        organism = synthetic construct
                        note = Synthetic
SEQUENCE: 801
ttggataata ttctgttgtc gg                                                    22

SEQ ID NO: 802          moltype = RNA   length = 22
FEATURE                 Location/Qualifiers
source                  1..22
                        mol_type = other RNA
                        organism = synthetic construct
                        note = Synthetic
SEQUENCE: 802
tccttgataa ctctgtccat gg                                                    22

SEQ ID NO: 803          moltype = RNA   length = 22
FEATURE                 Location/Qualifiers
source                  1..22
                        mol_type = other RNA
                        organism = synthetic construct
                        note = Synthetic
SEQUENCE: 803
ttggataata ttctgttgtc gg                                                    22

SEQ ID NO: 804          moltype = RNA   length = 19
FEATURE                 Location/Qualifiers
source                  1..19
                        mol_type = other RNA
                        organism = synthetic construct
                        note = Synthetic
SEQUENCE: 804
ctgagcaaag ccatgtggt                                                        19

SEQ ID NO: 805          moltype = RNA   length = 19
FEATURE                 Location/Qualifiers
source                  1..19
                        mol_type = other RNA
                        organism = synthetic construct
                        note = Synthetic
SEQUENCE: 805
agcaaagcca tgtggtcca                                                        19

SEQ ID NO: 806          moltype = RNA   length = 19
FEATURE                 Location/Qualifiers
source                  1..19
                        mol_type = other RNA
                        organism = synthetic construct
                        note = Synthetic
SEQUENCE: 806
aagccatgtg gtccaggat                                                        19

SEQ ID NO: 807          moltype = RNA   length = 19
FEATURE                 Location/Qualifiers
source                  1..19
                        mol_type = other RNA
                        organism = synthetic construct
```

```
                            note = Synthetic
SEQUENCE: 807
agccatgtgg tccaggatt                                                         19

SEQ ID NO: 808          moltype = RNA   length = 19
FEATURE                 Location/Qualifiers
source                  1..19
                        mol_type = other RNA
                        organism = synthetic construct
                        note = Synthetic
SEQUENCE: 808
gccatgtggt ccaggattg                                                         19

SEQ ID NO: 809          moltype = RNA   length = 19
FEATURE                 Location/Qualifiers
source                  1..19
                        mol_type = other RNA
                        organism = synthetic construct
                        note = Synthetic
SEQUENCE: 809
ccatgtggtc caggattgc                                                         19

SEQ ID NO: 810          moltype = RNA   length = 19
FEATURE                 Location/Qualifiers
source                  1..19
                        mol_type = other RNA
                        organism = synthetic construct
                        note = Synthetic
SEQUENCE: 810
catgtggtcc aggattgct                                                         19

SEQ ID NO: 811          moltype = RNA   length = 19
FEATURE                 Location/Qualifiers
source                  1..19
                        mol_type = other RNA
                        organism = synthetic construct
                        note = Synthetic
SEQUENCE: 811
atgtggtcca ggattgcta                                                         19

SEQ ID NO: 812          moltype = RNA   length = 19
FEATURE                 Location/Qualifiers
source                  1..19
                        mol_type = other RNA
                        organism = synthetic construct
                        note = Synthetic
SEQUENCE: 812
tgtggtccag gattgctac                                                         19

SEQ ID NO: 813          moltype = RNA   length = 19
FEATURE                 Location/Qualifiers
source                  1..19
                        mol_type = other RNA
                        organism = synthetic construct
                        note = Synthetic
SEQUENCE: 813
ggtgatggac agagttatc                                                         19

SEQ ID NO: 814          moltype = RNA   length = 19
FEATURE                 Location/Qualifiers
source                  1..19
                        mol_type = other RNA
                        organism = synthetic construct
                        note = Synthetic
SEQUENCE: 814
tccaccactg tcacaggaa                                                         19

SEQ ID NO: 815          moltype = RNA   length = 19
FEATURE                 Location/Qualifiers
source                  1..19
                        mol_type = other RNA
                        organism = synthetic construct
                        note = Synthetic
SEQUENCE: 815
ccaccactgt cacaggaag                                                         19

SEQ ID NO: 816          moltype = RNA   length = 19
FEATURE                 Location/Qualifiers
source                  1..19
```

|     |     |     |
| --- | --- | --- |
|  | moltype = other RNA<br>organism = synthetic construct<br>note = Synthetic |  |
| SEQUENCE: 816<br>ctgtcacagg aaggacctg |  | 19 |
| SEQ ID NO: 817<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 817<br>ggaaggacct gccaagctt |  | 19 |
| SEQ ID NO: 818<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 818<br>gaaggacctg ccaagcttg |  | 19 |
| SEQ ID NO: 819<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 819<br>aggacctgcc aagcttggt |  | 19 |
| SEQ ID NO: 820<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 820<br>ggacctgcca agcttggtc |  | 19 |
| SEQ ID NO: 821<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 821<br>gacctgccaa gcttggtca |  | 19 |
| SEQ ID NO: 822<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 822<br>acctgccaag cttggtcat |  | 19 |
| SEQ ID NO: 823<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 823<br>cctgccaagc ttggtcatc |  | 19 |
| SEQ ID NO: 824<br>FEATURE<br>source | moltype = RNA   length = 19<br>Location/Qualifiers<br>1..19<br>mol_type = other RNA<br>organism = synthetic construct<br>note = Synthetic |  |
| SEQUENCE: 824<br>agcttggtca tctatgaca |  | 19 |
| SEQ ID NO: 825 | moltype = RNA   length = 19 |  |

```
FEATURE                 Location/Qualifiers
source                  1..19
                        mol_type = other RNA
                        organism = synthetic construct
                        note = Synthetic
SEQUENCE: 825
gtcatctatg acaccacat                                                    19

SEQ ID NO: 826          moltype = RNA  length = 19
FEATURE                 Location/Qualifiers
source                  1..19
                        mol_type = other RNA
                        organism = synthetic construct
                        note = Synthetic
SEQUENCE: 826
cacagaaaac tacccaaat                                                    19

SEQ ID NO: 827          moltype = RNA  length = 19
FEATURE                 Location/Qualifiers
source                  1..19
                        mol_type = other RNA
                        organism = synthetic construct
                        note = Synthetic
SEQUENCE: 827
agaaaactac ccaaatgct                                                    19

SEQ ID NO: 828          moltype = RNA  length = 19
FEATURE                 Location/Qualifiers
source                  1..19
                        mol_type = other RNA
                        organism = synthetic construct
                        note = Synthetic
SEQUENCE: 828
aaaactaccc aaatgctgg                                                    19

SEQ ID NO: 829          moltype = RNA  length = 19
FEATURE                 Location/Qualifiers
source                  1..19
                        mol_type = other RNA
                        organism = synthetic construct
                        note = Synthetic
SEQUENCE: 829
acccaaatgc tggcttgat                                                    19

SEQ ID NO: 830          moltype = RNA  length = 19
FEATURE                 Location/Qualifiers
source                  1..19
                        mol_type = other RNA
                        organism = synthetic construct
                        note = Synthetic
SEQUENCE: 830
cccaaatgct ggcttgatc                                                    19

SEQ ID NO: 831          moltype = RNA  length = 19
FEATURE                 Location/Qualifiers
source                  1..19
                        mol_type = other RNA
                        organism = synthetic construct
                        note = Synthetic
SEQUENCE: 831
gaactactgc aggaatcca                                                    19

SEQ ID NO: 832          moltype = RNA  length = 19
FEATURE                 Location/Qualifiers
source                  1..19
                        mol_type = other RNA
                        organism = synthetic construct
                        note = Synthetic
SEQUENCE: 832
tactgcagga atccagatg                                                    19

SEQ ID NO: 833          moltype = RNA  length = 19
FEATURE                 Location/Qualifiers
source                  1..19
                        mol_type = other RNA
                        organism = synthetic construct
                        note = Synthetic
SEQUENCE: 833
actgcaggaa tccagatgc                                                    19
```

```
SEQ ID NO: 834           moltype = RNA   length = 19
FEATURE                  Location/Qualifiers
source                   1..19
                         mol_type = other RNA
                         organism = synthetic construct
                         note = Synthetic
SEQUENCE: 834
tgcaggaatc cagatgctg                                                     19

SEQ ID NO: 835           moltype = RNA   length = 19
FEATURE                  Location/Qualifiers
source                   1..19
                         mol_type = other RNA
                         organism = synthetic construct
                         note = Synthetic
SEQUENCE: 835
aggtgggagt actgcaacc                                                     19

SEQ ID NO: 836           moltype = RNA   length = 19
FEATURE                  Location/Qualifiers
source                   1..19
                         mol_type = other RNA
                         organism = synthetic construct
                         note = Synthetic
SEQUENCE: 836
aatgctcaga cgcagaagg                                                     19

SEQ ID NO: 837           moltype = RNA   length = 19
FEATURE                  Location/Qualifiers
source                   1..19
                         mol_type = other RNA
                         organism = synthetic construct
                         note = Synthetic
SEQUENCE: 837
gactgttacc ccggttcca                                                     19

SEQ ID NO: 838           moltype = RNA   length = 19
FEATURE                  Location/Qualifiers
source                   1..19
                         mol_type = other RNA
                         organism = synthetic construct
                         note = Synthetic
SEQUENCE: 838
actgttaccc cggttccaa                                                     19

SEQ ID NO: 839           moltype = RNA   length = 19
FEATURE                  Location/Qualifiers
source                   1..19
                         mol_type = other RNA
                         organism = synthetic construct
                         note = Synthetic
SEQUENCE: 839
ctgttacccc ggttccaag                                                     19

SEQ ID NO: 840           moltype = RNA   length = 19
FEATURE                  Location/Qualifiers
source                   1..19
                         mol_type = other RNA
                         organism = synthetic construct
                         note = Synthetic
SEQUENCE: 840
tgttaccccg gttccaagc                                                     19

SEQ ID NO: 841           moltype = RNA   length = 19
FEATURE                  Location/Qualifiers
source                   1..19
                         mol_type = other RNA
                         organism = synthetic construct
                         note = Synthetic
SEQUENCE: 841
gttaccccgg ttccaagcc                                                     19

SEQ ID NO: 842           moltype = RNA   length = 19
FEATURE                  Location/Qualifiers
source                   1..19
                         mol_type = other RNA
                         organism = synthetic construct
                         note = Synthetic
```

| | | |
|---|---|---|
| SEQUENCE: 842 ttaccccggt tccaagcct | | 19 |
| SEQ ID NO: 843 FEATURE source | moltype = RNA length = 19 Location/Qualifiers 1..19 mol_type = other RNA organism = synthetic construct note = Synthetic | |
| SEQUENCE: 843 taccccggtt ccaagccta | | 19 |
| SEQ ID NO: 844 FEATURE source | moltype = RNA length = 19 Location/Qualifiers 1..19 mol_type = other RNA organism = synthetic construct note = Synthetic | |
| SEQUENCE: 844 gtgctaccat ggtaatgga | | 19 |
| SEQ ID NO: 845 FEATURE source | moltype = RNA length = 19 Location/Qualifiers 1..19 mol_type = other RNA organism = synthetic construct note = Synthetic | |
| SEQUENCE: 845 tgctaccatg gtaatggac | | 19 |
| SEQ ID NO: 846 FEATURE source | moltype = RNA length = 19 Location/Qualifiers 1..19 mol_type = other RNA organism = synthetic construct note = Synthetic | |
| SEQUENCE: 846 gctaccatgg taatggaca | | 19 |
| SEQ ID NO: 847 FEATURE source | moltype = RNA length = 19 Location/Qualifiers 1..19 mol_type = other RNA organism = synthetic construct note = Synthetic | |
| SEQUENCE: 847 ctaccatggt aatggacag | | 19 |
| SEQ ID NO: 848 FEATURE source | moltype = RNA length = 19 Location/Qualifiers 1..19 mol_type = other RNA organism = synthetic construct note = Synthetic | |
| SEQUENCE: 848 taccatggta atggacaga | | 19 |
| SEQ ID NO: 849 FEATURE source | moltype = RNA length = 19 Location/Qualifiers 1..19 mol_type = other RNA organism = synthetic construct note = Synthetic | |
| SEQUENCE: 849 accatggtaa tggacagag | | 19 |
| SEQ ID NO: 850 FEATURE source | moltype = RNA length = 19 Location/Qualifiers 1..19 mol_type = other RNA organism = synthetic construct note = Synthetic | |
| SEQUENCE: 850 ccatggtaat ggacagagt | | 19 |
| SEQ ID NO: 851 FEATURE source | moltype = RNA length = 19 Location/Qualifiers 1..19 mol_type = other RNA | |

```
                            organism = synthetic construct
                            note = Synthetic
SEQUENCE: 851
catggtaatg gacagagtt                                                   19

SEQ ID NO: 852              moltype = RNA   length = 19
FEATURE                     Location/Qualifiers
source                      1..19
                            mol_type = other RNA
                            organism = synthetic construct
                            note = Synthetic
SEQUENCE: 852
atggtaatgg acagagtta                                                   19

SEQ ID NO: 853              moltype = RNA   length = 19
FEATURE                     Location/Qualifiers
source                      1..19
                            mol_type = other RNA
                            organism = synthetic construct
                            note = Synthetic
SEQUENCE: 853
tggtaatgga cagagttat                                                   19

SEQ ID NO: 854              moltype = RNA   length = 19
FEATURE                     Location/Qualifiers
source                      1..19
                            mol_type = other RNA
                            organism = synthetic construct
                            note = Synthetic
SEQUENCE: 854
ggtaatggac agagttatc                                                   19

SEQ ID NO: 855              moltype = RNA   length = 19
FEATURE                     Location/Qualifiers
source                      1..19
                            mol_type = other RNA
                            organism = synthetic construct
                            note = Synthetic
SEQUENCE: 855
gtaatggaca gagttatcg                                                   19

SEQ ID NO: 856              moltype = RNA   length = 19
FEATURE                     Location/Qualifiers
source                      1..19
                            mol_type = other RNA
                            organism = synthetic construct
                            note = Synthetic
SEQUENCE: 856
ggcacatact ccaccactg                                                   19

SEQ ID NO: 857              moltype = RNA   length = 19
FEATURE                     Location/Qualifiers
source                      1..19
                            mol_type = other RNA
                            organism = synthetic construct
                            note = Synthetic
SEQUENCE: 857
cttggtcatc tatgacacc                                                   19

SEQ ID NO: 858              moltype = RNA   length = 19
FEATURE                     Location/Qualifiers
source                      1..19
                            mol_type = other RNA
                            organism = synthetic construct
                            note = Synthetic
SEQUENCE: 858
gtcatctatg acaccacac                                                   19

SEQ ID NO: 859              moltype = RNA   length = 19
FEATURE                     Location/Qualifiers
source                      1..19
                            mol_type = other RNA
                            organism = synthetic construct
                            note = Synthetic
SEQUENCE: 859
tcatctatga caccacact                                                   19

SEQ ID NO: 860              moltype = RNA   length = 19
FEATURE                     Location/Qualifiers
```

```
source                  1..19
                        mol_type = other RNA
                        organism = synthetic construct
                        note = Synthetic
SEQUENCE: 860
catctatgac accacactc                                                    19

SEQ ID NO: 861          moltype = RNA   length = 19
FEATURE                 Location/Qualifiers
source                  1..19
                        mol_type = other RNA
                        organism = synthetic construct
                        note = Synthetic
SEQUENCE: 861
gcacatactc caccactgt                                                    19

SEQ ID NO: 862          moltype = RNA   length = 19
FEATURE                 Location/Qualifiers
source                  1..19
                        mol_type = other RNA
                        organism = synthetic construct
                        note = Synthetic
SEQUENCE: 862
agcccttat tgttatacg                                                     19

SEQ ID NO: 863          moltype = RNA   length = 19
FEATURE                 Location/Qualifiers
source                  1..19
                        mol_type = other RNA
                        organism = synthetic construct
                        note = Synthetic
SEQUENCE: 863
gcccttatt gttatacga                                                     19

SEQ ID NO: 864          moltype = RNA   length = 19
FEATURE                 Location/Qualifiers
source                  1..19
                        mol_type = other RNA
                        organism = synthetic construct
                        note = Synthetic
SEQUENCE: 864
ccaagcctag aggctcctt                                                    19

SEQ ID NO: 865          moltype = RNA   length = 19
FEATURE                 Location/Qualifiers
source                  1..19
                        mol_type = other RNA
                        organism = synthetic construct
                        note = Synthetic
SEQUENCE: 865
aggctccttc tgaacaagc                                                    19

SEQ ID NO: 866          moltype = RNA   length = 19
FEATURE                 Location/Qualifiers
source                  1..19
                        mol_type = other RNA
                        organism = synthetic construct
                        note = Synthetic
SEQUENCE: 866
atggacagag ttatcaagg                                                    19

SEQ ID NO: 867          moltype = RNA   length = 19
FEATURE                 Location/Qualifiers
source                  1..19
                        mol_type = other RNA
                        organism = synthetic construct
                        note = Synthetic
SEQUENCE: 867
tggacagagt tatcaaggc                                                    19

SEQ ID NO: 868          moltype = RNA   length = 19
FEATURE                 Location/Qualifiers
source                  1..19
                        mol_type = other RNA
                        organism = synthetic construct
                        note = Synthetic
SEQUENCE: 868
ggacagagtt atcaaggca                                                    19
```

| | | |
|---|---|---|
| SEQ ID NO: 869<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 869<br>gacagagtta tcaaggcac | | 19 |
| SEQ ID NO: 870<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 870<br>acagagttat caaggcaca | | 19 |
| SEQ ID NO: 871<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 871<br>cagagttatc aaggcacat | | 19 |
| SEQ ID NO: 872<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 872<br>tacccaaatg ctggcttga | | 19 |
| SEQ ID NO: 873<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 873<br>ccaaatgctg gcttgatca | | 19 |
| SEQ ID NO: 874<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 874<br>tcaagaacta ctgccgaaa | | 19 |
| SEQ ID NO: 875<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 875<br>caagaactac tgccgaaat | | 19 |
| SEQ ID NO: 876<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 876<br>aagaactact gccgaaatc | | 19 |
| SEQ ID NO: 877<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 877 | | |

-continued

```
gaactactgc cgaaatcca                                                      19

SEQ ID NO: 878         moltype = RNA   length = 19
FEATURE                Location/Qualifiers
source                 1..19
                       mol_type = other RNA
                       organism = synthetic construct
                       note = Synthetic
SEQUENCE: 878
ctactgccga aatccagat                                                      19

SEQ ID NO: 879         moltype = RNA   length = 19
FEATURE                Location/Qualifiers
source                 1..19
                       mol_type = other RNA
                       organism = synthetic construct
                       note = Synthetic
SEQUENCE: 879
tgtggcagcc ccttggtgt                                                      19

SEQ ID NO: 880         moltype = RNA   length = 19
FEATURE                Location/Qualifiers
source                 1..19
                       mol_type = other RNA
                       organism = synthetic construct
                       note = Synthetic
SEQUENCE: 880
gtggcagccc cttggtgtt                                                      19

SEQ ID NO: 881         moltype = RNA   length = 19
FEATURE                Location/Qualifiers
source                 1..19
                       mol_type = other RNA
                       organism = synthetic construct
                       note = Synthetic
SEQUENCE: 881
tggcagcccc ttggtgtta                                                      19

SEQ ID NO: 882         moltype = RNA   length = 19
FEATURE                Location/Qualifiers
source                 1..19
                       mol_type = other RNA
                       organism = synthetic construct
                       note = Synthetic
SEQUENCE: 882
ggcagcccct tggtgttat                                                      19

SEQ ID NO: 883         moltype = RNA   length = 19
FEATURE                Location/Qualifiers
source                 1..19
                       mol_type = other RNA
                       organism = synthetic construct
                       note = Synthetic
SEQUENCE: 883
gcagcccctt ggtgttata                                                      19

SEQ ID NO: 884         moltype = RNA   length = 19
FEATURE                Location/Qualifiers
source                 1..19
                       mol_type = other RNA
                       organism = synthetic construct
                       note = Synthetic
SEQUENCE: 884
cagcccettg gtgttatac                                                      19

SEQ ID NO: 885         moltype = RNA   length = 19
FEATURE                Location/Qualifiers
source                 1..19
                       mol_type = other RNA
                       organism = synthetic construct
                       note = Synthetic
SEQUENCE: 885
agccccttgg tgttataca                                                      19

SEQ ID NO: 886         moltype = RNA   length = 19
FEATURE                Location/Qualifiers
source                 1..19
                       mol_type = other RNA
                       organism = synthetic construct
```

-continued

```
                          note = Synthetic
SEQUENCE: 886
gccccttggt gttatacaa                                                19

SEQ ID NO: 887         moltype = RNA   length = 19
FEATURE                Location/Qualifiers
source                 1..19
                       mol_type = other RNA
                       organism = synthetic construct
                       note = Synthetic
SEQUENCE: 887
ccccttggtg ttatacaac                                                19

SEQ ID NO: 888         moltype = RNA   length = 19
FEATURE                Location/Qualifiers
source                 1..19
                       mol_type = other RNA
                       organism = synthetic construct
                       note = Synthetic
SEQUENCE: 888
ggtgggagta ctgcaacct                                                19

SEQ ID NO: 889         moltype = RNA   length = 19
FEATURE                Location/Qualifiers
source                 1..19
                       mol_type = other RNA
                       organism = synthetic construct
                       note = Synthetic
SEQUENCE: 889
gtgggagtac tgcaacctg                                                19

SEQ ID NO: 890         moltype = RNA   length = 19
FEATURE                Location/Qualifiers
source                 1..19
                       mol_type = other RNA
                       organism = synthetic construct
                       note = Synthetic
SEQUENCE: 890
ggagtactgc aacctgaca                                                19

SEQ ID NO: 891         moltype = RNA   length = 19
FEATURE                Location/Qualifiers
source                 1..19
                       mol_type = other RNA
                       organism = synthetic construct
                       note = Synthetic
SEQUENCE: 891
gagtactgca acctgacac                                                19

SEQ ID NO: 892         moltype = RNA   length = 19
FEATURE                Location/Qualifiers
source                 1..19
                       mol_type = other RNA
                       organism = synthetic construct
                       note = Synthetic
SEQUENCE: 892
gtactgcaac ctgacacga                                                19

SEQ ID NO: 893         moltype = RNA   length = 19
FEATURE                Location/Qualifiers
source                 1..19
                       mol_type = other RNA
                       organism = synthetic construct
                       note = Synthetic
SEQUENCE: 893
tactgcaacc tgacacgat                                                19

SEQ ID NO: 894         moltype = RNA   length = 19
FEATURE                Location/Qualifiers
source                 1..19
                       mol_type = other RNA
                       organism = synthetic construct
                       note = Synthetic
SEQUENCE: 894
actgcaacct gacacgatg                                                19

SEQ ID NO: 895         moltype = RNA   length = 19
FEATURE                Location/Qualifiers
source                 1..19
```

-continued

```
                        mol_type = other RNA
                        organism = synthetic construct
                        note = Synthetic
SEQUENCE: 895
ctgcaacctg acacgatgc                                                19

SEQ ID NO: 896          moltype = RNA   length = 19
FEATURE                 Location/Qualifiers
source                  1..19
                        mol_type = other RNA
                        organism = synthetic construct
                        note = Synthetic
SEQUENCE: 896
tgcaacctga cacgatgct                                                19

SEQ ID NO: 897          moltype = RNA   length = 19
FEATURE                 Location/Qualifiers
source                  1..19
                        mol_type = other RNA
                        organism = synthetic construct
                        note = Synthetic
SEQUENCE: 897
caacctgaca cgatgctca                                                19

SEQ ID NO: 898          moltype = RNA   length = 19
FEATURE                 Location/Qualifiers
source                  1..19
                        mol_type = other RNA
                        organism = synthetic construct
                        note = Synthetic
SEQUENCE: 898
acctgacacg atgctcaga                                                19

SEQ ID NO: 899          moltype = RNA   length = 19
FEATURE                 Location/Qualifiers
source                  1..19
                        mol_type = other RNA
                        organism = synthetic construct
                        note = Synthetic
SEQUENCE: 899
cctgacacga tgctcagat                                                19

SEQ ID NO: 900          moltype = RNA   length = 19
FEATURE                 Location/Qualifiers
source                  1..19
                        mol_type = other RNA
                        organism = synthetic construct
                        note = Synthetic
SEQUENCE: 900
ctgacacgat gctcagatg                                                19

SEQ ID NO: 901          moltype = RNA   length = 19
FEATURE                 Location/Qualifiers
source                  1..19
                        mol_type = other RNA
                        organism = synthetic construct
                        note = Synthetic
SEQUENCE: 901
tgacacgatg ctcagatgc                                                19

SEQ ID NO: 902          moltype = RNA   length = 19
FEATURE                 Location/Qualifiers
source                  1..19
                        mol_type = other RNA
                        organism = synthetic construct
                        note = Synthetic
SEQUENCE: 902
gacacgatgc tcagatgca                                                19

SEQ ID NO: 903          moltype = RNA   length = 19
FEATURE                 Location/Qualifiers
source                  1..19
                        mol_type = other RNA
                        organism = synthetic construct
                        note = Synthetic
SEQUENCE: 903
acacgatgct cagatgcag                                                19

SEQ ID NO: 904          moltype = RNA   length = 19
```

| | | |
|---|---|---|
| FEATURE<br>source | Location/Qualifiers<br>1..19<br>mol_type = other RNA<br>organism = synthetic construct<br>note = Synthetic | |
| SEQUENCE: 904<br>cacgatgctc agatgcaga | | 19 |
| SEQ ID NO: 905<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 905<br>tgctactacc attatggac | | 19 |
| SEQ ID NO: 906<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 906<br>gctactacca ttatggaca | | 19 |
| SEQ ID NO: 907<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 907<br>ctactaccat tatggacag | | 19 |
| SEQ ID NO: 908<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 908<br>tactaccatt atggacaga | | 19 |
| SEQ ID NO: 909<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 909<br>actaccatta tggacagag | | 19 |
| SEQ ID NO: 910<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 910<br>ctaccattat ggacagagt | | 19 |
| SEQ ID NO: 911<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 911<br>taccattatg gacagagtt | | 19 |
| SEQ ID NO: 912<br>FEATURE<br>source | moltype = RNA   length = 19<br>Location/Qualifiers<br>1..19<br>mol_type = other RNA<br>organism = synthetic construct<br>note = Synthetic | |
| SEQUENCE: 912<br>accattatgg acagagtta | | 19 |

```
SEQ ID NO: 913           moltype = RNA   length = 19
FEATURE                  Location/Qualifiers
source                   1..19
                         mol_type = other RNA
                         organism = synthetic construct
                         note = Synthetic
SEQUENCE: 913
gaggcacata ctccaccac                                                   19

SEQ ID NO: 914           moltype = RNA   length = 19
FEATURE                  Location/Qualifiers
source                   1..19
                         mol_type = other RNA
                         organism = synthetic construct
                         note = Synthetic
SEQUENCE: 914
ctccaccact gtcacagga                                                   19

SEQ ID NO: 915           moltype = RNA   length = 19
FEATURE                  Location/Qualifiers
source                   1..19
                         mol_type = other RNA
                         organism = synthetic construct
                         note = Synthetic
SEQUENCE: 915
acaggaagaa cttgccaag                                                   19

SEQ ID NO: 916           moltype = RNA   length = 19
FEATURE                  Location/Qualifiers
source                   1..19
                         mol_type = other RNA
                         organism = synthetic construct
                         note = Synthetic
SEQUENCE: 916
caggaagaac ttgccaagc                                                   19

SEQ ID NO: 917           moltype = RNA   length = 19
FEATURE                  Location/Qualifiers
source                   1..19
                         mol_type = other RNA
                         organism = synthetic construct
                         note = Synthetic
SEQUENCE: 917
aggaagaact tgccaagct                                                   19

SEQ ID NO: 918           moltype = RNA   length = 19
FEATURE                  Location/Qualifiers
source                   1..19
                         mol_type = other RNA
                         organism = synthetic construct
                         note = Synthetic
SEQUENCE: 918
ggaagaactt gccaagctt                                                   19

SEQ ID NO: 919           moltype = RNA   length = 19
FEATURE                  Location/Qualifiers
source                   1..19
                         mol_type = other RNA
                         organism = synthetic construct
                         note = Synthetic
SEQUENCE: 919
gaagaacttg ccaagcttg                                                   19

SEQ ID NO: 920           moltype = RNA   length = 19
FEATURE                  Location/Qualifiers
source                   1..19
                         mol_type = other RNA
                         organism = synthetic construct
                         note = Synthetic
SEQUENCE: 920
aagaacttgc caagcttgg                                                   19

SEQ ID NO: 921           moltype = RNA   length = 19
FEATURE                  Location/Qualifiers
source                   1..19
                         mol_type = other RNA
                         organism = synthetic construct
                         note = Synthetic
```

```
SEQUENCE: 921
agaacttgcc aagcttggt                                                          19

SEQ ID NO: 922         moltype = RNA  length = 19
FEATURE                Location/Qualifiers
source                 1..19
                       mol_type = other RNA
                       organism = synthetic construct
                       note = Synthetic SEQUENCE: 922
gaacttgcca agcttggtc                                                          19

SEQ ID NO: 923         moltype = RNA  length = 19
FEATURE                Location/Qualifiers
source                 1..19
                       mol_type = other RNA
                       organism = synthetic construct
                       note = Synthetic SEQUENCE: 923
aacttgccaa gcttggtca                                                          19

SEQ ID NO: 924         moltype = RNA  length = 19
FEATURE                Location/Qualifiers
source                 1..19
                       mol_type = other RNA
                       organism = synthetic construct
                       note = Synthetic SEQUENCE: 924
acttgccaag cttggtcat                                                          19

SEQ ID NO: 925         moltype = RNA  length = 19
FEATURE                Location/Qualifiers
source                 1..19
                       mol_type = other RNA
                       organism = synthetic construct
                       note = Synthetic SEQUENCE: 925
cttgccaagc ttggtcatc                                                          19

SEQ ID NO: 926         moltype = RNA  length = 19
FEATURE                Location/Qualifiers
source                 1..19
                       mol_type = other RNA
                       organism = synthetic construct
                       note = Synthetic SEQUENCE: 926
ttgccaagct tggtcatct                                                          19

SEQ ID NO: 927         moltype = RNA  length = 19
FEATURE                Location/Qualifiers
source                 1..19
                       mol_type = other RNA
                       organism = synthetic construct
                       note = Synthetic SEQUENCE: 927
tgccaagctt ggtcatcta                                                          19

SEQ ID NO: 928         moltype = RNA  length = 19
FEATURE                Location/Qualifiers
source                 1..19
                       mol_type = other RNA
                       organism = synthetic construct
                       note = Synthetic SEQUENCE: 928
gcttggtcat ctatgacac                                                          19

SEQ ID NO: 929         moltype = RNA  length = 19
FEATURE                Location/Qualifiers
source                 1..19
                       mol_type = other RNA
                       organism = synthetic construct
                       note = Synthetic SEQUENCE: 929
ttggtcatct atgacacca                                                          19

SEQ ID NO: 930         moltype = RNA  length = 19
FEATURE                Location/Qualifiers
source                 1..19
                       mol_type = other RNA
```

```
                                   -continued
                        organism = synthetic construct
                        note = Synthetic
SEQUENCE: 930
tggtcatcta tgacaccac                                                    19

SEQ ID NO: 931          moltype = RNA   length = 19
FEATURE                 Location/Qualifiers
source                  1..19
                        mol_type = other RNA
                        organism = synthetic construct
                        note = Synthetic
SEQUENCE: 931
gtcatctatg acaccacac                                                    19

SEQ ID NO: 932          moltype = RNA   length = 19
FEATURE                 Location/Qualifiers
source                  1..19
                        mol_type = other RNA
                        organism = synthetic construct
                        note = Synthetic
SEQUENCE: 932
catctatgac accacacca                                                    19

SEQ ID NO: 933          moltype = RNA   length = 19
FEATURE                 Location/Qualifiers
source                  1..19
                        mol_type = other RNA
                        organism = synthetic construct
                        note = Synthetic
SEQUENCE: 933
atctatgaca ccacaccag                                                    19

SEQ ID NO: 934          moltype = RNA   length = 19
FEATURE                 Location/Qualifiers
source                  1..19
                        mol_type = other RNA
                        organism = synthetic construct
                        note = Synthetic
SEQUENCE: 934
ctatgacacc acaccagca                                                    19

SEQ ID NO: 935          moltype = RNA   length = 19
FEATURE                 Location/Qualifiers
source                  1..19
                        mol_type = other RNA
                        organism = synthetic construct
                        note = Synthetic
SEQUENCE: 935
gtcggacccc agaaaacta                                                    19

SEQ ID NO: 936          moltype = RNA   length = 19
FEATURE                 Location/Qualifiers
source                  1..19
                        mol_type = other RNA
                        organism = synthetic construct
                        note = Synthetic
SEQUENCE: 936
tcggacccca gaaaactac                                                    19

SEQ ID NO: 937          moltype = RNA   length = 19
FEATURE                 Location/Qualifiers
source                  1..19
                        mol_type = other RNA
                        organism = synthetic construct
                        note = Synthetic
SEQUENCE: 937
gaaaactacc caaatgctg                                                    19

SEQ ID NO: 938          moltype = RNA   length = 19
FEATURE                 Location/Qualifiers
source                  1..19
                        mol_type = other RNA
                        organism = synthetic construct
                        note = Synthetic
SEQUENCE: 938
gctgagattc gcccttggt                                                    19

SEQ ID NO: 939          moltype = RNA   length = 19
FEATURE                 Location/Qualifiers
```

-continued

| | | |
|---|---|---|
| source | 1..19<br>mol_type = other RNA<br>organism = synthetic construct<br>note = Synthetic | |
| SEQUENCE: 939<br>ctgagattcg cccttggtg | | 19 |
| SEQ ID NO: 940<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 940<br>gagattcgcc cttggtgtt | | 19 |
| SEQ ID NO: 941<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 941<br>agattcgccc ttggtgtta | | 19 |
| SEQ ID NO: 942<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 942<br>ttcgcccttg gtgttacac | | 19 |
| SEQ ID NO: 943<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 943<br>cttggtgtta caccatgga | | 19 |
| SEQ ID NO: 944<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 944<br>ttggtgttac accatggat | | 19 |
| SEQ ID NO: 945<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 945<br>tggtgttaca ccatggatc | | 19 |
| SEQ ID NO: 946<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 946<br>ggtgttacac catggatcc | | 19 |
| SEQ ID NO: 947<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 947<br>tgttacacca tggatccca | | 19 |

```
SEQ ID NO: 948         moltype = RNA   length = 19
FEATURE                Location/Qualifiers
source                 1..19
                       mol_type = other RNA
                       organism = synthetic construct
                       note = Synthetic
SEQUENCE: 948
gaatcaagtg tccttgcaa                                                   19

SEQ ID NO: 949         moltype = RNA   length = 19
FEATURE                Location/Qualifiers
source                 1..19
                       mol_type = other RNA
                       organism = synthetic construct
                       note = Synthetic
SEQUENCE: 949
aatcaagtgt ccttgcaac                                                   19

SEQ ID NO: 950         moltype = RNA   length = 19
FEATURE                Location/Qualifiers
source                 1..19
                       mol_type = other RNA
                       organism = synthetic construct
                       note = Synthetic
SEQUENCE: 950
atcaagtgtc cttgcaact                                                   19

SEQ ID NO: 951         moltype = RNA   length = 19
FEATURE                Location/Qualifiers
source                 1..19
                       mol_type = other RNA
                       organism = synthetic construct
                       note = Synthetic
SEQUENCE: 951
atggacagag ttatcgagg                                                   19

SEQ ID NO: 952         moltype = RNA   length = 19
FEATURE                Location/Qualifiers
source                 1..19
                       mol_type = other RNA
                       organism = synthetic construct
                       note = Synthetic
SEQUENCE: 952
tggacagagt tatcgaggc                                                   19

SEQ ID NO: 953         moltype = RNA   length = 19
FEATURE                Location/Qualifiers
source                 1..19
                       mol_type = other RNA
                       organism = synthetic construct
                       note = Synthetic
SEQUENCE: 953
acaccacact ggcatcaga                                                   19

SEQ ID NO: 954         moltype = RNA   length = 19
FEATURE                Location/Qualifiers
source                 1..19
                       mol_type = other RNA
                       organism = synthetic construct
                       note = Synthetic
SEQUENCE: 954
ttggtgttat accatggat                                                   19

SEQ ID NO: 955         moltype = RNA   length = 19
FEATURE                Location/Qualifiers
source                 1..19
                       mol_type = other RNA
                       organism = synthetic construct
                       note = Synthetic
SEQUENCE: 955
tggtgttata ccatggatc                                                   19

SEQ ID NO: 956         moltype = RNA   length = 19
FEATURE                Location/Qualifiers
source                 1..19
                       mol_type = other RNA
                       organism = synthetic construct
                       note = Synthetic
SEQUENCE: 956
```

```
ggtgttatac catggatcc                                                  19

SEQ ID NO: 957          moltype = RNA   length = 19
FEATURE                 Location/Qualifiers
source                  1..19
                        mol_type = other RNA
                        organism = synthetic construct
                        note = Synthetic
SEQUENCE: 957
gtgttatacc atggatccc                                                  19

SEQ ID NO: 958          moltype = RNA   length = 19
FEATURE                 Location/Qualifiers
source                  1..19
                        mol_type = other RNA
                        organism = synthetic construct
                        note = Synthetic
SEQUENCE: 958
tcagatggga gtactgcaa                                                  19

SEQ ID NO: 959          moltype = RNA   length = 19
FEATURE                 Location/Qualifiers
source                  1..19
                        mol_type = other RNA
                        organism = synthetic construct
                        note = Synthetic
SEQUENCE: 959
gatgggagta ctgcaacct                                                  19

SEQ ID NO: 960          moltype = RNA   length = 19
FEATURE                 Location/Qualifiers
source                  1..19
                        mol_type = other RNA
                        organism = synthetic construct
                        note = Synthetic
SEQUENCE: 960
atgggagtac tgcaacctg                                                  19

SEQ ID NO: 961          moltype = RNA   length = 19
FEATURE                 Location/Qualifiers
source                  1..19
                        mol_type = other RNA
                        organism = synthetic construct
                        note = Synthetic
SEQUENCE: 961
tgggagtact gcaacctga                                                  19

SEQ ID NO: 962          moltype = RNA   length = 19
FEATURE                 Location/Qualifiers
source                  1..19
                        mol_type = other RNA
                        organism = synthetic construct
                        note = Synthetic
SEQUENCE: 962
gggagtactg caacctgac                                                  19

SEQ ID NO: 963          moltype = RNA   length = 19
FEATURE                 Location/Qualifiers
source                  1..19
                        mol_type = other RNA
                        organism = synthetic construct
                        note = Synthetic
SEQUENCE: 963
ggctgtttct gaacaagca                                                  19

SEQ ID NO: 964          moltype = RNA   length = 19
FEATURE                 Location/Qualifiers
source                  1..19
                        mol_type = other RNA
                        organism = synthetic construct
                        note = Synthetic
SEQUENCE: 964
gtttctgaac aagcaccaa                                                  19

SEQ ID NO: 965          moltype = RNA   length = 19
FEATURE                 Location/Qualifiers
source                  1..19
                        mol_type = other RNA
                        organism = synthetic construct
```

```
                              note = Synthetic
SEQUENCE: 965
ctccaccact gttacagga                                                    19

SEQ ID NO: 966          moltype = RNA   length = 19
FEATURE                 Location/Qualifiers
source                  1..19
                        mol_type = other RNA
                        organism = synthetic construct
                        note = Synthetic
SEQUENCE: 966
tccaccactg ttacaggaa                                                    19

SEQ ID NO: 967          moltype = RNA   length = 19
FEATURE                 Location/Qualifiers
source                  1..19
                        mol_type = other RNA
                        organism = synthetic construct
                        note = Synthetic
SEQUENCE: 967
ccaccactgt tacaggaag                                                    19

SEQ ID NO: 968          moltype = RNA   length = 19
FEATURE                 Location/Qualifiers
source                  1..19
                        mol_type = other RNA
                        organism = synthetic construct
                        note = Synthetic
SEQUENCE: 968
gacaccacac tggcatcag                                                    19

SEQ ID NO: 969          moltype = RNA   length = 19
FEATURE                 Location/Qualifiers
source                  1..19
                        mol_type = other RNA
                        organism = synthetic construct
                        note = Synthetic
SEQUENCE: 969
acaccacact ggcatcaga                                                    19

SEQ ID NO: 970          moltype = RNA   length = 19
FEATURE                 Location/Qualifiers
source                  1..19
                        mol_type = other RNA
                        organism = synthetic construct
                        note = Synthetic
SEQUENCE: 970
agaatactac ccaaatggt                                                    19

SEQ ID NO: 971          moltype = RNA   length = 19
FEATURE                 Location/Qualifiers
source                  1..19
                        mol_type = other RNA
                        organism = synthetic construct
                        note = Synthetic
SEQUENCE: 971
gaatactacc caaatggtg                                                    19

SEQ ID NO: 972          moltype = RNA   length = 19
FEATURE                 Location/Qualifiers
source                  1..19
                        mol_type = other RNA
                        organism = synthetic construct
                        note = Synthetic
SEQUENCE: 972
aatactaccc aaatggtgg                                                    19

SEQ ID NO: 973          moltype = RNA   length = 19
FEATURE                 Location/Qualifiers
source                  1..19
                        mol_type = other RNA
                        organism = synthetic construct
                        note = Synthetic
SEQUENCE: 973
tccttctgaa gaagcacca                                                    19

SEQ ID NO: 974          moltype = RNA   length = 19
FEATURE                 Location/Qualifiers
source                  1..19
```

```
                          mol_type = other RNA
                          organism = synthetic construct
                          note = Synthetic
SEQUENCE: 974
ccttctgaag aagcaccaa                                          19

SEQ ID NO: 975            moltype = RNA   length = 19
FEATURE                   Location/Qualifiers
source                    1..19
                          mol_type = other RNA
                          organism = synthetic construct
                          note = Synthetic
SEQUENCE: 975
cttctgaaga agcaccaac                                          19

SEQ ID NO: 976            moltype = RNA   length = 19
FEATURE                   Location/Qualifiers
source                    1..19
                          mol_type = other RNA
                          organism = synthetic construct
                          note = Synthetic
SEQUENCE: 976
ttctgaagaa gcaccaact                                          19

SEQ ID NO: 977            moltype = RNA   length = 19
FEATURE                   Location/Qualifiers
source                    1..19
                          mol_type = other RNA
                          organism = synthetic construct
                          note = Synthetic
SEQUENCE: 977
tctgaagaag caccaactg                                          19

SEQ ID NO: 978            moltype = RNA   length = 19
FEATURE                   Location/Qualifiers
source                    1..19
                          mol_type = other RNA
                          organism = synthetic construct
                          note = Synthetic
SEQUENCE: 978
ctgaagaagc accaactga                                          19

SEQ ID NO: 979            moltype = RNA   length = 19
FEATURE                   Location/Qualifiers
source                    1..19
                          mol_type = other RNA
                          organism = synthetic construct
                          note = Synthetic
SEQUENCE: 979
tgaagaagca ccaactgaa                                          19

SEQ ID NO: 980            moltype = RNA   length = 19
FEATURE                   Location/Qualifiers
source                    1..19
                          mol_type = other RNA
                          organism = synthetic construct
                          note = Synthetic
SEQUENCE: 980
gaagaagcac caactgaaa                                          19

SEQ ID NO: 981            moltype = RNA   length = 19
FEATURE                   Location/Qualifiers
source                    1..19
                          mol_type = other RNA
                          organism = synthetic construct
                          note = Synthetic
SEQUENCE: 981
aagaagcacc aactgaaaa                                          19

SEQ ID NO: 982            moltype = RNA   length = 19
FEATURE                   Location/Qualifiers
source                    1..19
                          mol_type = other RNA
                          organism = synthetic construct
                          note = Synthetic
SEQUENCE: 982
agaagcacca actgaaaac                                          19

SEQ ID NO: 983            moltype = RNA   length = 19
```

```
FEATURE                 Location/Qualifiers
source                  1..19
                        mol_type = other RNA
                        organism = synthetic construct
                        note = Synthetic SEQUENCE: 983
gaagcaccaa ctgaaaaca                                                 19

SEQ ID NO: 984          moltype = RNA  length = 19
FEATURE                 Location/Qualifiers
source                  1..19
                        mol_type = other RNA
                        organism = synthetic construct
                        note = Synthetic SEQUENCE: 984
aagcaccaac tgaaaacag                                                 19

SEQ ID NO: 985          moltype = RNA  length = 19
FEATURE                 Location/Qualifiers
source                  1..19
                        mol_type = other RNA
                        organism = synthetic construct
                        note = Synthetic SEQUENCE: 985
aggtgatgga cagagttat                                                 19

SEQ ID NO: 986          moltype = RNA  length = 19
FEATURE                 Location/Qualifiers
source                  1..19
                        mol_type = other RNA
                        organism = synthetic construct
                        note = Synthetic SEQUENCE: 986
ctccaccact atcacagga                                                 19

SEQ ID NO: 987          moltype = RNA  length = 19
FEATURE                 Location/Qualifiers
source                  1..19
                        mol_type = other RNA
                        organism = synthetic construct
                        note = Synthetic SEQUENCE: 987
tccaccacta tcacaggaa                                                 19

SEQ ID NO: 988          moltype = RNA  length = 19
FEATURE                 Location/Qualifiers
source                  1..19
                        mol_type = other RNA
                        organism = synthetic construct
                        note = Synthetic SEQUENCE: 988
ccaccactat cacaggaag                                                 19

SEQ ID NO: 989          moltype = RNA  length = 19
FEATURE                 Location/Qualifiers
source                  1..19
                        mol_type = other RNA
                        organism = synthetic construct
                        note = Synthetic SEQUENCE: 989
caccactatc acaggaaga                                                 19

SEQ ID NO: 990          moltype = RNA  length = 19
FEATURE                 Location/Qualifiers
source                  1..19
                        mol_type = other RNA
                        organism = synthetic construct
                        note = Synthetic SEQUENCE: 990
accactatca caggaagaa                                                 19

SEQ ID NO: 991          moltype = RNA  length = 19
FEATURE                 Location/Qualifiers
source                  1..19
                        mol_type = other RNA
                        organism = synthetic construct
                        note = Synthetic SEQUENCE: 991
ccactatcac aggaagaac                                                 19
```

| | | |
|---|---|---|
| SEQ ID NO: 992<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 992<br>cactatcaca ggaagaaca | | 19 |
| SEQ ID NO: 993<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 993<br>actatcacag gaagaacat | | 19 |
| SEQ ID NO: 994<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 994<br>ctatcacagg aagaacatg | | 19 |
| SEQ ID NO: 995<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 995<br>tatcacagga agaacatgt | | 19 |
| SEQ ID NO: 996<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 996<br>atcacaggaa gaacatgtc | | 19 |
| SEQ ID NO: 997<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 997<br>tcacaggaag aacatgtca | | 19 |
| SEQ ID NO: 998<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 998<br>cacaggaaga acatgtcag | | 19 |
| SEQ ID NO: 999<br>FEATURE<br>source | moltype = RNA  length = 19<br>Location/Qualifiers<br>1..19<br>mol_type = other RNA<br>organism = synthetic construct<br>note = Synthetic | |
| SEQUENCE: 999<br>acaggaagaa catgtcagt | | 19 |
| SEQ ID NO: 1000<br>FEATURE<br>source | moltype = RNA  length = 19<br>Location/Qualifiers<br>1..19<br>mol_type = other RNA<br>organism = synthetic construct<br>note = Synthetic | |

```
SEQUENCE: 1000
ggaagaacat gtcagtctt                                                              19

SEQ ID NO: 1001         moltype = RNA   length = 19
FEATURE                 Location/Qualifiers
source                  1..19
                        mol_type = other RNA
                        organism = synthetic construct
                        note = Synthetic
SEQUENCE: 1001
gaagaacatg tcagtcttg                                                              19

SEQ ID NO: 1002         moltype = RNA   length = 19
FEATURE                 Location/Qualifiers
source                  1..19
                        mol_type = other RNA
                        organism = synthetic construct
                        note = Synthetic
SEQUENCE: 1002
aagaacatgt cagtcttgg                                                              19

SEQ ID NO: 1003         moltype = RNA   length = 19
FEATURE                 Location/Qualifiers
source                  1..19
                        mol_type = other RNA
                        organism = synthetic construct
                        note = Synthetic
SEQUENCE: 1003
agaacatgtc agtcttggt                                                              19

SEQ ID NO: 1004         moltype = RNA   length = 19
FEATURE                 Location/Qualifiers
source                  1..19
                        mol_type = other RNA
                        organism = synthetic construct
                        note = Synthetic
SEQUENCE: 1004
ggcatcggag gatcccatt                                                              19

SEQ ID NO: 1005         moltype = RNA   length = 19
FEATURE                 Location/Qualifiers
source                  1..19
                        mol_type = other RNA
                        organism = synthetic construct
                        note = Synthetic
SEQUENCE: 1005
actatccaaa tgctggcct                                                              19

SEQ ID NO: 1006         moltype = RNA   length = 19
FEATURE                 Location/Qualifiers
source                  1..19
                        mol_type = other RNA
                        organism = synthetic construct
                        note = Synthetic
SEQUENCE: 1006
gcacagaggc tccttctga                                                              19

SEQ ID NO: 1007         moltype = RNA   length = 19
FEATURE                 Location/Qualifiers
source                  1..19
                        mol_type = other RNA
                        organism = synthetic construct
                        note = Synthetic
SEQUENCE: 1007
tccttctgaa caagcacca                                                              19

SEQ ID NO: 1008         moltype = RNA   length = 19
FEATURE                 Location/Qualifiers
source                  1..19
                        mol_type = other RNA
                        organism = synthetic construct
                        note = Synthetic
SEQUENCE: 1008
ccttctgaac aagcaccac                                                              19

SEQ ID NO: 1009         moltype = RNA   length = 19
FEATURE                 Location/Qualifiers
source                  1..19
                        mol_type = other RNA
```

```
                              organism = synthetic construct
                              note = Synthetic
SEQUENCE: 1009
cttctgaaca agcaccacc                                                        19

SEQ ID NO: 1010               moltype = RNA   length = 19
FEATURE                       Location/Qualifiers
source                        1..19
                              mol_type = other RNA
                              organism = synthetic construct
                              note = Synthetic
SEQUENCE: 1010
ttctgaacaa gcaccacct                                                        19

SEQ ID NO: 1011               moltype = RNA   length = 19
FEATURE                       Location/Qualifiers
source                        1..19
                              mol_type = other RNA
                              organism = synthetic construct
                              note = Synthetic
SEQUENCE: 1011
tctgaacaag caccacctg                                                        19

SEQ ID NO: 1012               moltype = RNA   length = 19
FEATURE                       Location/Qualifiers
source                        1..19
                              mol_type = other RNA
                              organism = synthetic construct
                              note = Synthetic
SEQUENCE: 1012
ctgaacaagc accacctga                                                        19

SEQ ID NO: 1013               moltype = RNA   length = 19
FEATURE                       Location/Qualifiers
source                        1..19
                              mol_type = other RNA
                              organism = synthetic construct
                              note = Synthetic
SEQUENCE: 1013
tgaacaagca ccacctgag                                                        19

SEQ ID NO: 1014               moltype = RNA   length = 19
FEATURE                       Location/Qualifiers
source                        1..19
                              mol_type = other RNA
                              organism = synthetic construct
                              note = Synthetic
SEQUENCE: 1014
gaacaagcac cacctgaga                                                        19

SEQ ID NO: 1015               moltype = RNA   length = 19
FEATURE                       Location/Qualifiers
source                        1..19
                              mol_type = other RNA
                              organism = synthetic construct
                              note = Synthetic
SEQUENCE: 1015
aacaagcacc acctgagaa                                                        19

SEQ ID NO: 1016               moltype = RNA   length = 19
FEATURE                       Location/Qualifiers
source                        1..19
                              mol_type = other RNA
                              organism = synthetic construct
                              note = Synthetic
SEQUENCE: 1016
caagcaccac ctgagaaaa                                                        19

SEQ ID NO: 1017               moltype = RNA   length = 19
FEATURE                       Location/Qualifiers
source                        1..19
                              mol_type = other RNA
                              organism = synthetic construct
                              note = Synthetic
SEQUENCE: 1017
aagcaccacc tgagaaaag                                                        19

SEQ ID NO: 1018               moltype = RNA   length = 19
FEATURE                       Location/Qualifiers
```

```
source             1..19
                   mol_type = other RNA
                   organism = synthetic construct
                   note = Synthetic
SEQUENCE: 1018
agcaccacct gagaaaagc                                               19

SEQ ID NO: 1019    moltype = RNA   length = 19
FEATURE            Location/Qualifiers
source             1..19
                   mol_type = other RNA
                   organism = synthetic construct
                   note = Synthetic
SEQUENCE: 1019
ctgagaaaag ccctgtggt                                               19

SEQ ID NO: 1020    moltype = RNA   length = 19
FEATURE            Location/Qualifiers
source             1..19
                   mol_type = other RNA
                   organism = synthetic construct
                   note = Synthetic
SEQUENCE: 1020
gccctgtggt ccaggattg                                               19

SEQ ID NO: 1021    moltype = RNA   length = 19
FEATURE            Location/Qualifiers
source             1..19
                   mol_type = other RNA
                   organism = synthetic construct
                   note = Synthetic
SEQUENCE: 1021
ctgtggtcca ggattgcta                                               19

SEQ ID NO: 1022    moltype = RNA   length = 19
FEATURE            Location/Qualifiers
source             1..19
                   mol_type = other RNA
                   organism = synthetic construct
                   note = Synthetic
SEQUENCE: 1022
ctccaccact gtcacagga                                               19

SEQ ID NO: 1023    moltype = RNA   length = 19
FEATURE            Location/Qualifiers
source             1..19
                   mol_type = other RNA
                   organism = synthetic construct
                   note = Synthetic
SEQUENCE: 1023
tccaccactg tcacaggaa                                               19

SEQ ID NO: 1024    moltype = RNA   length = 19
FEATURE            Location/Qualifiers
source             1..19
                   mol_type = other RNA
                   organism = synthetic construct
                   note = Synthetic
SEQUENCE: 1024
tcttggtcat ctatgatac                                               19

SEQ ID NO: 1025    moltype = RNA   length = 19
FEATURE            Location/Qualifiers
source             1..19
                   mol_type = other RNA
                   organism = synthetic construct
                   note = Synthetic
SEQUENCE: 1025
cttggtcatc tatgatacc                                               19

SEQ ID NO: 1026    moltype = RNA   length = 19
FEATURE            Location/Qualifiers
source             1..19
                   mol_type = other RNA
                   organism = synthetic construct
                   note = Synthetic
SEQUENCE: 1026
ttggtcatct atgatacca                                               19
```

```
SEQ ID NO: 1027            moltype = RNA  length = 19
FEATURE                    Location/Qualifiers
source                     1..19
                           mol_type = other RNA
                           organism = synthetic construct
                           note = Synthetic
SEQUENCE: 1027
tggtcatcta tgataccac                                               19

SEQ ID NO: 1028            moltype = RNA  length = 19
FEATURE                    Location/Qualifiers
source                     1..19
                           mol_type = other RNA
                           organism = synthetic construct
                           note = Synthetic
SEQUENCE: 1028
ggtcatctat gataccaca                                               19

SEQ ID NO: 1029            moltype = RNA  length = 19
FEATURE                    Location/Qualifiers
source                     1..19
                           mol_type = other RNA
                           organism = synthetic construct
                           note = Synthetic
SEQUENCE: 1029
gtcatctatg ataccacac                                               19

SEQ ID NO: 1030            moltype = RNA  length = 19
FEATURE                    Location/Qualifiers
source                     1..19
                           mol_type = other RNA
                           organism = synthetic construct
                           note = Synthetic
SEQUENCE: 1030
tcatctatga taccacact                                               19

SEQ ID NO: 1031            moltype = RNA  length = 19
FEATURE                    Location/Qualifiers
source                     1..19
                           mol_type = other RNA
                           organism = synthetic construct
                           note = Synthetic
SEQUENCE: 1031
catctatgat accacactg                                               19

SEQ ID NO: 1032            moltype = RNA  length = 19
FEATURE                    Location/Qualifiers
source                     1..19
                           mol_type = other RNA
                           organism = synthetic construct
                           note = Synthetic
SEQUENCE: 1032
atctatgata ccacactgg                                               19

SEQ ID NO: 1033            moltype = RNA  length = 19
FEATURE                    Location/Qualifiers
source                     1..19
                           mol_type = other RNA
                           organism = synthetic construct
                           note = Synthetic
SEQUENCE: 1033
tctatgatac cacactggc                                               19

SEQ ID NO: 1034            moltype = RNA  length = 19
FEATURE                    Location/Qualifiers
source                     1..19
                           mol_type = other RNA
                           organism = synthetic construct
                           note = Synthetic
SEQUENCE: 1034
ctatgatacc acactggca                                               19

SEQ ID NO: 1035            moltype = RNA  length = 19
FEATURE                    Location/Qualifiers
source                     1..19
                           mol_type = other RNA
                           organism = synthetic construct
                           note = Synthetic
SEQUENCE: 1035
```

```
tgataccaca ctggcatca                                              19

SEQ ID NO: 1036         moltype = RNA   length = 19
FEATURE                 Location/Qualifiers
source                  1..19
                        mol_type = other RNA
                        organism = synthetic construct
                        note = Synthetic
SEQUENCE: 1036
ataccacact ggcatcaga                                              19

SEQ ID NO: 1037         moltype = RNA   length = 19
FEATURE                 Location/Qualifiers
source                  1..19
                        mol_type = other RNA
                        organism = synthetic construct
                        note = Synthetic
SEQUENCE: 1037
agaggacccc agaaaacta                                              19

SEQ ID NO: 1038         moltype = RNA   length = 19
FEATURE                 Location/Qualifiers
source                  1..19
                        mol_type = other RNA
                        organism = synthetic construct
                        note = Synthetic
SEQUENCE: 1038
gaggacccca gaaaactac                                              19

SEQ ID NO: 1039         moltype = RNA   length = 19
FEATURE                 Location/Qualifiers
source                  1..19
                        mol_type = other RNA
                        organism = synthetic construct
                        note = Synthetic
SEQUENCE: 1039
agaactactg caggaatcc                                              19

SEQ ID NO: 1040         moltype = RNA   length = 19
FEATURE                 Location/Qualifiers
source                  1..19
                        mol_type = other RNA
                        organism = synthetic construct
                        note = Synthetic
SEQUENCE: 1040
actactgcag gaatccaga                                              19

SEQ ID NO: 1041         moltype = RNA   length = 19
FEATURE                 Location/Qualifiers
source                  1..19
                        mol_type = other RNA
                        organism = synthetic construct
                        note = Synthetic
SEQUENCE: 1041
tactgcagga atccagatt                                              19

SEQ ID NO: 1042         moltype = RNA   length = 19
FEATURE                 Location/Qualifiers
source                  1..19
                        mol_type = other RNA
                        organism = synthetic construct
                        note = Synthetic
SEQUENCE: 1042
actgcaggaa tccagattc                                              19

SEQ ID NO: 1043         moltype = RNA   length = 19
FEATURE                 Location/Qualifiers
source                  1..19
                        mol_type = other RNA
                        organism = synthetic construct
                        note = Synthetic
SEQUENCE: 1043
ctgcaggaat ccagattct                                              19

SEQ ID NO: 1044         moltype = RNA   length = 19
FEATURE                 Location/Qualifiers
source                  1..19
                        mol_type = other RNA
                        organism = synthetic construct
```

```
                              note = Synthetic
SEQUENCE: 1044
tgcaggaatc cagattctg                                                      19

SEQ ID NO: 1045               moltype = RNA   length = 19
FEATURE                       Location/Qualifiers
source                        1..19
                              mol_type = other RNA
                              organism = synthetic construct
                              note = Synthetic
SEQUENCE: 1045
gcaggaatcc agattctgg                                                      19

SEQ ID NO: 1046               moltype = RNA   length = 19
FEATURE                       Location/Qualifiers
source                        1..19
                              mol_type = other RNA
                              organism = synthetic construct
                              note = Synthetic
SEQUENCE: 1046
ggaatccaga ttctgggaa                                                      19

SEQ ID NO: 1047               moltype = RNA   length = 19
FEATURE                       Location/Qualifiers
source                        1..19
                              mol_type = other RNA
                              organism = synthetic construct
                              note = Synthetic
SEQUENCE: 1047
gggaaacaac cctggtgtt                                                      19

SEQ ID NO: 1048               moltype = RNA   length = 19
FEATURE                       Location/Qualifiers
source                        1..19
                              mol_type = other RNA
                              organism = synthetic construct
                              note = Synthetic
SEQUENCE: 1048
ggaaacaacc ctggtgtta                                                      19

SEQ ID NO: 1049               moltype = RNA   length = 19
FEATURE                       Location/Qualifiers
source                        1..19
                              mol_type = other RNA
                              organism = synthetic construct
                              note = Synthetic
SEQUENCE: 1049
tgtgtgaggt gggagtact                                                      19

SEQ ID NO: 1050               moltype = RNA   length = 19
FEATURE                       Location/Qualifiers
source                        1..19
                              mol_type = other RNA
                              organism = synthetic construct
                              note = Synthetic
SEQUENCE: 1050
gtgtgaggtg ggagtactg                                                      19

SEQ ID NO: 1051               moltype = RNA   length = 19
FEATURE                       Location/Qualifiers
source                        1..19
                              mol_type = other RNA
                              organism = synthetic construct
                              note = Synthetic
SEQUENCE: 1051
gtgaggtggg agtactgca                                                      19

SEQ ID NO: 1052               moltype = RNA   length = 19
FEATURE                       Location/Qualifiers
source                        1..19
                              mol_type = other RNA
                              organism = synthetic construct
                              note = Synthetic
SEQUENCE: 1052
tgaggtggga gtactgcaa                                                      19

SEQ ID NO: 1053               moltype = RNA   length = 19
FEATURE                       Location/Qualifiers
source                        1..19
```

```
                        mol_type = other RNA
                        organism = synthetic construct
                        note = Synthetic
SEQUENCE: 1053
ctgacacaat gctcagaaa                                                       19

SEQ ID NO: 1054         moltype = RNA   length = 19
FEATURE                 Location/Qualifiers
source                  1..19
                        mol_type = other RNA
                        organism = synthetic construct
                        note = Synthetic
SEQUENCE: 1054
tgacacaatg ctcagaaac                                                       19

SEQ ID NO: 1055         moltype = RNA   length = 19
FEATURE                 Location/Qualifiers
source                  1..19
                        mol_type = other RNA
                        organism = synthetic construct
                        note = Synthetic
SEQUENCE: 1055
gacacaatgc tcagaaaca                                                       19

SEQ ID NO: 1056         moltype = RNA   length = 19
FEATURE                 Location/Qualifiers
source                  1..19
                        mol_type = other RNA
                        organism = synthetic construct
                        note = Synthetic
SEQUENCE: 1056
acacaatgct cagaaacag                                                       19

SEQ ID NO: 1057         moltype = RNA   length = 19
FEATURE                 Location/Qualifiers
source                  1..19
                        mol_type = other RNA
                        organism = synthetic construct
                        note = Synthetic
SEQUENCE: 1057
cacaatgctc agaaacaga                                                       19

SEQ ID NO: 1058         moltype = RNA   length = 19
FEATURE                 Location/Qualifiers
source                  1..19
                        mol_type = other RNA
                        organism = synthetic construct
                        note = Synthetic
SEQUENCE: 1058
acaatgctca gaaacagaa                                                       19

SEQ ID NO: 1059         moltype = RNA   length = 19
FEATURE                 Location/Qualifiers
source                  1..19
                        mol_type = other RNA
                        organism = synthetic construct
                        note = Synthetic
SEQUENCE: 1059
caatgctcag aaacagaat                                                       19

SEQ ID NO: 1060         moltype = RNA   length = 19
FEATURE                 Location/Qualifiers
source                  1..19
                        mol_type = other RNA
                        organism = synthetic construct
                        note = Synthetic
SEQUENCE: 1060
aatgctcaga aacagaatc                                                       19

SEQ ID NO: 1061         moltype = RNA   length = 19
FEATURE                 Location/Qualifiers
source                  1..19
                        mol_type = other RNA
                        organism = synthetic construct
                        note = Synthetic
SEQUENCE: 1061
atgctcagaa acagaatca                                                       19

SEQ ID NO: 1062         moltype = RNA   length = 19
```

-continued

| FEATURE | Location/Qualifiers |
| --- | --- |
| source | 1..19<br>mol_type = other RNA<br>organism = synthetic construct<br>note = Synthetic |

SEQUENCE: 1062
tgctcagaaa cagaatcag                                                    19

SEQ ID NO: 1063      moltype = RNA   length = 19
FEATURE              Location/Qualifiers
source               1..19
                     mol_type = other RNA
                     organism = synthetic construct
                     note = Synthetic SEQUENCE: 1063
ctcagaaaca gaatcaggt                                                    19

SEQ ID NO: 1064      moltype = RNA   length = 19
FEATURE              Location/Qualifiers
source               1..19
                     mol_type = other RNA
                     organism = synthetic construct
                     note = Synthetic SEQUENCE: 1064
cagaaacaga atcaggtgt                                                    19

SEQ ID NO: 1065      moltype = RNA   length = 19
FEATURE              Location/Qualifiers
source               1..19
                     mol_type = other RNA
                     organism = synthetic construct
                     note = Synthetic SEQUENCE: 1065
agaaacagaa tcaggtgtc                                                    19

SEQ ID NO: 1066      moltype = RNA   length = 19
FEATURE              Location/Qualifiers
source               1..19
                     mol_type = other RNA
                     organism = synthetic construct
                     note = Synthetic SEQUENCE: 1066
gaaacagaat caggtgtcc                                                    19

SEQ ID NO: 1067      moltype = RNA   length = 19
FEATURE              Location/Qualifiers
source               1..19
                     mol_type = other RNA
                     organism = synthetic construct
                     note = Synthetic SEQUENCE: 1067
aaacagaatc aggtgtcct                                                    19

SEQ ID NO: 1068      moltype = RNA   length = 19
FEATURE              Location/Qualifiers
source               1..19
                     mol_type = other RNA
                     organism = synthetic construct
                     note = Synthetic SEQUENCE: 1068
aacagaatca ggtgtccta                                                    19

SEQ ID NO: 1069      moltype = RNA   length = 19
FEATURE              Location/Qualifiers
source               1..19
                     mol_type = other RNA
                     organism = synthetic construct
                     note = Synthetic SEQUENCE: 1069
cagaatcagg tgtcctaga                                                    19

SEQ ID NO: 1070      moltype = RNA   length = 19
FEATURE              Location/Qualifiers
source               1..19
                     mol_type = other RNA
                     organism = synthetic construct
                     note = Synthetic SEQUENCE: 1070
gaatcaggtg tcctagaga                                                    19

-continued

```
SEQ ID NO: 1071          moltype = RNA  length = 19
FEATURE                  Location/Qualifiers
source                   1..19
                         mol_type = other RNA
                         organism = synthetic construct
                         note = Synthetic
SEQUENCE: 1071
atcaggtgtc ctagagact                                                      19

SEQ ID NO: 1072          moltype = RNA  length = 19
FEATURE                  Location/Qualifiers
source                   1..19
                         mol_type = other RNA
                         organism = synthetic construct
                         note = Synthetic
SEQUENCE: 1072
ggtgtcctag agactccca                                                      19

SEQ ID NO: 1073          moltype = RNA  length = 19
FEATURE                  Location/Qualifiers
source                   1..19
                         mol_type = other RNA
                         organism = synthetic construct
                         note = Synthetic
SEQUENCE: 1073
cctagagact cccactgtt                                                      19

SEQ ID NO: 1074          moltype = RNA  length = 19
FEATURE                  Location/Qualifiers
source                   1..19
                         mol_type = other RNA
                         organism = synthetic construct
                         note = Synthetic
SEQUENCE: 1074
ctagagactc ccactgttg                                                      19

SEQ ID NO: 1075          moltype = RNA  length = 19
FEATURE                  Location/Qualifiers
source                   1..19
                         mol_type = other RNA
                         organism = synthetic construct
                         note = Synthetic
SEQUENCE: 1075
tagagactcc cactgttgt                                                      19

SEQ ID NO: 1076          moltype = RNA  length = 19
FEATURE                  Location/Qualifiers
source                   1..19
                         mol_type = other RNA
                         organism = synthetic construct
                         note = Synthetic
SEQUENCE: 1076
agagactccc actgttgtt                                                      19

SEQ ID NO: 1077          moltype = RNA  length = 19
FEATURE                  Location/Qualifiers
source                   1..19
                         mol_type = other RNA
                         organism = synthetic construct
                         note = Synthetic
SEQUENCE: 1077
gagactccca ctgttgttc                                                      19

SEQ ID NO: 1078          moltype = RNA  length = 19
FEATURE                  Location/Qualifiers
source                   1..19
                         mol_type = other RNA
                         organism = synthetic construct
                         note = Synthetic
SEQUENCE: 1078
agactcccac tgttgttcc                                                      19

SEQ ID NO: 1079          moltype = RNA  length = 19
FEATURE                  Location/Qualifiers
source                   1..19
                         mol_type = other RNA
                         organism = synthetic construct
                         note = Synthetic
```

| | | |
|---|---|---|
| SEQUENCE: 1079 gctcattctg aagcagcac | | 19 |
| SEQ ID NO: 1080 FEATURE source | moltype = RNA  length = 19 Location/Qualifiers 1..19 mol_type = other RNA organism = synthetic construct note = Synthetic | |
| SEQUENCE: 1080 ctcattctga agcagcacc | | 19 |
| SEQ ID NO: 1081 FEATURE source | moltype = RNA  length = 19 Location/Qualifiers 1..19 mol_type = other RNA organism = synthetic construct note = Synthetic | |
| SEQUENCE: 1081 tcattctgaa gcagcacca | | 19 |
| SEQ ID NO: 1082 FEATURE source | moltype = RNA  length = 19 Location/Qualifiers 1..19 mol_type = other RNA organism = synthetic construct note = Synthetic | |
| SEQUENCE: 1082 cattctgaag cagcaccaa | | 19 |
| SEQ ID NO: 1083 FEATURE source | moltype = RNA  length = 19 Location/Qualifiers 1..19 mol_type = other RNA organism = synthetic construct note = Synthetic | |
| SEQUENCE: 1083 attctgaagc agcaccaac | | 19 |
| SEQ ID NO: 1084 FEATURE source | moltype = RNA  length = 19 Location/Qualifiers 1..19 mol_type = other RNA organism = synthetic construct note = Synthetic | |
| SEQUENCE: 1084 ttctgaagca gcaccaact | | 19 |
| SEQ ID NO: 1085 FEATURE source | moltype = RNA  length = 19 Location/Qualifiers 1..19 mol_type = other RNA organism = synthetic construct note = Synthetic | |
| SEQUENCE: 1085 tctgaagcag caccaactg | | 19 |
| SEQ ID NO: 1086 FEATURE source | moltype = RNA  length = 19 Location/Qualifiers 1..19 mol_type = other RNA organism = synthetic construct note = Synthetic | |
| SEQUENCE: 1086 ctgaagcagc accaactga | | 19 |
| SEQ ID NO: 1087 FEATURE source | moltype = RNA  length = 19 Location/Qualifiers 1..19 mol_type = other RNA organism = synthetic construct note = Synthetic | |
| SEQUENCE: 1087 tgaagcagca ccaactgag | | 19 |
| SEQ ID NO: 1088 FEATURE source | moltype = RNA  length = 19 Location/Qualifiers 1..19 mol_type = other RNA | |

```
                                organism = synthetic construct
                                note = Synthetic
SEQUENCE: 1088
gaagcagcac caactgagc                                                     19

SEQ ID NO: 1089                 moltype = RNA   length = 19
FEATURE                         Location/Qualifiers
source                          1..19
                                mol_type = other RNA
                                organism = synthetic construct
                                note = Synthetic
SEQUENCE: 1089
aagcagcacc aactgagca                                                     19

SEQ ID NO: 1090                 moltype = RNA   length = 19
FEATURE                         Location/Qualifiers
source                          1..19
                                mol_type = other RNA
                                organism = synthetic construct
                                note = Synthetic
SEQUENCE: 1090
cagtgctacc atggtaatg                                                     19

SEQ ID NO: 1091                 moltype = RNA   length = 19
FEATURE                         Location/Qualifiers
source                          1..19
                                mol_type = other RNA
                                organism = synthetic construct
                                note = Synthetic
SEQUENCE: 1091
agtgctacca tggtaatgg                                                     19

SEQ ID NO: 1092                 moltype = RNA   length = 19
FEATURE                         Location/Qualifiers
source                          1..19
                                mol_type = other RNA
                                organism = synthetic construct
                                note = Synthetic
SEQUENCE: 1092
acattctcca ccactgtca                                                     19

SEQ ID NO: 1093                 moltype = RNA   length = 19
FEATURE                         Location/Qualifiers
source                          1..19
                                mol_type = other RNA
                                organism = synthetic construct
                                note = Synthetic
SEQUENCE: 1093
cactgtcaca ggaaggaca                                                     19

SEQ ID NO: 1094                 moltype = RNA   length = 19
FEATURE                         Location/Qualifiers
source                          1..19
                                mol_type = other RNA
                                organism = synthetic construct
                                note = Synthetic
SEQUENCE: 1094
actgtcacag gaaggacat                                                     19

SEQ ID NO: 1095                 moltype = RNA   length = 19
FEATURE                         Location/Qualifiers
source                          1..19
                                mol_type = other RNA
                                organism = synthetic construct
                                note = Synthetic
SEQUENCE: 1095
ctgtcacagg aaggacatg                                                     19

SEQ ID NO: 1096                 moltype = RNA   length = 19
FEATURE                         Location/Qualifiers
source                          1..19
                                mol_type = other RNA
                                organism = synthetic construct
                                note = Synthetic
SEQUENCE: 1096
tgtcacagga aggacatgt                                                     19

SEQ ID NO: 1097                 moltype = RNA   length = 19
FEATURE                         Location/Qualifiers
```

```
source                1..19
                      mol_type = other RNA
                      organism = synthetic construct
                      note = Synthetic
SEQUENCE: 1097
gtcacaggaa ggacatgtc                                              19

SEQ ID NO: 1098       moltype = RNA   length = 19
FEATURE               Location/Qualifiers
source                1..19
                      mol_type = other RNA
                      organism = synthetic construct
                      note = Synthetic
SEQUENCE: 1098
tcacaggaag gacatgtca                                              19

SEQ ID NO: 1099       moltype = RNA   length = 19
FEATURE               Location/Qualifiers
source                1..19
                      mol_type = other RNA
                      organism = synthetic construct
                      note = Synthetic
SEQUENCE: 1099
acaggaagga catgtcaat                                              19

SEQ ID NO: 1100       moltype = RNA   length = 19
FEATURE               Location/Qualifiers
source                1..19
                      mol_type = other RNA
                      organism = synthetic construct
                      note = Synthetic
SEQUENCE: 1100
caggaaggac atgtcaatc                                              19

SEQ ID NO: 1101       moltype = RNA   length = 19
FEATURE               Location/Qualifiers
source                1..19
                      mol_type = other RNA
                      organism = synthetic construct
                      note = Synthetic
SEQUENCE: 1101
aggaaggaca tgtcaatct                                              19

SEQ ID NO: 1102       moltype = RNA   length = 19
FEATURE               Location/Qualifiers
source                1..19
                      mol_type = other RNA
                      organism = synthetic construct
                      note = Synthetic
SEQUENCE: 1102
ggaaggacat gtcaatctt                                              19

SEQ ID NO: 1103       moltype = RNA   length = 19
FEATURE               Location/Qualifiers
source                1..19
                      mol_type = other RNA
                      organism = synthetic construct
                      note = Synthetic
SEQUENCE: 1103
gaaggacatg tcaatcttg                                              19

SEQ ID NO: 1104       moltype = RNA   length = 19
FEATURE               Location/Qualifiers
source                1..19
                      mol_type = other RNA
                      organism = synthetic construct
                      note = Synthetic
SEQUENCE: 1104
aaggacatgt caatcttgg                                              19

SEQ ID NO: 1105       moltype = RNA   length = 19
FEATURE               Location/Qualifiers
source                1..19
                      mol_type = other RNA
                      organism = synthetic construct
                      note = Synthetic
SEQUENCE: 1105
aggacatgtc aatcttggt                                              19
```

```
SEQ ID NO: 1106         moltype = RNA  length = 19
FEATURE                 Location/Qualifiers
source                  1..19
                        mol_type = other RNA
                        organism = synthetic construct
                        note = Synthetic
SEQUENCE: 1106
ggacatgtca atcttggtc                                                    19

SEQ ID NO: 1107         moltype = RNA  length = 19
FEATURE                 Location/Qualifiers
source                  1..19
                        mol_type = other RNA
                        organism = synthetic construct
                        note = Synthetic
SEQUENCE: 1107
gacatgtcaa tcttggtca                                                    19

SEQ ID NO: 1108         moltype = RNA  length = 19
FEATURE                 Location/Qualifiers
source                  1..19
                        mol_type = other RNA
                        organism = synthetic construct
                        note = Synthetic
SEQUENCE: 1108
acatgtcaat cttggtcat                                                    19

SEQ ID NO: 1109         moltype = RNA  length = 19
FEATURE                 Location/Qualifiers
source                  1..19
                        mol_type = other RNA
                        organism = synthetic construct
                        note = Synthetic
SEQUENCE: 1109
catgtcaatc ttggtcatc                                                    19

SEQ ID NO: 1110         moltype = RNA  length = 19
FEATURE                 Location/Qualifiers
source                  1..19
                        mol_type = other RNA
                        organism = synthetic construct
                        note = Synthetic
SEQUENCE: 1110
atgtcaatct tggtcatcc                                                    19

SEQ ID NO: 1111         moltype = RNA  length = 19
FEATURE                 Location/Qualifiers
source                  1..19
                        mol_type = other RNA
                        organism = synthetic construct
                        note = Synthetic
SEQUENCE: 1111
tgtcaatctt ggtcatcca                                                    19

SEQ ID NO: 1112         moltype = RNA  length = 19
FEATURE                 Location/Qualifiers
source                  1..19
                        mol_type = other RNA
                        organism = synthetic construct
                        note = Synthetic
SEQUENCE: 1112
gtcaatcttg gtcatccat                                                    19

SEQ ID NO: 1113         moltype = RNA  length = 19
FEATURE                 Location/Qualifiers
source                  1..19
                        mol_type = other RNA
                        organism = synthetic construct
                        note = Synthetic
SEQUENCE: 1113
tcaatcttgg tcatccatg                                                    19

SEQ ID NO: 1114         moltype = RNA  length = 19
FEATURE                 Location/Qualifiers
source                  1..19
                        mol_type = other RNA
                        organism = synthetic construct
                        note = Synthetic
SEQUENCE: 1114
```

```
caatcttggt catccatga                                             19

SEQ ID NO: 1115         moltype = RNA   length = 19
FEATURE                 Location/Qualifiers
source                  1..19
                        mol_type = other RNA
                        organism = synthetic construct
                        note = Synthetic
SEQUENCE: 1115
aatcttggtc atccatgac                                             19

SEQ ID NO: 1116         moltype = RNA   length = 19
FEATURE                 Location/Qualifiers
source                  1..19
                        mol_type = other RNA
                        organism = synthetic construct
                        note = Synthetic
SEQUENCE: 1116
atcttggtca tccatgaca                                             19

SEQ ID NO: 1117         moltype = RNA   length = 19
FEATURE                 Location/Qualifiers
source                  1..19
                        mol_type = other RNA
                        organism = synthetic construct
                        note = Synthetic
SEQUENCE: 1117
tgacaatgaa ctactgcag                                             19

SEQ ID NO: 1118         moltype = RNA   length = 19
FEATURE                 Location/Qualifiers
source                  1..19
                        mol_type = other RNA
                        organism = synthetic construct
                        note = Synthetic
SEQUENCE: 1118
gacaatgaac tactgcagg                                             19

SEQ ID NO: 1119         moltype = RNA   length = 19
FEATURE                 Location/Qualifiers
source                  1..19
                        mol_type = other RNA
                        organism = synthetic construct
                        note = Synthetic
SEQUENCE: 1119
acaatgaact actgcagga                                             19

SEQ ID NO: 1120         moltype = RNA   length = 19
FEATURE                 Location/Qualifiers
source                  1..19
                        mol_type = other RNA
                        organism = synthetic construct
                        note = Synthetic
SEQUENCE: 1120
caatgaacta ctgcaggaa                                             19

SEQ ID NO: 1121         moltype = RNA   length = 19
FEATURE                 Location/Qualifiers
source                  1..19
                        mol_type = other RNA
                        organism = synthetic construct
                        note = Synthetic
SEQUENCE: 1121
aatgaactac tgcaggaat                                             19

SEQ ID NO: 1122         moltype = RNA   length = 19
FEATURE                 Location/Qualifiers
source                  1..19
                        mol_type = other RNA
                        organism = synthetic construct
                        note = Synthetic
SEQUENCE: 1122
atgaactact gcaggaatc                                             19

SEQ ID NO: 1123         moltype = RNA   length = 19
FEATURE                 Location/Qualifiers
source                  1..19
                        mol_type = other RNA
                        organism = synthetic construct
```

SEQUENCE: 1123
tgaactactg caggaatcc                                                19

SEQ ID NO: 1124         moltype = RNA   length = 19
FEATURE                 Location/Qualifiers
source                  1..19
                        mol_type = other RNA
                        organism = synthetic construct
                        note = Synthetic
SEQUENCE: 1124
ctactgcagg aatccagat                                                19

SEQ ID NO: 1125         moltype = RNA   length = 19
FEATURE                 Location/Qualifiers
source                  1..19
                        mol_type = other RNA
                        organism = synthetic construct
                        note = Synthetic
SEQUENCE: 1125
caggcccttg gtgttttac                                                19

SEQ ID NO: 1126         moltype = RNA   length = 19
FEATURE                 Location/Qualifiers
source                  1..19
                        mol_type = other RNA
                        organism = synthetic construct
                        note = Synthetic
SEQUENCE: 1126
cttggtgttt taccatgga                                                19

SEQ ID NO: 1127         moltype = RNA   length = 19
FEATURE                 Location/Qualifiers
source                  1..19
                        mol_type = other RNA
                        organism = synthetic construct
                        note = Synthetic
SEQUENCE: 1127
ttggtgtttt accatggac                                                19

SEQ ID NO: 1128         moltype = RNA   length = 19
FEATURE                 Location/Qualifiers
source                  1..19
                        mol_type = other RNA
                        organism = synthetic construct
                        note = Synthetic
SEQUENCE: 1128
tggtgtttta ccatggacc                                                19

SEQ ID NO: 1129         moltype = RNA   length = 19
FEATURE                 Location/Qualifiers
source                  1..19
                        mol_type = other RNA
                        organism = synthetic construct
                        note = Synthetic
SEQUENCE: 1129
ggtgttttac catggaccc                                                19

SEQ ID NO: 1130         moltype = RNA   length = 19
FEATURE                 Location/Qualifiers
source                  1..19
                        mol_type = other RNA
                        organism = synthetic construct
                        note = Synthetic
SEQUENCE: 1130
gtgttttacc atggacccc                                                19

SEQ ID NO: 1131         moltype = RNA   length = 19
FEATURE                 Location/Qualifiers
source                  1..19
                        mol_type = other RNA
                        organism = synthetic construct
                        note = Synthetic
SEQUENCE: 1131
gttttaccat ggaccccag                                                19

SEQ ID NO: 1132         moltype = RNA   length = 19
FEATURE                 Location/Qualifiers
source                  1..19

-continued

```
                    mol_type = other RNA
                    organism = synthetic construct
                    note = Synthetic
SEQUENCE: 1132
ggagtactgc aacctgacg                                                19

SEQ ID NO: 1133     moltype = RNA   length = 19
FEATURE             Location/Qualifiers
source              1..19
                    mol_type = other RNA
                    organism = synthetic construct
                    note = Synthetic
SEQUENCE: 1133
gagtactgca acctgacgc                                                19

SEQ ID NO: 1134     moltype = RNA   length = 19
FEATURE             Location/Qualifiers
source              1..19
                    mol_type = other RNA
                    organism = synthetic construct
                    note = Synthetic
SEQUENCE: 1134
gtactgcaac ctgacgcga                                                19

SEQ ID NO: 1135     moltype = RNA   length = 19
FEATURE             Location/Qualifiers
source              1..19
                    mol_type = other RNA
                    organism = synthetic construct
                    note = Synthetic
SEQUENCE: 1135
tactgcaacc tgacgcgat                                                19

SEQ ID NO: 1136     moltype = RNA   length = 19
FEATURE             Location/Qualifiers
source              1..19
                    mol_type = other RNA
                    organism = synthetic construct
                    note = Synthetic
SEQUENCE: 1136
tgcaacctga cgcgatgct                                                19

SEQ ID NO: 1137     moltype = RNA   length = 19
FEATURE             Location/Qualifiers
source              1..19
                    mol_type = other RNA
                    organism = synthetic construct
                    note = Synthetic
SEQUENCE: 1137
cctgacgcga tgctcagac                                                19

SEQ ID NO: 1138     moltype = RNA   length = 19
FEATURE             Location/Qualifiers
source              1..19
                    mol_type = other RNA
                    organism = synthetic construct
                    note = Synthetic
SEQUENCE: 1138
ctgacgcgat gctcagaca                                                19

SEQ ID NO: 1139     moltype = RNA   length = 19
FEATURE             Location/Qualifiers
source              1..19
                    mol_type = other RNA
                    organism = synthetic construct
                    note = Synthetic
SEQUENCE: 1139
gatgctcaga cacagaagg                                                19

SEQ ID NO: 1140     moltype = RNA   length = 19
FEATURE             Location/Qualifiers
source              1..19
                    mol_type = other RNA
                    organism = synthetic construct
                    note = Synthetic
SEQUENCE: 1140
atgctcagac acagaaggg                                                19

SEQ ID NO: 1141     moltype = RNA   length = 19
```

```
FEATURE                 Location/Qualifiers
source                  1..19
                        mol_type = other RNA
                        organism = synthetic construct
                        note = Synthetic
SEQUENCE: 1141
agacacagaa gggactgtg                                                      19

SEQ ID NO: 1142         moltype = RNA  length = 19
FEATURE                 Location/Qualifiers
source                  1..19
                        mol_type = other RNA
                        organism = synthetic construct
                        note = Synthetic
SEQUENCE: 1142
gcatcctctt catttgatt                                                      19

SEQ ID NO: 1143         moltype = RNA  length = 19
FEATURE                 Location/Qualifiers
source                  1..19
                        mol_type = other RNA
                        organism = synthetic construct
                        note = Synthetic
SEQUENCE: 1143
catcctcttc atttgattg                                                      19

SEQ ID NO: 1144         moltype = RNA  length = 19
FEATURE                 Location/Qualifiers
source                  1..19
                        mol_type = other RNA
                        organism = synthetic construct
                        note = Synthetic
SEQUENCE: 1144
atcctcttca tttgattgt                                                      19

SEQ ID NO: 1145         moltype = RNA  length = 19
FEATURE                 Location/Qualifiers
source                  1..19
                        mol_type = other RNA
                        organism = synthetic construct
                        note = Synthetic
SEQUENCE: 1145
tcctcttcat tgattgtg                                                       19

SEQ ID NO: 1146         moltype = RNA  length = 19
FEATURE                 Location/Qualifiers
source                  1..19
                        mol_type = other RNA
                        organism = synthetic construct
                        note = Synthetic
SEQUENCE: 1146
cctcttcatt tgattgtgg                                                      19

SEQ ID NO: 1147         moltype = RNA  length = 19
FEATURE                 Location/Qualifiers
source                  1..19
                        mol_type = other RNA
                        organism = synthetic construct
                        note = Synthetic
SEQUENCE: 1147
cttcatttga ttgtgggaa                                                      19

SEQ ID NO: 1148         moltype = RNA  length = 19
FEATURE                 Location/Qualifiers
source                  1..19
                        mol_type = other RNA
                        organism = synthetic construct
                        note = Synthetic
SEQUENCE: 1148
ttcatttgat tgtgggaag                                                      19

SEQ ID NO: 1149         moltype = RNA  length = 19
FEATURE                 Location/Qualifiers
source                  1..19
                        mol_type = other RNA
                        organism = synthetic construct
                        note = Synthetic
SEQUENCE: 1149
tcatttgatt gtgggaagc                                                      19
```

| | |
|---|---|
| SEQ ID NO: 1150<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1150<br>catttgattg tgggaagcc | 19 |
| SEQ ID NO: 1151<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1151<br>atttgattgt gggaagcct | 19 |
| SEQ ID NO: 1152<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1152<br>gtgggaagcc tcaagtgga | 19 |
| SEQ ID NO: 1153<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1153<br>aagaaatgtc ctggaagca | 19 |
| SEQ ID NO: 1154<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1154<br>agaaatgtcc tggaagcat | 19 |
| SEQ ID NO: 1155<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1155<br>gaaatgtcct ggaagcatt | 19 |
| SEQ ID NO: 1156<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1156<br>aatgtcctgg aagcattgt | 19 |
| SEQ ID NO: 1157<br>FEATURE<br>source | moltype = RNA  length = 19<br>Location/Qualifiers<br>1..19<br>mol_type = other RNA<br>organism = synthetic construct<br>note = Synthetic |
| SEQUENCE: 1157<br>atgtcctgga agcattgta | 19 |
| SEQ ID NO: 1158<br>FEATURE<br>source | moltype = RNA  length = 19<br>Location/Qualifiers<br>1..19<br>mol_type = other RNA<br>organism = synthetic construct<br>note = Synthetic |

```
SEQUENCE: 1158
agaacaaggt tggaaagc                                                         19

SEQ ID NO: 1159         moltype = RNA   length = 19
FEATURE                 Location/Qualifiers
source                  1..19
                        mol_type = other RNA
                        organism = synthetic construct
                        note = Synthetic
SEQUENCE: 1159
gaacaaggtt tggaaagca                                                        19

SEQ ID NO: 1160         moltype = RNA   length = 19
FEATURE                 Location/Qualifiers
source                  1..19
                        mol_type = other RNA
                        organism = synthetic construct
                        note = Synthetic
SEQUENCE: 1160
aacaaggttt ggaaagcac                                                        19

SEQ ID NO: 1161         moltype = RNA   length = 19
FEATURE                 Location/Qualifiers
source                  1..19
                        mol_type = other RNA
                        organism = synthetic construct
                        note = Synthetic
SEQUENCE: 1161
acaaggtttg gaaagcact                                                        19

SEQ ID NO: 1162         moltype = RNA   length = 19
FEATURE                 Location/Qualifiers
source                  1..19
                        mol_type = other RNA
                        organism = synthetic construct
                        note = Synthetic
SEQUENCE: 1162
caaggtttgg aaagcactt                                                        19

SEQ ID NO: 1163         moltype = RNA   length = 19
FEATURE                 Location/Qualifiers
source                  1..19
                        mol_type = other RNA
                        organism = synthetic construct
                        note = Synthetic
SEQUENCE: 1163
aaggtttgga aagcacttc                                                        19

SEQ ID NO: 1164         moltype = RNA   length = 19
FEATURE                 Location/Qualifiers
source                  1..19
                        mol_type = other RNA
                        organism = synthetic construct
                        note = Synthetic
SEQUENCE: 1164
aggtttggaa agcacttct                                                        19

SEQ ID NO: 1165         moltype = RNA   length = 19
FEATURE                 Location/Qualifiers
source                  1..19
                        mol_type = other RNA
                        organism = synthetic construct
                        note = Synthetic
SEQUENCE: 1165
tggaaagcac ttctgtgga                                                        19

SEQ ID NO: 1166         moltype = RNA   length = 19
FEATURE                 Location/Qualifiers
source                  1..19
                        mol_type = other RNA
                        organism = synthetic construct
                        note = Synthetic
SEQUENCE: 1166
gtggaggcac cttaatatc                                                        19

SEQ ID NO: 1167         moltype = RNA   length = 19
FEATURE                 Location/Qualifiers
source                  1..19
                        mol_type = other RNA
```

-continued

```
                            organism = synthetic construct
                            note = Synthetic
SEQUENCE: 1167
cttaatatcc ccagagtgg                                                        19

SEQ ID NO: 1168             moltype = RNA   length = 19
FEATURE                     Location/Qualifiers
source                      1..19
                            mol_type = other RNA
                            organism = synthetic construct
                            note = Synthetic
SEQUENCE: 1168
taatatcccc agagtgggt                                                        19

SEQ ID NO: 1169             moltype = RNA   length = 19
FEATURE                     Location/Qualifiers
source                      1..19
                            mol_type = other RNA
                            organism = synthetic construct
                            note = Synthetic
SEQUENCE: 1169
agagtgggtg ctgactgct                                                        19

SEQ ID NO: 1170             moltype = RNA   length = 19
FEATURE                     Location/Qualifiers
source                      1..19
                            mol_type = other RNA
                            organism = synthetic construct
                            note = Synthetic
SEQUENCE: 1170
caaggtcatc ctgggtgca                                                        19

SEQ ID NO: 1171             moltype = RNA   length = 19
FEATURE                     Location/Qualifiers
source                      1..19
                            mol_type = other RNA
                            organism = synthetic construct
                            note = Synthetic
SEQUENCE: 1171
cctgggtgca caccaagaa                                                        19

SEQ ID NO: 1172             moltype = RNA   length = 19
FEATURE                     Location/Qualifiers
source                      1..19
                            mol_type = other RNA
                            organism = synthetic construct
                            note = Synthetic
SEQUENCE: 1172
gtgcacacca agaagtgaa                                                        19

SEQ ID NO: 1173             moltype = RNA   length = 19
FEATURE                     Location/Qualifiers
source                      1..19
                            mol_type = other RNA
                            organism = synthetic construct
                            note = Synthetic
SEQUENCE: 1173
agcagatatt gccttgcta                                                        19

SEQ ID NO: 1174             moltype = RNA   length = 19
FEATURE                     Location/Qualifiers
source                      1..19
                            mol_type = other RNA
                            organism = synthetic construct
                            note = Synthetic
SEQUENCE: 1174
gcagatattg ccttgctaa                                                        19

SEQ ID NO: 1175             moltype = RNA   length = 19
FEATURE                     Location/Qualifiers
source                      1..19
                            mol_type = other RNA
                            organism = synthetic construct
                            note = Synthetic
SEQUENCE: 1175
cagatattgc cttgctaaa                                                        19

SEQ ID NO: 1176             moltype = RNA   length = 19
FEATURE                     Location/Qualifiers
```

```
source                   1..19
                         mol_type = other RNA
                         organism = synthetic construct
                         note = Synthetic
SEQUENCE: 1176
agatattgcc ttgctaaag                                                      19

SEQ ID NO: 1177          moltype = RNA   length = 19
FEATURE                  Location/Qualifiers
source                   1..19
                         mol_type = other RNA
                         organism = synthetic construct
                         note = Synthetic
SEQUENCE: 1177
gatattgcct tgctaaagc                                                      19

SEQ ID NO: 1178          moltype = RNA   length = 19
FEATURE                  Location/Qualifiers
source                   1..19
                         mol_type = other RNA
                         organism = synthetic construct
                         note = Synthetic
SEQUENCE: 1178
atattgcctt gctaaagct                                                      19

SEQ ID NO: 1179          moltype = RNA   length = 19
FEATURE                  Location/Qualifiers
source                   1..19
                         mol_type = other RNA
                         organism = synthetic construct
                         note = Synthetic
SEQUENCE: 1179
tattgccttg ctaaagcta                                                      19

SEQ ID NO: 1180          moltype = RNA   length = 19
FEATURE                  Location/Qualifiers
source                   1..19
                         mol_type = other RNA
                         organism = synthetic construct
                         note = Synthetic
SEQUENCE: 1180
tcatcactga caaagtaat                                                      19

SEQ ID NO: 1181          moltype = RNA   length = 19
FEATURE                  Location/Qualifiers
source                   1..19
                         mol_type = other RNA
                         organism = synthetic construct
                         note = Synthetic
SEQUENCE: 1181
ggactgaatg ttacatcac                                                      19

SEQ ID NO: 1182          moltype = RNA   length = 19
FEATURE                  Location/Qualifiers
source                   1..19
                         mol_type = other RNA
                         organism = synthetic construct
                         note = Synthetic
SEQUENCE: 1182
gactgaatgt tacatcact                                                      19

SEQ ID NO: 1183          moltype = RNA   length = 19
FEATURE                  Location/Qualifiers
source                   1..19
                         mol_type = other RNA
                         organism = synthetic construct
                         note = Synthetic
SEQUENCE: 1183
actgaatgtt acatcactg                                                      19

SEQ ID NO: 1184          moltype = RNA   length = 19
FEATURE                  Location/Qualifiers
source                   1..19
                         mol_type = other RNA
                         organism = synthetic construct
                         note = Synthetic
SEQUENCE: 1184
ctgaatgtta catcactgg                                                      19
```

```
SEQ ID NO: 1185        moltype = RNA   length = 19
FEATURE                Location/Qualifiers
source                 1..19
                       mol_type = other RNA
                       organism = synthetic construct
                       note = Synthetic
SEQUENCE: 1185
tgaatgttac atcactggc                                                    19

SEQ ID NO: 1186        moltype = RNA   length = 19
FEATURE                Location/Qualifiers
source                 1..19
                       mol_type = other RNA
                       organism = synthetic construct
                       note = Synthetic
SEQUENCE: 1186
aatgttacat cactggctg                                                    19

SEQ ID NO: 1187        moltype = RNA   length = 19
FEATURE                Location/Qualifiers
source                 1..19
                       mol_type = other RNA
                       organism = synthetic construct
                       note = Synthetic
SEQUENCE: 1187
gaaacccaag gtacctttg                                                    19

SEQ ID NO: 1188        moltype = RNA   length = 36
FEATURE                Location/Qualifiers
source                 1..36
                       mol_type = other RNA
                       organism = synthetic construct
                       note = Synthetic
SEQUENCE: 1188
gacaacagaa tattatccaa gcagccgaaa ggctgc                                 36

SEQ ID NO: 1189        moltype = RNA   length = 22
FEATURE                Location/Qualifiers
source                 1..22
                       mol_type = other RNA
                       organism = synthetic construct
                       note = Synthetic
SEQUENCE: 1189
ttggataata ttctgttgtc gg                                                22

SEQ ID NO: 1190        moltype = RNA   length = 19
FEATURE                Location/Qualifiers
source                 1..19
                       mol_type = other RNA
                       organism = synthetic construct
                       note = Synthetic
SEQUENCE: 1190
gacaacagaa tattatcca                                                    19

SEQ ID NO: 1191        moltype = RNA   length = 24
FEATURE                Location/Qualifiers
source                 1..24
                       mol_type = other RNA
                       organism = synthetic construct
                       note = Synthetic
```

```
SEQUENCE: 1191
cgttaatcgc gtataatacg cgta                                          24

SEQ ID NO: 1192         moltype = RNA  length = 27
FEATURE                 Location/Qualifiers
source                  1..27
                        mol_type = other RNA
                        organism = synthetic construct
                        note = Synthetic
SEQUENCE: 1192
atacgcgtat tatacgcgat taacgac                                       27

SEQ ID NO: 1193         moltype = RNA  length = 25
FEATURE                 Location/Qualifiers
source                  1..25
                        mol_type = other RNA
                        organism = synthetic construct
                        note = Synthetic
SEQUENCE: 1193
catattgcgc gtatagtcgc gttag                                         25

SEQ ID NO: 1194         moltype = RNA  length = 27
FEATURE                 Location/Qualifiers
source                  1..27
                        mol_type = other RNA
                        organism = synthetic construct
                        note = Synthetic
SEQUENCE: 1194
ctaacgcgac tatacgcgca atatggt                                       27

SEQ ID NO: 1195         moltype = RNA  length = 24
FEATURE                 Location/Qualifiers
source                  1..24
                        mol_type = other RNA
                        organism = synthetic construct
                        note = Synthetic
SEQUENCE: 1195
ggcgcgtata gtcgcgcgta tagc                                          24

SEQ ID NO: 1196         moltype = RNA  length = 27
FEATURE                 Location/Qualifiers
source                  1..27
                        mol_type = other RNA
                        organism = synthetic construct
                        note = Synthetic
SEQUENCE: 1196
gactatacgc gcgactatac gcgcctc                                       27

SEQ ID NO: 1197         moltype = RNA  length = 16
FEATURE                 Location/Qualifiers
source                  1..16
                        mol_type = other RNA
                        organism = synthetic construct
                        note = Synthetic
SEQUENCE: 1197
gcagccgaaa ggctgc                                                   16
```